United States Patent [19]

Fischer et al.

[11] Patent Number: 5,171,353
[45] Date of Patent: Dec. 15, 1992

[54] SULFONAMIDES

[75] Inventors: Klaus Fischer, Speyer; Horst Mayer, Ludwigshafen; Klaus Ditrich, Bad Duerkheim; Gerhard Hamprecht, Weinheim; Bruno Wuerzer, Otterstadt; Karl-Otto Westphalen, Speyer, all of Fed. Rep. of Germany

[73] Assignee: BASF Akteingesellschaft, Ludwigshafen, Fed. Rep. of Germany

[21] Appl. No.: 521,032

[22] Filed: May 9, 1990

[30] Foreign Application Priority Data

May 20, 1989 [DE] Fed. Rep. of Germany ..... 39160496

[51] Int. Cl.$^5$ .................. A01N 43/48; A01N 43/64; C07D 471/02; C07D 473/00
[52] U.S. Cl. ........................... 71/92; 544/264; 544/265; 544/266; 544/267; 544/268; 544/269; 544/270; 544/271; 544/272; 544/276; 544/277; 546/118
[58] Field of Search ............... 544/264, 265, 267, 269, 544/270, 272, 276, 277, 271; 546/118; 71/92

[56] References Cited

U.S. PATENT DOCUMENTS

| | | | |
|---|---|---|---|
| 4,761,173 | 8/1988 | Dean | 71/92 |
| 4,859,231 | 8/1989 | Westermann et al. | 71/93 |
| 4,881,969 | 11/1989 | Saupe et al. | 71/94 |
| 4,908,056 | 3/1990 | Tseng | 71/90 |

FOREIGN PATENT DOCUMENTS 0150974 6/1985 European Pat. Off.

OTHER PUBLICATIONS

Rapoport et al., J. Org. Chem. (1977) 42(18) 3065-70.

Primary Examiner—Mukund J. Shah
Assistant Examiner—Matthew V. Grumbling
Attorney, Agent, or Firm—Keil & Weinkauf

[57] ABSTRACT

Sulfonamides of the general formula I

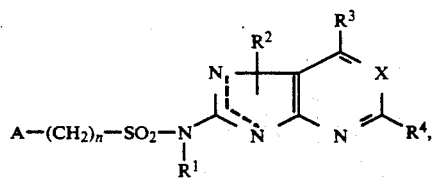

where
- $R^1$ is hydrogen of $C_1$–$C_4$-alkyl,
- $R^2$ is hydrogen or substituted or unsubstituted $C_1$–$C_6$-alkyl; $C_3$–$C_4$-alkenyl; $C_3$–$C_4$-alkynyl or substituted or unsubstituted saturated or singly unsaturated 5- to 7-membered heteroaryl;
- $R^3$ and $R^4$ are halogen; substituted or unsubstituted $C_1$–$C_4$-alkoxy $C_1$–$C_4$-alkylthio, $C_2$–$C_6$-alkenyl, $C_2$–$C_6$-alkenyloxy, $C_2$–$C_6$-alkenylthio, $C_2$–$C_6$-alkynyl, $C_2$–$C_6$-alkynyloxy, $C_2$–$C_6$-alkynylthio, $C_3$–$C_6$-cycloalkyl, $C_3$–$C_6$-cycloalkylthio, $C_5$–$C_6$-cycloalkenyl, $C_3$–$C_6$-cycloalkoxy, $C_5$–$C_6$-cycloalkenyloxy, $C_5$–$C_6$-cycloalkenylthio, phenyl, phenoxy, phenylthio, benzyl, benzyloxy or benzylthio; the group given for $R^2$, or $NR^7R^8$, where $R^7$ and $R^8$ are hydrogen, $C_1$–$C_6$-alkyl, $C_3$–$C_6$-alkenyl, $C_3$–$C_6$-alkynyl, $C_3$–$C_6$-cycloalkyl, $C_5$–$C_6$-cycloalkenyl, substituted or unsubstituted phenyl and/or benzyl bedeuten, or is substituted or unsubstituted $C_4$–$C_6$-alkylene which may be interrupted ar oxygen, sulfur or nitrogen;
- X is nitrogen or $=CR^514$, where $R^5$ is one of the radicals $R^3$,
- n is 0 or 1 and
- A is substituted or unsubstituted mono- or dinuclear aryl containing one or two nitrogen, oxygen and/or sulfur atoms, and their agriculturally useful salts, and herbicidal and growth-regulating agents containing them.

8 Claims, No Drawings

SULFONAMIDES

The present invention relates to sulfonamides of the general formula I

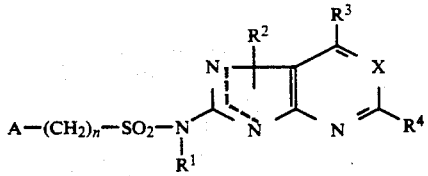

where
R$^1$ is hydrogen or C$_1$–C$_4$-alkyl,
R$^2$ is hydrogen,
   a C$_1$–C$_6$-alkyl which can be substituted by one to five halogens and/or one of the following: C$_1$–C$_4$-alkoxy, C$_1$–C$_4$-haloalkoxy, C$_1$–C$_4$-alkylthio, C$_1$–C$_4$-haloalkylthio, phenyl, phenoxy or phenylthio;
   a C$_3$–C$_4$-alkenyl, a C$_3$–C$_4$-alkynyl;
   a saturated or singly unsaturated 5- to 7-membered heterocycle which contains one or two nitrogen, oxygen and/or sulfur atoms and which can have one to three of the following substituents: halogen, C$_1$–C$_4$-alkyl, C$_1$–C$_4$-alkoxy, C$_1$–C$_4$-haloalkyl, C$_1$–C$_4$-haloalkoxy, C$_1$–C$_4$-alkylthio, C$_1$–C$_4$-haloalkylthio and/or phenyl, phenoxy and/or phenylthio;
R$^3$ and R$^4$ are halogen;
   C$_1$–C$_4$-alkoxy, C$_1$–C$_4$-alkylthio, C$_2$–C$_6$-alkenyl, C$_2$–C$_6$-alkenyloxy, C$_2$–C$_6$-alkenylthio, C$_2$–C$_6$-alkynyl, C$_2$–C$_6$-alkynyloxy and/or C$_2$–C$_6$-alkynylthio, it being possible for these radicals to be substituted by one to five halogens and/or by one of the following groups: C$_1$–C$_4$-alkoxy, C$_1$–C$_4$-haloalkoxy, C$_1$–C$_4$-alkylthio, C$_1$–C$_4$-haloalkylthio, phenyl, phenoxy or phenylthio;
   C$_3$–C$_6$-cycloalkyl, C$_3$–C$_6$-cycloalkylthio, C$_5$–C$_6$-cycloalkenyl, C$_3$–C$_6$-cycloalkoxy, C$_5$–C$_6$-cycloalkenyloxy, C$_5$–C$_6$-cycloalkenylthio, phenyl, phenoxy, phenylthio, benzyl, benzyloxy or benzylthio, it being possible for these cyclic groups to be substituted by one to five halogens and/or one to three of the following:
   C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, phenyl, phenoxy, phenylthio, benzyl, benzyloxy and/or benzylthio; the groups mentioned under R$^2$ or
NR$^7$R$^8$ where
   R$^7$ and R$^8$ are hydrogen, C$_1$–C$_6$-alkyl, C$_3$–C$_6$-alkenyl, C$_3$–C$_6$-alkynyl, C$_3$–C$_6$-cycloalkyl, C$_5$–C$_6$-cycloalkenyl, phenyl and/or benzyl, it being possible for the aromatic rings in turn to be substituted once to five times by halogen and/or once to three times by C$_1$–C$_4$-alkyl, C$_1$–C$_4$-haloalkyl, C$_1$–C$_4$-alkoxy and/or C$_1$–C$_4$-haloalkoxy or together are a C$_4$–C$_6$-alkylene bridge which can be interrupted by an oxygen, sulfur or a nitrogen atom, it being possible for these bridges in turn to carry one to three C$_1$–C$_4$-alkyl groups;
X is nitrogen or =CR$^5$— where R$^5$ is one of the radicals R$^3$,
n is 0 or 1 and
A is a mono- or dinuclear aromatic radical which can contain one or two nitrogen, oxygen and/or sulfur atoms and can carry one to five halogens and/or one to three of the following: cyano, nitro, thiocyanato, the radicals R$^3$, COR$^6$ where R$^6$ is hydroxyl, amino or one of the radicals R$^3$ and SO$_m$R$^6$ where m is 1 or 2,
and the salts thereof which can be used in agriculture.

The present invention also relates to a process for the preparation of these compounds and to the use thereof for controlling undesired plant growth and for influencing plant growth.

EP-A-150,974 describes sulfonamides which have a herbicidal action. However, they do not meet all requirements, e.g. with regard to selectivity and specific action.

Hence the object of the present invention was to find and synthesize substances with satisfactory properties. In accordance with this object, we have found the sulfonamides I defined in the first paragraph.

The present invention also relates to processes for the preparation of these compounds I, herbicides and agents for influencing plant growth, which contain the novel compounds as active ingredients, and a process for influencing and controlling plant growth with these compounds.

The compounds I according to the invention can be obtained in a variety of ways similar to known conversion methods. As Examples, seven processes (A to G) are explained below.

Process A

The compounds I are obtained in a conventional manner (J. Med. Chem. 9 (1966), 373) by reacting an appropriate sulfonamide II in an inert organic solvent in the presence of a base with a heteroaryl halide III as shown below.

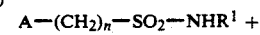

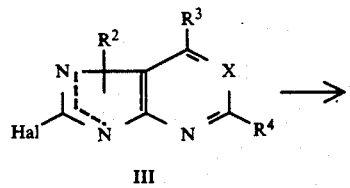

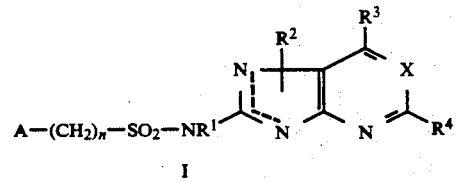

Hal in formula III is a halogen such as fluorine, chlorine, bromine and iodine, and particularly suitable compounds III are those in which Hal is chlorine or bromine.

Solvents expediently used for these reactions are halohydrocarbons, e.g. tetrachloroethane, methylene chloride, chloroform, dichloroethane, chlorobenzene and 1,2-dichlorobenzene; ethers, e.g. diethyl ether, methyl tert-butyl ether, dimethoxyethane, diethylene glycol dimethyl ether, tetrahydrofuran and dioxane; dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one; aromatics, e.g. benzene, toluene, xylene, pyridine and quinoline; ketones, e.g. acetone, methyl ethyl ketone; alcohols, e.g. methanol, ethanol, isopropanol and t-butanol, or mixtures thereof.

The reaction can be carried out at from 25° C. to the reflux temperature of the particular solvent or mixture thereof.

Bases used as catalysts in this reaction are aromatic nitrogen bases such as pyridine, 4-dimethylaminopyridine and quinoline; tertiary aliphatic amines such as triethylamine, ethyldiisopropylamine and N-methylmorpholine; bi- and tricyclic amines such as diazabicycloundecene (DBU) or diazabicyclooctane (DABCO), and hydroxides, hydrides, alkoxides, carbonates and bicarbonates of alkali metals and alkaline earth metals, in particular NaOH, KOH, NaH, KH, CaH$_2$, LiH, NaOMe, NaOEt, KOtBu, Na$_2$CO$_3$, K$_2$CO$_3$, NaHCO$_3$, KHCO$_3$. It is also sometimes useful to employ combinations of these bases.

The molar ratios of the starting compounds used in the reaction are generally from 1:1 to 1:3 for the ratio of sulfonamide II to heteroaryl halide III and from 1:1 to 1:3 for the ratio of sulfonamide II to catalytic base.

The concentration of the precursors in the solvent is generally from 0.1 to 5 mol/l, preferably from 0.2 to 2 mol/l.

The reaction is particularly preferably carried out in aprotic dipolar solvents such as acetonitrile, dimethylformamide, dimethyl sulfoxide, N-methylpyrrolidone, 1,3-dimethyltetrahydro-2(1H)-pyrimidinone, 1,3-dimethylimidazolidin-2-one or ethers such as 1,2-dimethoxyethane, diethylene glycol dimethyl ether, tetrahydrofuran or dioxane, at from 80° C. to 150° C., using sodium hydride, sodium methylate, sodium ethylate or potassium tert-butylate as bases. It has proven particularly advantageous initially to convert the sulfonamide II, by reaction with the base, into its salt and then to react the latter with the heteroaryl halide III. It is possible to isolate the sulfonamide salt, but it is unnecessary and, in fact, it is extremely expedient merely to generate the sulfonamide salt in situ and react it further with the heteroaryl halide III in the same reaction medium.

Many of the sulfonamides of the general formula II which are required are commercially available. Novel sulfonamides of the formula II can be prepared by conventional methods (Pawlenko, Houben-Weyl, Methoden der organischen Chemie, volume E 11, Organic Sulfur Compounds, G. Thieme Verlag, Stuttgart (1985), pp. 1098 et seq.).

The heteroaryl halides of the general formula III which are required can also be obtained by conventional methods (Shaw; Comprehensive Heterocyclic Chemistry (The Structure, Reaction, Synthesis and Uses of Heterocyclic Compounds), Vol. 5, 1st ed. (1984), Chapter 4.09, pp. 499 et seq.; Montgomery, J. A. Secrist III in Comprehensive Heterocyclic Chemistry, Vol. 5, 1st ed. (1984), Chapter 4.10, pp. 615 et seq., and pp. 635 et seq.; Lister, The Chemistry of Heterocyclic Compounds, Fused Pyrimidines, Part II, Purines (1971) and Robins, Heterocyclic Compounds, Vol. 8, pp. 162 et seq. (1967)).

Process B

The compounds I with R$^2$≠H are also obtained by reacting an appropriate sulfonyl halide IV in a conventional manner in an inert organic solvent in the presence of a base with a heteroarylamine V where R$^2$ is not hydrogen, as shown below:

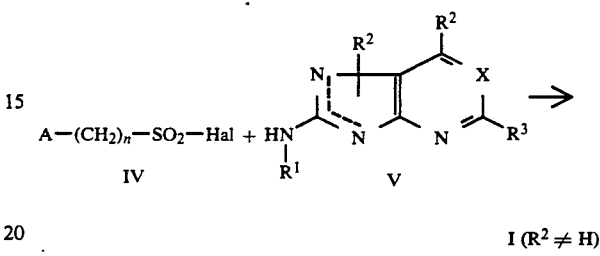

Hal in formula IV is a halogen such as fluorine, chlorine and bromine, especially chlorine.

It is possible in principle to use for this reaction the solvents and bases, and combinations thereof, mentioned for process A, at from 25° C. to the reflux temperature of the particular solvent or mixture thereof. Addition of a base is unnecessary with basic solvents such as pyridine.

The molar ratio of the starting compounds is generally from 1:1 to 1:3 for the ratio of heteroarylamine V to catalytic base. However, it is also possible for the sulfonyl halides IV and the reaction-accelerating bases to be employed in less than the stoichiometric amount in each case.

The concentration of the precursors in the solvent is generally from 0.1 to 5 mol/l, preferably from 0.2 to 2 mol/l.

The sulfonyl halides of the general formula IV which are required are commercially available or can be prepared by conventional methods (Clarke et al., Org. Synth. Coll. Vol. I, 2nd ed., 1941, pp. 85 et seq.; Hoffmann, Org, Synth., Vol. 60, pp. 121 et seq.). The heteroarylamines of the general formula V required for the reaction can be prepared by conventional methods. These methods are described in the literature cited in connection with the heteroaryl halides of the general formula II in process A.

Process C

Compounds I where R$^1$ is hydrogen are obtained, for example, by reacting a sulfonyl isocyanide derivative of the formula VI in a conventional manner (Synthesis 11 (1982), 984; Chem. Ber. 99 (1966), 2885) with a diaminoheteroaryl derivative of the formula VIIa or VIIb, in the presence or absence of a base, as shown below.

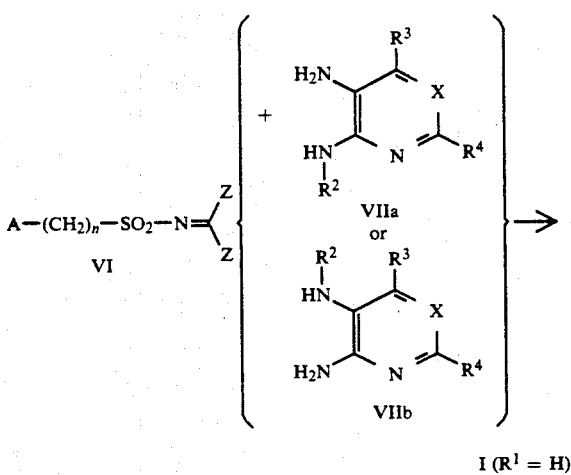

Z in formula VI is a halogen such as chlorine or bromine, or $C_1$–$C_4$-alkylthio or benzylthio, with chlorine and methylthio being preferred.

These reactions are carried out in one of the chlorohydrocarbons, ethers, aromatic or aprotic dipolar solvents or mixtures thereof mentioned in process A, at from 25° C. to the boiling point of the solvent or mixture.

The reactions in this process are particularly preferably carried out in halohydrocarbons such as chlorobenzene, 1,2-dichlorobenzene; aromatics such as toluene, xylene; ethers such as 1,2-dimethoxyethane, diethylene glycol dimethyl ether, dioxane or aprotic dipolar solvents such as acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one at from 80° C. to 150° C. The molar ratio of the starting compounds used in the reaction is generally from 1:1 to 1:5 for the ratio of derivatives of the general formula VI to diaminoheteroaryl compounds of the general formula VIIa or VIIb, with the concentration of the precursors in the solvent being from 0.1 to 5 mol/l, preferably from 0.2 to 2 mol/l.

It is advantageous, particularly in reactions of sulfonyl isocyanide dihalides of the general formula VI where Z is halogen, to carry out the reaction in the presence of at least 2 mol-equivalents of a base to bind the hydrogen halide produced in the reaction.

Preferred bases are aromatic nitrogen bases such as pyridine, 4-dimethylaminopyridine or quinoline, tertiary aliphatic amines such as triethylamine, ethyldiisopropylamine or N-methylmorpholine, bi- and tricyclic amines such as diazabicycloundecene (DBU) or diazabicyclooctane (DABCO) or, particularly advantageously, diaminoheteroaryl derivatives of the general formula VIIa or VIIb.

The sulfonyl isocyanide derivatives of the general formula VI which are required can be prepared by conventional methods (Kühler, Houben-Weyl, Methoden der Organischen Chemie, Volume E4, Carbonic acid derivatives, G. Thieme Verlag, Stuttgart (1983), pp. 540 et seq., 584 et seq.). The diaminoheteroaryl derivatives of the general formula VIIa or VIIb required for the reaction can be prepared by conventional methods (J. Brown, Comprehensive Heterocyclic Chemistry, Vol. 3, 1st ed. (1984), Chapter 2.13, pp. 57 et seq.; Jones, Comprehensive Chemistry, vol. 2, 1st ed. (1984), Chapter 2.08, pp. 395 et seq.).

Process D

In a modification of the process described under C, the compounds I where $R^1$ is hydrogen are also obtained by reacting a suitable N-sulfonylhalothioformimidic alkyl or benzyl ester VIa with a diaminoheteroaryl derivative VIIa or VIIb and subsequently cyclizing the isothiourea VIIIa or VIIIb to give the desired sulfonamide I (J. Org. Chem. 42 (1977), 3065).

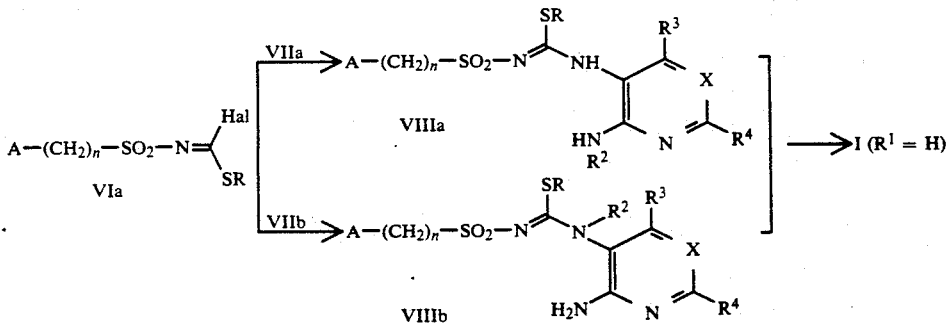

Hal in formula VIa is chlorine or bromine, and R is $C_1$–$C_4$-alkyl or benzyl, with chlorine and methyl being preferred.

It is possible in principle to employ for the reactions shown in the diagram to give the isothiourea derivatives of the general formula VIIIa or VIIIb the solvents mentioned in process A, in combination with the bases listed in process C, preferably at from 0° C. to 50° C.

The subsequent cyclization of the isothioureas VIIIa or VIIIb to give the sulfonamides I is carried out in all cases using the diluents and bases mentioned in process C, similar to Rapoport et al. (Journal of Organic Chemistry, 42 (1977), 2065) in the presence of at least one mol-equivalent of a silver salt, with silver nitrate being preferred. The precursors of the general formula VIa required for the reaction are obtained by conventional methods (e.g. Kühle, Houbey-Weyl, Methoden der organische Chemie, Volume E4, Carbonic acid derivatives, G. Thieme Verlag, Stuttgart (1983), p. 551 and literature cited therein).

Process E

Compounds I where neither $R^1$ nor $R^2$ is hydrogen are also obtained, for example, by reacting an appropriate sulfonamide IX in a conventional manner in an organic solvent in the presence of a base with an alkylating reagent X where Nu is a nucleophilic leaving group and $R^1$ is not hydrogen, as shown below.

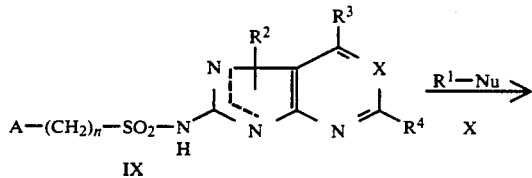

I (R¹, R² ≠ H)

It is expedient to use for this reaction inert solvents and mixtures thereof, as detailed in process A.

These reactions can be carried out at from 25° C. to the reflux temperature of the solvent or mixture thereof.

The bases used are those detailed in process A. It is possible to use the base as solvent, in which case no additional solvent is necessary.

The molar ratio of the starting compounds is generally from 1:1 to 1:3 (compound IX to electrophile X) or 1:1 to 1:5 (compound IX to base). The concentration of the precursors in the solvent is generally from 0.1 to 5 mol/l, preferably from 0.2 to 2 mol/l.

The alkylating reagents X used are, in particular, $C_1$–$C_4$-alkyl chlorides, bromides, iodides, benzenesulfonates, p-bromobenzenesulfonates, p-methylbenzenesulfonates, di-$C_1$–$C_4$-alkyl sulfates and tri-$C_1$–$C_4$-alkyloxonium tetrafluoroborates. The compounds X are generally commercially available or can be prepared by conventional methods.

The sulfonamides of the general formula IX with $R^2 \neq H$ can be obtained by processes A–D described above.

Process F

Compounds of the general formula I where $R^3$ and/or $R^4$ is alkoxy, alkylthio, phenoxy or a substituted amino, and X is nitrogen, are obtained particularly advantageously by reacting a sulfonamide derivative XIa or XIb where Hal is halogen such as fluorine, chlorine, bromine, especially chlorine, and $R^3$ in the formula XIb is not halogen or phenoxy, with an appropriate alcohol, thiol, phenol or amine XIIa or XIIb in a conventional manner in an organic solvent in the presence of a base as shown below.

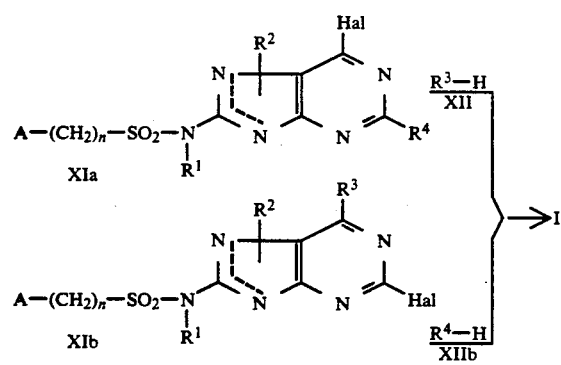

It is possible in principle to use for these reactions the solvents and bases, and the combinations thereof, mentioned in process A. The ratio of the reagent of the formula XIIa or XIIb to the sulfonamide XIa or XIb is preferably from 1:1 to 5:1, especially 3:1 to 5:1, and the reaction is carried out in a solvent such as an alcohol, e.g. methanol, ethanol, propanol, iso-propanol, n-butanol, iso-butanol, tert-butanol, ether, e.g. diethyl ether, methyl tert-butyl ether, 1,2-dimethoxyethane, tetrahydrofuran, dioxane, or aprotic dipolar solvent, e.g. acetonitrile, dimethylformamide or dimethyl sulfoxide, at from room temperature to 130° C.

Process G

In a modification of the process described under F, compounds of the general formula I where $R^3$ and $R^4$ are identical alkoxy, alkylthio, phenoxy, alkylamino, dialkylamino or alkyleneamino groups, and X is nitrogen, are obtained by reacting an appropriate sulfonamide derivative XIc with the derivative XIIa or XII in an organic solvent in the presence of a base as shown below.

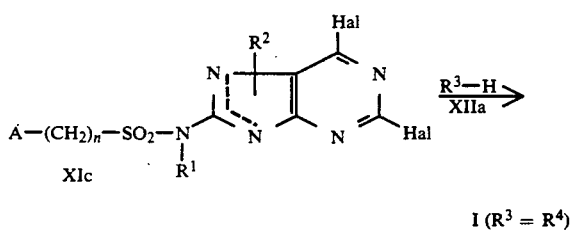

I ($R^3 = R^4$)

Hal in the formula XIc is fluorine, chlorine or bromine, especially chlorine.

The reaction is carried out under conditions similar to those described in process F.

The nucleophiles of the general formula XIIa or XIIb are generally commercially available or can be prepared from known precursors in a straightforward and conventional manner. The sulfonamides XIa, XIb and XIc can be obtained by processes A–E described above.

Suitable and preferred substituents having regard to the intended use of the compounds I are the following:

$R^1$ is hydrogen or $C_1$–$C_4$-alkyl such as methyl, ethyl, n-propyl, iso-propyl, n-butyl, sec-butyl, iso-butyl and tert-butyl, especially methyl, ethyl, propyl and iso-propyl $R^2$ is hydrogen, allyl; propargyl; alkyl as mentioned for $R^1$, and pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, especially methyl, ethyl, propyl and iso-propyl, which can be substituted by one to five halogens, especially fluorine and/or chlorine, or one of the following: alkoxy such as methoxy, ethoxy, n-propoxy, 2-methylethoxy, n-butoxy, 1-methylpropoxy, 2-methylpropoxy and 1,1-dimethylethoxy, especially methoxy, ethoxy, 1-methylethoxy and 1,1-dimethylethoxy;

haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy and pentafluoroethoxy;

alkylthio such as methylthio, ethylthio, propylthio, 1-methylethylthio, butylthio, 1-methylpropylthio, 2-methylpropylthio and 1,1-dimethylethylthio, especially methylthio and ethylthio;

haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, especially difluoromethylthio and pentafluoroethylthio; phenyl or phenylthio;

a 5- to 7-membered saturated or singly unsaturated heterocycle such as tetrahydrofuryl, tetrahydrothienyl, dioxolanyl, dithiolanyl, oxathiolanyl, pyrazolidinyl, dihydropyrazolyl, imidazolidinyl, dihydroimidazolyl, isoxazolidinyl, dihydroisoxazolyl, oxazolidinyl, dihydrooxazolyl, isothioazolidinyl, dihydroisothiazolyl, thiazolidinyl, dihydrothiazolyl, tetrahydropyran-3-yl, dihydropyran-3-yl, tetrahydropyran-4-yl, tetrahydropyran-2-yl, dihydropyran-4-yl, tetrahydrothiopyran-3-yl, dihydrothiopyran-3-yl, tetrahydrothiopyran-4-yl, dihydrothiopyran-4-yl and dioxepan-5-yl, piperidinyl, tetrahydro-1,3-oxazinyl, tetrahydro-1,4-oxazinyl, tetrahydro-1,3-thiazinyl, tetrahydro-1,4-thiazinyl, perhydro-1,3-oxazepinyl, perhydro-1,4-oxazepinyl, perhydro-1,3-thiazepinyl, perhydro-1,4-thiazepinyl and perhydroazepinyl, it being possible for this ring to carry one to three of the following substituents:

halogen, such as fluorine, chlorine, bromine and iodine, especially fluorine and chlorine; alkyl as mentioned for $R^1$, especially methyl, ethyl, propyl and iso-propyl;

alkoxy as mentioned above, especially methoxy, ethoxy, 1-methylethoxy and 1,1-dimethylethoxy; haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, especially trifluoromethyl;

haloalkoxy as mentioned above, especially trifluoromethoxy, trifluoroethoxy and chloroethoxy;

alkylthio as mentioned above, especially methylthio and ethylthio;

haloalkylthio as mentioned above, especially difluoromethylthio and pentafluoroethylthio and/or phenyl, phenoxy or phenylthio;

$R^3$ and $R^4$ are, independently of one another, halogen as mentioned for $R^2$, especially fluorine and chlorine; alkoxy as mentioned for $R^2$, especially methoxy, ethoxy, 1-methylethoxy and 1,1-dimethylethoxy; alkylthio as mentioned for $R^2$, especially methylthio and ethylthio;

alkenyl such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-2-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, especially allyl and, in general and in particular, corresponding alkenyloxy and/or alkenylthio;

alkynyl such as ethynyl, 1-propynyl, propargyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, especially propargyl and, in general and in particular, corresponding alkynyloxy and/or alkynylthio;

it being possible for these radicals to be substituted by one to five halogens and/or by one of the following: alkoxy, haloalkoxy, alkylthio and haloalkylthio as mentioned for $R^2$, especially fluorine, chlorine, methoxy, ethoxy, 1-methylethoxy, 1,1-dimethylethoxy, trifluoromethoxy, pentafluoroethoxy, methylthio, ethylthio, difluoromethylthio and pentafluoroethylthio, and phenyl, phenoxy or phenylthio;

cycloalkyl such as cyclopropyl, cyclobutyl, cyclopentyl and cyclohexyl, especially cyclopropyl, cyclopentyl and cyclohexyl, and corresponding cycloalkoxy and/or cycloalkylthio, especially cyclopentyloxy, cyclohexyloxy, cyclopentylthio, cyclohexylthio;

cycloalkenyl such as cyclopentenyl, cyclohexenyl, cyclohexadienyl, especially cyclopentenyl and cyclohexenyl, and corresponding cycloalkenyloxy and/or cycloalkenylthio, especially cyclopentenyloxy, cyclohexenyloxy, cyclopentenylthio and cyclohexenylthio;

phenyl, phenoxy, phenylthio, benzyl, benzyloxy and/or benzylthio, it being possible for these cyclic radicals to carry one to five halogens as mentioned for $R^2$, especially fluorine and chlorine, and/or one to three of the following: alkyl as mentioned for $R^1$, especially methyl, ethyl, propyl, iso-propyl;

haloalkyl as mentioned for $R^2$, especially trifluoromethyl, alkoxy as mentioned for $R^2$, especially methoxy, ethoxy, 1-methylethoxy and 1,1-dimethylethoxy;

haloalkoxy as mentioned for $R^2$, especially trifluoromethoxy and trifluoroethoxy and chloroethoxy; alkylthio as mentioned for $R^2$, especially methylthio and ethylthio; haloalkylthio as mentioned for $R^2$, especially difluoromethylthio and pentafluoroethylthio; phenyl, phenoxy, phenylthio, benzyl, benzyloxy and/or benzylthio;

in general and in particular the groups mentioned for $R^2$, or $NR^7R^8$ where $R^7$ and $R^8$ are hydrogen; alkyl as mentioned for $R^2$, especially as mentioned in general for $R^1$; alkenyl, alkynyl or cycloalkyl of 3 to 6 carbons in each case, as mentioned in general and in particular for $R^3$;

cycloalkenyl as mentioned in general and in particular for $R^3$;

phenyl and/or benzyl, it being possible for the aromatic rings in turn to be substituted once to five times by the halogens mentioned for $R^3$ and/or once to three times by alkyl, haloalkyl, alkoxy and/or haloalkoxy of 1 to 4 carbons in each case, as mentioned in general and in particular for $R^2$, or $R^7$ and $R^8$ together are $C_4$-$C_6$-alkylene which can be interrupted by a hetero atom such as oxygen, sulfur or nitrogen, such as —$(CH_2)_4$—, —$(CH_2)_5$—, —$(CH_2)_6$—, —$(CH_2)_2$—O—$(CH_2)_2$—, —$(CH_2)_2$—S—$(CH_2)_2$— and —$(CH_2)_2$—NH—$(CH_2)_2$—, it being possible for these bridges in turn to carry one to three of the alkyl groups mentioned in general and in particular for $R^1$;

X is nitrogen or =$CR^5$— where $R^5$ is in general and in particular one of the groups mentioned for $R^3$, n is 0 or 1 and A is aryl or heteroaryl such as phenyl, naphthyl, six-membered heterocycles with one or more hetero atoms such as pyridyl, pyridazinyl, pyrimidinyl, pyrazinyl, 1,3,5-triazinyl, 1,2,4-triazinyl, 1,2,3-triazinyl, tetrazinyl, five-membered heterocycles with one or more hetero atoms such as pyrrolyl, furyl, thienyl, pyrazolyl, imidazolyl, oxazolyl, isoxazolyl, thiazolyl, isothiazolyl, 1,2,3-triazolyl, 1,2,4-triazolyl, tetrazolyl, thiadiazolyl, fused heteroaryls such as indolyl, isoindolyl, thionaphthyl, quinolyl, isoquinolyl, cinnolinyl, phthalazinyl, quinazolyl, quinoxalyl, indazolyl, naphthyridinyl, benzothiazolyl, benzimidazolyl, benzofuryl, benzoxazolyl and benzotriazolyl, especially phenyl, naphthyl, thienyl, pyridyl, pyrazolyl, quinolyl, it being possible for these aromatic rings to carry one to five halogens, especially fluorine, chlorine and bromine, and/or one to three of the following: cyano, nitro, thiocyanato, —$COR^6$ where $R^6$ is hydroxyl, amino or one of the radicals $R^3$, —$SO_mR^6$ where m is 1 or 2, and/or the radicals mentioned for $R^3$.

Particularly preferred sulfonamides are compounds of the general formula Ia

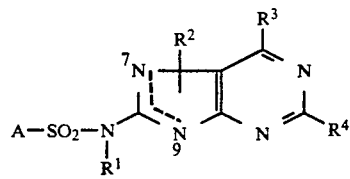

where the substituents have the following meanings, in particular:

$R^1$ is hydrogen or methyl;

$R^2$ is hydrogen or methyl, it being impossible, as a consequence of tautomerism, in the cases where $R^2$ is hydrogen to specify on which of the two nitrogens (N-7 or N-9) the hydrogen is located;

$R^3$ and $R^4$ are hydrogen, fluorine, chlorine, methyl, ethyl, n-propyl, iso-propyl, trifluoromethyl, methoxy, ethoxy, propoxy, 1-methylethoxy, methylthio, ethylthio, allyl, propargyl, allyloxy, allylthio, propargyloxy, propargylthio, trifluoromethoxy, methylamino, phenylamino, dimethylamino, pyrrolidino, piperidino, morpholino, 3,5-dimethylmorpholino, phenoxy, benzyloxy, phenylthio, benzylthio and/or phenyl;

A is phenyl, pyridyl, naphthyl, quinolyl, thienyl or pyrazolyl, it being possible for these aromatic radicals to carry one to three of the following, in particular: nitro, cyano, fluorine, chlorine, ethyl, propyl, isopropyl, trifluoromethyl, methoxy, ethoxy, 1-methylethoxy, 1,1-dimethylethoxy, trifluoromethoxy, trifluoroethoxy, chloroethoxy, methoxymethyl, ethoxymethyl, methoxyethyl, ethoxyethyl, methoxyethoxy, ethoxyethoxy, methylthio, ethylthio, methyl- and ethylsulfonyl, methoxycarbonyl, ethoxycarbonyl, iso-propoxycarbonyl, methyl- and ethylcarbonyl, N,N-dimethylsulfamoyl and N,N-dimethylcarbamoyl and the salts thereof.

The compounds Ib are additionally preferred,

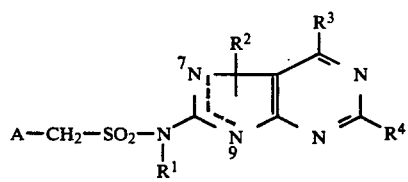

where $R^1$, $R^2$, $R^3$ and $R^4$ have the meaning stated for formula Ia, and the salts thereof.

Additional preferred compounds are sulfonamides of the general formula Ic

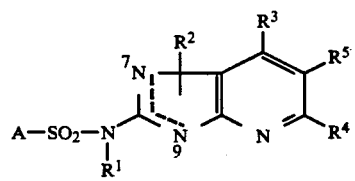

where $R^1$, $R^2$, $R^3$, $R^4$ and A have the meaning stated for formula Ia, and $R^5$ is hydrogen, methyl, fluorine or chlorine, and the salts thereof.

Additionally preferred are sulfonamides of the formula Id

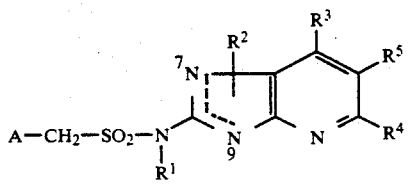

where $R^1$, $R^2$, $R^3$, $R^4$, $R^5$ and A have the meaning given for formula Ic, and the salts thereof.

Examples of very active compounds of the formulae Ia, Ib, Ic and Id are listed in Tables I, II, III and IV which follow.

TABLE I

Ia $$A-SO_2-NR^1-\text{[structure]}$$

| A | $R^1$ | $R^2$ | Pos. | $R^3$ | $R^4$ |
|---|---|---|---|---|---|
| phenyl | H | H | 7/9 | CH$_3$ | CH$_3$ |
| phenyl | H | CH$_3$ | 7 | CH$_3$ | CH$_3$ |
| phenyl | H | H | 7/9 | Cl | CH$_3$ |
| phenyl | H | CH$_3$ | 7 | Cl | CH$_3$ |
| phenyl | H | H | 7/9 | CH$_3$ | Cl |
| phenyl | H | CH$_3$ | 7 | CH$_3$ | Cl |
| phenyl | H | H | 7/9 | Cl | Cl |
| phenyl | H | CH$_3$ | 7 | Cl | Cl |
| phenyl | H | H | 7/9 | OCH$_3$ | OCH$_3$ |
| phenyl | H | CH$_3$ | 7 | OCH$_3$ | OCH$_3$ |
| phenyl | H | H | 7/9 | CH$_3$ | OCH$_3$ |
| phenyl | H | CH$_3$ | 7 | CH$_3$ | OCH$_3$ |
| phenyl | H | H | 7/9 | OCH$_3$ | CH$_3$ |
| phenyl | H | CH$_3$ | 7 | OCH$_3$ | CH$_3$ |
| phenyl | H | H | 7/9 | Cl | OCH$_3$ |
| phenyl | H | CH$_3$ | 7 | Cl | OCH$_3$ |
| phenyl | H | H | 7/9 | OCH$_3$ | Cl |
| phenyl | H | CH$_3$ | 7 | OCH$_3$ | Cl |
| 2-Cl-phenyl | H | H | 7/9 | CH$_3$ | CH$_3$ |
| 2-Cl-phenyl | H | CH$_3$ | 7 | CH$_3$ | CH$_3$ |
| 2-Cl-phenyl | H | H | 7/9 | Cl | CH$_3$ |
| 2-Cl-phenyl | H | CH$_3$ | 7 | Cl | CH$_3$ |
| 2-Cl-phenyl | H | H | 7/9 | CH$_3$ | Cl |
| 2-Cl-phenyl | H | CH$_3$ | 7 | CH$_3$ | Cl |
| 2-Cl-phenyl | H | H | 7/9 | Cl | Cl |
| 2-Cl-phenyl | H | CH$_3$ | 7 | Cl | Cl |
| 2-Cl-phenyl | H | H | 7/9 | OCH$_3$ | OCH$_3$ |
| 2-Cl-phenyl | H | CH$_3$ | 7 | OCH$_3$ | OCH$_3$ |
| 2-Cl-phenyl | H | H | 7/9 | CH$_3$ | OCH$_3$ |
| 2-Cl-phenyl | H | CH$_3$ | 7 | CH$_3$ | OCH$_3$ |
| 2-Cl-phenyl | H | H | 7/9 | OCH$_3$ | CH$_3$ |
| 2-Cl-phenyl | H | CH$_3$ | 7 | OCH$_3$ | CH$_3$ |
| 2-Cl-phenyl | H | H | 7/9 | Cl | OCH$_3$ |
| 2-Cl-phenyl | H | CH$_3$ | 7 | Cl | OCH$_3$ |
| 2-Cl-phenyl | H | H | 7/9 | OCH$_3$ | Cl |
| 2-Cl-phenyl | H | CH$_3$ | 7 | OCH$_3$ | Cl |
| 2-Cl-phenyl | CH$_3$ | H | 7/9 | CH$_3$ | CH$_3$ |
| 2-Cl-phenyl | CH$_3$ | CH$_3$ | 7 | CH$_3$ | CH$_3$ |
| 2-Cl-phenyl | CH$_3$ | H | 7/9 | Cl | CH$_3$ |
| 2-Cl-phenyl | CH$_3$ | CH$_3$ | 7 | Cl | CH$_3$ |
| 2-Cl-phenyl | CH$_3$ | H | 7/9 | CH$_3$ | Cl |
| 2-Cl-phenyl | CH$_3$ | CH$_3$ | 7 | CH$_3$ | Cl |
| 2-Cl-phenyl | CH$_3$ | H | 7/9 | Cl | Cl |
| 2-Cl-phenyl | CH$_3$ | CH$_3$ | 7 | Cl | Cl |
| 2-Cl-phenyl | CH$_3$ | H | 7/9 | OCH$_3$ | OCH$_3$ |
| 2-Cl-phenyl | CH$_3$ | CH$_3$ | 7 | OCH$_3$ | OCH$_3$ |
| 2-Cl-phenyl | CH$_3$ | H | 7/9 | CH$_3$ | OCH$_3$ |
| 2-Cl-phenyl | CH$_3$ | CH$_3$ | 7 | CH$_3$ | OCH$_3$ |
| 2-Cl-phenyl | CH$_3$ | H | 7/9 | OCH$_3$ | CH$_3$ |
| 2-Cl-phenyl | CH$_3$ | CH$_3$ | 7 | OCH$_3$ | CH$_3$ |
| 2-Cl-phenyl | CH$_3$ | H | 7/9 | Cl | OCH$_3$ |
| 2-Cl-phenyl | CH$_3$ | CH$_3$ | 7 | Cl | OCH$_3$ |
| 2-Cl-phenyl | CH$_3$ | H | 7/9 | OCH$_3$ | Cl |
| 2-Cl-phenyl | CH$_3$ | CH$_3$ | 7 | OCH$_3$ | Cl |
| 2-Cl-phenyl | H | H | 7/9 | CF$_3$ | CF$_3$ |
| 2-Cl-phenyl | H | CH$_3$ | 7 | CF$_3$ | CF$_3$ |
| 2-Cl-phenyl | H | H | 7/9 | Cl | CF$_3$ |
| 2-Cl-phenyl | H | CH$_3$ | 7 | Cl | CF$_3$ |
| 2-Cl-phenyl | H | H | 7/9 | CF$_3$ | Cl |
| 2-Cl-phenyl | H | CH$_3$ | 7 | CF$_3$ | Cl |
| 2-Cl-phenyl | H | H | 7/9 | F | CF$_3$ |

TABLE I-continued

Ia

A—SO₂—NR¹ ... structure with R², R³, R⁴

| A | R¹ | R² | Pos. | R³ | R⁴ |
|---|---|---|---|---|---|
| 2-Cl-phenyl | H | CH₃ | 7 | F | CF₃ |
| 2-Cl-phenyl | H | H | 7/9 | CF₃ | F |
| 2-Cl-phenyl | H | CH₃ | 7 | CF₃ | F |
| 2-Cl-phenyl | H | H | 7/9 | CH₃ | CF₃ |
| 2-Cl-phenyl | H | CH₃ | 7 | CH₃ | CF₃ |
| 2-Cl-phenyl | H | H | 7/9 | CF₃ | CH₃ |
| 2-Cl-phenyl | H | CH₃ | 7 | CF₃ | CH₃ |
| 2-Cl-phenyl | H | H | 7/9 | OCH₃ | CF₃ |
| 2-Cl-phenyl | H | CH₃ | 7 | OCH₃ | CF₃ |
| 2-Cl-phenyl | H | H | 7/9 | CF₃ | OCH₃ |
| 2-Cl-phenyl | H | CH₃ | 7 | CF₃ | OCH₃ |
| 2-Cl-phenyl | H | H | 7/9 | F | F |
| 2-Cl-phenyl | H | CH₃ | 7 | F | F |
| 2-Cl-phenyl | H | H | 7/9 | F | Cl |
| 2-Cl-phenyl | H | CH₃ | 7 | F | Cl |
| 2-Cl-phenyl | H | H | 7/9 | Cl | F |
| 2-Cl-phenyl | H | CH₃ | 7 | Cl | F |
| 2-Cl-phenyl | H | H | 7/9 | F | CH₃ |
| 2-Cl-phenyl | H | CH₃ | 7 | F | CH₃ |
| 2-Cl-phenyl | H | H | 7/9 | CH₃ | F |
| 2-Cl-phenyl | H | CH₃ | 7 | CH₃ | F |
| 2-Cl-phenyl | H | H | 7/9 | F | OCH₃ |
| 2-Cl-phenyl | H | CH₃ | 7 | F | OCH₃ |
| 2-Cl-phenyl | H | H | 7/9 | OCH₃ | F |
| 2-Cl-phenyl | H | CH₃ | 7 | OCH₃ | F |
| 2-Cl-phenyl | H | H | 7/9 | N(CH₃)₂ | Cl |
| 2-Cl-phenyl | H | CH₃ | 7 | N(CH₃)₂ | Cl |
| 2-Cl-phenyl | H | H | 7/9 | SCH₃ | Cl |
| 2-Cl-phenyl | H | CH₃ | 7 | SCH₃ | Cl |
| 2-F-phenyl | H | H | 7/9 | CH₃ | CH₃ |
| 2-F-phenyl | H | CH₃ | 7 | CH₃ | CH₃ |
| 2-F-phenyl | H | H | 7/9 | Cl | CH₃ |
| 2-F-phenyl | H | CH₃ | 7 | Cl | CH₃ |
| 2-F-phenyl | H | H | 7/9 | CH₃ | Cl |
| 2-F-phenyl | H | CH₃ | 7 | CH₃ | Cl |
| 2-F-phenyl | H | H | 7/9 | Cl | Cl |
| 2-F-phenyl | H | CH₃ | 7 | Cl | Cl |
| 2-F-phenyl | H | H | 7/9 | OCH₃ | OCH₃ |
| 2-F-phenyl | H | CH₃ | 7 | OCH₃ | OCH₃ |
| 2-F-phenyl | H | H | 7/9 | CH₃ | OCH₃ |
| 2-F-phenyl | H | CH₃ | 7 | CH₃ | OCH₃ |
| 2-F-phenyl | H | H | 7/9 | OCH₃ | CH₃ |
| 2-F-phenyl | H | CH₃ | 7 | OCH₃ | CH₃ |
| 2-F-phenyl | H | H | 7/9 | Cl | OCH₃ |
| 2-F-phenyl | H | CH₃ | 7 | Cl | OCH₃ |
| 2-F-phenyl | H | H | 7/9 | OCH₃ | Cl |
| 2-F-phenyl | H | CH₃ | 7 | OCH₃ | Cl |
| 2-Br-phenyl | H | H | 7/9 | CH₃ | CH₃ |
| 2-Br-phenyl | H | CH₃ | 7 | CH₃ | CH₃ |
| 2-Br-phenyl | H | H | 7/9 | Cl | CH₃ |
| 2-Br-phenyl | H | CH₃ | 7 | Cl | CH₃ |
| 2-Br-phenyl | H | H | 7/9 | CH₃ | Cl |
| 2-Br-phenyl | H | CH₃ | 7 | CH₃ | Cl |
| 2-Br-phenyl | H | H | 7/9 | Cl | Cl |
| 2-Br-phenyl | H | CH₃ | 7 | Cl | Cl |
| 2-Br-phenyl | H | H | 7/9 | OCH₃ | OCH₃ |
| 2-Br-phenyl | H | CH₃ | 7 | OCH₃ | OCH₃ |
| 2-Br-phenyl | H | H | 7/9 | CH₃ | OCH₃ |
| 2-Br-phenyl | H | CH₃ | 7 | CH₃ | OCH₃ |
| 2-Br-phenyl | H | H | 7/9 | OCH₃ | CH₃ |
| 2-Br-phenyl | H | CH₃ | 7 | OCH₃ | CH₃ |
| 2-Br-phenyl | H | H | 7/9 | Cl | OCH₃ |
| 2-Br-phenyl | H | CH₃ | 7 | Cl | OCH₃ |
| 2-Br-phenyl | H | H | 7/9 | OCH₃ | Cl |
| 2-Br-phenyl | H | CH₃ | 7 | OCH₃ | Cl |
| 2-CN-phenyl | H | H | 7/9 | CH₃ | CH₃ |
| 2-CN-phenyl | H | CH₃ | 7 | CH₃ | CH₃ |
| 2-CN-phenyl | H | H | 7/9 | Cl | CH₃ |
| 2-CN-phenyl | H | CH₃ | 7 | Cl | CH₃ |
| 2-CN-phenyl | H | H | 7/9 | CH₃ | Cl |
| 2-CN-phenyl | H | CH₃ | 7 | CH₃ | Cl |
| 2-CN-phenyl | H | H | 7/9 | Cl | Cl |
| 2-CN-phenyl | H | CH₃ | 7 | Cl | Cl |

TABLE I-continued

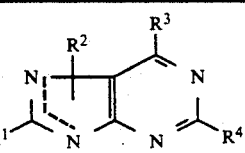

| A | $R^1$ | $R^2$ | Pos. | $R^3$ | $R^4$ |
|---|---|---|---|---|---|
| 2-CN-phenyl | H | H | 7/9 | $OCH_3$ | $OCH_3$ |
| 2-CN-phenyl | H | $CH_3$ | 7 | $OCH_3$ | $OCH_3$ |
| 2-CN-phenyl | H | H | 7/9 | $CH_3$ | $OCH_3$ |
| 2-CN-phenyl | H | $CH_3$ | 7 | $CH_3$ | $OCH_3$ |
| 2-CN-phenyl | H | H | 7/9 | $OCH_3$ | $CH_3$ |
| 2-CN-phenyl | H | $CH_3$ | 7 | $OCH_3$ | $CH_3$ |
| 2-CN-phenyl | H | H | 7/9 | Cl | $OCH_3$ |
| 2-CN-phenyl | H | $CH_3$ | 7 | Cl | $OCH_3$ |
| 2-CN-phenyl | H | H | 7/9 | $OCH_3$ | Cl |
| 2-CN-phenyl | H | $CH_3$ | 7 | $OCH_3$ | Cl |
| 2-$CF_3$-phenyl | H | H | 7/9 | $CH_3$ | $CH_3$ |
| 2-$CF_3$-phenyl | H | $CH_3$ | 7 | $CH_3$ | $CH_3$ |
| 2-$CF_3$-phenyl | H | H | 7/9 | Cl | $CH_3$ |
| 2-$CF_3$-phenyl | H | $CH_3$ | 7 | Cl | $CH_3$ |
| 2-$CF_3$-phenyl | H | H | 7/9 | $CH_3$ | Cl |
| 2-$CF_3$-phenyl | H | $CH_3$ | 7 | $CH_3$ | Cl |
| 2-$CF_3$-phenyl | H | H | 7/9 | Cl | Cl |
| 2-$CF_3$-phenyl | H | $CH_3$ | 7 | Cl | Cl |
| 2-$CF_3$-phenyl | H | H | 7/9 | $OCH_3$ | $OCH_3$ |
| 2-$CF_3$-phenyl | H | $CH_3$ | 7 | $OCH_3$ | $OCH_3$ |
| 2-$CF_3$-phenyl | H | H | 7/9 | $CH_3$ | $OCH_3$ |
| 2-$CF_3$-phenyl | H | $CH_3$ | 7 | $CH_3$ | $OCH_3$ |
| 2-$CF_3$-phenyl | H | H | 7/9 | $OCH_3$ | $CH_3$ |
| 2-$CF_3$-phenyl | H | $CH_3$ | 7 | $OCH_3$ | $CH_3$ |
| 2-$CF_3$-phenyl | H | H | 7/9 | Cl | $OCH_3$ |
| 2-$CF_3$-phenyl | H | $CH_3$ | 7 | Cl | $OCH_3$ |
| 2-$CF_3$-phenyl | H | H | 7/9 | $OCH_3$ | Cl |
| 2-$CF_3$-phenyl | H | $CH_3$ | 7 | $OCH_3$ | Cl |
| 2-$NO_2$-phenyl | H | H | 7/9 | $CH_3$ | $CH_3$ |
| 2-$NO_2$-phenyl | H | $CH_3$ | 7 | $CH_3$ | $CH_3$ |
| 2-$NO_2$-phenyl | H | H | 7/9 | Cl | $CH_3$ |
| 2-$NO_2$-phenyl | H | $CH_3$ | 7 | Cl | $CH_3$ |
| 2-$NO_2$-phenyl | H | H | 7/9 | $CH_3$ | Cl |
| 2-$NO_2$-phenyl | H | $CH_3$ | 7 | $CH_3$ | Cl |
| 2-$NO_2$-phenyl | H | H | 7/9 | Cl | Cl |
| 2-$NO_2$-phenyl | H | $CH_3$ | 7 | Cl | Cl |
| 2-$NO_2$-phenyl | H | H | 7/9 | $OCH_3$ | $OCH_3$ |
| 2-$NO_2$-phenyl | H | $CH_3$ | 7 | $OCH_3$ | $OCH_3$ |
| 2-$NO_2$-phenyl | H | H | 7/9 | $CH_3$ | $OCH_3$ |
| 2-$NO_2$-phenyl | H | $CH_3$ | 7 | $CH_3$ | $OCH_3$ |
| 2-$NO_2$-phenyl | H | H | 7/9 | $OCH_3$ | $CH_3$ |
| 2-$NO_2$-phenyl | H | $CH_3$ | 7 | $OCH_3$ | $CH_3$ |
| 2-$NO_2$-phenyl | H | H | 7/9 | Cl | $OCH_3$ |
| 2-$NO_2$-phenyl | H | $CH_3$ | 7 | Cl | $OCH_3$ |
| 2-$NO_2$-phenyl | H | H | 7/9 | $OCH_3$ | Cl |
| 2-$NO_2$-phenyl | H | $CH_3$ | 7 | $OCH_3$ | Cl |
| 2-$CH_3$-phenyl | H | H | 7/9 | $CH_3$ | $CH_3$ |
| 2-$CH_3$-phenyl | H | $CH_3$ | 7 | $CH_3$ | $CH_3$ |
| 2-$CH_3$-phenyl | H | H | 7/9 | Cl | $CH_3$ |
| 2-$CH_3$-phenyl | H | $CH_3$ | 7 | Cl | $CH_3$ |
| 2-$CH_3$-phenyl | H | H | 7/9 | $CH_3$ | Cl |
| 2-$CH_3$-phenyl | H | $CH_3$ | 7 | $CH_3$ | Cl |
| 2-$CH_3$-phenyl | H | H | 7/9 | Cl | Cl |
| 2-$CH_3$-phenyl | H | $CH_3$ | 7 | Cl | Cl |
| 2-$CH_3$-phenyl | H | H | 7/9 | $OCH_3$ | $OCH_3$ |
| 2-$CH_3$-phenyl | H | $CH_3$ | 7 | $OCH_3$ | $OCH_3$ |
| 2-$CH_3$-phenyl | H | H | 7/9 | $CH_3$ | $OCH_3$ |
| 2-$CH_3$-phenyl | H | $CH_3$ | 7 | $CH_3$ | $OCH_3$ |
| 2-$CH_3$-phenyl | H | H | 7/9 | $OCH_3$ | $CH_3$ |
| 2-$CH_3$-phenyl | H | $CH_3$ | 7 | $OCH_3$ | $CH_3$ |
| 2-$CH_3$-phenyl | H | H | 7/9 | Cl | $OCH_3$ |
| 2-$CH_3$-phenyl | H | $CH_3$ | 7 | Cl | $OCH_3$ |
| 2-$CH_3$-phenyl | H | H | 7/9 | $OCH_3$ | Cl |
| 2-$CH_3$-phenyl | H | $CH_3$ | 7 | $OCH_3$ | Cl |
| 2-$CO_2CH_3$-phenyl | H | H | 7/9 | $CH_3$ | $CH_3$ |
| 2-$CO_2CH_3$-phenyl | H | $CH_3$ | 7 | $CH_3$ | $CH_3$ |
| 2-$CO_2CH_3$-phenyl | H | H | 7/9 | Cl | $CH_3$ |
| 2-$CO_2CH_3$-phenyl | H | $CH_3$ | 7 | Cl | $CH_3$ |
| 2-$CO_2CH_3$-phenyl | H | H | 7/9 | $CH_3$ | Cl |
| 2-$CO_2CH_3$-phenyl | H | $CH_3$ | 7 | $CH_3$ | Cl |
| 2-$CO_2CH_3$-phenyl | H | H | 7/9 | Cl | Cl |
| 2-$CO_2CH_3$-phenyl | H | $CH_3$ | 7 | Cl | Cl |
| 2-$CO_2CH_3$-phenyl | H | H | 7/9 | $OCH_3$ | $OCH_3$ |

TABLE I-continued

Ia

A—SO$_2$—NR$^1$ [structure with R$^2$, R$^3$, R$^4$ substituents on fused ring system]

| A | R$^1$ | R$^2$ | Pos. | R$^3$ | R$^4$ |
|---|---|---|---|---|---|
| 2-CO$_2$CH$_3$-phenyl | H | CH$_3$ | 7 | OCH$_3$ | OCH$_3$ |
| 2-CO$_2$CH$_3$-phenyl | H | H | 7/9 | CH$_3$ | OCH$_3$ |
| 2-CO$_2$CH$_3$-phenyl | H | CH$_3$ | 7 | CH$_3$ | OCH$_3$ |
| 2-CO$_2$CH$_3$-phenyl | H | H | 7/9 | OCH$_3$ | CH$_3$ |
| 2-CO$_2$CH$_3$-phenyl | H | CH$_3$ | 7 | OCH$_3$ | CH$_3$ |
| 2-CO$_2$CH$_3$-phenyl | H | H | 7/9 | Cl | OCH$_3$ |
| 2-CO$_2$CH$_3$-phenyl | H | CH$_3$ | 7 | Cl | OCH$_3$ |
| 2-CO$_2$CH$_3$-phenyl | H | H | 7/9 | OCH$_3$ | Cl |
| 2-CO$_2$CH$_3$-phenyl | H | CH$_3$ | 7 | OCH$_3$ | Cl |
| 2-CO$_2$CH$_3$-phenyl | CH$_3$ | H | 7/9 | CH$_3$ | CH$_3$ |
| 2-CO$_2$CH$_3$-phenyl | CH$_3$ | CH$_3$ | 7 | CH$_3$ | CH$_3$ |
| 2-CO$_2$CH$_3$-phenyl | CH$_3$ | H | 7/9 | Cl | CH$_3$ |
| 2-CO$_2$CH$_3$-phenyl | CH$_3$ | CH$_3$ | 7 | Cl | CH$_3$ |
| 2-CO$_2$CH$_3$-phenyl | CH$_3$ | H | 7/9 | CH$_3$ | Cl |
| 2-CO$_2$CH$_3$-phenyl | CH$_3$ | CH$_3$ | 7 | CH$_3$ | Cl |
| 2-CO$_2$CH$_3$-phenyl | CH$_3$ | H | 7/9 | Cl | Cl |
| 2-CO$_2$CH$_3$-phenyl | CH$_3$ | CH$_3$ | 7 | Cl | Cl |
| 2-CO$_2$CH$_3$-phenyl | CH$_3$ | H | 7/9 | OCH$_3$ | OCH$_3$ |
| 2-CO$_2$CH$_3$-phenyl | CH$_3$ | CH$_3$ | 7 | OCH$_3$ | OCH$_3$ |
| 2-CO$_2$CH$_3$-phenyl | CH$_3$ | H | 7/9 | CH$_3$ | OCH$_3$ |
| 2-CO$_2$CH$_3$-phenyl | CH$_3$ | CH$_3$ | 7 | CH$_3$ | OCH$_3$ |
| 2-CO$_2$CH$_3$-phenyl | CH$_3$ | H | 7/9 | OCH$_3$ | CH$_3$ |
| 2-CO$_2$CH$_3$-phenyl | CH$_3$ | CH$_3$ | 7 | OCH$_3$ | CH$_3$ |
| 2-CO$_2$CH$_3$-phenyl | CH$_3$ | H | 7/9 | Cl | OCH$_3$ |
| 2-CO$_2$CH$_3$-phenyl | CH$_3$ | CH$_3$ | 7 | Cl | OCH$_3$ |
| 2-CO$_2$CH$_3$-phenyl | CH$_3$ | H | 7/9 | OCH$_3$ | Cl |
| 2-CO$_2$CH$_3$-phenyl | CH$_3$ | CH$_3$ | 7 | OCH$_3$ | Cl |
| 2-CO$_2$CH$_3$-phenyl | H | H | 7/9 | CF$_3$ | CF$_3$ |
| 2-CO$_2$CH$_3$-phenyl | H | CH$_3$ | 7 | CF$_3$ | CF$_3$ |
| 2-CO$_2$CH$_3$-phenyl | H | H | 7/9 | Cl | CF$_3$ |
| 2-CO$_2$CH$_3$-phenyl | H | CH$_3$ | 7 | Cl | CF$_3$ |
| 2-CO$_2$CH$_3$-phenyl | H | H | 7/9 | CF$_3$ | Cl |
| 2-CO$_2$CH$_3$-phenyl | H | CH$_3$ | 7 | CF$_3$ | Cl |
| 2-CO$_2$CH$_3$-phenyl | H | H | 7/9 | F | CF$_3$ |
| 2-CO$_2$CH$_3$-phenyl | H | CH$_3$ | 7 | F | CF$_3$ |
| 2-CO$_2$CH$_3$-phenyl | H | H | 7/9 | CF$_3$ | F |
| 2-CO$_2$CH$_3$-phenyl | H | CH$_3$ | 7 | CF$_3$ | F |
| 2-CO$_2$CH$_3$-phenyl | H | H | 7/9 | CH$_3$ | CF$_3$ |
| 2-CO$_2$CH$_3$-phenyl | H | CH$_3$ | 7 | CH$_3$ | CF$_3$ |
| 2-CO$_2$CH$_3$-phenyl | H | H | 7/9 | CF$_3$ | CH$_3$ |
| 2-CO$_2$CH$_3$-phenyl | H | CH$_3$ | 7 | CF$_3$ | CH$_3$ |
| 2-CO$_2$CH$_3$-phenyl | H | H | 7/9 | OCH$_3$ | CF$_3$ |
| 2-CO$_2$CH$_3$-phenyl | H | CH$_3$ | 7 | OCH$_3$ | CF$_3$ |
| 2-CO$_2$CH$_3$-phenyl | H | H | 7/9 | CF$_3$ | OCH$_3$ |
| 2-CO$_2$CH$_3$-phenyl | H | CH$_3$ | 7 | CF$_3$ | OCH$_3$ |
| 2-CO$_2$CH$_3$-phenyl | H | H | 7/9 | F | F |
| 2-CO$_2$CH$_3$-phenyl | H | CH$_3$ | 7 | F | F |
| 2-CO$_2$CH$_3$-phenyl | H | H | 7/9 | F | Cl |
| 2-CO$_2$CH$_3$-phenyl | H | CH$_3$ | 7 | F | Cl |
| 2-CO$_2$CH$_3$-phenyl | H | H | 7/9 | Cl | F |
| 2-CO$_2$CH$_3$-phenyl | H | CH$_3$ | 7 | Cl | F |
| 2-CO$_2$CH$_3$-phenyl | H | H | 7/9 | F | CH$_3$ |
| 2-CO$_2$CH$_3$-phenyl | H | CH$_3$ | 7 | F | CH$_3$ |
| 2-CO$_2$CH$_3$-phenyl | H | H | 7/9 | CH$_3$ | F |
| 2-CO$_2$CH$_3$-phenyl | H | CH$_3$ | 7 | CH$_3$ | F |
| 2-CO$_2$CH$_3$-phenyl | H | H | 7/9 | F | OCH$_3$ |
| 2-CO$_2$CH$_3$-phenyl | H | CH$_3$ | 7 | F | OCH$_3$ |
| 2-CO$_2$CH$_3$-phenyl | H | H | 7/9 | OCH$_3$ | F |
| 2-CO$_2$CH$_3$-phenyl | H | CH$_3$ | 7 | OCH$_3$ | F |
| 2-CO$_2$CH$_3$-phenyl | H | H | 7/9 | N(CH$_3$)$_2$ | Cl |
| 2-CO$_2$CH$_3$-phenyl | H | CH$_3$ | 7 | N(CH$_3$)$_2$ | Cl |
| 2-CO$_2$CH$_3$-phenyl | H | H | 7/9 | SCH$_3$ | Cl |
| 2-CO$_2$CH$_3$-phenyl | H | CH$_3$ | 7 | SCH$_3$ | Cl |
| 2-CO$_2$C$_2$H$_5$-phenyl | H | H | 7/9 | CH$_3$ | CH$_3$ |
| 2-CO$_2$C$_2$H$_5$-phenyl | H | CH$_3$ | 7 | CH$_3$ | CH$_3$ |
| 2-CO$_2$C$_2$H$_5$-phenyl | H | H | 7/9 | Cl | CH$_3$ |
| 2-CO$_2$C$_2$H$_5$-phenyl | H | CH$_3$ | 7 | Cl | CH$_3$ |
| 2-CO$_2$C$_2$H$_5$-phenyl | H | H | 7/9 | CH$_3$ | Cl |
| 2-CO$_2$C$_2$H$_5$-phenyl | H | CH$_3$ | 7 | CH$_3$ | Cl |
| 2-CO$_2$C$_2$H$_5$-phenyl | H | H | 7/9 | Cl | Cl |
| 2-CO$_2$C$_2$H$_5$-phenyl | H | CH$_3$ | 7 | Cl | Cl |
| 2-CO$_2$C$_2$H$_5$-phenyl | H | H | 7/9 | OCH$_3$ | OCH$_3$ |
| 2-CO$_2$C$_2$H$_5$-phenyl | H | H | 7/9 | CH$_3$ | OCH$_3$ |

TABLE I-continued

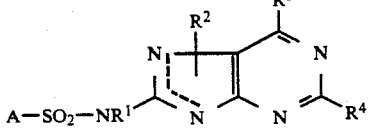

| A | $R^1$ | $R^2$ | Pos. | $R^3$ | $R^4$ |
|---|---|---|---|---|---|
| 2-$CO_2C_2H_5$-phenyl | H | $CH_3$ | 7 | $CH_3$ | $OCH_3$ |
| 2-$CO_2C_2H_5$-phenyl | H | H | 7/9 | $OCH_3$ | $CH_3$ |
| 2-$CO_2C_2H_5$-phenyl | H | $CH_3$ | 7 | $OCH_3$ | $CH_3$ |
| 2-$CO_2C_2H_5$-phenyl | H | H | 7/9 | Cl | $OCH_3$ |
| 2-$CO_2C_2H_5$-phenyl | H | $CH_3$ | 7 | Cl | $OCH_3$ |
| 2-$CO_2C_2H_5$-phenyl | H | H | 7/9 | $OCH_3$ | Cl |
| 2-$CO_2C_2H_5$-phenyl | H | $CH_3$ | 7 | $OCH_3$ | Cl |
| 2-$CON(CH_3)_2$-phenyl | H | H | 7/9 | $CH_3$ | $CH_3$ |
| 2-$CON(CH_3)_2$-phenyl | H | $CH_3$ | 7 | $CH_3$ | $CH_3$ |
| 2-$CON(CH_3)_2$-phenyl | H | H | 7/9 | Cl | $CH_3$ |
| 2-$CON(CH_3)_2$-phenyl | H | $CH_3$ | 7 | Cl | $CH_3$ |
| 2-$CON(CH_3)_2$-phenyl | H | H | 7/9 | $CH_3$ | Cl |
| 2-$CON(CH_3)_2$-phenyl | H | $CH_3$ | 7 | $CH_3$ | Cl |
| 2-$CON(CH_3)_2$-phenyl | H | H | 7/9 | Cl | Cl |
| 2-$CON(CH_3)_2$-phenyl | H | $CH_3$ | 7 | Cl | Cl |
| 2-$CON(CH_3)_2$-phenyl | H | H | 7/9 | $OCH_3$ | $OCH_3$ |
| 2-$CON(CH_3)_2$-phenyl | H | $CH_3$ | 7 | $OCH_3$ | $OCH_3$ |
| 2-$CON(CH_3)_2$-phenyl | H | H | 7/9 | $CH_3$ | $OCH_3$ |
| 2-$CON(CH_3)_2$-phenyl | H | $CH_3$ | 7 | $CH_3$ | $OCH_3$ |
| 2-$CON(CH_3)_2$-phenyl | H | H | 7/9 | $OCH_3$ | $CH_3$ |
| 2-$CON(CH_3)_2$-phenyl | H | $CH_3$ | 7 | $OCH_3$ | $CH_3$ |
| 2-$CON(CH_3)_2$-phenyl | H | H | 7/9 | Cl | $OCH_3$ |
| 2-$CON(CH_3)_2$-phenyl | H | $CH_3$ | 7 | Cl | $OCH_3$ |
| 2-$CON(CH_3)_2$-phenyl | H | H | 7/9 | $OCH_3$ | Cl |
| 2-$CON(CH_3)_2$-phenyl | H | $CH_3$ | 7 | $OCH_3$ | Cl |
| 2-$COCH_3$-phenyl | H | H | 7/9 | $CH_3$ | $CH_3$ |
| 2-$COCH_3$-phenyl | H | $CH_3$ | 7 | $CH_3$ | $CH_3$ |
| 2-$COCH_3$-phenyl | H | H | 7/9 | Cl | $CH_3$ |
| 2-$COCH_3$-phenyl | H | $CH_3$ | 7 | Cl | $CH_3$ |
| 2-$COCH_3$-phenyl | H | H | 7/9 | $CH_3$ | Cl |
| 2-$COCH_3$-phenyl | H | $CH_3$ | 7 | $CH_3$ | Cl |
| 2-$COCH_3$-phenyl | H | H | 7/9 | Cl | Cl |
| 2-$COCH_3$-phenyl | H | $CH_3$ | 7 | Cl | Cl |
| 2-$COCH_3$-phenyl | H | H | 7/9 | $OCH_3$ | $OCH_3$ |
| 2-$COCH_3$-phenyl | H | $CH_3$ | 7 | $OCH_3$ | $OCH_3$ |
| 2-$COCH_3$-phenyl | H | H | 7/9 | $CH_3$ | $OCH_3$ |
| 2-$COCH_3$-phenyl | H | $CH_3$ | 7 | $CH_3$ | $OCH_3$ |
| 2-$COCH_3$-phenyl | H | H | 7/9 | $OCH_3$ | $CH_3$ |
| 2-$COCH_3$-phenyl | H | $CH_3$ | 7 | $OCH_3$ | $CH_3$ |
| 2-$COCH_3$-phenyl | H | H | 7/9 | Cl | $OCH_3$ |
| 2-$COCH_3$-phenyl | H | $CH_3$ | 7 | Cl | $OCH_3$ |
| 2-$COCH_3$-phenyl | H | H | 7/9 | $OCH_3$ | Cl |
| 2-$COCH_3$-phenyl | H | $CH_3$ | 7 | $OCH_3$ | Cl |
| 2-$OCH_3$-phenyl | H | H | 7/9 | $CH_3$ | $CH_3$ |
| 2-$OCH_3$-phenyl | H | $CH_3$ | 7 | $CH_3$ | $CH_3$ |
| 2-$OCH_3$-phenyl | H | H | 7/9 | Cl | $CH_3$ |
| 2-$OCH_3$-phenyl | H | $CH_3$ | 7 | Cl | $CH_3$ |
| 2-$OCH_3$-phenyl | H | H | 7/9 | $CH_3$ | Cl |
| 2-$OCH_3$-phenyl | H | $CH_3$ | 7 | $CH_3$ | Cl |
| 2-$OCH_3$-phenyl | H | H | 7/9 | Cl | Cl |
| 2-$OCH_3$-phenyl | H | $CH_3$ | 7 | Cl | Cl |
| 2-$OCH_3$-phenyl | H | H | 7/9 | $OCH_3$ | $OCH_3$ |
| 2-$OCH_3$-phenyl | H | $CH_3$ | 7 | $OCH_3$ | $OCH_3$ |
| 2-$OCH_3$-phenyl | H | H | 7/9 | $CH_3$ | $OCH_3$ |
| 2-$OCH_3$-phenyl | H | $CH_3$ | 7 | $CH_3$ | $OCH_3$ |
| 2-$OCH_3$-phenyl | H | H | 7/9 | $OCH_3$ | $CH_3$ |
| 2-$OCH_3$-phenyl | H | $CH_3$ | 7 | $OCH_3$ | $CH_3$ |
| 2-$OCH_3$-phenyl | H | H | 7/9 | Cl | $OCH_3$ |
| 2-$OCH_3$-phenyl | H | $CH_3$ | 7 | Cl | $OCH_3$ |
| 2-$OCH_3$-phenyl | H | H | 7/9 | $OCH_3$ | Cl |
| 2-$OCH_3$-phenyl | H | $CH_3$ | 7 | $OCH_3$ | Cl |
| 2-$OCH_2CH_2OCH_3$-phenyl | H | H | 7/9 | $CH_3$ | $CH_3$ |
| 2-$OCH_2CH_2OCH_3$-phenyl | H | $CH_3$ | 7 | $CH_3$ | $CH_3$ |
| 2-$OCH_2CH_2OCH_3$-phenyl | H | H | 7/9 | Cl | $CH_3$ |
| 2-$OCH_2CH_2OCH_3$-phenyl | H | $CH_3$ | 7 | Cl | $CH_3$ |
| 2-$OCH_2CH_2OCH_3$-phenyl | H | H | 7/9 | $CH_3$ | Cl |
| 2-$OCH_2CH_2OCH_3$-phenyl | H | $CH_3$ | 7 | $CH_3$ | Cl |
| 2-$OCH_2CH_2OCH_3$-phenyl | H | H | 7/9 | Cl | Cl |
| 2-$OCH_2CH_2OCH_3$-phenyl | H | $CH_3$ | 7 | Cl | Cl |
| 2-$OCH_2CH_2OCH_3$-phenyl | H | H | 7/9 | $OCH_3$ | $OCH_3$ |
| 2-$OCH_2CH_2OCH_3$-phenyl | H | $CH_3$ | 7 | $OCH_3$ | $OCH_3$ |
| 2-$OCH_2CH_2OCH_3$-phenyl | H | H | 7/9 | $CH_3$ | $OCH_3$ |
| 2-$OCH_2CH_2OCH_3$-phenyl | H | $CH_3$ | 7 | $CH_3$ | $OCH_3$ |

TABLE I-continued

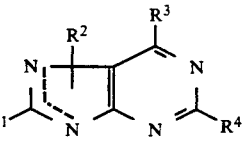

| A | $R^1$ | $R^2$ | Pos. | $R^3$ | $R^4$ |
|---|---|---|---|---|---|
| 2-OCH$_2$CH$_2$OCH$_3$-phenyl | H | H | 7/9 | OCH$_3$ | CH$_3$ |
| 2-OCH$_2$CH$_2$OCH$_3$-phenyl | H | CH$_3$ | 7 | OCH$_3$ | CH$_3$ |
| 2-OCH$_2$CH$_2$OCH$_3$-phenyl | H | H | 7/9 | Cl | OCH$_3$ |
| 2-OCH$_2$CH$_2$OCH$_3$-phenyl | H | CH$_3$ | 7 | Cl | OCH$_3$ |
| 2-OCH$_2$CH$_2$OCH$_3$-phenyl | H | H | 7/9 | OCH$_3$ | Cl |
| 2-OCH$_2$CH$_2$OCH$_3$-phenyl | H | CH$_3$ | 7 | OCH$_3$ | Cl |
| 2-OCH$_2$CH$_2$Cl-phenyl | H | H | 7/9 | CH$_3$ | CH$_3$ |
| 2-OCH$_2$CH$_2$Cl-phenyl | H | CH$_3$ | 7 | CH$_3$ | CH$_3$ |
| 2-OCH$_2$CH$_2$Cl-phenyl | H | H | 7/9 | Cl | CH$_3$ |
| 2-OCH$_2$CH$_2$Cl-phenyl | H | CH$_3$ | 7 | Cl | CH$_3$ |
| 2-OCH$_2$CH$_2$Cl-phenyl | H | H | 7/9 | CH$_3$ | Cl |
| 2-OCH$_2$CH$_2$Cl-phenyl | H | CH$_3$ | 7 | CH$_3$ | Cl |
| 2-OCH$_2$CH$_2$Cl-phenyl | H | H | 7/9 | Cl | Cl |
| 2-OCH$_2$CH$_2$Cl-phenyl | H | CH$_3$ | 7 | Cl | Cl |
| 2-OCH$_2$CH$_2$Cl-phenyl | H | H | 7/9 | OCH$_3$ | OCH$_3$ |
| 2-OCH$_2$CH$_2$Cl-phenyl | H | CH$_3$ | 7 | OCH$_3$ | OCH$_3$ |
| 2-OCH$_2$CH$_2$Cl-phenyl | H | H | 7/9 | CH$_3$ | OCH$_3$ |
| 2-OCH$_2$CH$_2$Cl-phenyl | H | CH$_3$ | 7 | CH$_3$ | OCH$_3$ |
| 2-OCH$_2$CH$_2$Cl-phenyl | H | H | 7/9 | OCH$_3$ | CH$_3$ |
| 2-OCH$_2$CH$_2$Cl-phenyl | H | CH$_3$ | 7 | OCH$_3$ | CH$_3$ |
| 2-OCH$_2$CH$_2$Cl-phenyl | H | H | 7/9 | Cl | OCH$_3$ |
| 2-OCH$_2$CH$_2$Cl-phenyl | H | CH$_3$ | 7 | Cl | OCH$_3$ |
| 2-OCH$_2$CH$_2$Cl-phenyl | H | H | 7/9 | OCH$_3$ | Cl |
| 2-OCH$_2$CH$_2$Cl-phenyl | H | CH$_3$ | 7 | OCH$_3$ | Cl |
| 2-OCH$_2$CH$_2$Cl-phenyl | CH$_3$ | H | 7/9 | CH$_3$ | CH$_3$ |
| 2-OCH$_2$CH$_2$Cl-phenyl | CH$_3$ | CH$_3$ | 7 | CH$_3$ | CH$_3$ |
| 2-OCH$_2$CH$_2$Cl-phenyl | CH$_3$ | H | 7/9 | Cl | CH$_3$ |
| 2-OCH$_2$CH$_2$Cl-phenyl | CH$_3$ | CH$_3$ | 7 | Cl | CH$_3$ |
| 2-OCH$_2$CH$_2$Cl-phenyl | CH$_3$ | H | 7/9 | CH$_3$ | Cl |
| 2-OCH$_2$CH$_2$Cl-phenyl | CH$_3$ | CH$_3$ | 7 | CH$_3$ | Cl |
| 2-OCH$_2$CH$_2$Cl-phenyl | CH$_3$ | H | 7/9 | Cl | Cl |
| 2-OCH$_2$CH$_2$Cl-phenyl | CH$_3$ | CH$_3$ | 7 | Cl | Cl |
| 2-OCH$_2$CH$_2$Cl-phenyl | CH$_3$ | H | 7/9 | OCH$_3$ | OCH$_3$ |
| 2-OCH$_2$CH$_2$Cl-phenyl | CH$_3$ | CH$_3$ | 7 | OCH$_3$ | OCH$_3$ |
| 2-OCH$_2$CH$_2$Cl-phenyl | CH$_3$ | H | 7/9 | CH$_3$ | OCH$_3$ |
| 2-OCH$_2$CH$_2$Cl-phenyl | CH$_3$ | CH$_3$ | 7 | CH$_3$ | OCH$_3$ |
| 2-OCH$_2$CH$_2$Cl-phenyl | CH$_3$ | H | 7/9 | OCH$_3$ | CH$_3$ |
| 2-OCH$_2$CH$_2$Cl-phenyl | CH$_3$ | CH$_3$ | 7 | OCH$_3$ | CH$_3$ |
| 2-OCH$_2$CH$_2$Cl-phenyl | CH$_3$ | H | 7/9 | Cl | OCH$_3$ |
| 2-OCH$_2$CH$_2$Cl-phenyl | CH$_3$ | CH$_3$ | 7 | Cl | OCH$_3$ |
| 2-OCH$_2$CH$_2$Cl-phenyl | CH$_3$ | H | 7/9 | OCH$_3$ | Cl |
| 2-OCH$_2$CH$_2$Cl-phenyl | CH$_3$ | CH$_3$ | 7 | OCH$_3$ | Cl |
| 2-OCH$_2$CH$_2$Cl-phenyl | H | H | 7/9 | CF$_3$ | CF$_3$ |
| 2-OCH$_2$CH$_2$Cl-phenyl | H | CH$_3$ | 7 | CF$_3$ | CF$_3$ |
| 2-OCH$_2$CH$_2$Cl-phenyl | H | H | 7/9 | Cl | CF$_3$ |
| 2-OCH$_2$CH$_2$Cl-phenyl | H | CH$_3$ | 7 | Cl | CF$_3$ |
| 2-OCH$_2$CH$_2$Cl-phenyl | H | H | 7/9 | CF$_3$ | Cl |
| 2-OCH$_2$CH$_2$Cl-phenyl | H | CH$_3$ | 7 | CF$_3$ | Cl |
| 2-OCH$_2$CH$_2$Cl-phenyl | H | H | 7/9 | F | CF$_3$ |
| 2-OCH$_2$CH$_2$Cl-phenyl | H | CH$_3$ | 7 | F | CF$_3$ |
| 2-OCH$_2$CH$_2$Cl-phenyl | H | H | 7/9 | CF$_3$ | F |
| 2-OCH$_2$CH$_2$Cl-phenyl | H | CH$_3$ | 7 | CF$_3$ | F |
| 2-OCH$_2$CH$_2$Cl-phenyl | H | H | 7/9 | CH$_3$ | CF$_3$ |
| 2-OCH$_2$CH$_2$Cl-phenyl | H | CH$_3$ | 7 | CH$_3$ | CF$_3$ |
| 2-OCH$_2$CH$_2$Cl-phenyl | H | H | 7/9 | CF$_3$ | CH$_3$ |
| 2-OCH$_2$CH$_2$Cl-phenyl | H | CH$_3$ | 7 | CF$_3$ | CH$_3$ |
| 2-OCH$_2$CH$_2$Cl-phenyl | H | H | 7/9 | OCH$_3$ | CF$_3$ |
| 2-OCH$_2$CH$_2$Cl-phenyl | H | CH$_3$ | 7 | OCH$_3$ | CF$_3$ |
| 2-OCH$_2$CH$_2$Cl-phenyl | H | H | 7/9 | CF$_3$ | OCH$_3$ |
| 2-OCH$_2$CH$_2$Cl-phenyl | H | CH$_3$ | 7 | CF$_3$ | OCH$_3$ |
| 2-OCH$_2$CH$_2$Cl-phenyl | H | H | 7/9 | F | F |
| 2-OCH$_2$CH$_2$Cl-phenyl | H | CH$_3$ | 7 | F | F |
| 2-OCH$_2$CH$_2$Cl-phenyl | H | H | 7/9 | F | Cl |
| 2-OCH$_2$CH$_2$Cl-phenyl | H | CH$_3$ | 7 | F | Cl |
| 2-OCH$_2$CH$_2$Cl-phenyl | H | H | 7/9 | Cl | F |
| 2-OCH$_2$CH$_2$Cl-phenyl | H | CH$_3$ | 7 | Cl | F |
| 2-OCH$_2$CH$_2$Cl-phenyl | H | H | 7/9 | F | CH$_3$ |
| 2-OCH$_2$CH$_2$Cl-phenyl | H | CH$_3$ | 7 | F | CH$_3$ |
| 2-OCH$_2$CH$_2$Cl-phenyl | H | H | 7/9 | CH$_3$ | F |
| 2-OCH$_2$CH$_2$Cl-phenyl | H | CH$_3$ | 7 | CH$_3$ | F |
| 2-OCH$_2$CH$_2$Cl-phenyl | H | H | 7/9 | F | OCH$_3$ |
| 2-OCH$_2$CH$_2$Cl-phenyl | H | CH$_3$ | 7 | F | OCH$_3$ |
| 2-OCH$_2$CH$_2$Cl-phenyl | H | H | 7/9 | OCH$_3$ | F |

TABLE I-continued

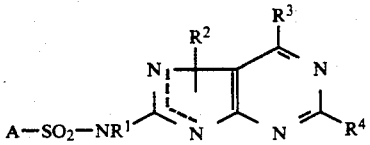

Ia

| A | R¹ | R² | Pos. | R³ | R⁴ |
|---|---|---|---|---|---|
| 2-OCH₂CH₂Cl-phenyl | H | CH₃ | 7 | OCH₃ | F |
| 2-OCH₂CH₂Cl-phenyl | H | H | 7/9 | N(CH₃)₂ | Cl |
| 2-OCH₂CH₂Cl-phenyl | H | CH₃ | 7 | N(CH₃)₂ | Cl |
| 2-OCH₂CH₂Cl-phenyl | H | H | 7/9 | SCH₃ | Cl |
| 2-OCH₂CH₂Cl-phenyl | H | CH₃ | 7 | SCH₃ | Cl |
| 2-OCH₂CO₂CH₃-phenyl | H | H | 7/9 | CH₃ | CH₃ |
| 2-OCH₂CO₂CH₃-phenyl | H | CH₃ | 7 | CH₃ | CH₃ |
| 2-OCH₂CO₂CH₃-phenyl | H | H | 7/9 | Cl | CH₃ |
| 2-OCH₂CO₂CH₃-phenyl | H | CH₃ | 7 | Cl | CH₃ |
| 2-OCH₂CO₂CH₃-phenyl | H | H | 7/9 | CH₃ | Cl |
| 2-OCH₂CO₂CH₃-phenyl | H | CH₃ | 7 | CH₃ | Cl |
| 2-OCH₂CO₂CH₃-phenyl | H | H | 7/9 | Cl | Cl |
| 2-OCH₂CO₂CH₃-phenyl | H | CH₃ | 7 | Cl | Cl |
| 2-OCH₂CO₂CH₃-phenyl | H | H | 7/9 | OCH₃ | OCH₃ |
| 2-OCH₂CO₂CH₃-phenyl | H | CH₃ | 7 | OCH₃ | OCH₃ |
| 2-OCH₂CO₂CH₃-phenyl | H | H | 7/9 | CH₃ | OCH₃ |
| 2-OCH₂CO₂CH₃-phenyl | H | CH₃ | 7 | CH₃ | OCH₃ |
| 2-OCH₂CO₂CH₃-phenyl | H | H | 7/9 | OCH₃ | CH₃ |
| 2-OCH₂CO₂CH₃-phenyl | H | CH₃ | 7 | OCH₃ | CH₃ |
| 2-OCH₂CO₂CH₃-phenyl | H | H | 7/9 | Cl | OCH₃ |
| 2-OCH₂CO₂CH₃-phenyl | H | CH₃ | 7 | Cl | OCH₃ |
| 2-OCH₂CO₂CH₃-phenyl | H | H | 7/9 | OCH₃ | Cl |
| 2-OCH₂CO₂CH₃-phenyl | H | CH₃ | 7 | OCH₃ | Cl |
| 2-SCH₃-phenyl | H | H | 7/9 | CH₃ | CH₃ |
| 2-SCH₃-phenyl | H | CH₃ | 7 | CH₃ | CH₃ |
| 2-SCH₃-phenyl | H | H | 7/9 | Cl | CH₃ |
| 2-SCH₃-phenyl | H | CH₃ | 7 | Cl | CH₃ |
| 2-SCH₃-phenyl | H | H | 7/9 | CH₃ | Cl |
| 2-SCH₃-phenyl | H | CH₃ | 7 | CH₃ | Cl |
| 2-SCH₃-phenyl | H | H | 7/9 | Cl | Cl |
| 2-SCH₃-phenyl | H | CH₃ | 7 | Cl | Cl |
| 2-SCH₃-phenyl | H | H | 7/9 | OCH₃ | OCH₃ |
| 2-SCH₃-phenyl | H | CH₃ | 7 | OCH₃ | OCH₃ |
| 2-SCH₃-phenyl | H | H | 7/9 | CH₃ | OCH₃ |
| 2-SCH₃-phenyl | H | CH₃ | 7 | CH₃ | OCH₃ |
| 2-SCH₃-phenyl | H | H | 7/9 | OCH₃ | CH₃ |
| 2-SCH₃-phenyl | H | CH₃ | 7 | OCH₃ | CH₃ |
| 2-SCH₃-phenyl | H | H | 7/9 | Cl | OCH₃ |
| 2-SCH₃-phenyl | H | CH₃ | 7 | Cl | OCH₃ |
| 2-SCH₃-phenyl | H | H | 7/9 | OCH₃ | Cl |
| 2-SCH₃-phenyl | H | CH₃ | 7 | OCH₃ | Cl |
| 2-SO₂CH₃-phenyl | H | H | 7/9 | CH₃ | CH₃ |
| 2-SO₂CH₃-phenyl | H | CH₃ | 7 | CH₃ | CH₃ |
| 2-SO₂CH₃-phenyl | H | H | 7/9 | Cl | CH₃ |
| 2-SO₂CH₃-phenyl | H | CH₃ | 7 | Cl | CH₃ |
| 2-SO₂CH₃-phenyl | H | H | 7/9 | CH₃ | Cl |
| 2-SO₂CH₃-phenyl | H | CH₃ | 7 | CH₃ | Cl |
| 2-SO₂CH₃-phenyl | H | H | 7/9 | Cl | Cl |
| 2-SO₂CH₃-phenyl | H | CH₃ | 7 | Cl | Cl |
| 2-SO₂CH₃-phenyl | H | H | 7/9 | OCH₃ | OCH₃ |
| 2-SO₂CH₃-phenyl | H | CH₃ | 7 | OCH₃ | OCH₃ |
| 2-SO₂CH₃-phenyl | H | H | 7/9 | CH₃ | OCH₃ |
| 2-SO₂CH₃-phenyl | H | CH₃ | 7 | CH₃ | OCH₃ |
| 2-SO₂CH₃-phenyl | H | H | 7/9 | OCH₃ | CH₃ |
| 2-SO₂CH₃-phenyl | H | CH₃ | 7 | OCH₃ | CH₃ |
| 2-SO₂CH₃-phenyl | H | H | 7/9 | Cl | OCH₃ |
| 2-SO₂CH₃-phenyl | H | CH₃ | 7 | Cl | OCH₃ |
| 2-SO₂CH₃-phenyl | H | H | 7/9 | OCH₃ | Cl |
| 2-SO₂CH₃-phenyl | H | CH₃ | 7 | OCH₃ | Cl |
| 2-SO₂N(CH₃)₂-phenyl | H | H | 7/9 | CH₃ | CH₃ |
| 2-SO₂N(CH₃)₂-phenyl | H | CH₃ | 7 | CH₃ | CH₃ |
| 2-SO₂N(CH₃)₂-phenyl | H | H | 7/9 | Cl | CH₃ |
| 2-SO₂N(CH₃)₂-phenyl | H | CH₃ | 7 | Cl | CH₃ |
| 2-SO₂N(CH₃)₂-phenyl | H | H | 7/9 | CH₃ | Cl |
| 2-SO₂N(CH₃)₂-phenyl | H | CH₃ | 7 | CH₃ | Cl |
| 2-SO₂N(CH₃)₂-phenyl | H | H | 7/9 | Cl | Cl |
| 2-SO₂N(CH₃)₂-phenyl | H | CH₃ | 7 | Cl | Cl |
| 2-SO₂N(CH₃)₂-phenyl | H | H | 7/9 | OCH₃ | OCH₃ |
| 2-SO₂N(CH₃)₂-phenyl | H | CH₃ | 7 | OCH₃ | OCH₃ |
| 2-SO₂N(CH₃)₂-phenyl | H | H | 7/9 | CH₃ | OCH₃ |
| 2-SO₂N(CH₃)₂-phenyl | H | CH₃ | 7 | CH₃ | OCH₃ |
| 2-SO₂N(CH₃)₂-phenyl | H | H | 7/9 | OCH₃ | CH₃ |
| 2-SO₂N(CH₃)₂-phenyl | H | CH₃ | 7 | OCH₃ | CH₃ |

TABLE I-continued

| A | R¹ | R² | Pos. | R³ | R⁴ |
|---|---|---|---|---|---|
| 2-SO₂N(CH₃)₂-phenyl | H | H | 7/9 | Cl | OCH₃ |
| 2-SO₂N(CH₃)₂-phenyl | H | CH₃ | 7 | Cl | OCH₃ |
| 2-SO₂N(CH₃)₂-phenyl | H | H | 7/9 | OCH₃ | Cl |
| 2-SO₂N(CH₃)₂-phenyl | H | CH₃ | 7 | OCH₃ | Cl |
| 2,6-Cl,Cl-phenyl | H | H | 7/9 | CH₃ | CH₃ |
| 2,6-Cl,Cl-phenyl | H | CH₃ | 7 | CH₃ | CH₃ |
| 2,6-Cl,Cl-phenyl | H | H | 7/9 | Cl | CH₃ |
| 2,6-Cl,Cl-phenyl | H | CH₃ | 7 | Cl | CH₃ |
| 2,6-Cl,Cl-phenyl | H | H | 7/9 | CH₃ | Cl |
| 2,6-Cl,Cl-phenyl | H | CH₃ | 7 | CH₃ | Cl |
| 2,6-Cl,Cl-phenyl | H | H | 7/9 | Cl | Cl |
| 2,6-Cl,Cl-phenyl | H | CH₃ | 7 | Cl | Cl |
| 2,6-Cl,Cl-phenyl | H | H | 7/9 | OCH₃ | OCH₃ |
| 2,6-Cl,Cl-phenyl | H | CH₃ | 7 | OCH₃ | OCH₃ |
| 2,6-Cl,Cl-phenyl | H | H | 7/9 | CH₃ | OCH₃ |
| 2,6-Cl,Cl-phenyl | H | CH₃ | 7 | CH₃ | OCH₃ |
| 2,6-Cl,Cl-phenyl | H | H | 7/9 | OCH₃ | CH₃ |
| 2,6-Cl,Cl-phenyl | H | CH₃ | 7 | OCH₃ | CH₃ |
| 2,6-Cl,Cl-phenyl | H | H | 7/9 | Cl | OCH₃ |
| 2,6-Cl,Cl-phenyl | H | CH₃ | 7 | Cl | OCH₃ |
| 2,6-Cl,Cl-phenyl | H | H | 7/9 | OCH₃ | Cl |
| 2,6-Cl,Cl-phenyl | H | CH₃ | 7 | OCH₃ | Cl |
| 2,6-Cl,Cl-phenyl | CH₃ | H | 7/9 | CH₃ | CH₃ |
| 2,6-Cl,Cl-phenyl | CH₃ | CH₃ | 7 | CH₃ | CH₃ |
| 2,6-Cl,Cl-phenyl | CH₃ | H | 7/9 | Cl | CH₃ |
| 2,6-Cl,Cl-phenyl | CH₃ | CH₃ | 7 | Cl | CH₃ |
| 2,6-Cl,Cl-phenyl | CH₃ | H | 7/9 | CH₃ | Cl |
| 2,6-Cl,Cl-phenyl | CH₃ | CH₃ | 7 | CH₃ | Cl |
| 2,6-Cl,Cl-phenyl | CH₃ | H | 7/9 | Cl | Cl |
| 2,6-Cl,Cl-phenyl | CH₃ | CH₃ | 7 | Cl | Cl |
| 2,6-Cl,Cl-phenyl | CH₃ | H | 7/9 | OCH₃ | OCH₃ |
| 2,6-Cl,Cl-phenyl | CH₃ | CH₃ | 7 | OCH₃ | OCH₃ |
| 2,6-Cl,Cl-phenyl | CH₃ | H | 7/9 | CH₃ | OCH₃ |
| 2,6-Cl,Cl-phenyl | CH₃ | CH₃ | 7 | CH₃ | OCH₃ |
| 2,6-Cl,Cl-phenyl | CH₃ | H | 7/9 | OCH₃ | CH₃ |
| 2,6-Cl,Cl-phenyl | CH₃ | CH₃ | 7 | OCH₃ | CH₃ |
| 2,6-Cl,Cl-phenyl | CH₃ | H | 7/9 | Cl | OCH₃ |
| 2,6-Cl,Cl-phenyl | CH₃ | CH₃ | 7 | Cl | OCH₃ |
| 2,6-Cl,Cl-phenyl | CH₃ | H | 7/9 | OCH₃ | Cl |
| 2,6-Cl,Cl-phenyl | CH₃ | CH₃ | 7 | OCH₃ | Cl |
| 2,6-Cl,Cl-phenyl | H | H | 7/9 | CF₃ | CF₃ |
| 2,6-Cl,Cl-phenyl | H | CH₃ | 7 | CF₃ | CF₃ |
| 2,6-Cl,Cl-phenyl | H | H | 7/9 | Cl | CF₃ |
| 2,6-Cl,Cl-phenyl | H | CH₃ | 7 | Cl | CF₃ |
| 2,6-Cl,Cl-phenyl | H | H | 7/9 | CF₃ | Cl |
| 2,6-Cl,Cl-phenyl | H | CH₃ | 7 | CF₃ | Cl |
| 2,6-Cl,Cl-phenyl | H | H | 7/9 | F | CF₃ |
| 2,6-Cl,Cl-phenyl | H | CH₃ | 7 | F | CF₃ |
| 2,6-Cl,Cl-phenyl | H | H | 7/9 | CF₃ | F |
| 2,6-Cl,Cl-phenyl | H | CH₃ | 7 | CF₃ | F |
| 2,6-Cl,Cl-phenyl | H | H | 7/9 | CH₃ | CF₃ |
| 2,6-Cl,Cl-phenyl | H | CH₃ | 7 | CH₃ | CF₃ |
| 2,6-Cl,Cl-phenyl | H | H | 7/9 | CF₃ | CH₃ |
| 2,6-Cl,Cl-phenyl | H | CH₃ | 7 | CF₃ | CH₃ |
| 2,6-Cl,Cl-phenyl | H | H | 7/9 | OCH₃ | CF₃ |
| 2,6-Cl,Cl-phenyl | H | CH₃ | 7 | OCH₃ | CF₃ |
| 2,6-Cl,Cl-phenyl | H | H | 7/9 | CF₃ | OCH₃ |
| 2,6-Cl,Cl-phenyl | H | CH₃ | 7 | CF₃ | OCH₃ |
| 2,6-Cl,Cl-phenyl | H | H | 7/9 | F | F |
| 2,6-Cl,Cl-phenyl | H | CH₃ | 7 | F | F |
| 2,6-Cl,Cl-phenyl | H | H | 7/9 | F | Cl |
| 2,6-Cl,Cl-phenyl | H | CH₃ | 7 | F | Cl |
| 2,6-Cl,Cl-phenyl | H | H | 7/9 | Cl | F |
| 2,6-Cl,Cl-phenyl | H | CH₃ | 7 | Cl | F |
| 2,6-Cl,Cl-phenyl | H | H | 7/9 | F | CH₃ |
| 2,6-Cl,Cl-phenyl | H | CH₃ | 7 | F | CH₃ |
| 2,6-Cl,Cl-phenyl | H | H | 7/9 | CH₃ | F |
| 2,6-Cl,Cl-phenyl | H | CH₃ | 7 | CH₃ | F |
| 2,6-Cl,Cl-phenyl | H | H | 7/9 | F | OCH₃ |
| 2,6-Cl,Cl-phenyl | H | CH₃ | 7 | F | OCH₃ |
| 2,6-Cl,Cl-phenyl | H | H | 7/9 | OCH₃ | F |
| 2,6-Cl,Cl-phenyl | H | CH₃ | 7 | OCH₃ | F |
| 2,6-Cl,Cl-phenyl | H | H | 7/9 | N(CH₃)₂ | Cl |

TABLE I-continued

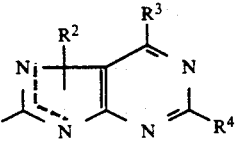

| A | R¹ | R² | Pos. | R³ | R⁴ |
|---|---|---|---|---|---|
| 2,6-Cl,Cl-phenyl | H | CH₃ | 7 | N(CH₃)₂ | Cl |
| 2,6-Cl,Cl-phenyl | H | H | 7/9 | SCH₃ | Cl |
| 2,6-Cl,Cl-phenyl | H | CH₃ | 7 | SCH₃ | Cl |
| 2-Cl,6-CH₃-phenyl | H | H | 7/9 | CH₃ | CH₃ |
| 2-Cl,6-CH₃-phenyl | H | CH₃ | 7 | CH₃ | CH₃ |
| 2-Cl,6-CH₃-phenyl | H | H | 7/9 | Cl | CH₃ |
| 2-Cl,6-CH₃-phenyl | H | CH₃ | 7 | Cl | CH₃ |
| 2-Cl,6-CH₃-phenyl | H | H | 7/9 | CH₃ | Cl |
| 2-Cl,6-CH₃-phenyl | H | CH₃ | 7 | CH₃ | Cl |
| 2-Cl,6-CH₃-phenyl | H | H | 7/9 | Cl | Cl |
| 2-Cl,6-CH₃-phenyl | H | CH₃ | 7 | Cl | Cl |
| 2-Cl,6-CH₃-phenyl | H | H | 7/9 | OCH₃ | OCH₃ |
| 2-Cl,6-CH₃-phenyl | H | CH₃ | 7 | OCH₃ | OCH₃ |
| 2-Cl,6-CH₃-phenyl | H | H | 7/9 | CH₃ | OCH₃ |
| 2-Cl,6-CH₃-phenyl | H | CH₃ | 7 | CH₃ | OCH₃ |
| 2-Cl,6-CH₃-phenyl | H | H | 7/9 | OCH₃ | CH₃ |
| 2-Cl,6-CH₃-phenyl | H | CH₃ | 7 | OCH₃ | CH₃ |
| 2-Cl,6-CH₃-phenyl | H | H | 7/9 | Cl | OCH₃ |
| 2-Cl,6-CH₃-phenyl | H | CH₃ | 7 | Cl | OCH₃ |
| 2-Cl,6-CH₃-phenyl | H | H | 7/9 | OCH₃ | Cl |
| 2-Cl,6-CH₃-phenyl | H | CH₃ | 7 | OCH₃ | Cl |
| 2-Cl,6-CH₃-phenyl | CH₃ | H | 7/9 | CH₃ | CH₃ |
| 2-Cl,6-CH₃-phenyl | CH₃ | CH₃ | 7 | CH₃ | CH₃ |
| 2-Cl,6-CH₃-phenyl | CH₃ | H | 7/9 | Cl | CH₃ |
| 2-Cl,6-CH₃-phenyl | CH₃ | CH₃ | 7 | Cl | CH₃ |
| 2-Cl,6-CH₃-phenyl | CH₃ | H | 7/9 | CH₃ | Cl |
| 2-Cl,6-CH₃-phenyl | CH₃ | CH₃ | 7 | CH₃ | Cl |
| 2-Cl,6-CH₃-phenyl | CH₃ | H | 7/9 | Cl | Cl |
| 2-Cl,6-CH₃-phenyl | CH₃ | CH₃ | 7 | Cl | Cl |
| 2-Cl,6-CH₃-phenyl | CH₃ | H | 7/9 | OCH₃ | OCH₃ |
| 2-Cl,6-CH₃-phenyl | CH₃ | CH₃ | 7 | OCH₃ | OCH₃ |
| 2-Cl,6-CH₃-phenyl | CH₃ | H | 7/9 | CH₃ | OCH₃ |
| 2-Cl,6-CH₃-phenyl | CH₃ | CH₃ | 7 | CH₃ | OCH₃ |
| 2-Cl,6-CH₃-phenyl | CH₃ | H | 7/9 | OCH₃ | CH₃ |
| 2-Cl,6-CH₃-phenyl | CH₃ | CH₃ | 7 | OCH₃ | CH₃ |
| 2-Cl,6-CH₃-phenyl | CH₃ | H | 7/9 | Cl | OCH₃ |
| 2-Cl,6-CH₃-phenyl | CH₃ | CH₃ | 7 | Cl | OCH₃ |
| 2-Cl,6-CH₃-phenyl | CH₃ | H | 7/9 | OCH₃ | Cl |
| 2-Cl,6-CH₃-phenyl | CH₃ | CH₃ | 7 | OCH₃ | Cl |
| 2-Cl,6-CH₃-phenyl | H | H | 7/9 | CF₃ | CF₃ |
| 2-Cl,6-CH₃-phenyl | H | CH₃ | 7 | CF₃ | CF₃ |
| 2-Cl,6-CH₃-phenyl | H | H | 7/9 | Cl | CF₃ |
| 2-Cl,6-CH₃-phenyl | H | CH₃ | 7 | Cl | CF₃ |
| 2-Cl,6-CH₃-phenyl | H | H | 7/9 | CF₃ | Cl |
| 2-Cl,6-CH₃-phenyl | H | CH₃ | 7 | CF₃ | Cl |
| 2-Cl,6-CH₃-phenyl | H | H | 7/9 | F | CF₃ |
| 2-Cl,6-CH₃-phenyl | H | CH₃ | 7 | F | CF₃ |
| 2-Cl,6-CH₃-phenyl | H | H | 7/9 | CF₃ | F |
| 2-Cl,6-CH₃-phenyl | H | CH₃ | 7 | CF₃ | F |
| 2-Cl,6-CH₃-phenyl | H | H | 7/9 | CH₃ | CF₃ |
| 2-Cl,6-CH₃-phenyl | H | CH₃ | 7 | CH₃ | CF₃ |
| 2-Cl,6-CH₃-phenyl | H | H | 7/9 | CF₃ | CH₃ |
| 2-Cl,6-CH₃-phenyl | H | CH₃ | 7 | CF₃ | CH₃ |
| 2-Cl,6-CH₃-phenyl | H | H | 7/9 | OCH₃ | CF₃ |
| 2-Cl,6-CH₃-phenyl | H | CH₃ | 7 | OCH₃ | CF₃ |
| 2-Cl,6-CH₃-phenyl | H | H | 7/9 | CF₃ | OCH₃ |
| 2-Cl,6-CH₃-phenyl | H | CH₃ | 7 | CF₃ | OCH₃ |
| 2-Cl,6-CH₃-phenyl | H | H | 7/9 | F | F |
| 2-Cl,6-CH₃-phenyl | H | CH₃ | 7 | F | F |
| 2-Cl,6-CH₃-phenyl | H | H | 7/9 | F | Cl |
| 2-Cl,6-CH₃-phenyl | H | CH₃ | 7 | F | Cl |
| 2-Cl,6-CH₃-phenyl | H | H | 7/9 | Cl | F |
| 2-Cl,6-CH₃-phenyl | H | CH₃ | 7 | Cl | F |
| 2-Cl,6-CH₃-phenyl | H | H | 7/9 | F | CH₃ |
| 2-Cl,6-CH₃-phenyl | H | CH₃ | 7 | F | CH₃ |
| 2-Cl,6-CH₃-phenyl | H | H | 7/9 | CH₃ | F |
| 2-Cl,6-CH₃-phenyl | H | CH₃ | 7 | CH₃ | F |
| 2-Cl,6-CH₃-phenyl | H | H | 7/9 | F | OCH₃ |
| 2-Cl,6-CH₃-phenyl | H | CH₃ | 7 | F | OCH₃ |
| 2-Cl,6-CH₃-phenyl | H | H | 7/9 | OCH₃ | F |
| 2-Cl,6-CH₃-phenyl | H | CH₃ | 7 | OCH₃ | F |
| 2-Cl,6-CH₃-phenyl | H | H | 7/9 | N(CH₃)₂ | Cl |
| 2-Cl,6-CH₃-phenyl | H | CH₃ | 7 | N(CH₃)₂ | Cl |
| 2-Cl,6-CH₃-phenyl | H | H | 7/9 | SCH₃ | Cl |

TABLE I-continued

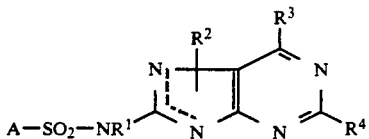

Ia

| A | $R^1$ | $R^2$ | Pos. | $R^3$ | $R^4$ |
|---|---|---|---|---|---|
| 2-Cl,6-CH$_3$-phenyl | H | CH$_3$ | 7 | SCH$_3$ | Cl |
| 2-Cl,6-CO$_2$CH$_3$-phenyl | H | H | 7/9 | CH$_3$ | CH$_3$ |
| 2-Cl,6-CO$_2$CH$_3$-phenyl | H | CH$_3$ | 7 | CH$_3$ | CH$_3$ |
| 2-Cl,6-CO$_2$CH$_3$-phenyl | H | H | 7/9 | Cl | CH$_3$ |
| 2-Cl,6-CO$_2$CH$_3$-phenyl | H | CH$_3$ | 7 | Cl | CH$_3$ |
| 2-Cl,6-CO$_2$CH$_3$-phenyl | H | H | 7/9 | CH$_3$ | Cl |
| 2-Cl,6-CO$_2$CH$_3$-phenyl | H | CH$_3$ | 7 | CH$_3$ | Cl |
| 2-Cl,6-CO$_2$CH$_3$-phenyl | H | H | 7/9 | Cl | Cl |
| 2-Cl,6-CO$_2$CH$_3$-phenyl | H | CH$_3$ | 7 | Cl | Cl |
| 2-Cl,6-CO$_2$CH$_3$-phenyl | H | H | 7/9 | OCH$_3$ | OCH$_3$ |
| 2-Cl,6-CO$_2$CH$_3$-phenyl | H | CH$_3$ | 7 | OCH$_3$ | OCH$_3$ |
| 2-Cl,6-CO$_2$CH$_3$-phenyl | H | H | 7/9 | CH$_3$ | OCH$_3$ |
| 2-Cl,6-CO$_2$CH$_3$-phenyl | H | CH$_3$ | 7 | CH$_3$ | OCH$_3$ |
| 2-Cl,6-CO$_2$CH$_3$-phenyl | H | H | 7/9 | OCH$_3$ | CH$_3$ |
| 2-Cl,6-CO$_2$CH$_3$-phenyl | H | CH$_3$ | 7 | OCH$_3$ | CH$_3$ |
| 2-Cl,6-CO$_2$CH$_3$-phenyl | H | H | 7/9 | Cl | OCH$_3$ |
| 2-Cl,6-CO$_2$CH$_3$-phenyl | H | CH$_3$ | 7 | Cl | OCH$_3$ |
| 2-Cl,6-CO$_2$CH$_3$-phenyl | H | H | 7/9 | OCH$_3$ | Cl |
| 2-Cl,6-CO$_2$CH$_3$-phenyl | H | CH$_3$ | 7 | OCH$_3$ | Cl |
| 2-Cl,6-OCH$_3$-phenyl | H | H | 7/9 | CH$_3$ | CH$_3$ |
| 2-Cl,6-OCH$_3$-phenyl | H | CH$_3$ | 7 | CH$_3$ | CH$_3$ |
| 2-Cl,6-OCH$_3$-phenyl | H | H | 7/9 | Cl | CH$_3$ |
| 2-Cl,6-OCH$_3$-phenyl | H | CH$_3$ | 7 | Cl | CH$_3$ |
| 2-Cl,6-OCH$_3$-phenyl | H | H | 7/9 | CH$_3$ | Cl |
| 2-Cl,6-OCH$_3$-phenyl | H | CH$_3$ | 7 | CH$_3$ | Cl |
| 2-Cl,6-OCH$_3$-phenyl | H | H | 7/9 | Cl | Cl |
| 2-Cl,6-OCH$_3$-phenyl | H | CH$_3$ | 7 | Cl | Cl |
| 2-Cl,6-OCH$_3$-phenyl | H | H | 7/9 | OCH$_3$ | OCH$_3$ |
| 2-Cl,6-OCH$_3$-phenyl | H | CH$_3$ | 7 | OCH$_3$ | OCH$_3$ |
| 2-Cl,6-OCH$_3$-phenyl | H | H | 7/9 | CH$_3$ | OCH$_3$ |
| 2-Cl,6-OCH$_3$-phenyl | H | CH$_3$ | 7 | CH$_3$ | OCH$_3$ |
| 2-Cl,6-OCH$_3$-phenyl | H | H | 7/9 | OCH$_3$ | CH$_3$ |
| 2-Cl,6-OCH$_3$-phenyl | H | CH$_3$ | 7 | OCH$_3$ | CH$_3$ |
| 2-Cl,6-OCH$_3$-phenyl | H | H | 7/9 | Cl | OCH$_3$ |
| 2-Cl,6-OCH$_3$-phenyl | H | CH$_3$ | 7 | Cl | OCH$_3$ |
| 2-Cl,6-OCH$_3$-phenyl | H | H | 7/9 | OCH$_3$ | Cl |
| 2-Cl,6-OCH$_3$-phenyl | H | CH$_3$ | 7 | OCH$_3$ | Cl |
| 2-OCH$_3$,6-CO$_2$CH$_3$-phenyl | H | H | 7/9 | CH$_3$ | CH$_3$ |
| 2-OCH$_3$,6-CO$_2$CH$_3$-phenyl | H | CH$_3$ | 7 | CH$_3$ | CH$_3$ |
| 2-OCH$_3$,6-CO$_2$CH$_3$-phenyl | H | H | 7/9 | Cl | CH$_3$ |
| 2-OCH$_3$,6-CO$_2$CH$_3$-phenyl | H | CH$_3$ | 7 | Cl | CH$_3$ |
| 2-OCH$_3$,6-CO$_2$CH$_3$-phenyl | H | H | 7/9 | CH$_3$ | Cl |
| 2-OCH$_3$,6-CO$_2$CH$_3$-phenyl | H | CH$_3$ | 7 | CH$_3$ | Cl |
| 2-OCH$_3$,6-CO$_2$CH$_3$-phenyl | H | H | 7/9 | Cl | Cl |
| 2-OCH$_3$,6-CO$_2$CH$_3$-phenyl | H | CH$_3$ | 7 | Cl | Cl |
| 2-OCH$_3$,6-CO$_2$CH$_3$-phenyl | H | H | 7/9 | OCH$_3$ | OCH$_3$ |
| 2-OCH$_3$,6-CO$_2$CH$_3$-phenyl | H | CH$_3$ | 7 | OCH$_3$ | OCH$_3$ |
| 2-OCH$_3$,6-CO$_2$CH$_3$-phenyl | H | H | 7/9 | CH$_3$ | OCH$_3$ |
| 2-OCH$_3$,6-CO$_2$CH$_3$-phenyl | H | CH$_3$ | 7 | CH$_3$ | OCH$_3$ |
| 2-OCH$_3$,6-CO$_2$CH$_3$-phenyl | H | H | 7/9 | OCH$_3$ | CH$_3$ |
| 2-OCH$_3$,6-CO$_2$CH$_3$-phenyl | H | CH$_3$ | 7 | OCH$_3$ | CH$_3$ |
| 2-OCH$_3$,6-CO$_2$CH$_3$-phenyl | H | H | 7/9 | Cl | OCH$_3$ |
| 2-OCH$_3$,6-CO$_2$CH$_3$-phenyl | H | CH$_3$ | 7 | Cl | OCH$_3$ |
| 2-OCH$_3$,6-CO$_2$CH$_3$-phenyl | H | H | 7/9 | OCH$_3$ | Cl |
| 2-OCH$_3$,6-CO$_2$CH$_3$-phenyl | H | CH$_3$ | 7 | OCH$_3$ | Cl |
| 2-CO$_2$CH$_3$,6-CH$_3$-phenyl | H | H | 7/9 | CH$_3$ | CH$_3$ |
| 2-CO$_2$CH$_3$,6-CH$_3$-phenyl | H | CH$_3$ | 7 | CH$_3$ | CH$_3$ |
| 2-CO$_2$CH$_3$,6-CH$_3$-phenyl | H | H | 7/9 | Cl | CH$_3$ |
| 2-CO$_2$CH$_3$,6-CH$_3$-phenyl | H | CH$_3$ | 7 | Cl | CH$_3$ |
| 2-CO$_2$CH$_3$,6-CH$_3$-phenyl | H | H | 7/9 | CH$_3$ | Cl |
| 2-CO$_2$CH$_3$,6-CH$_3$-phenyl | H | CH$_3$ | 7 | CH$_3$ | Cl |
| 2-CO$_2$CH$_3$,6-CH$_3$-phenyl | H | H | 7/9 | Cl | Cl |
| 2-CO$_2$CH$_3$,6-CH$_3$-phenyl | H | CH$_3$ | 7 | Cl | Cl |
| 2-CO$_2$CH$_3$,6-CH$_3$-phenyl | H | H | 7/9 | OCH$_3$ | OCH$_3$ |
| 2-CO$_2$CH$_3$,6-CH$_3$-phenyl | H | CH$_3$ | 7 | OCH$_3$ | OCH$_3$ |
| 2-CO$_2$CH$_3$,6-CH$_3$-phenyl | H | H | 7/9 | CH$_3$ | OCH$_3$ |
| 2-CO$_2$CH$_3$,6-CH$_3$-phenyl | H | CH$_3$ | 7 | CH$_3$ | OCH$_3$ |
| 2-CO$_2$CH$_3$,6-CH$_3$-phenyl | H | H | 7/9 | OCH$_3$ | CH$_3$ |
| 2-CO$_2$CH$_3$,6-CH$_3$-phenyl | H | CH$_3$ | 7 | OCH$_3$ | CH$_3$ |
| 2-CO$_2$CH$_3$,6-CH$_3$-phenyl | H | H | 7/9 | Cl | OCH$_3$ |
| 2-CO$_2$CH$_3$,6-CH$_3$-phenyl | H | CH$_3$ | 7 | Cl | OCH$_3$ |
| 2-CO$_2$CH$_3$,6-CH$_3$-phenyl | H | H | 7/9 | OCH$_3$ | Cl |
| 2-CO$_2$CH$_3$,6-CH$_3$-phenyl | H | CH$_3$ | 7 | OCH$_3$ | Cl |

TABLE I-continued

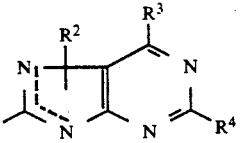

| A | R[1] | R[2] | Pos. | R[3] | R[4] |
|---|---|---|---|---|---|
| 2,5-Cl,Cl-phenyl | H | H | 7/9 | $CH_3$ | $CH_3$ |
| 2,5-Cl,Cl-phenyl | H | $CH_3$ | 7 | $CH_3$ | $CH_3$ |
| 2,5-Cl,Cl-phenyl | H | H | 7/9 | Cl | $CH_3$ |
| 2,5-Cl,Cl-phenyl | H | $CH_3$ | 7 | Cl | $CH_3$ |
| 2,5-Cl,Cl-phenyl | H | H | 7/9 | $CH_3$ | Cl |
| 2,5-Cl,Cl-phenyl | H | $CH_3$ | 7 | $CH_3$ | Cl |
| 2,5-Cl,Cl-phenyl | H | H | 7/9 | Cl | Cl |
| 2,5-Cl,Cl-phenyl | H | $CH_3$ | 7 | Cl | Cl |
| 2,5-Cl,Cl-phenyl | H | H | 7/9 | $OCH_3$ | $OCH_3$ |
| 2,5-Cl,Cl-phenyl | H | $CH_3$ | 7 | $OCH_3$ | $OCH_3$ |
| 2,5-Cl,Cl-phenyl | H | H | 7/9 | $CH_3$ | $OCH_3$ |
| 2,5-Cl,Cl-phenyl | H | $CH_3$ | 7 | $CH_3$ | $OCH_3$ |
| 2,5-Cl,Cl-phenyl | H | H | 7/9 | $OCH_3$ | $CH_3$ |
| 2,5-Cl,Cl-phenyl | H | $CH_3$ | 7 | $OCH_3$ | $CH_3$ |
| 2,5-Cl,Cl-phenyl | H | H | 7/9 | Cl | $OCH_3$ |
| 2,5-Cl,Cl-phenyl | H | $CH_3$ | 7 | Cl | $OCH_3$ |
| 2,5-Cl,Cl-phenyl | H | H | 7/9 | $OCH_3$ | Cl |
| 2,5-Cl,Cl-phenyl | H | $CH_3$ | 7 | $OCH_3$ | Cl |
| 2,5-Cl,Cl-phenyl | $CH_3$ | H | 7/9 | $CH_3$ | $CH_3$ |
| 2,5-Cl,Cl-phenyl | $CH_3$ | $CH_3$ | 7 | $CH_3$ | $CH_3$ |
| 2,5-Cl,Cl-phenyl | $CH_3$ | H | 7/9 | Cl | $CH_3$ |
| 2,5-Cl,Cl-phenyl | $CH_3$ | $CH_3$ | 7 | Cl | $CH_3$ |
| 2,5-Cl,Cl-phenyl | $CH_3$ | H | 7/9 | $CH_3$ | Cl |
| 2,5-Cl,Cl-phenyl | $CH_3$ | $CH_3$ | 7 | $CH_3$ | Cl |
| 2,5-Cl,Cl-phenyl | $CH_3$ | H | 7/9 | Cl | Cl |
| 2,5-Cl,Cl-phenyl | $CH_3$ | $CH_3$ | 7 | Cl | Cl |
| 2,5-Cl,Cl-phenyl | $CH_3$ | H | 7/9 | $OCH_3$ | $OCH_3$ |
| 2,5-Cl,Cl-phenyl | $CH_3$ | $CH_3$ | 7 | $OCH_3$ | $OCH_3$ |
| 2,5-Cl,Cl-phenyl | $CH_3$ | H | 7/9 | $CH_3$ | $OCH_3$ |
| 2,5-Cl,Cl-phenyl | $CH_3$ | $CH_3$ | 7 | $CH_3$ | $OCH_3$ |
| 2,5-Cl,Cl-phenyl | $CH_3$ | H | 7/9 | $OCH_3$ | $CH_3$ |
| 2,5-Cl,Cl-phenyl | $CH_3$ | $CH_3$ | 7 | $OCH_3$ | $CH_3$ |
| 2,5-Cl,Cl-phenyl | $CH_3$ | H | 7/9 | Cl | $OCH_3$ |
| 2,5-Cl,Cl-phenyl | $CH_3$ | $CH_3$ | 7 | Cl | $OCH_3$ |
| 2,5-Cl,Cl-phenyl | $CH_3$ | H | 7/9 | $OCH_3$ | Cl |
| 2,5-Cl,Cl-phenyl | $CH_3$ | $CH_3$ | 7 | $OCH_3$ | Cl |
| 2,5-Cl,Cl-phenyl | H | H | 7/9 | $CF_3$ | $CF_3$ |
| 2,5-Cl,Cl-phenyl | H | $CH_3$ | 7 | $CF_3$ | $CF_3$ |
| 2,5-Cl,Cl-phenyl | H | H | 7/9 | Cl | $CF_3$ |
| 2,5-Cl,Cl-phenyl | H | $CH_3$ | 7 | Cl | $CF_3$ |
| 2,5-Cl,Cl-phenyl | H | H | 7/9 | $CF_3$ | Cl |
| 2,5-Cl,Cl-phenyl | H | $CH_3$ | 7 | $CF_3$ | Cl |
| 2,5-Cl,Cl-phenyl | H | H | 7/9 | F | $CF_3$ |
| 2,5-Cl,Cl-phenyl | H | $CH_3$ | 7 | F | $CF_3$ |
| 2,5-Cl,Cl-phenyl | H | H | 7/9 | $CF_3$ | F |
| 2,5-Cl,Cl-phenyl | H | $CH_3$ | 7 | $CF_3$ | F |
| 2,5-Cl,Cl-phenyl | H | H | 7/9 | $CH_3$ | $CF_3$ |
| 2,5-Cl,Cl-phenyl | H | $CH_3$ | 7 | $CH_3$ | $CF_3$ |
| 2,5-Cl,Cl-phenyl | H | H | 7/9 | $CF_3$ | $CH_3$ |
| 2,5-Cl,Cl-phenyl | H | $CH_3$ | 7 | $CF_3$ | $CH_3$ |
| 2,5-Cl,Cl-phenyl | H | H | 7/9 | $OCH_3$ | $CF_3$ |
| 2,5-Cl,Cl-phenyl | H | $CH_3$ | 7 | $OCH_3$ | $CF_3$ |
| 2,5-Cl,Cl-phenyl | H | H | 7/9 | $CF_3$ | $OCH_3$ |
| 2,5-Cl,Cl-phenyl | H | $CH_3$ | 7 | $CF_3$ | $OCH_3$ |
| 2,5-Cl,Cl-phenyl | H | H | 7/9 | F | F |
| 2,5-Cl,Cl-phenyl | H | $CH_3$ | 7 | F | F |
| 2,5-Cl,Cl-phenyl | H | H | 7/9 | F | Cl |
| 2,5-Cl,Cl-phenyl | H | $CH_3$ | 7 | F | Cl |
| 2,5-Cl,Cl-phenyl | H | H | 7/9 | Cl | F |
| 2,5-Cl,Cl-phenyl | H | $CH_3$ | 7 | Cl | F |
| 2,5-Cl,Cl-phenyl | H | H | 7/9 | F | $CH_3$ |
| 2,5-Cl,Cl-phenyl | H | $CH_3$ | 7 | F | $CH_3$ |
| 2,5-Cl,Cl-phenyl | H | H | 7/9 | $CH_3$ | F |
| 2,5-Cl,Cl-phenyl | H | $CH_3$ | 7 | $CH_3$ | F |
| 2,5-Cl,Cl-phenyl | H | H | 7/9 | F | $OCH_3$ |
| 2,5-Cl,Cl-phenyl | H | $CH_3$ | 7 | F | $OCH_3$ |
| 2,5-Cl,Cl-phenyl | H | H | 7/9 | $OCH_3$ | F |
| 2,5-Cl,Cl-phenyl | H | $CH_3$ | 7 | $OCH_3$ | F |
| 2,5-Cl,Cl-phenyl | H | H | 7/9 | $N(CH_3)_2$ | Cl |
| 2,5-Cl,Cl-phenyl | H | $CH_3$ | 7 | $N(CH_3)_2$ | Cl |
| 2,5-Cl,Cl-phenyl | H | H | 7/9 | $SCH_3$ | Cl |
| 2,5-Cl,Cl-phenyl | H | $CH_3$ | 7 | $SCH_3$ | Cl |
| 2-$OCH_3$,5-Br-phenyl | H | H | 7/9 | $CH_3$ | $CH_3$ |

TABLE I-continued

Ia

A—SO₂—NR¹— [structure with R², R³, R⁴ substituents on fused pyrimidine ring system]

| A | R¹ | R² | Pos. | R³ | R⁴ |
|---|----|----|------|----|----|
| 2-OCH₃,5-Br-phenyl | H | CH₃ | 7 | CH₃ | CH₃ |
| 2-OCH₃,5-Br-phenyl | H | H | 7/9 | Cl | CH₃ |
| 2-OCH₃,5-Br-phenyl | H | CH₃ | 7 | Cl | CH₃ |
| 2-OCH₃,5-Br-phenyl | H | H | 7/9 | CH₃ | Cl |
| 2-OCH₃,5-Br-phenyl | H | CH₃ | 7 | CH₃ | Cl |
| 2-OCH₃,5-Br-phenyl | H | H | 7/9 | Cl | Cl |
| 2-OCH₃,5-Br-phenyl | H | CH₃ | 7 | Cl | Cl |
| 2-OCH₃,5-Br-phenyl | H | H | 7/9 | OCH₃ | OCH₃ |
| 2-OCH₃,5-Br-phenyl | H | CH₃ | 7 | OCH₃ | OCH₃ |
| 2-OCH₃,5-Br-phenyl | H | H | 7/9 | CH₃ | OCH₃ |
| 2-OCH₃,5-Br-phenyl | H | CH₃ | 7 | CH₃ | OCH₃ |
| 2-OCH₃,5-Br-phenyl | H | H | 7/9 | OCH₃ | CH₃ |
| 2-OCH₃,5-Br-phenyl | H | CH₃ | 7 | OCH₃ | CH₃ |
| 2-OCH₃,5-Br-phenyl | H | H | 7/9 | Cl | OCH₃ |
| 2-OCH₃,5-Br-phenyl | H | CH₃ | 7 | Cl | OCH₃ |
| 2-OCH₃,5-Br-phenyl | H | H | 7/9 | OCH₃ | Cl |
| 2-OCH₃,5-Br-phenyl | H | CH₃ | 7 | OCH₃ | Cl |
| 2,5-Di-OCH₂CF₃-phenyl | H | H | 7/9 | CH³ | CH³ |
| 2,5-Di-OCH₂CF₃-phenyl | H | CH³ | 7 | CH³ | CH³ |
| 2,5-Di-OCH₂CF₃-phenyl | H | H | 7/9 | Cl | CH³ |
| 2,5-Di-OCH₂CF₃-phenyl | H | CH³ | 7 | Cl | CH³ |
| 2,5-Di-OCH₂CF₃-phenyl | H | H | 7/9 | CH³ | Cl |
| 2,5-Di-OCH₂CF₃-phenyl | H | CH³ | 7 | CH³ | Cl |
| 2,5-Di-OCH₂CF₃-phenyl | H | H | 7/9 | Cl | Cl |
| 2,5-Di-OCH₂CF₃-phenyl | H | CH³ | 7 | Cl | Cl |
| 2,5-Di-OCH₂CF₃-phenyl | H | H | 7/9 | OCH³ | OCH³ |
| 2,5-Di-OCH₂CF₃-phenyl | H | CH³ | 7 | OCH³ | OCH³ |
| 2,5-Di-OCH₂CF₃-phenyl | H | H | 7/9 | CH³ | OCH³ |
| 2,5-Di-OCH₂CF₃-phenyl | H | CH³ | 7 | CH³ | OCH³ |
| 2,5-Di-OCH₂CF₃-phenyl | H | H | 7/9 | OCH³ | CH³ |
| 2,5-Di-OCH₂CF₃-phenyl | H | CH³ | 7 | OCH³ | CH³ |
| 2,5-Di-OCH₂CF₃-phenyl | H | H | 7/9 | Cl | OCH³ |
| 2,5-Di-OCH₂CF₃-phenyl | H | CH³ | 7 | Cl | OCH³ |
| 2,5-Di-OCH₂CF₃-phenyl | H | H | 7/9 | OCH³ | Cl |
| 2,5-Di-OCH₂CF₃-phenyl | H | CH₃ | 7 | OCH₃ | Cl |
| 2,5-Di-OCH₃-phenyl | H | H | 7/9 | CH₃ | CH₃ |
| 2,5-Di-OCH₃-phenyl | H | CH₃ | 7 | CH₃ | CH₃ |
| 2,5-Di-OCH₃-phenyl | H | H | 7/9 | Cl | CH₃ |
| 2,5-Di-OCH₃-phenyl | H | CH₃ | 7 | Cl | CH₃ |
| 2,5-Di-OCH₃-phenyl | H | H | 7/9 | CH₃ | Cl |
| 2,5-Di-OCH₃-phenyl | H | CH₃ | 7 | CH₃ | Cl |
| 2,5-Di-OCH₃-phenyl | H | H | 7/9 | Cl | Cl |
| 2,5-Di-OCH₃-phenyl | H | CH₃ | 7 | Cl | Cl |
| 2,5-Di-OCH₃-phenyl | H | H | 7/9 | OCH₃ | OCH₃ |
| 2,5-Di-OCH₃-phenyl | H | CH₃ | 7 | OCH₃ | OCH₃ |
| 2,5-Di-OCH₃-phenyl | H | H | 7/9 | CH₃ | OCH₃ |
| 2,5-Di-OCH₃-phenyl | H | CH₃ | 7 | CH₃ | OCH₃ |
| 2,5-Di-OCH₃-phenyl | H | H | 7/9 | OCH₃ | CH₃ |
| 2,5-Di-OCH₃-phenyl | H | CH₃ | 7 | OCH₃ | CH₃ |
| 2,5-Di-OCH₃-phenyl | H | H | 7/9 | Cl | OCH₃ |
| 2,5-Di-OCH₃-phenyl | H | CH₃ | 7 | Cl | OCH₃ |
| 2,5-Di-OCH₃-phenyl | H | H | 7/9 | OCH₃ | Cl |
| 2,5-Di-OCH₃-phenyl | H | CH₃ | 7 | OCH₃ | Cl |
| 2-Cl,5-CO₂CH₃-phenyl | H | H | 7/9 | CH₃ | CH₃ |
| 2-Cl,5-CO₂CH₃-phenyl | H | CH₃ | 7 | CH₃ | CH₃ |
| 2-Cl,5-CO₂CH₃-phenyl | H | H | 7/9 | Cl | CH₃ |
| 2-Cl,5-CO₂CH₃-phenyl | H | CH₃ | 7 | Cl | CH₃ |
| 2-Cl,5-CO₂CH₃-phenyl | H | H | 7/9 | CH₃ | Cl |
| 2-Cl,5-CO₂CH₃-phenyl | H | CH₃ | 7 | CH₃ | Cl |
| 2-Cl,5-CO₂CH₃-phenyl | H | H | 7/9 | Cl | Cl |
| 2-Cl,5-CO₂CH₃-phenyl | H | CH₃ | 7 | Cl | Cl |
| 2-Cl,5-CO₂CH₃-phenyl | H | H | 7/9 | OCH₃ | OCH₃ |
| 2-Cl,5-CO₂CH₃-phenyl | H | CH₃ | 7 | OCH₃ | OCH₃ |
| 2-Cl,5-CO₂CH₃-phenyl | H | H | 7/9 | CH₃ | OCH₃ |
| 2-Cl,5-CO₂CH₃-phenyl | H | CH₃ | 7 | CH₃ | OCH₃ |
| 2-Cl,5-CO₂CH₃-phenyl | H | H | 7/9 | OCH₃ | CH₃ |
| 2-Cl,5-CO₂CH₃-phenyl | H | CH₃ | 7 | OCH₃ | CH₃ |
| 2-Cl,5-CO₂CH₃-phenyl | H | H | 7/9 | Cl | OCH₃ |
| 2-Cl,5-CO₂CH₃-phenyl | H | CH₃ | 7 | Cl | OCH₃ |
| 2-Cl,5-CO₂CH₃-phenyl | H | H | 7/9 | OCH₃ | Cl |
| 2-Cl,5-CO₂CH₃-phenyl | H | CH₃ | 7 | OCH₃ | Cl |
| 2-CH₃,5-OCH₃-phenyl | H | H | 7/9 | CH₃ | CH₃ |
| 2-CH₃,5-OCH₃-phenyl | H | CH₃ | 7 | CH₃ | CH₃ |

TABLE I-continued

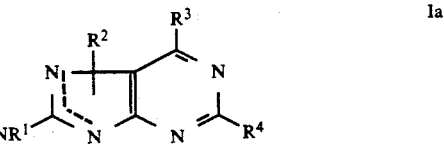

| A | R¹ | R² | Pos. | R³ | R⁴ |
|---|---|---|---|---|---|
| 2-CH₃,5-OCH₃-phenyl | H | H | 7/9 | Cl | CH₃ |
| 2-CH₃,5-OCH₃-phenyl | H | CH₃ | 7 | Cl | CH₃ |
| 2-CH₃,5-OCH₃-phenyl | H | H | 7/9 | CH₃ | Cl |
| 2-CH₃,5-OCH₃-phenyl | H | CH₃ | 7 | CH₃ | Cl |
| 2-CH₃,5-OCH₃-phenyl | H | H | 7/9 | Cl | Cl |
| 2-CH₃,5-OCH₃-phenyl | H | CH₃ | 7 | Cl | Cl |
| 2-CH₃,5-OCH₃-phenyl | H | H | 7/9 | OCH₃ | OCH₃ |
| 2-CH₃,5-OCH₃-phenyl | H | CH₃ | 7 | OCH₃ | OCH₃ |
| 2-CH₃,5-OCH₃-phenyl | H | H | 7/9 | CH₃ | OCH₃ |
| 2-CH₃,5-OCH₃-phenyl | H | CH₃ | 7 | CH₃ | OCH₃ |
| 2-CH₃,5-OCH₃-phenyl | H | H | 7/9 | OCH₃ | CH₃ |
| 2-CH₃,5-OCH₃-phenyl | H | CH₃ | 7 | OCH₃ | CH₃ |
| 2-CH₃,5-OCH₃-phenyl | H | H | 7/9 | Cl | OCH₃ |
| 2-CH₃,5-OCH₃-phenyl | H | CH₃ | 7 | Cl | OCH₃ |
| 2-CH₃,5-OCH₃-phenyl | H | H | 7/9 | OCH₃ | Cl |
| 2-CH₃,5-OCH₃-phenyl | H | CH₃ | 7 | OCH₃ | Cl |
| 2-Cl,5-NO₂-phenyl | H | H | 7/9 | CH₃ | CH₃ |
| 2-Cl,5-NO₂-phenyl | H | CH₃ | 7 | CH₃ | CH₃ |
| 2-Cl,5-NO₂-phenyl | H | H | 7/9 | Cl | CH₃ |
| 2-Cl,5-NO₂-phenyl | H | CH₃ | 7 | Cl | CH₃ |
| 2-Cl,5-NO₂-phenyl | H | H | 7/9 | CH₃ | Cl |
| 2-Cl,5-NO₂-phenyl | H | CH₃ | 7 | CH₃ | Cl |
| 2-Cl,5-NO₂-phenyl | H | H | 7/9 | Cl | Cl |
| 2-Cl,5-NO₂-phenyl | H | CH₃ | 7 | Cl | Cl |
| 2-Cl,5-NO₂-phenyl | H | H | 7/9 | OCH₃ | OCH₃ |
| 2-Cl,5-NO₂-phenyl | H | CH₃ | 7 | OCH₃ | OCH₃ |
| 2-Cl,5-NO₂-phenyl | H | H | 7/9 | CH₃ | OCH₃ |
| 2-Cl,5-NO₂-phenyl | H | CH₃ | 7 | CH₃ | OCH₃ |
| 2-Cl,5-NO₂-phenyl | H | H | 7/9 | OCH₃ | CH₃ |
| 2-Cl,5-NO₂-phenyl | H | CH₃ | 7 | OCH₃ | CH₃ |
| 2-Cl,5-NO₂-phenyl | H | H | 7/9 | Cl | OCH₃ |
| 2-Cl,5-NO₂-phenyl | H | CH₃ | 7 | Cl | OCH₃ |
| 2-Cl,5-NO₂-phenyl | H | H | 7/9 | OCH₃ | Cl |
| 2-Cl,5-NO₂-phenyl | H | CH₃ | 7 | OCH₃ | Cl |
| 2-Cl,5-CH₃-phenyl | H | H | 7/9 | CH₃ | CH₃ |
| 2-Cl,5-CH₃-phenyl | H | CH₃ | 7 | CH₃ | CH₃ |
| 2-Cl,5-CH₃-phenyl | H | H | 7/9 | Cl | CH₃ |
| 2-Cl,5-CH₃-phenyl | H | CH₃ | 7 | Cl | CH₃ |
| 2-Cl,5-CH₃-phenyl | H | H | 7/9 | CH₃ | Cl |
| 2-Cl,5-CH₃-phenyl | H | CH₃ | 7 | CH₃ | Cl |
| 2-Cl,5-CH₃-phenyl | H | H | 7/9 | Cl | Cl |
| 2-Cl,5-CH₃-phenyl | H | CH₃ | 7 | Cl | Cl |
| 2-Cl,5-CH₃-phenyl | H | H | 7/9 | OCH₃ | OCH₃ |
| 2-Cl,5-CH₃-phenyl | H | CH₃ | 7 | OCH₃ | OCH₃ |
| 2-Cl,5-CH₃-phenyl | H | H | 7/9 | CH₃ | OCH₃ |
| 2-Cl,5-CH₃-phenyl | H | CH₃ | 7 | CH₃ | OCH₃ |
| 2-Cl,5-CH₃-phenyl | H | H | 7/9 | OCH₃ | CH₃ |
| 2-Cl,5-CH₃-phenyl | H | CH₃ | 7 | OCH₃ | CH₃ |
| 2-Cl,5-CH₃-phenyl | H | H | 7/9 | Cl | OCH₃ |
| 2-Cl,5-CH₃-phenyl | H | CH₃ | 7 | Cl | OCH₃ |
| 2-Cl,5-CH₃-phenyl | H | H | 7/9 | OCH₃ | Cl |
| 2-Cl,5-CH₃-phenyl | H | CH₃ | 7 | OCH₃ | Cl |
| 2,5-Di-CH₃-phenyl | H | H | 7/9 | CH₃ | CH₃ |
| 2,5-Di-CH₃-phenyl | H | CH₃ | 7 | CH₃ | CH₃ |
| 2,5-Di-CH₃-phenyl | H | H | 7/9 | Cl | CH₃ |
| 2,5-Di-CH₃-phenyl | H | CH₃ | 7 | Cl | CH₃ |
| 2,5-Di-CH₃-phenyl | H | H | 7/9 | CH₃ | Cl |
| 2,5-Di-CH₃-phenyl | H | CH₃ | 7 | CH₃ | Cl |
| 2,5-Di-CH₃-phenyl | H | H | 7/9 | Cl | Cl |
| 2,5-Di-CH₃-phenyl | H | CH₃ | 7 | Cl | Cl |
| 2,5-Di-CH₃-phenyl | H | H | 7/9 | OCH₃ | OCH₃ |
| 2,5-Di-CH₃-phenyl | H | CH₃ | 7 | OCH₃ | OCH₃ |
| 2,5-Di-CH₃-phenyl | H | H | 7/9 | CH₃ | OCH₃ |
| 2,5-Di-CH₃-phenyl | H | CH₃ | 7 | CH₃ | OCH₃ |
| 2,5-Di-CH₃-phenyl | H | H | 7/9 | OCH₃ | CH₃ |
| 2,5-Di-CH₃-phenyl | H | CH₃ | 7 | OCH₃ | CH₃ |
| 2,5-Di-CH₃-phenyl | H | H | 7/9 | Cl | OCH₃ |
| 2,5-Di-CH₃-phenyl | H | CH₃ | 7 | Cl | OCH₃ |
| 2,5-Di-CH₃-phenyl | H | H | 7/9 | OCH₃ | Cl |
| 2,5-Di-CH₃-phenyl | H | CH₃ | 7 | OCH₃ | Cl |
| 2,3-Cl,Cl-phenyl | H | H | 7/9 | CH₃ | CH₃ |
| 2,3-Cl,Cl-phenyl | H | CH₃ | 7 | CH₃ | CH₃ |
| 2,3-Cl,Cl-phenyl | H | H | 7/9 | Cl | CH₃ |

TABLE I-continued

Ia $$A-SO_2-NR^1 \text{ [pyrazolo-pyrimidine structure with } R^2, R^3, R^4\text{]}$$

| A | $R^1$ | $R^2$ | Pos. | $R^3$ | $R^4$ |
|---|---|---|---|---|---|
| 2,3-Cl,Cl-phenyl | H | $CH_3$ | 7 | Cl | $CH_3$ |
| 2,3-Cl,Cl-phenyl | H | H | 7/9 | $CH_3$ | Cl |
| 2,3-Cl,Cl-phenyl | H | $CH_3$ | 7 | $CH_3$ | Cl |
| 2,3-Cl,Cl-phenyl | H | H | 7/9 | Cl | Cl |
| 2,3-Cl,Cl-phenyl | H | $CH_3$ | 7 | Cl | Cl |
| 2,3-Cl,Cl-phenyl | H | H | 7/9 | $OCH_3$ | $OCH_3$ |
| 2,3-Cl,Cl-phenyl | H | $CH_3$ | 7 | $OCH_3$ | $OCH_3$ |
| 2,3-Cl,Cl-phenyl | H | H | 7/9 | $CH_3$ | $OCH_3$ |
| 2,3-Cl,Cl-phenyl | H | $CH_3$ | 7 | $CH_3$ | $OCH_3$ |
| 2,3-Cl,Cl-phenyl | H | H | 7/9 | $OCH_3$ | $CH_3$ |
| 2,3-Cl,Cl-phenyl | H | $CH_3$ | 7 | $OCH_3$ | $CH_3$ |
| 2,3-Cl,Cl-phenyl | H | H | 7/9 | Cl | $OCH_3$ |
| 2,3-Cl,Cl-phenyl | H | $CH_3$ | 7 | Cl | $OCH_3$ |
| 2,3-Cl,Cl-phenyl | H | H | 7/9 | $OCH_3$ | Cl |
| 2,3-Cl,Cl-phenyl | H | $CH_3$ | 7 | $OCH_3$ | Cl |
| 2-$CO_2CH_3$,3-Cl-phenyl | H | H | 7/9 | $CH_3$ | $CH_3$ |
| 2-$CO_2CH_3$,3-Cl-phenyl | H | $CH_3$ | 7 | $CH_3$ | $CH_3$ |
| 2-$CO_2CH_3$,3-Cl-phenyl | H | H | 7/9 | Cl | $CH_3$ |
| 2-$CO_2CH_3$,3-Cl-phenyl | H | $CH_3$ | 7 | $CH_3$ | $CH_3$ |
| 2-$CO_2CH_3$,3-Cl-phenyl | H | H | 7/9 | $CH_3$ | Cl |
| 2-$CO_2CH_3$,3-Cl-phenyl | H | $CH_3$ | 7 | $CH_3$ | Cl |
| 2-$CO_2CH_3$,3-Cl-phenyl | H | H | 7/9 | Cl | Cl |
| 2-$CO_2CH_3$,3-Cl-phenyl | H | $CH_3$ | 7 | Cl | Cl |
| 2-$CO_2CH_3$,3-Cl-phenyl | H | H | 7/9 | $OCH_3$ | $OCH_3$ |
| 2-$CO_2CH_3$,3-Cl-phenyl | H | $CH_3$ | 7 | $OCH_3$ | $OCH_3$ |
| 2-$CO_2CH_3$,3-Cl-phenyl | H | H | 7/9 | $CH_3$ | $OCH_3$ |
| 2-$CO_2CH_3$,3-Cl-phenyl | H | $CH_3$ | 7 | $CH_3$ | $OCH_3$ |
| 2-$CO_2CH_3$,3-Cl-phenyl | H | H | 7/9 | $OCH_3$ | $CH_3$ |
| 2-$CO_2CH_3$,3-Cl-phenyl | H | $CH_3$ | 7 | $OCH_3$ | $CH_3$ |
| 2-$CO_2CH_3$,3-Cl-phenyl | H | H | 7/9 | Cl | $OCH_3$ |
| 2-$CO_2CH_3$,3-Cl-phenyl | H | $CH_3$ | 7 | Cl | $OCH_3$ |
| 2-$CO_2CH_3$,3-Cl-phenyl | H | H | 7/9 | $OCH_3$ | Cl |
| 2-$CO_2CH_3$,3-Cl-phenyl | H | $CH_3$ | 7 | $OCH_3$ | Cl |
| 2-$CON(CH_3)_2$,3-Cl-phenyl | H | H | 7/9 | $CH_3$ | $CH_3$ |
| 2-$CON(CH_3)_2$,3-Cl-phenyl | H | $CH_3$ | 7 | $CH_3$ | $CH_3$ |
| 2-$CON(CH_3)_2$,3-Cl-phenyl | H | H | 7/9 | Cl | $CH_3$ |
| 2-$CON(CH_3)_2$,3-Cl-phenyl | H | $CH_3$ | 7 | Cl | $CH_3$ |
| 2-$CON(CH_3)_2$,3-Cl-phenyl | H | H | 7/9 | $CH_3$ | Cl |
| 2-$CON(CH_3)_2$,3-Cl-phenyl | H | $CH_3$ | 7 | $CH_3$ | Cl |
| 2-$CON(CH_3)_2$,3-Cl-phenyl | H | H | 7/9 | Cl | Cl |
| 2-$CON(CH_3)_2$,3-Cl-phenyl | H | $CH_3$ | 7 | Cl | Cl |
| 2-$CON(CH_3)_2$,3-Cl-phenyl | H | H | 7/9 | $OCH_3$ | $OCH_3$ |
| 2-$CON(CH_3)_2$,3-Cl-phenyl | H | $CH_3$ | 7 | $OCH_3$ | $OCH_3$ |
| 2-$CON(CH_3)_2$,3-Cl-phenyl | H | H | 7/9 | $CH_3$ | $OCH_3$ |
| 2-$CON(CH_3)_2$,3-Cl-phenyl | H | $CH_3$ | 7 | $CH_3$ | $OCH_3$ |
| 2-$CON(CH_3)_2$,3-Cl-phenyl | H | H | 7/9 | $OCH_3$ | $CH_3$ |
| 2-$CON(CH_3)_2$,3-Cl-phenyl | H | $CH_3$ | 7 | $OCH_3$ | $CH_3$ |
| 2-$CON(CH_3)_2$,3-Cl-phenyl | H | H | 7/9 | Cl | $OCH_3$ |
| 2-$CON(CH_3)_2$,3-Cl-phenyl | H | $CH_3$ | 7 | Cl | $OCH_3$ |
| 2-$CON(CH_3)_2$,3-Cl-phenyl | H | H | 7/9 | $OCH_3$ | Cl |
| 2-$CON(CH_3)_2$,3-Cl-phenyl | H | $CH_3$ | 7 | $OCH_3$ | Cl |
| 2-$CO_2CH_3$,3-F-phenyl | H | H | 7/9 | $CH_3$ | $CH_3$ |
| 2-$CO_2CH_3$,3-F-phenyl | H | $CH_3$ | 7 | $CH_3$ | $CH_3$ |
| 2-$CO_2CH_3$,3-F-phenyl | H | H | 7/9 | Cl | $CH_3$ |
| 2-$CO_2CH_3$,3-F-phenyl | H | $CH_3$ | 7 | Cl | $CH_3$ |
| 2-$CO_2CH_3$,3-F-phenyl | H | H | 7/9 | $CH_3$ | Cl |
| 2-$CO_2CH_3$,3-F-phenyl | H | $CH_3$ | 7 | $CH_3$ | Cl |
| 2-$CO_2CH_3$,3-F-phenyl | H | H | 7/9 | Cl | Cl |
| 2-$CO_2CH_3$,3-F-phenyl | H | $CH_3$ | 7 | Cl | Cl |
| 2-$CO_2CH_3$,3-F-phenyl | H | H | 7/9 | $OCH_3$ | $OCH_3$ |
| 2-$CO_2CH_3$,3-F-phenyl | H | $CH_3$ | 7 | $OCH_3$ | $OCH_3$ |
| 2-$CO_2CH_3$,3-F-phenyl | H | H | 7/9 | $CH_3$ | $OCH_3$ |
| 2-$CO_2CH_3$,3-F-phenyl | H | $CH_3$ | 7 | $CH_3$ | $OCH_3$ |
| 2-$CO_2CH_3$,3-F-phenyl | H | H | 7/9 | $OCH_3$ | $CH_3$ |
| 2-$CO_2CH_3$,3-F-phenyl | H | $CH_3$ | 7 | $OCH_3$ | $CH_3$ |
| 2-$CO_2CH_3$,3-F-phenyl | H | H | 7/9 | Cl | $OCH_3$ |
| 2-$CO_2CH_3$,3-F-phenyl | H | $CH_3$ | 7 | Cl | $OCH_3$ |
| 2-$CO_2CH_3$,3-F-phenyl | H | H | 7/9 | $OCH_3$ | Cl |
| 2-$CO_2CH_3$,3-F-phenyl | H | $CH_3$ | 7 | $OCH_3$ | Cl |
| 2-$CO_2CH_3$,3-F-phenyl | $CH_3$ | H | 7/9 | $CH_3$ | $CH_3$ |
| 2-$CO_2CH_3$,3-F-phenyl | $CH_3$ | $CH_3$ | 7 | $CH_3$ | $CH_3$ |
| 2-$CO_2CH_3$,3-F-phenyl | $CH_3$ | H | 7/9 | Cl | $CH_3$ |
| 2-$CO_2CH_3$,3-F-phenyl | $CH_3$ | $CH_3$ | 7 | Cl | $CH_3$ |

TABLE I-continued

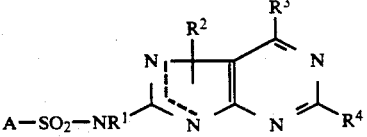

Ia

| A | R¹ | R² | Pos. | R³ | R⁴ |
|---|---|---|---|---|---|
| 2-CO₂CH₃,3-F-phenyl | CH₃ | H | 7/9 | CH₃ | Cl |
| 2-CO₂CH₃,3-F-phenyl | CH₃ | CH₃ | 7 | CH₃ | Cl |
| 2-CO₂CH₃,3-F-phenyl | CH₃ | H | 7/9 | Cl | Cl |
| 2-CO₂CH₃,3-F-phenyl | CH₃ | CH₃ | 7 | Cl | Cl |
| 2-CO₂CH₃,3-F-phenyl | CH₃ | H | 7/9 | OCH₃ | OCH₃ |
| 2-CO₂CH₃,3-F-phenyl | CH₃ | CH₃ | 7 | OCH₃ | OCH₃ |
| 2-CO₂CH₃,3-F-phenyl | CH₃ | H | 7/9 | CH₃ | OCH₃ |
| 2-CO₂CH₃,3-F-phenyl | CH₃ | CH₃ | 7 | CH₃ | OCH₃ |
| 2-CO₂CH₃,3-F-phenyl | CH₃ | H | 7/9 | OCH₃ | CH₃ |
| 2-CO₂CH₃,3-F-phenyl | CH₃ | CH₃ | 7 | OCH₃ | CH₃ |
| 2-CO₂CH₃,3-F-phenyl | CH₃ | H | 7/9 | Cl | OCH₃ |
| 2-CO₂CH₃,3-F-phenyl | CH₃ | CH₃ | 7 | Cl | OCH₃ |
| 2-CO₂CH₃,3-F-phenyl | CH₃ | H | 7/9 | OCH₃ | Cl |
| 2-CO₂CH₃,3-F-phenyl | CH₃ | CH₃ | 7 | OCH₃ | Cl |
| 2-CO₂CH₃,3-F-phenyl | H | H | 7/9 | CF₃ | CF₃ |
| 2-CO₂CH₃,3-F-phenyl | H | CH₃ | 7 | CF₃ | CF₃ |
| 2-CO₂CH₃,3-F-phenyl | H | H | 7/9 | Cl | CF₃ |
| 2-CO₂CH₃,3-F-phenyl | H | CH₃ | 7 | Cl | CF₃ |
| 2-CO₂CH₃,3-F-phenyl | H | H | 7/9 | CF₃ | Cl |
| 2-CO₂CH₃,3-F-phenyl | H | CH₃ | 7 | CF₃ | Cl |
| 2-CO₂CH₃,3-F-phenyl | H | H | 7/9 | F | CF₃ |
| 2-CO₂CH₃,3-F-phenyl | H | CH₃ | 7 | F | CF₃ |
| 2-CO₂CH₃,3-F-phenyl | H | H | 7/9 | CF₃ | F |
| 2-CO₂CH₃,3-F-phenyl | H | CH₃ | 7 | CF₃ | F |
| 2-CO₂CH₃,3-F-phenyl | H | H | 7/9 | CH₃ | CF₃ |
| 2-CO₂CH₃,3-F-phenyl | H | CH₃ | 7 | CH₃ | CF₃ |
| 2-CO₂CH₃,3-F-phenyl | H | H | 7/9 | CF₃ | CH₃ |
| 2-CO₂CH₃,3-F-phenyl | H | CH₃ | 7 | CF₃ | CH₃ |
| 2-CO₂CH₃,3-F-phenyl | H | H | 7/9 | OCH₃ | CF₃ |
| 2-CO₂CH₃,3-F-phenyl | H | CH₃ | 7 | OCH₃ | CF₃ |
| 2-CO₂CH₃,3-F-phenyl | H | H | 7/9 | CF₃ | OCH₃ |
| 2-CO₂CH₃,3-F-phenyl | H | CH₃ | 7 | CF₃ | OCH₃ |
| 2-CO₂CH₃,3-F-phenyl | H | H | 7/9 | F | F |
| 2-CO₂CH₃,3-F-phenyl | H | CH₃ | 7 | F | F |
| 2-CO₂CH₃,3-F-phenyl | H | H | 7/9 | F | Cl |
| 2-CO₂CH₃,3-F-phenyl | H | CH₃ | 7 | F | Cl |
| 2-CO₂CH₃,3-F-phenyl | H | H | 7/9 | Cl | F |
| 2-CO₂CH₃,3-F-phenyl | H | CH₃ | 7 | Cl | F |
| 2-CO₂CH₃,3-F-phenyl | H | H | 7/9 | F | CH₃ |
| 2-CO₂CH₃,3-F-phenyl | H | CH₃ | 7 | F | CH₃ |
| 2-CO₂CH₃,3-F-phenyl | H | H | 7/9 | CH₃ | F |
| 2-CO₂CH₃,3-F-phenyl | H | CH₃ | 7 | CH₃ | F |
| 2-CO₂CH₃,3-F-phenyl | H | H | 7/9 | F | OCH₃ |
| 2-CO₂CH₃,3-F-phenyl | H | CH₃ | 7 | F | OCH₃ |
| 2-CO₂CH₃,3-F-phenyl | H | H | 7/9 | OCH₃ | F |
| 2-CO₂CH₃,3-F-phenyl | H | CH₃ | 7 | OCH₃ | F |
| 2-CO₂CH₃,3-F-phenyl | H | H | 7/9 | N(CH₃)₂ | Cl |
| 2-CO₂CH₃,3-F-phenyl | H | CH₃ | 7 | N(CH₃)₂ | Cl |
| 2-CO₂CH₃,3-F-phenyl | H | H | 7/9 | SCH₃ | Cl |
| 2-CO₂CH₃,3-F-phenyl | H | CH₃ | 7 | SCH₃ | Cl |
| 2-CON(CH₃)₂,3-F-phenyl | H | H | 7/9 | CH₃ | CH₃ |
| 2-CON(CH₃)₂,3-F-phenyl | H | CH₃ | 7 | CH₃ | CH₃ |
| 2-CON(CH₃)₂,3-F-phenyl | H | H | 7/9 | Cl | CH₃ |
| 2-CON(CH₃)₂,3-F-phenyl | H | CH₃ | 7 | Cl | CH₃ |
| 2-CON(CH₃)₂,3-F-phenyl | H | H | 7/9 | CH₃ | Cl |
| 2-CON(CH₃)₂,3-F-phenyl | H | CH₃ | 7 | CH₃ | Cl |
| 2-CON(CH₃)₂,3-F-phenyl | H | H | 7/9 | Cl | Cl |
| 2-CON(CH₃)₂,3-F-phenyl | H | CH₃ | 7 | Cl | Cl |
| 2-CON(CH₃)₂,3-F-phenyl | H | H | 7/9 | OCH₃ | OCH₃ |
| 2-CON(CH₃)₂,3-F-phenyl | H | CH₃ | 7 | OCH₃ | OCH₃ |
| 2-CON(CH₃)₂,3-F-phenyl | H | H | 7/9 | CH₃ | OCH₃ |
| 2-CON(CH₃)₂,3-F-phenyl | H | CH₃ | 7 | CH₃ | OCH₃ |
| 2-CON(CH₃)₂,3-F-phenyl | H | H | 7/9 | OCH₃ | CH₃ |
| 2-CON(CH₃)₂,3-F-phenyl | H | CH₃ | 7 | OCH₃ | CH₃ |
| 2-CON(CH₃)₂,3-F-phenyl | H | H | 7/9 | Cl | OCH₃ |
| 2-CON(CH₃)₂,3-F-phenyl | H | CH₃ | 7 | Cl | OCH₃ |
| 2-CON(CH₃)₂,3-F-phenyl | H | H | 7/9 | OCH₃ | Cl |
| 2-CON(CH₃)₂,3-F-phenyl | H | CH₃ | 7 | OCH₃ | Cl |
| 2,5,6-Cl,Cl,Cl-phenyl | CH₃ | H | 7/9 | CH₃ | CH₃ |
| 2,5,6-Cl,Cl,Cl-phenyl | CH₃ | CH₃ | 7 | CH₃ | CH₃ |
| 2,5,6-Cl,Cl,Cl-phenyl | CH₃ | H | 7/9 | Cl | CH₃ |
| 2,5,6-Cl,Cl,Cl-phenyl | CH₃ | CH₃ | 7 | Cl | CH₃ |
| 2,5,6-Cl,Cl,Cl-phenyl | CH₃ | H | 7/9 | CH₃ | Cl |

TABLE I-continued $$A-SO_2-NR^1 \text{ (structure Ia with } R^2, R^3, R^4\text{)}$$

| A | R¹ | R² | Pos. | R³ | R⁴ |
|---|---|---|---|---|---|
| 2,5,6-Cl,Cl,Cl-phenyl | CH₃ | CH₃ | 7 | CH₃ | Cl |
| 2,5,6-Cl,Cl,Cl-phenyl | CH₃ | H | 7/9 | Cl | Cl |
| 2,5,6-Cl,Cl,Cl-phenyl | CH₃ | CH₃ | 7 | Cl | Cl |
| 2,5,6-Cl,Cl,Cl-phenyl | CH₃ | H | 7/9 | OCH₃ | OCH₃ |
| 2,5,6-Cl,Cl,Cl-phenyl | CH₃ | CH₃ | 7 | OCH₃ | OCH₃ |
| 2,5,6-Cl,Cl,Cl-phenyl | CH₃ | H | 7/9 | CH₃ | OCH₃ |
| 2,5,6-Cl,Cl,Cl-phenyl | CH₃ | CH₃ | 7 | CH₃ | OCH₃ |
| 2,5,6-Cl,Cl,Cl-phenyl | CH₃ | H | 7/9 | OCH₃ | CH₃ |
| 2,5,6-Cl,Cl,Cl-phenyl | CH₃ | CH₃ | 7 | OCH₃ | CH₃ |
| 2,5,6-Cl,Cl,Cl-phenyl | CH₃ | H | 7/9 | Cl | OCH₃ |
| 2,5,6-Cl,Cl,Cl-phenyl | CH₃ | CH₃ | 7 | Cl | OCH₃ |
| 2,5,6-Cl,Cl,Cl-phenyl | CH₃ | H | 7/9 | OCH₃ | Cl |
| 2,5,6-Cl,Cl,Cl-phenyl | CH₃ | CH₃ | 7 | OCH₃ | Cl |
| 2,5,6-Cl,Cl,Cl-phenyl | H | H | 7/9 | CH₃ | CH₃ |
| 2,5,6-Cl,Cl,Cl-phenyl | H | CH₃ | 7 | CH₃ | CH₃ |
| 2,5,6-Cl,Cl,Cl-phenyl | H | H | 7/9 | Cl | CH₃ |
| 2,5,6-Cl,Cl,Cl-phenyl | H | CH₃ | 7 | Cl | CH₃ |
| 2,5,6-Cl,Cl,Cl-phenyl | H | H | 7/9 | CH₃ | Cl |
| 2,5,6-Cl,Cl,Cl-phenyl | H | CH₃ | 7 | CH₃ | Cl |
| 2,5,6-Cl,Cl,Cl-phenyl | H | H | 7/9 | Cl | Cl |
| 2,5,6-Cl,Cl,Cl-phenyl | H | CH₃ | 7 | Cl | Cl |
| 2,5,6-Cl,Cl,Cl-phenyl | H | H | 7/9 | OCH₃ | OCH₃ |
| 2,5,6-Cl,Cl,Cl-phenyl | H | CH₃ | 7 | OCH₃ | OCH₃ |
| 2,5,6-Cl,Cl,Cl-phenyl | H | H | 7/9 | CH₃ | OCH₃ |
| 2,5,6-Cl,Cl,Cl-phenyl | H | CH₃ | 7 | CH₃ | OCH₃ |
| 2,5,6-Cl,Cl,Cl-phenyl | H | H | 7/9 | OCH₃ | CH₃ |
| 2,5,6-Cl,Cl,Cl-phenyl | H | CH₃ | 7 | OCH₃ | CH₃ |
| 2,5,6-Cl,Cl,Cl-phenyl | H | H | 7/9 | Cl | OCH₃ |
| 2,5,6-Cl,Cl,Cl-phenyl | H | CH₃ | 7 | Cl | OCH₃ |
| 2,5,6-Cl,Cl,Cl-phenyl | H | H | 7/9 | OCH₃ | Cl |
| 2,5,6-Cl,Cl,Cl-phenyl | H | CH₃ | 7 | OCH₃ | Cl |
| 2,3,5-Cl,Cl,Cl-phenyl | H | H | 7/9 | CH₃ | CH₃ |
| 2,3,5-Cl,Cl,Cl-phenyl | H | CH₃ | 7 | CH₃ | CH₃ |
| 2,3,5-Cl,Cl,Cl-phenyl | H | H | 7/9 | Cl | CH₃ |
| 2,3,5-Cl,Cl,Cl-phenyl | H | CH₃ | 7 | Cl | CH₃ |
| 2,3,5-Cl,Cl,Cl-phenyl | H | H | 7/9 | CH₃ | Cl |
| 2,3,5-Cl,Cl,Cl-phenyl | H | CH₃ | 7 | CH₃ | Cl |
| 2,3,5-Cl,Cl,Cl-phenyl | H | H | 7/9 | Cl | Cl |
| 2,3,5-Cl,Cl,Cl-phenyl | H | CH₃ | 7 | Cl | Cl |
| 2,3,5-Cl,Cl,Cl-phenyl | H | H | 7/9 | OCH₃ | OCH₃ |
| 2,3,5-Cl,Cl,Cl-phenyl | H | CH₃ | 7 | OCH₃ | OCH₃ |
| 2,3,5-Cl,Cl,Cl-phenyl | H | H | 7/9 | CH₃ | OCH₃ |
| 2,3,5-Cl,Cl,Cl-phenyl | H | CH₃ | 7 | CH₃ | OCH₃ |
| 2,3,5-Cl,Cl,Cl-phenyl | H | H | 7/9 | OCH₃ | CH₃ |
| 2,3,5-Cl,Cl,Cl-phenyl | H | CH₃ | 7 | OCH₃ | CH₃ |
| 2,3,5-Cl,Cl,Cl-phenyl | H | H | 7/9 | Cl | OCH₃ |
| 2,3,5-Cl,Cl,Cl-phenyl | H | CH₃ | 7 | Cl | OCH₃ |
| 2,3,5-Cl,Cl,Cl-phenyl | H | H | 7/9 | OCH₃ | Cl |
| 2,3,5-Cl,Cl,Cl-phenyl | H | CH₃ | 7 | OCH₃ | Cl |
| 1-naphthyl | H | H | 7/9 | CH₃ | CH₃ |
| 1-naphthyl | H | CH₃ | 7 | CH₃ | CH₃ |
| 1-naphthyl | H | H | 7/9 | Cl | CH₃ |
| 1-naphthyl | H | CH₃ | 7 | Cl | CH₃ |
| 1-naphthyl | H | H | 7/9 | CH₃ | Cl |
| 1-naphthyl | H | CH₃ | 7 | CH₃ | Cl |
| 1-naphthyl | H | H | 7/9 | Cl | Cl |
| 1-naphthyl | H | CH₃ | 7 | Cl | Cl |
| 1-naphthyl | H | H | 7/9 | OCH₃ | OCH₃ |
| 1-naphthyl | H | CH₃ | 7 | OCH₃ | OCH₃ |
| 1-naphthyl | H | H | 7/9 | CH₃ | OCH₃ |
| 1-naphthyl | H | CH₃ | 7 | CH₃ | OCH₃ |
| 1-naphthyl | H | H | 7/9 | OCH₃ | CH₃ |
| 1-naphthyl | H | CH₃ | 7 | OCH₃ | CH₃ |
| 1-naphthyl | H | H | 7/9 | Cl | OCH₃ |
| 1-naphthyl | H | CH₃ | 7 | Cl | OCH₃ |
| 1-naphthyl | H | H | 7/9 | OCH₃ | Cl |
| 1-naphthyl | H | CH₃ | 7 | OCH₃ | Cl |
| 8-Cl,1-naphthyl | H | H | 7/9 | CH₃ | CH₃ |
| 8-Cl,1-naphthyl | H | CH₃ | 7 | CH₃ | CH₃ |
| 8-Cl,1-naphthyl | H | H | 7/9 | Cl | CH₃ |
| 8-Cl,1-naphthyl | H | CH₃ | 7 | Cl | CH₃ |
| 8-Cl,1-naphthyl | H | H | 7/9 | CH₃ | Cl |
| 8-Cl,1-naphthyl | H | CH₃ | 7 | CH₃ | Cl |

TABLE I-continued

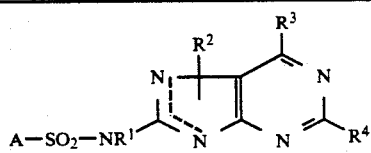

Ia

| A | $R^1$ | $R^2$ | Pos. | $R^3$ | $R^4$ |
|---|---|---|---|---|---|
| 8-Cl,1-naphthyl | H | H | 7/9 | Cl | Cl |
| 8-Cl,1-naphthyl | H | CH$_3$ | 7 | Cl | Cl |
| 8-Cl,1-naphthyl | H | H | 7/9 | OCH$_3$ | OCH$_3$ |
| 8-Cl,1-naphthyl | H | CH$_3$ | 7 | OCH$_3$ | OCH$_3$ |
| 8-Cl,1-naphthyl | H | H | 7/9 | CH$_3$ | OCH$_3$ |
| 8-Cl,1-naphthyl | H | CH$_3$ | 7 | CH$_3$ | OCH$_3$ |
| 8-Cl,1-naphthyl | H | H | 7/9 | OCH$_3$ | CH$_3$ |
| 8-Cl,1-naphthyl | H | CH$_3$ | 7 | OCH$_3$ | CH$_3$ |
| 8-Cl,1-naphthyl | H | H | 7/9 | Cl | OCH$_3$ |
| 8-Cl,1-naphthyl | H | CH$_3$ | 7 | Cl | OCH$_3$ |
| 8-Cl,1-naphthyl | H | H | 7/9 | OCH$_3$ | Cl |
| 8-Cl,1-naphthyl | H | CH$_3$ | 7 | OCH$_3$ | Cl |
| 8-CO$_2$CH$_3$,1-naphthyl | H | H | 7/9 | CH$_3$ | CH$_3$ |
| 8-CO$_2$CH$_3$,1-naphthyl | H | CH$_3$ | 7 | CH$_3$ | CH$_3$ |
| 8-CO$_2$CH$_3$,1-naphthyl | H | H | 7/9 | Cl | CH$_3$ |
| 8-CO$_2$CH$_3$,1-naphthyl | H | CH$_3$ | 7 | Cl | CH$_3$ |
| 8-CO$_2$CH$_3$,1-naphthyl | H | H | 7/9 | CH$_3$ | Cl |
| 8-CO$_2$CH$_3$,1-naphthyl | H | CH$_3$ | 7 | CH$_3$ | Cl |
| 8-CO$_2$CH$_3$,1-naphthyl | H | H | 7/9 | Cl | Cl |
| 8-CO$_2$CH$_3$,1-naphthyl | H | CH$_3$ | 7 | Cl | Cl |
| 8-CO$_2$CH$_3$,1-naphthyl | H | H | 7/9 | OCH$_3$ | OCH$_3$ |
| 8-CO$_2$CH$_3$,1-naphthyl | H | CH$_3$ | 7 | OCH$_3$ | OCH$_3$ |
| 8-CO$_2$CH$_3$,1-naphthyl | H | H | 7/9 | CH$_3$ | OCH$_3$ |
| 8-CO$_2$CH$_3$,1-naphthyl | H | CH$_3$ | 7 | CH$_3$ | OCH$_3$ |
| 8-CO$_2$CH$_3$,1-naphthyl | H | H | 7/9 | OCH$_3$ | CH$_3$ |
| 8-CO$_2$CH$_3$,1-naphthyl | H | CH$_3$ | 7 | OCH$_3$ | CH$_3$ |
| 8-CO$_2$CH$_3$,1-naphthyl | H | H | 7/9 | Cl | OCH$_3$ |
| 8-CO$_2$CH$_3$,1-naphthyl | H | CH$_3$ | 7 | Cl | OCH$_3$ |
| 8-CO$_2$CH$_3$,1-naphthyl | H | H | 7/9 | OCH$_3$ | Cl |
| 8-CO$_2$CH$_3$,1-naphthyl | H | CH$_3$ | 7 | OCH$_3$ | Cl |
| 8-OCH$_3$,1-naphthyl | H | H | 7/9 | CH$_3$ | CH$_3$ |
| 8-OCH$_3$,1-naphthyl | H | CH$_3$ | 7 | CH$_3$ | CH$_3$ |
| 8-OCH$_3$,1-naphthyl | H | H | 7/9 | Cl | CH$_3$ |
| 8-OCH$_3$,1-naphthyl | H | CH$_3$ | 7 | Cl | CH$_3$ |
| 8-OCH$_3$,1-naphthyl | H | H | 7/9 | CH$_3$ | Cl |
| 8-OCH$_3$,1-naphthyl | H | CH$_3$ | 7 | CH$_3$ | Cl |
| 8-OCH$_3$,1-naphthyl | H | H | 7/9 | Cl | Cl |
| 8-OCH$_3$,1-naphthyl | H | CH$_3$ | 7 | Cl | Cl |
| 8-OCH$_3$,1-naphthyl | H | H | 7/9 | OCH$_3$ | OCH$_3$ |
| 8-OCH$_3$,1-naphthyl | H | CH$_3$ | 7 | OCH$_3$ | OCH$_3$ |
| 8-OCH$_3$,1-naphthyl | H | H | 7/9 | CH$_3$ | OCH$_3$ |
| 8-OCH$_3$,1-naphthyl | H | CH$_3$ | 7 | CH$_3$ | OCH$_3$ |
| 8-OCH$_3$,1-naphthyl | H | H | 7/9 | OCH$_3$ | CH$_3$ |
| 8-OCH$_3$,1-naphthyl | H | CH$_3$ | 7 | OCH$_3$ | CH$_3$ |
| 8-OCH$_3$,1-naphthyl | H | H | 7/9 | Cl | OCH$_3$ |
| 8-OCH$_3$,1-naphthyl | H | CH$_3$ | 7 | Cl | OCH$_3$ |
| 8-OCH$_3$,1-naphthyl | H | H | 7/9 | OCH$_3$ | Cl |
| 8-OCH$_3$,1-naphthyl | H | CH$_3$ | 7 | OCH$_3$ | Cl |
| 8-OCH$_2$CH$_2$OCH$_3$,1-naphthyl | H | H | 7/9 | CH$_3$ | CH$_3$ |
| 8-OCH$_2$CH$_2$OCH$_3$,1-naphthyl | H | CH$_3$ | 7 | CH$_3$ | CH$_3$ |
| 8-OCH$_2$CH$_2$OCH$_3$,1-naphthyl | H | H | 7/9 | Cl | CH$_3$ |
| 8-OCH$_2$CH$_2$OCH$_3$,1-naphthyl | H | CH$_3$ | 7 | Cl | CH$_3$ |
| 8-OCH$_2$CH$_2$OCH$_3$,1-naphthyl | H | H | 7/9 | CH$_3$ | Cl |
| 8-OCH$_2$CH$_2$OCH$_3$,1-naphthyl | H | CH$_3$ | 7 | CH$_3$ | Cl |
| 8-OCH$_2$CH$_2$OCH$_3$,1-naphthyl | H | H | 7/9 | Cl | Cl |
| 8-OCH$_2$CH$_2$OCH$_3$,1-naphthyl | H | CH$_3$ | 7 | Cl | Cl |
| 8-OCH$_2$CH$_2$OCH$_3$,1-naphthyl | H | H | 7/9 | OCH$_3$ | OCH$_3$ |
| 8-OCH$_2$CH$_2$OCH$_3$,1-naphthyl | H | CH$_3$ | 7 | OCH$_3$ | OCH$_3$ |
| 8-OCH$_2$CH$_2$OCH$_3$,1-naphthyl | H | H | 7/9 | CH$_3$ | OCH$_3$ |
| 8-OCH$_2$CH$_2$OCH$_3$,1-naphthyl | H | CH$_3$ | 7 | CH$_3$ | OCH$_3$ |
| 8-OCH$_2$CH$_2$OCH$_3$,1-naphthyl | H | H | 7/9 | OCH$_3$ | CH$_3$ |
| 8-OCH$_2$CH$_2$OCH$_3$,1-naphthyl | H | CH$_3$ | 7 | OCH$_3$ | CH$_3$ |
| 8-OCH$_2$CH$_2$OCH$_3$,1-naphthyl | H | H | 7/9 | Cl | OCH$_3$ |
| 8-OCH$_2$CH$_2$OCH$_3$,1-naphthyl | H | CH$_3$ | 7 | Cl | OCH$_3$ |
| 8-OCH$_2$CH$_2$OCH$_3$,1-naphthyl | H | H | 7/9 | OCH$_3$ | Cl |
| 8-OCH$_2$CH$_2$OCH$_3$,1-naphthyl | H | CH$_3$ | 7 | OCH$_3$ | Cl |
| 8-OCH$_2$CH$_2$Cl,1-naphthyl | H | H | 7/9 | CH$_3$ | CH$_3$ |
| 8-OCH$_2$CH$_2$Cl,1-naphthyl | H | CH$_3$ | 7 | CH$_3$ | CH$_3$ |
| 8-OCH$_2$CH$_2$Cl,1-naphthyl | H | H | 7/9 | Cl | CH$_3$ |
| 8-OCH$_2$CH$_2$Cl,1-naphthyl | H | CH$_3$ | 7 | Cl | CH$_3$ |
| 8-OCH$_2$CH$_2$Cl,1-naphthyl | H | H | 7/9 | CH$_3$ | Cl |
| 8-OCH$_2$CH$_2$Cl,1-naphthyl | H | CH$_3$ | 7 | CH$_3$ | Cl |
| 8-OCH$_2$CH$_2$Cl,1-naphthyl | H | H | 7/9 | Cl | Cl |

TABLE I-continued $$\text{A-SO}_2\text{-NR}^1 \begin{array}{c} R^2 \\ \text{pyrrolopyrimidine core} \end{array} R^3, R^4 \quad \text{Ia}$$

| A | R¹ | R² | Pos. | R³ | R⁴ |
|---|---|---|---|---|---|
| 8-OCH₂CH₂Cl,1-naphthyl | H | CH₃ | 7 | Cl | Cl |
| 8-OCH₂CH₂Cl,1-naphthyl | H | H | 7/9 | OCH₃ | OCH₃ |
| 8-OCH₂CH₂Cl,1-naphthyl | H | CH₃ | 7 | OCH₃ | OCH₃ |
| 8-OCH₂CH₂Cl,1-naphthyl | H | H | 7/9 | CH₃ | OCH₃ |
| 8-OCH₂CH₂Cl,1-naphthyl | H | CH₃ | 7 | CH₃ | OCH₃ |
| 8-OCH₂CH₂Cl,1-naphthyl | H | H | 7/9 | OCH₃ | CH₃ |
| 8-OCH₂CH₂Cl,1-naphthyl | H | CH₃ | 7 | OCH₃ | CH₃ |
| 8-OCH₂CH₂Cl,1-naphthyl | H | H | 7/9 | Cl | OCH₃ |
| 8-OCH₂CH₂Cl,1-naphthyl | H | CH₃ | 7 | Cl | OCH₃ |
| 8-OCH₂CH₂Cl,1-naphthyl | H | H | 7/9 | OCH₃ | Cl |
| 8-OCH₂CH₂Cl,1-naphthyl | H | CH₃ | 7 | OCH₃ | Cl |
| 8-OCH₂CO₂CH₃,1-naphthyl | H | H | 7/9 | CH₃ | CH₃ |
| 8-OCH₂CO₂CH₃,1-naphthyl | H | CH₃ | 7 | CH₃ | CH₃ |
| 8-OCH₂CO₂CH₃,1-naphthyl | H | H | 7/9 | Cl | CH₃ |
| 8-OCH₂CO₂CH₃,1-naphthyl | H | CH₃ | 7 | Cl | CH₃ |
| 8-OCH₂CO₂CH₃,1-naphthyl | H | H | 7/9 | CH₃ | Cl |
| 8-OCH₂CO₂CH₃,1-naphthyl | H | CH₃ | 7 | CH₃ | Cl |
| 8-OCH₂CO₂CH₃,1-naphthyl | H | H | 7/9 | Cl | Cl |
| 8-OCH₂CO₂CH₃,1-naphthyl | H | CH₃ | 7 | Cl | Cl |
| 8-OCH₂CO₂CH₃,1-naphthyl | H | H | 7/9 | OCH₃ | OCH₃ |
| 8-OCH₂CO₂CH₃,1-naphthyl | H | CH₃ | 7 | OCH₃ | OCH₃ |
| 8-OCH₂CO₂CH₃,1-naphthyl | H | H | 7/9 | CH₃ | OCH₃ |
| 8-OCH₂CO₂CH₃,1-naphthyl | H | CH₃ | 7 | CH₃ | OCH₃ |
| 8-OCH₂CO₂CH₃,1-naphthyl | H | H | 7/9 | OCH₃ | CH₃ |
| 8-OCH₂CO₂CH₃,1-naphthyl | H | CH₃ | 7 | OCH₃ | CH₃ |
| 8-OCH₂CO₂CH₃,1-naphthyl | H | H | 7/9 | Cl | OCH₃ |
| 8-OCH₂CO₂CH₃,1-naphthyl | H | CH₃ | 7 | Cl | OCH₃ |
| 8-OCH₂CO₂CH₃,1-naphthyl | H | H | 7/9 | OCH₃ | Cl |
| 8-OCH₂CO₂CH₃,1-naphthyl | H | CH₃ | 7 | OCH₃ | Cl |
| 2-Cl,1-naphthyl | H | H | 7/9 | CH₃ | CH₃ |
| 2-Cl,1-naphthyl | H | CH₃ | 7 | CH₃ | CH₃ |
| 2-Cl,1-naphthyl | H | H | 7/9 | Cl | CH₃ |
| 2-Cl,1-naphthyl | H | CH₃ | 7 | Cl | CH₃ |
| 2-Cl,1-naphthyl | H | H | 7/9 | CH₃ | Cl |
| 2-Cl,1-naphthyl | H | CH₃ | 7 | CH₃ | Cl |
| 2-Cl,1-naphthyl | H | H | 7/9 | Cl | Cl |
| 2-Cl,1-naphthyl | H | CH₃ | 7 | Cl | Cl |
| 2-Cl,1-naphthyl | H | H | 7/9 | OCH₃ | OCH₃ |
| 2-Cl,1-naphthyl | H | CH₃ | 7 | OCH₃ | OCH₃ |
| 2-Cl,1-naphthyl | H | H | 7/9 | CH₃ | OCH₃ |
| 2-Cl,1-naphthyl | H | CH₃ | 7 | CH₃ | OCH₃ |
| 2-Cl,1-naphthyl | H | H | 7/9 | OCH₃ | CH₃ |
| 2-Cl,1-naphthyl | H | CH₃ | 7 | OCH₃ | CH₃ |
| 2-Cl,1-naphthyl | H | H | 7/9 | Cl | OCH₃ |
| 2-Cl,1-naphthyl | H | CH₃ | 7 | Cl | OCH₃ |
| 2-Cl,1-naphthyl | H | H | 7/9 | OCH₃ | Cl |
| 2-Cl,1-naphthyl | H | CH₃ | 7 | OCH₃ | Cl |
| 2-CO₂CH₃,1-naphthyl | H | H | 7/9 | CH₃ | CH₃ |
| 2-CO₂CH₃,1-naphthyl | H | CH₃ | 7 | CH₃ | CH₃ |
| 2-CO₂CH₃,1-naphthyl | H | H | 7/9 | Cl | CH₃ |
| 2-CO₂CH₃,1-naphthyl | H | CH₃ | 7 | Cl | CH₃ |
| 2-CO₂CH₃,1-naphthyl | H | H | 7/9 | CH₃ | Cl |
| 2-CO₂CH₃,1-naphthyl | H | CH₃ | 7 | CH₃ | Cl |
| 2-CO₂CH₃,1-naphthyl | H | H | 7/9 | Cl | Cl |
| 2-CO₂CH₃,1-naphthyl | H | CH₃ | 7 | Cl | Cl |
| 2-CO₂CH₃,1-naphthyl | H | H | 7/9 | OCH₃ | OCH₃ |
| 2-CO₂CH₃,1-naphthyl | H | CH₃ | 7 | OCH₃ | OCH₃ |
| 2-CO₂CH₃,1-naphthyl | H | H | 7/9 | CH₃ | OCH₃ |
| 2-CO₂CH₃,1-naphthyl | H | CH₃ | 7 | CH₃ | OCH₃ |
| 2-CO₂CH₃,1-naphthyl | H | H | 7/9 | OCH₃ | CH₃ |
| 2-CO₂CH₃,1-naphthyl | H | CH₃ | 7 | OCH₃ | CH₃ |
| 2-CO₂CH₃,1-naphthyl | H | H | 7/9 | Cl | OCH₃ |
| 2-CO₂CH₃,1-naphthyl | H | CH₃ | 7 | Cl | OCH₃ |
| 2-CO₂CH₃,1-naphthyl | H | H | 7/9 | OCH₃ | Cl |
| 2-CO₂CH₃,1-naphthyl | H | CH₃ | 7 | OCH₃ | Cl |
| 2-naphthyl | H | H | 7/9 | CH₃ | CH₃ |
| 2-naphthyl | H | CH₃ | 7 | CH₃ | CH₃ |
| 2-naphthyl | H | H | 7/9 | Cl | CH₃ |
| 2-naphthyl | H | CH₃ | 7 | Cl | CH₃ |
| 2-naphthyl | H | H | 7/9 | CH₃ | Cl |
| 2-naphthyl | H | CH₃ | 7 | CH₃ | Cl |
| 2-naphthyl | H | H | 7/9 | Cl | Cl |
| 2-naphthyl | H | CH₃ | 7 | Cl | Cl |

TABLE I-continued

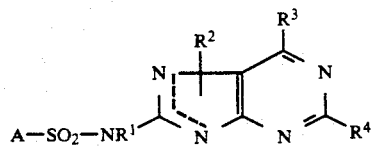

Ia

| A | $R^1$ | $R^2$ | Pos. | $R^3$ | $R^4$ |
|---|---|---|---|---|---|
| 2-naphthyl | H | H | 7/9 | $OCH_3$ | $OCH_3$ |
| 2-naphthyl | H | $CH_3$ | 7 | $OCH_3$ | $OCH_3$ |
| 2-naphthyl | H | H | 7/9 | $CH_3$ | $OCH_3$ |
| 2-naphthyl | H | $CH_3$ | 7 | $CH_3$ | $OCH_3$ |
| 2-naphthyl | H | H | 7/9 | $OCH_3$ | $CH_3$ |
| 2-naphthyl | H | $CH_3$ | 7 | $OCH_3$ | $CH_3$ |
| 2-naphthyl | H | H | 7/9 | Cl | $OCH_3$ |
| 2-naphthyl | H | $CH_3$ | 7 | Cl | $OCH_3$ |
| 2-naphthyl | H | H | 7/9 | $OCH_3$ | Cl |
| 2-naphthyl | H | $CH_3$ | 7 | $OCH_3$ | Cl |
| 1-Cl,2-napthyl | H | H | 7/9 | $CH_3$ | $CH_3$ |
| 1-Cl,2-napthyl | H | $CH_3$ | 7 | $CH_3$ | $CH_3$ |
| 1-Cl,2-napthyl | H | H | 7/9 | Cl | $CH_3$ |
| 1-Cl,2-napthyl | H | $CH_3$ | 7 | Cl | $CH_3$ |
| 1-Cl,2-napthyl | H | H | 7/9 | $CH_3$ | Cl |
| 1-Cl,2-napthyl | H | $CH_3$ | 7 | $CH_3$ | Cl |
| 1-Cl,2-napthyl | H | H | 7/9 | Cl | Cl |
| 1-Cl,2-napthyl | H | $CH_3$ | 7 | Cl | Cl |
| 1-Cl,2-napthyl | H | H | 7/9 | $OCH_3$ | $OCH_3$ |
| 1-Cl,2-napthyl | H | $CH_3$ | 7 | $OCH_3$ | $OCH_3$ |
| 1-Cl,2-napthyl | H | H | 7/9 | $CH_3$ | $OCH_3$ |
| 1-Cl,2-napthyl | H | $CH_3$ | 7 | $CH_3$ | $OCH_3$ |
| 1-Cl,2-napthyl | H | H | 7/9 | $OCH_3$ | $CH_3$ |
| 1-Cl,2-napthyl | H | $CH_3$ | 7 | $OCH_3$ | $CH_3$ |
| 1-Cl,2-napthyl | H | H | 7/9 | Cl | $OCH_3$ |
| 1-Cl,2-napthyl | H | $CH_3$ | 7 | Cl | $OCH_3$ |
| 1-Cl,2-napthyl | H | H | 7/9 | $OCH_3$ | Cl |
| 1-Cl,2-napthyl | H | $CH_3$ | 7 | $OCH_3$ | Cl |
| 1-$CO_2CH_3$,2-napthyl | H | H | 7/9 | $CH_3$ | $CH_3$ |
| 1-$CO_2CH_3$,2-napthyl | H | $CH_3$ | 7 | $CH_3$ | $CH_3$ |
| 1-$CO_2CH_3$,2-napthyl | H | H | 7/9 | Cl | $CH_3$ |
| 1-$CO_2CH_3$,2-napthyl | H | $CH_3$ | 7 | Cl | $CH_3$ |
| 1-$CO_2CH_3$,2-napthyl | H | H | 7/9 | $CH_3$ | Cl |
| 1-$CO_2CH_3$,2-napthyl | H | $CH_3$ | 7 | $CH_3$ | Cl |
| 1-$CO_2CH_3$,2-napthyl | H | H | 7/9 | Cl | Cl |
| 1-$CO_2CH_3$,2-napthyl | H | $CH_3$ | 7 | Cl | Cl |
| 1-$CO_2CH_3$,2-napthyl | H | H | 7/9 | $OCH_3$ | $OCH_3$ |
| 1-$CO_2CH_3$,2-napthyl | H | $CH_3$ | 7 | $OCH_3$ | $OCH_3$ |
| 1-$CO_2CH_3$,2-napthyl | H | H | 7/9 | $CH_3$ | $OCH_3$ |
| 1-$CO_2CH_3$,2-napthyl | H | $CH_3$ | 7 | $CH_3$ | $OCH_3$ |
| 1-$CO_2CH_3$,2-napthyl | H | H | 7/9 | $OCH_3$ | $CH_3$ |
| 1-$CO_2CH_3$,2-napthyl | H | $CH_3$ | 7 | $OCH_3$ | $CH_3$ |
| 1-$CO_2CH_3$,2-napthyl | H | H | 7/9 | Cl | $OCH_3$ |
| 1-$CO_2CH_3$,2-napthyl | H | $CH_3$ | 7 | Cl | $OCH_3$ |
| 1-$CO_2CH_3$,2-napthyl | H | H | 7/9 | $OCH_3$ | Cl |
| 1-$CO_2CH_3$,2-napthyl | H | $CH_3$ | 7 | $OCH_3$ | Cl |
| 1-$OCH_2CH_2OCH_3$,2-naphthyl | H | H | 7/9 | $CH_3$ | $CH_3$ |
| 1-$OCH_2CH_2OCH_3$,2-naphthyl | H | $CH_3$ | 7 | $CH_3$ | $CH_3$ |
| 1-$OCH_2CH_2OCH_3$,2-naphthyl | H | H | 7/9 | Cl | $CH_3$ |
| 1-$OCH_2CH_2OCH_3$,2-naphthyl | H | $CH_3$ | 7 | Cl | $CH_3$ |
| 1-$OCH_2CH_2OCH_3$,2-naphthyl | H | H | 7/9 | $CH_3$ | Cl |
| 1-$OCH_2CH_2OCH_3$,2-naphthyl | H | $CH_3$ | 7 | $CH_3$ | Cl |
| 1-$OCH_2CH_2OCH_3$,2-naphthyl | H | H | 7/9 | Cl | Cl |
| 1-$OCH_2CH_2OCH_3$,2-naphthyl | H | $CH_3$ | 7 | Cl | Cl |
| 1-$OCH_2CH_2OCH_3$,2-naphthyl | H | H | 7/9 | $OCH_3$ | $OCH_3$ |
| 1-$OCH_2CH_2OCH_3$,2-naphthyl | H | $CH_3$ | 7 | $OCH_3$ | $OCH_3$ |
| 1-$OCH_2CH_2OCH_3$,2-naphthyl | H | H | 7/9 | $CH_3$ | $OCH_3$ |
| 1-$OCH_2CH_2OCH_3$,2-naphthyl | H | $CH_3$ | 7 | $CH_3$ | $OCH_3$ |
| 1-$OCH_2CH_2OCH_3$,2-naphthyl | H | H | 7/9 | $OCH_3$ | $CH_3$ |
| 1-$OCH_2CH_2OCH_3$,2-naphthyl | H | $CH_3$ | 7 | $OCH_3$ | $CH_3$ |
| 1-$OCH_2CH_2OCH_3$,2-naphthyl | H | H | 7/9 | Cl | $OCH_3$ |
| 1-$OCH_2CH_2OCH_3$,2-naphthyl | H | $CH_3$ | 7 | Cl | $OCH_3$ |
| 1-$OCH_2CH_2OCH_3$,2-naphthyl | H | H | 7/9 | $OCH_3$ | Cl |
| 1-$OCH_2CH_2OCH_3$,2-naphthyl | H | $CH_3$ | 7 | $OCH_3$ | Cl |
| 1-$OCH_2CH_2Cl$,2-naphthyl | H | H | 7/9 | $CH_3$ | $CH_3$ |
| 1-$OCH_2CH_2Cl$,2-naphthyl | H | $CH_3$ | 7 | $CH_3$ | $CH_3$ |
| 1-$OCH_2CH_2Cl$,2-naphthyl | H | H | 7/9 | Cl | $CH_3$ |
| 1-$OCH_2CH_2Cl$,2-naphthyl | H | $CH_3$ | 7 | Cl | $CH_3$ |
| 1-$OCH_2CH_2Cl$,2-naphthyl | H | H | 7/9 | $CH_3$ | Cl |
| 1-$OCH_2CH_2Cl$,2-naphthyl | H | $CH_3$ | 7 | $CH_3$ | Cl |
| 1-$OCH_2CH_2Cl$,2-naphthyl | H | H | 7/9 | Cl | Cl |
| 1-$OCH_2CH_2Cl$,2-naphthyl | H | $CH_3$ | 7 | Cl | Cl |
| 1-$OCH_2CH_2Cl$,2-naphthyl | H | H | 7/9 | $OCH_3$ | $OCH_3$ |

TABLE I-continued

Ia

| A | R¹ | R² | Pos. | R³ | R⁴ |
|---|---|---|---|---|---|
| 1-OCH₂CH₂Cl,2-naphthyl | H | CH₃ | 7 | OCH₃ | OCH₃ |
| 1-OCH₂CH₂Cl,2-naphthyl | H | H | 7/9 | CH₃ | OCH₃ |
| 1-OCH₂CH₂Cl,2-naphthyl | H | CH₃ | 7 | CH₃ | OCH₃ |
| 1-OCH₂CH₂Cl,2-naphthyl | H | H | 7/9 | OCH₃ | CH₃ |
| 1-OCH₂CH₂Cl,2-naphthyl | H | CH₃ | 7 | OCH₃ | CH₃ |
| 1-OCH₂CH₂Cl,2-naphthyl | H | H | 7/9 | Cl | OCH₃ |
| 1-OCH₂CH₂Cl,2-naphthyl | H | CH₃ | 7 | Cl | OCH₃ |
| 1-OCH₂CH₂Cl,2-naphthyl | H | H | 7/9 | OCH₃ | Cl |
| 1-OCH₂CH₂Cl,2-naphthyl | H | CH₃ | 7 | OCH₃ | Cl |
| 1-OCH₂CO₂CH₃,2-naphthyl | H | H | 7/9 | CH₃ | CH₃ |
| 1-OCH₂CO₂CH₃,2-naphthyl | H | CH₃ | 7 | CH₃ | CH₃ |
| 1-OCH₂CO₂CH₃,2-naphthyl | H | H | 7/9 | Cl | CH₃ |
| 1-OCH₂CO₂CH₃,2-naphthyl | H | CH₃ | 7 | Cl | CH₃ |
| 1-OCH₂CO₂CH₃,2-naphthyl | H | H | 7/9 | CH₃ | Cl |
| 1-OCH₂CO₂CH₃,2-naphthyl | H | CH₃ | 7 | CH₃ | Cl |
| 1-OCH₂CO₂CH₃,2-naphthyl | H | H | 7/9 | Cl | Cl |
| 1-OCH₂CO₂CH₃,2-naphthyl | H | CH₃ | 7 | Cl | Cl |
| 1-OCH₂CO₂CH₃,2-naphthyl | H | H | 7/9 | OCH₃ | OCH₃ |
| 1-OCH₂CO₂CH₃,2-naphthyl | H | CH₃ | 7 | OCH₃ | OCH₃ |
| 1-OCH₂CO₂CH₃,2-naphthyl | H | H | 7/9 | CH₃ | OCH₃ |
| 1-OCH₂CO₂CH₃,2-naphthyl | H | CH₃ | 7 | CH₃ | OCH₃ |
| 1-OCH₂CO₂CH₃,2-naphthyl | H | H | 7/9 | OCH₃ | CH₃ |
| 1-OCH₂CO₂CH₃,2-naphthyl | H | CH₃ | 7 | OCH₃ | CH₃ |
| 1-OCH₂CO₂CH₃,2-naphthyl | H | H | 7/9 | Cl | OCH₃ |
| 1-OCH₂CO₂CH₃,2-naphthyl | H | CH₃ | 7 | Cl | OCH₃ |
| 1-OCH₂CO₂CH₃,2-naphthyl | H | H | 7/9 | OCH₃ | Cl |
| 1-OCH₂CO₂CH₃,2-naphthyl | H | CH₃ | 7 | OCH₃ | Cl |
| 2-thienyl | H | H | 7/9 | CH₃ | CH₃ |
| 2-thienyl | H | CH₃ | 7 | CH₃ | CH₃ |
| 2-thienyl | H | H | 7/9 | Cl | CH₃ |
| 2-thienyl | H | CH₃ | 7 | Cl | CH₃ |
| 2-thienyl | H | H | 7/9 | CH₃ | Cl |
| 2-thienyl | H | CH₃ | 7 | CH₃ | Cl |
| 2-thienyl | H | H | 7/9 | Cl | Cl |
| 2-thienyl | H | CH₃ | 7 | Cl | Cl |
| 2-thienyl | H | H | 7/9 | OCH₃ | OCH₃ |
| 2-thienyl | H | CH₃ | 7 | OCH₃ | OCH₃ |
| 2-thienyl | H | H | 7/9 | CH₃ | OCH₃ |
| 2-thienyl | H | CH₃ | 7 | CH₃ | OCH₃ |
| 2-thienyl | H | H | 7/9 | OCH₃ | CH₃ |
| 2-thienyl | H | CH₃ | 7 | OCH₃ | CH₃ |
| 2-thienyl | H | H | 7/9 | Cl | OCH₃ |
| 2-thienyl | H | CH₃ | 7 | Cl | OCH₃ |
| 2-thienyl | H | H | 7/9 | OCH₃ | Cl |
| 2-thienyl | H | CH₃ | 7 | OCH₃ | Cl |
| 3-Cl,2-thienyl | H | H | 7/9 | CH₃ | CH₃ |
| 3-Cl,2-thienyl | H | CH₃ | 7 | CH₃ | CH₃ |
| 3-Cl,2-thienyl | H | H | 7/9 | Cl | CH₃ |
| 3-Cl,2-thienyl | H | CH₃ | 7 | Cl | CH₃ |
| 3-Cl,2-thienyl | H | H | 7/9 | CH₃ | Cl |
| 3-Cl,2-thienyl | H | CH₃ | 7 | CH₃ | Cl |
| 3-Cl,2-thienyl | H | H | 7/9 | Cl | Cl |
| 3-Cl,2-thienyl | H | CH₃ | 7 | Cl | Cl |
| 3-Cl,2-thienyl | H | H | 7/9 | OCH₃ | OCH₃ |
| 3-Cl,2-thienyl | H | CH₃ | 7 | OCH₃ | OCH₃ |
| 3-Cl,2-thienyl | H | H | 7/9 | CH₃ | OCH₃ |
| 3-Cl,2-thienyl | H | CH₃ | 7 | CH₃ | OCH₃ |
| 3-Cl,2-thienyl | H | H | 7/9 | OCH₃ | CH₃ |
| 3-Cl,2-thienyl | H | CH₃ | 7 | OCH₃ | CH₃ |
| 3-Cl,2-thienyl | H | H | 7/9 | Cl | OCH₃ |
| 3-Cl,2-thienyl | H | CH₃ | 7 | Cl | OCH₃ |
| 3-Cl,2-thienyl | H | H | 7/9 | OCH₃ | Cl |
| 3-Cl,2-thienyl | H | CH₃ | 7 | OCH₃ | Cl |
| 3-Cl,2-thienyl | CH₃ | H | 7/9 | CH₃ | CH₃ |
| 3-Cl,2-thienyl | CH₃ | CH₃ | 7 | CH₃ | CH₃ |
| 3-Cl,2-thienyl | CH₃ | H | 7/9 | Cl | CH₃ |
| 3-Cl,2-thienyl | CH₃ | CH₃ | 7 | Cl | CH₃ |
| 3-Cl,2-thienyl | CH₃ | H | 7/9 | CH₃ | Cl |
| 3-Cl,2-thienyl | CH₃ | CH₃ | 7 | CH₃ | Cl |
| 3-Cl,2-thienyl | CH₃ | H | 7/9 | Cl | Cl |
| 3-Cl,2-thienyl | CH₃ | CH₃ | 7 | Cl | Cl |
| 3-Cl,2-thienyl | CH₃ | H | 7/9 | OCH₃ | OCH₃ |
| 3-Cl,2-thienyl | CH₃ | CH₃ | 7 | OCH₃ | OCH₃ |

TABLE I-continued

| A | R¹ | R² | Pos. | R³ | R⁴ |
|---|---|---|---|---|---|
| 3-Cl,2-thienyl | CH₃ | H | 7/9 | CH₃ | OCH₃ |
| 3-Cl,2-thienyl | CH₃ | CH₃ | 7 | CH₃ | OCH₃ |
| 3-Cl,2-thienyl | CH₃ | H | 7/9 | OCH₃ | CH₃ |
| 3-Cl,2-thienyl | CH₃ | CH₃ | 7 | OCH₃ | CH₃ |
| 3-Cl,2-thienyl | CH₃ | H | 7/9 | Cl | OCH₃ |
| 3-Cl,2-thienyl | CH₃ | CH₃ | 7 | Cl | OCH₃ |
| 3-Cl,2-thienyl | CH₃ | H | 7/9 | OCH₃ | Cl |
| 3-Cl,2-thienyl | CH₃ | CH₃ | 7 | OCH₃ | Cl |
| 3-Cl,2-thienyl | H | H | 7/9 | CF₃ | CF₃ |
| 3-Cl,2-thienyl | H | CH₃ | 7 | CF₃ | CF₃ |
| 3-Cl,2-thienyl | H | H | 7/9 | Cl | CF₃ |
| 3-Cl,2-thienyl | H | CH₃ | 7 | Cl | CF₃ |
| 3-Cl,2-thienyl | H | H | 7/9 | CF₃ | Cl |
| 3-Cl,2-thienyl | H | CH₃ | 7 | CF₃ | Cl |
| 3-Cl,2-thienyl | H | H | 7/9 | F | CF₃ |
| 3-Cl,2-thienyl | H | CH₃ | 7 | F | CF₃ |
| 3-Cl,2-thienyl | H | H | 7/9 | CF₃ | F |
| 3-Cl,2-thienyl | H | CH₃ | 7 | CF₃ | F |
| 3-Cl,2-thienyl | H | H | 7/9 | CH₃ | CF₃ |
| 3-Cl,2-thienyl | H | CH₃ | 7 | CH₃ | CF₃ |
| 3-Cl,2-thienyl | H | H | 7/9 | CF₃ | CH₃ |
| 3-Cl,2-thienyl | H | CH₃ | 7 | CF₃ | CH₃ |
| 3-Cl,2-thienyl | H | H | 7/9 | OCH₃ | CF₃ |
| 3-Cl,2-thienyl | H | CH₃ | 7 | OCH₃ | CF₃ |
| 3-Cl,2-thienyl | H | H | 7/9 | CF₃ | OCH₃ |
| 3-Cl,2-thienyl | H | CH₃ | 7 | CF₃ | OCH₃ |
| 3-Cl,2-thienyl | H | H | 7/9 | F | F |
| 3-Cl,2-thienyl | H | CH₃ | 7 | F | F |
| 3-Cl,2-thienyl | H | H | 7/9 | F | Cl |
| 3-Cl,2-thienyl | H | CH₃ | 7 | F | Cl |
| 3-Cl,2-thienyl | H | H | 7/9 | Cl | F |
| 3-Cl,2-thienyl | H | CH₃ | 7 | Cl | F |
| 3-Cl,2-thienyl | H | H | 7/9 | F | CH₃ |
| 3-Cl,2-thienyl | H | CH₃ | 7 | F | CH₃ |
| 3-Cl,2-thienyl | H | H | 7/9 | CH₃ | F |
| 3-Cl,2-thienyl | H | CH₃ | 7 | CH₃ | F |
| 3-Cl,2-thienyl | H | H | 7/9 | F | OCH₃ |
| 3-Cl,2-thienyl | H | CH₃ | 7 | F | OCH₃ |
| 3-Cl,2-thienyl | H | H | 7/9 | OCH₃ | F |
| 3-Cl,2-thienyl | H | CH₃ | 7 | OCH₃ | F |
| 3-Cl,2-thienyl | H | H | 7/9 | N(CH₃)₂ | Cl |
| 3-Cl,2-thienyl | H | CH₃ | 7 | N(CH₃)₂ | Cl |
| 3-Cl,2-thienyl | H | H | 7/9 | SCH₃ | Cl |
| 3-Cl,2-thienyl | H | CH₃ | 7 | SCH₃ | Cl |
| 4-Cl,2-thienyl | H | H | 7/9 | CH₃ | CH₃ |
| 4-Cl,2-thienyl | H | CH₃ | 7 | CH₃ | CH₃ |
| 4-Cl,2-thienyl | H | H | 7/9 | Cl | CH₃ |
| 4-Cl,2-thienyl | H | CH₃ | 7 | Cl | CH₃ |
| 4-Cl,2-thienyl | H | H | 7/9 | CH₃ | Cl |
| 4-Cl,2-thienyl | H | CH₃ | 7 | CH₃ | Cl |
| 4-Cl,2-thienyl | H | H | 7/9 | Cl | Cl |
| 4-Cl,2-thienyl | H | CH₃ | 7 | Cl | Cl |
| 4-Cl,2-thienyl | H | H | 7/9 | OCH₃ | OCH₃ |
| 4-Cl,2-thienyl | H | CH₃ | 7 | OCH₃ | OCH₃ |
| 4-Cl,2-thienyl | H | H | 7/9 | CH₃ | OCH₃ |
| 4-Cl,2-thienyl | H | CH₃ | 7 | CH₃ | OCH₃ |
| 4-Cl,2-thienyl | H | H | 7/9 | OCH₃ | CH₃ |
| 4-Cl,2-thienyl | H | CH₃ | 7 | OCH₃ | CH₃ |
| 4-Cl,2-thienyl | H | H | 7/9 | Cl | OCH₃ |
| 4-Cl,2-thienyl | H | CH₃ | 7 | Cl | OCH₃ |
| 4-Cl,2-thienyl | H | H | 7/9 | OCH₃ | Cl |
| 4-Cl,2-thienyl | H | CH₃ | 7 | OCH₃ | Cl |
| 5-Cl,2-thienyl | H | H | 7/9 | CH₃ | CH₃ |
| 5-Cl,2-thienyl | H | CH₃ | 7 | CH₃ | CH₃ |
| 5-Cl,2-thienyl | H | H | 7/9 | Cl | CH₃ |
| 5-Cl,2-thienyl | H | CH₃ | 7 | Cl | CH₃ |
| 5-Cl,2-thienyl | H | H | 7/9 | CH₃ | Cl |
| 5-Cl,2-thienyl | H | CH₃ | 7 | CH₃ | Cl |
| 5-Cl,2-thienyl | H | H | 7/9 | Cl | Cl |
| 5-Cl,2-thienyl | H | CH₃ | 7 | Cl | Cl |
| 5-Cl,2-thienyl | H | H | 7/9 | OCH₃ | OCH₃ |
| 5-Cl,2-thienyl | H | CH₃ | 7 | OCH₃ | OCH₃ |
| 5-Cl,2-thienyl | H | H | 7/9 | CH₃ | OCH₃ |

TABLE I-continued

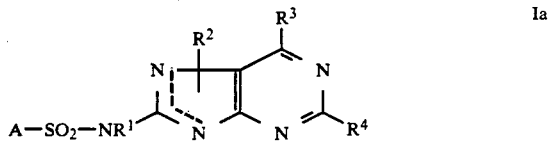

| A | R¹ | R² | Pos. | R³ | R⁴ |
|---|---|---|---|---|---|
| 5-Cl,2-thienyl | H | $CH_3$ | 7 | $CH_3$ | $OCH_3$ |
| 5-Cl,2-thienyl | H | H | 7/9 | $OCH_3$ | $CH_3$ |
| 5-Cl,2-thienyl | H | $CH_3$ | 7 | $OCH_3$ | $CH_3$ |
| 5-Cl,2-thienyl | H | H | 7/9 | Cl | $OCH_3$ |
| 5-Cl,2-thienyl | H | $CH_3$ | 7 | Cl | $OCH_3$ |
| 5-Cl,2-thienyl | H | H | 7/9 | $OCH_3$ | Cl |
| 5-Cl,2-thienyl | H | $CH_3$ | 7 | $OCH_3$ | Cl |
| 3-$CO_2CH_3$,2-thienyl | H | H | 7/9 | $CH_3$ | $CH_3$ |
| 3-$CO_2CH_3$,2-thienyl | H | $CH_3$ | 7 | $CH_3$ | $CH_3$ |
| 3-$CO_2CH_3$,2-thienyl | H | H | 7/9 | Cl | $CH_3$ |
| 3-$CO_2CH_3$,2-thienyl | H | $CH_3$ | 7 | Cl | $CH_3$ |
| 3-$CO_2CH_3$,2-thienyl | H | H | 7/9 | $CH_3$ | Cl |
| 3-$CO_2CH_3$,2-thienyl | H | $CH_3$ | 7 | $CH_3$ | Cl |
| 3-$CO_2CH_3$,2-thienyl | H | H | 7/9 | Cl | Cl |
| 3-$CO_2CH_3$,2-thienyl | H | $CH_3$ | 7 | Cl | Cl |
| 3-$CO_2CH_3$,2-thienyl | H | H | 7/9 | $OCH_3$ | $OCH_3$ |
| 3-$CO_2CH_3$,2-thienyl | H | $CH_3$ | 7 | $OCH_3$ | $OCH_3$ |
| 3-$CO_2CH_3$,2-thienyl | H | H | 7/9 | $CH_3$ | $OCH_3$ |
| 3-$CO_2CH_3$,2-thienyl | H | $CH_3$ | 7 | $CH_3$ | $OCH_3$ |
| 3-$CO_2CH_3$,2-thienyl | H | H | 7/9 | $OCH_3$ | $CH_3$ |
| 3-$CO_2CH_3$,2-thienyl | H | $CH_3$ | 7 | $OCH_3$ | $CH_3$ |
| 3-$CO_2CH_3$,2-thienyl | H | H | 7/9 | Cl | $OCH_3$ |
| 3-$CO_2CH_3$,2-thienyl | H | $CH_3$ | 7 | Cl | $OCH_3$ |
| 3-$CO_2CH_3$,2-thienyl | H | H | 7/9 | $OCH_3$ | Cl |
| 3-$CO_2CH_3$,2-thienyl | H | $CH_3$ | 7 | $OCH_3$ | Cl |
| 2-$CO_2CH_3$,3-thienyl | H | H | 7/9 | $CH_3$ | $CH_3$ |
| 2-$CO_2CH_3$,3-thienyl | H | $CH_3$ | 7 | $CH_3$ | $CH_3$ |
| 2-$CO_2CH_3$,3-thienyl | H | H | 7/9 | Cl | $CH_3$ |
| 2-$CO_2CH_3$,3-thienyl | H | $CH_3$ | 7 | Cl | $CH_3$ |
| 2-$CO_2CH_3$,3-thienyl | H | H | 7/9 | $CH_3$ | Cl |
| 2-$CO_2CH_3$,3-thienyl | H | $CH_3$ | 7 | $CH_3$ | Cl |
| 2-$CO_2CH_3$,3-thienyl | H | H | 7/9 | Cl | Cl |
| 2-$CO_2CH_3$,3-thienyl | H | $CH_3$ | 7 | Cl | Cl |
| 2-$CO_2CH_3$,3-thienyl | H | H | 7/9 | $OCH_3$ | $OCH_3$ |
| 2-$CO_2CH_3$,3-thienyl | H | $CH_3$ | 7 | $OCH_3$ | $OCH_3$ |
| 2-$CO_2CH_3$,3-thienyl | H | H | 7/9 | $CH_3$ | $OCH_3$ |
| 2-$CO_2CH_3$,3-thienyl | H | $CH_3$ | 7 | $CH_3$ | $OCH_3$ |
| 2-$CO_2CH_3$,3-thienyl | H | H | 7/9 | $OCH_3$ | $CH_3$ |
| 2-$CO_2CH_3$,3-thienyl | H | $CH_3$ | 7 | $OCH_3$ | $CH_3$ |
| 2-$CO_2CH_3$,3-thienyl | H | H | 7/9 | Cl | $OCH_3$ |
| 2-$CO_2CH_3$,3-thienyl | H | $CH_3$ | 7 | Cl | $OCH_3$ |
| 2-$CO_2CH_3$,3-thienyl | H | H | 7/9 | $OCH_3$ | Cl |
| 2-$CO_2CH_3$,3-thienyl | H | $CH_3$ | 7 | $OCH_3$ | Cl |
| 2-$CO_2CH_3$,3-thienyl | $CH_3$ | $CH_3$ | 7 | $CH_3$ | $CH_3$ |
| 2-$CO_2CH_3$,3-thienyl | $CH_3$ | H | 7/9 | Cl | $CH_3$ |
| 2-$CO_2CH_3$,3-thienyl | $CH_3$ | $CH_3$ | 7 | Cl | $CH_3$ |
| 2-$CO_2CH_3$,3-thienyl | $CH_3$ | H | 7/9 | $CH_3$ | Cl |
| 2-$CO_2CH_3$,3-thienyl | $CH_3$ | $CH_3$ | 7 | $CH_3$ | Cl |
| 2-$CO_2CH_3$,3-thienyl | $CH_3$ | H | 7/9 | Cl | Cl |
| 2-$CO_2CH_3$,3-thienyl | $CH_3$ | $CH_3$ | 7 | Cl | Cl |
| 2-$CO_2CH_3$,3-thienyl | $CH_3$ | H | 7/9 | $OCH_3$ | $OCH_3$ |
| 2-$CO_2CH_3$,3-thienyl | $CH_3$ | $CH_3$ | 7 | $OCH_3$ | $OCH_3$ |
| 2-$CO_2CH_3$,3-thienyl | $CH_3$ | H | 7/9 | $CH_3$ | $OCH_3$ |
| 2-$CO_2CH_3$,3-thienyl | $CH_3$ | $CH_3$ | 7 | $CH_3$ | $OCH_3$ |
| 2-$CO_2CH_3$,3-thienyl | $CH_3$ | H | 7/9 | $OCH_3$ | $CH_3$ |
| 2-$CO_2CH_3$,3-thienyl | $CH_3$ | $CH_3$ | 7 | $OCH_3$ | $CH_3$ |
| 2-$CO_2CH_3$,3-thienyl | $CH_3$ | H | 7/9 | Cl | $OCH_3$ |
| 2-$CO_2CH_3$,3-thienyl | $CH_3$ | $CH_3$ | 7 | Cl | $OCH_3$ |
| 2-$CO_2CH_3$,3-thienyl | $CH_3$ | H | 7/9 | $OCH_3$ | Cl |
| 2-$CO_2CH_3$,3-thienyl | $CH_3$ | $CH_3$ | 7 | $OCH_3$ | Cl |
| 2-$CO_2CH_3$,3-thienyl | H | H | 7/9 | $CF_3$ | $CF_3$ |
| 2-$CO_2CH_3$,3-thienyl | H | $CH_3$ | 7 | $CF_3$ | $CF_3$ |
| 2-$CO_2CH_3$,3-thienyl | H | H | 7/9 | Cl | $CF_3$ |
| 2-$CO_2CH_3$,3-thienyl | H | $CH_3$ | 7 | Cl | $CF_3$ |
| 2-$CO_2CH_3$,3-thienyl | H | H | 7/9 | $CF_3$ | Cl |
| 2-$CO_2CH_3$,3-thienyl | H | $CH_3$ | 7 | $CF_3$ | Cl |
| 2-$CO_2CH_3$,3-thienyl | H | H | 7/9 | F | $CF_3$ |
| 2-$CO_2CH_3$,3-thienyl | H | $CH_3$ | 7 | F | $CF_3$ |
| 2-$CO_2CH_3$,3-thienyl | H | H | 7/9 | $CF_3$ | F |
| 2-$CO_2CH_3$,3-thienyl | H | $CH_3$ | 7 | $CF_3$ | F |
| 2-$CO_2CH_3$,3-thienyl | H | H | 7/9 | $CH_3$ | $CF_3$ |
| 2-$CO_2CH_3$,3-thienyl | H | $CH_3$ | 7 | $CH_3$ | $CF_3$ |
| 2-$CO_2CH_3$,3-thienyl | H | H | 7/9 | $CF_3$ | $CH_3$ |

TABLE I-continued

Ia $$A-SO_2-NR^1 \text{—[pyrrolo-pyrimidine with } R^2, R^3, R^4\text{]}$$

| A | R¹ | R² | Pos. | R³ | R⁴ |
|---|---|---|---|---|---|
| 2-CO₂CH₃,3-thienyl | H | CH₃ | 7 | CF₃ | CH₃ |
| 2-CO₂CH₃,3-thienyl | H | H | 7/9 | OCH₃ | CF₃ |
| 2-CO₂CH₃,3-thienyl | H | CH₃ | 7 | OCH₃ | CF₃ |
| 2-CO₂CH₃,3-thienyl | H | H | 7/9 | CF₃ | OCH₃ |
| 2-CO₂CH₃,3-thienyl | H | CH₃ | 7 | CF₃ | OCH₃ |
| 2-CO₂CH₃,3-thienyl | H | H | 7/9 | F | F |
| 2-CO₂CH₃,3-thienyl | H | CH₃ | 7 | F | F |
| 2-CO₂CH₃,3-thienyl | H | H | 7/9 | F | Cl |
| 2-CO₂CH₃,3-thienyl | H | CH₃ | 7 | F | Cl |
| 2-CO₂CH₃,3-thienyl | H | H | 7/9 | Cl | F |
| 2-CO₂CH₃,3-thienyl | H | CH₃ | 7 | Cl | F |
| 2-CO₂CH₃,3-thienyl | H | H | 7/9 | F | CH₃ |
| 2-CO₂CH₃,3-thienyl | H | CH₃ | 7 | F | CH₃ |
| 2-CO₂CH₃,3-thienyl | H | H | 7/9 | CH₃ | F |
| 2-CO₂CH₃,3-thienyl | H | CH₃ | 7 | CH₃ | F |
| 2-CO₂CH₃,3-thienyl | H | H | 7/9 | F | OCH₃ |
| 2-CO₂CH₃,3-thienyl | H | CH₃ | 7 | F | OCH₃ |
| 2-CO₂CH₃,3-thienyl | H | H | 7/9 | OCH₃ | F |
| 2-CO₂CH₃,3-thienyl | H | CH₃ | 7 | OCH₃ | F |
| 2-CO₂CH₃,3-thienyl | H | H | 7/9 | N(CH₃)₂ | Cl |
| 2-CO₂CH₃,3-thienyl | H | CH₃ | 7 | N(CH₃)₂ | Cl |
| 2-CO₂CH₃,3-thienyl | H | H | 7/9 | SCH₃ | Cl |
| 2-CO₂CH₃,3-thienyl | H | CH₃ | 7 | SCH₃ | Cl |
| 2-Cl,5-CH₃,3-thienyl | H | H | 7/9 | CH₃ | CH₃ |
| 2-Cl,5-CH₃,3-thienyl | H | CH₃ | 7 | CH₃ | CH₃ |
| 2-Cl,5-CH₃,3-thienyl | H | H | 7/9 | Cl | CH₃ |
| 2-Cl,5-CH₃,3-thienyl | H | CH₃ | 7 | Cl | CH₃ |
| 2-Cl,5-CH₃,3-thienyl | H | H | 7/9 | CH₃ | Cl |
| 2-Cl,5-CH₃,3-thienyl | H | CH₃ | 7 | CH₃ | Cl |
| 2-Cl,5-CH₃,3-thienyl | H | H | 7/9 | Cl | Cl |
| 2-Cl,5-CH₃,3-thienyl | H | CH₃ | 7 | Cl | Cl |
| 2-Cl,5-CH₃,3-thienyl | H | H | 7/9 | OCH₃ | OCH₃ |
| 2-Cl,5-CH₃,3-thienyl | H | CH₃ | 7 | OCH₃ | OCH₃ |
| 2-Cl,5-CH₃,3-thienyl | H | H | 7/9 | CH₃ | OCH₃ |
| 2-Cl,5-CH₃,3-thienyl | H | CH₃ | 7 | CH₃ | OCH₃ |
| 2-Cl,5-CH₃,3-thienyl | H | H | 7/9 | OCH₃ | CH₃ |
| 2-Cl,5-CH₃,3-thienyl | H | CH₃ | 7 | OCH₃ | CH₃ |
| 2-Cl,5-CH₃,3-thienyl | H | H | 7/9 | Cl | OCH₃ |
| 2-Cl,5-CH₃,3-thienyl | H | CH₃ | 7 | Cl | OCH₃ |
| 2-Cl,5-CH₃,3-thienyl | H | H | 7/9 | OCH₃ | Cl |
| 2-Cl,5-CH₃,3-thienyl | H | CH₃ | 7 | OCH₃ | Cl |
| 4-CO₂CH₃,3-thienyl | H | H | 7/9 | CH₃ | CH₃ |
| 4-CO₂CH₃,3-thienyl | H | CH₃ | 7 | CH₃ | CH₃ |
| 4-CO₂CH₃,3-thienyl | H | H | 7/9 | Cl | CH₃ |
| 4-CO₂CH₃,3-thienyl | H | CH₃ | 7 | Cl | CH₃ |
| 4-CO₂CH₃,3-thienyl | H | H | 7/9 | CH₃ | Cl |
| 4-CO₂CH₃,3-thienyl | H | CH₃ | 7 | CH₃ | Cl |
| 4-CO₂CH₃,3-thienyl | H | H | 7/9 | Cl | Cl |
| 4-CO₂CH₃,3-thienyl | H | CH₃ | 7 | Cl | Cl |
| 4-CO₂CH₃,3-thienyl | H | H | 7/9 | OCH₃ | OCH₃ |
| 4-CO₂CH₃,3-thienyl | H | CH₃ | 7 | OCH₃ | OCH₃ |
| 4-CO₂CH₃,3-thienyl | H | H | 7/9 | CH₃ | OCH₃ |
| 4-CO₂CH₃,3-thienyl | H | CH₃ | 7 | CH₃ | OCH₃ |
| 4-CO₂CH₃,3-thienyl | H | H | 7/9 | OCH₃ | CH₃ |
| 4-CO₂CH₃,3-thienyl | H | CH₃ | 7 | OCH₃ | CH₃ |
| 4-CO₂CH₃,3-thienyl | H | H | 7/9 | Cl | OCH₃ |
| 4-CO₂CH₃,3-thienyl | H | CH₃ | 7 | Cl | OCH₃ |
| 4-CO₂CH₃,3-thienyl | H | H | 7/9 | OCH₃ | Cl |
| 4-CO₂CH₃,3-thienyl | H | CH₃ | 7 | OCH₃ | Cl |
| 1-CH₃,4-CO₂CH₃,5-pyrazolyl | H | H | 7/9 | CH₃ | CH₃ |
| 1-CH₃,4-CO₂CH₃,5-pyrazolyl | H | CH₃ | 7 | CH₃ | CH₃ |
| 1-CH₃,4-CO₂CH₃,5-pyrazolyl | H | H | 7/9 | Cl | CH₃ |
| 1-CH₃,4-CO₂CH₃,5-pyrazolyl | H | CH₃ | 7 | Cl | CH₃ |
| 1-CH₃,4-CO₂CH₃,5-pyrazolyl | H | H | 7/9 | CH₃ | Cl |
| 1-CH₃,4-CO₂CH₃,5-pyrazolyl | H | CH₃ | 7 | CH₃ | Cl |
| 1-CH₃,4-CO₂CH₃,5-pyrazolyl | H | H | 7/9 | Cl | Cl |
| 1-CH₃,4-CO₂CH₃,5-pyrazolyl | H | CH₃ | 7 | Cl | Cl |
| 1-CH₃,4-CO₂CH₃,5-pyrazolyl | H | H | 7/9 | OCH₃ | OCH₃ |
| 1-CH₃,4-CO₂CH₃,5-pyrazolyl | H | CH₃ | 7 | OCH₃ | OCH₃ |
| 1-CH₃,4-CO₂CH₃,5-pyrazolyl | H | H | 7/9 | CH₃ | OCH₃ |
| 1-CH₃,4-CO₂CH₃,5-pyrazolyl | H | CH₃ | 7 | CH₃ | OCH₃ |
| 1-CH₃,4-CO₂CH₃,5-pyrazolyl | H | H | 7/9 | OCH₃ | CH₃ |
| 1-CH₃,4-CO₂CH₃,5-pyrazolyl | H | CH₃ | 7 | OCH₃ | CH₃ |

TABLE I-continued

| A | R¹ | R² | Pos. | R³ | R⁴ |
|---|---|---|---|---|---|
| 1-CH₃,4-CO₂CH₃,5-pyrazolyl | H | H | 7/9 | Cl | OCH₃ |
| 1-CH₃,4-CO₂CH₃,5-pyrazolyl | H | CH₃ | 7 | Cl | OCH₃ |
| 1-CH₃,4-CO₂CH₃,5-pyrazolyl | H | H | 7/9 | OCH₃ | Cl |
| 1-CH₃,4-CO₂CH₃,5-pyrazolyl | H | CH₃ | 7 | OCH₃ | Cl |
| 1-CH₃,4-CO₂CH₃,5-pyrazolyl | CH₃ | H | 7/9 | CH₃ | CH₃ |
| 1-CH₃,4-CO₂CH₃,5-pyrazolyl | CH₃ | CH₃ | 7 | CH₃ | CH₃ |
| 1-CH₃,4-CO₂CH₃,5-pyrazolyl | CH₃ | H | 7/9 | Cl | CH₃ |
| 1-CH₃,4-CO₂CH₃,5-pyrazolyl | CH₃ | CH₃ | 7 | Cl | CH₃ |
| 1-CH₃,4-CO₂CH₃,5-pyrazolyl | CH₃ | H | 7/9 | CH₃ | Cl |
| 1-CH₃,4-CO₂CH₃,5-pyrazolyl | CH₃ | CH₃ | 7 | CH₃ | Cl |
| 1-CH₃,4-CO₂CH₃,5-pyrazolyl | CH₃ | H | 7/9 | Cl | Cl |
| 1-CH₃,4-CO₂CH₃,5-pyrazolyl | CH₃ | CH₃ | 7 | Cl | Cl |
| 1-CH₃,4-CO₂CH₃,5-pyrazolyl | CH₃ | H | 7/9 | OCH₃ | OCH₃ |
| 1-CH₃,4-CO₂CH₃,5-pyrazolyl | CH₃ | CH₃ | 7 | OCH₃ | OCH₃ |
| 1-CH₃,4-CO₂CH₃,5-pyrazolyl | CH₃ | H | 7/9 | CH₃ | OCH₃ |
| 1-CH₃,4-CO₂CH₃,5-pyrazolyl | CH₃ | CH₃ | 7 | CH₃ | OCH₃ |
| 1-CH₃,4-CO₂CH₃,5-pyrazolyl | CH₃ | H | 7/9 | OCH₃ | CH₃ |
| 1-CH₃,4-CO₂CH₃,5-pyrazolyl | CH₃ | CH₃ | 7 | OCH₃ | CH₃ |
| 1-CH₃,4-CO₂CH₃,5-pyrazolyl | CH₃ | H | 7/9 | Cl | OCH₃ |
| 1-CH₃,4-CO₂CH₃,5-pyrazolyl | CH₃ | CH₃ | 7 | Cl | OCH₃ |
| 1-CH₃,4-CO₂CH₃,5-pyrazolyl | CH₃ | H | 7/9 | OCH₃ | Cl |
| 1-CH₃,4-CO₂CH₃,5-pyrazolyl | CH₃ | CH₃ | 7 | OCH₃ | Cl |
| 1-CH₃,4-CO₂CH₃,5-pyrazolyl | H | H | 7/9 | CF₃ | CF₃ |
| 1-CH₃,4-CO₂CH₃,5-pyrazolyl | H | CH₃ | 7 | CF₃ | CF₃ |
| 1-CH₃,4-CO₂CH₃,5-pyrazolyl | H | H | 7/9 | Cl | CF₃ |
| 1-CH₃,4-CO₂CH₃,5-pyrazolyl | H | CH₃ | 7 | Cl | CF₃ |
| 1-CH₃,4-CO₂CH₃,5-pyrazolyl | H | H | 7/9 | CF₃ | Cl |
| 1-CH₃,4-CO₂CH₃,5-pyrazolyl | H | CH₃ | 7 | CF₃ | Cl |
| 1-CH₃,4-CO₂CH₃,5-pyrazolyl | H | H | 7/9 | F | CF₃ |
| 1-CH₃,4-CO₂CH₃,5-pyrazolyl | H | CH₃ | 7 | F | CF₃ |
| 1-CH₃,4-CO₂CH₃,5-pyrazolyl | H | H | 7/9 | CF₃ | F |
| 1-CH₃,4-CO₂CH₃,5-pyrazolyl | H | CH₃ | 7 | CF₃ | F |
| 1-CH₃,4-CO₂CH₃,5-pyrazolyl | H | H | 7/9 | CH₃ | CF₃ |
| 1-CH₃,4-CO₂CH₃,5-pyrazolyl | H | CH₃ | 7 | CH₃ | CF₃ |
| 1-CH₃,4-CO₂CH₃,5-pyrazolyl | H | H | 7/9 | CF₃ | CH₃ |
| 1-CH₃,4-CO₂CH₃,5-pyrazolyl | H | CH₃ | 7 | CF₃ | CH₃ |
| 1-CH₃,4-CO₂CH₃,5-pyrazolyl | H | H | 7/9 | OCH₃ | CF₃ |
| 1-CH₃,4-CO₂CH₃,5-pyrazolyl | H | CH₃ | 7 | OCH₃ | CF₃ |
| 1-CH₃,4-CO₂CH₃,5-pyrazolyl | H | H | 7/9 | CF₃ | OCH₃ |
| 1-CH₃,4-CO₂CH₃,5-pyrazolyl | H | CH₃ | 7 | CF₃ | OCH₃ |
| 1-CH₃,4-CO₂CH₃,5-pyrazolyl | H | H | 7/9 | F | F |
| 1-CH₃,4-CO₂CH₃,5-pyrazolyl | H | CH₃ | 7 | F | F |
| 1-CH₃,4-CO₂CH₃,5-pyrazolyl | H | H | 7/9 | F | Cl |
| 1-CH₃,4-CO₂CH₃,5-pyrazolyl | H | CH₃ | 7 | F | Cl |
| 1-CH₃,4-CO₂CH₃,5-pyrazolyl | H | H | 7/9 | Cl | F |
| 1-CH₃,4-CO₂CH₃,5-pyrazolyl | H | CH₃ | 7 | Cl | F |
| 1-CH₃,4-CO₂CH₃,5-pyrazolyl | H | H | 7/9 | F | CH₃ |
| 1-CH₃,4-CO₂CH₃,5-pyrazolyl | H | CH₃ | 7 | F | CH₃ |
| 1-CH₃,4-CO₂CH₃,5-pyrazolyl | H | H | 7/9 | CH₃ | F |
| 1-CH₃,4-CO₂CH₃,5-pyrazolyl | H | CH₃ | 7 | CH₃ | F |
| 1-CH₃,4-CO₂CH₃,5-pyrazolyl | H | H | 7/9 | F | OCH₃ |
| 1-CH₃,4-CO₂CH₃,5-pyrazolyl | H | CH₃ | 7 | F | OCH₃ |
| 1-CH₃,4-CO₂CH₃,5-pyrazolyl | H | H | 7/9 | OCH₃ | F |
| 1-CH₃,4-CO₂CH₃,5-pyrazolyl | H | CH₃ | 7 | OCH₃ | F |
| 1-CH₃,4-CO₂CH₃,5-pyrazolyl | H | H | 7/9 | N(CH₃)₂ | Cl |
| 1-CH₃,4-CO₂CH₃,5-pyrazolyl | H | CH₃ | 7 | N(CH₃)₂ | Cl |
| 1-CH₃,4-CO₂CH₃,5-pyrazolyl | H | H | 7/9 | SCH₃ | Cl |
| 1-CH₃,4-CO₂CH₃,5-pyrazolyl | H | CH₃ | 7 | SCH₃ | Cl |
| 2-pyridyl | H | H | 7/9 | CH₃ | CH₃ |
| 2-pyridyl | H | CH₃ | 7 | CH₃ | CH₃ |
| 2-pyridyl | H | H | 7/9 | Cl | CH₃ |
| 2-pyridyl | H | CH₃ | 7 | Cl | CH₃ |
| 2-pyridyl | H | H | 7/9 | CH₃ | Cl |
| 2-pyridyl | H | CH₃ | 7 | CH₃ | Cl |
| 2-pyridyl | H | H | 7/9 | Cl | Cl |
| 2-pyridyl | H | CH₃ | 7 | Cl | Cl |
| 2-pyridyl | H | H | 7/9 | OCH₃ | OCH₃ |
| 2-pyridyl | H | CH₃ | 7 | OCH₃ | OCH₃ |
| 2-pyridyl | H | H | 7/9 | CH₃ | OCH₃ |
| 2-pyridyl | H | CH₃ | 7 | CH₃ | OCH₃ |
| 2-pyridyl | H | H | 7/9 | OCH₃ | CH₃ |
| 2-pyridyl | H | CH₃ | 7 | OCH₃ | CH₃ |
| 2-pyridyl | H | H | 7/9 | Cl | OCH₃ |

TABLE I-continued

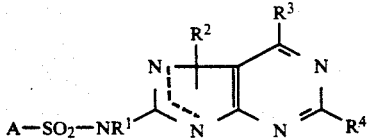

Ia

| A | $R^1$ | $R^2$ | Pos. | $R^3$ | $R^4$ |
|---|---|---|---|---|---|
| 2-pyridyl | H | CH$_3$ | 7 | Cl | OCH$_3$ |
| 2-pyridyl | H | H | 7/9 | OCH$_3$ | Cl |
| 2-pyridyl | H | CH$_3$ | 7 | OCH$_3$ | Cl |
| 3-Cl,2-pyridyl | H | H | 7/9 | CH$_3$ | CH$_3$ |
| 3-Cl,2-pyridyl | H | CH$_3$ | 7 | CH$_3$ | CH$_3$ |
| 3-Cl,2-pyridyl | H | H | 7/9 | Cl | CH$_3$ |
| 3-Cl,2-pyridyl | H | CH$_3$ | 7 | Cl | CH$_3$ |
| 3-Cl,2-pyridyl | H | H | 7/9 | CH$_3$ | Cl |
| 3-Cl,2-pyridyl | H | CH$_3$ | 7 | CH$_3$ | Cl |
| 3-Cl,2-pyridyl | H | H | 7/9 | Cl | Cl |
| 3-Cl,2-pyridyl | H | CH$_3$ | 7 | Cl | Cl |
| 3-Cl,2-pyridyl | H | H | 7/9 | OCH$_3$ | OCH$_3$ |
| 3-Cl,2-pyridyl | H | CH$_3$ | 7 | OCH$_3$ | OCH$_3$ |
| 3-Cl,2-pyridyl | H | H | 7/9 | CH$_3$ | OCH$_3$ |
| 3-Cl,2-pyridyl | H | CH$_3$ | 7 | CH$_3$ | OCH$_3$ |
| 3-Cl,2-pyridyl | H | H | 7/9 | OCH$_3$ | CH$_3$ |
| 3-Cl,2-pyridyl | H | CH$_3$ | 7 | OCH$_3$ | CH$_3$ |
| 3-Cl,2-pyridyl | H | H | 7/9 | Cl | OCH$_3$ |
| 3-Cl,2-pyridyl | H | CH$_3$ | 7 | Cl | OCH$_3$ |
| 3-Cl,2-pyridyl | H | H | 7/9 | OCH$_3$ | Cl |
| 3-Cl,2-pyridyl | H | CH$_3$ | 7 | OCH$_3$ | Cl |
| 3-CO$_2$CH$_3$,2-pyridyl | H | H | 7/9 | CH$_3$ | CH$_3$ |
| 3-CO$_2$CH$_3$,2-pyridyl | H | CH$_3$ | 7 | CH$_3$ | CH$_3$ |
| 3-CO$_2$CH$_3$,2-pyridyl | H | H | 7/9 | Cl | CH$_3$ |
| 3-CO$_2$CH$_3$,2-pyridyl | H | CH$_3$ | 7 | Cl | CH$_3$ |
| 3-CO$_2$CH$_3$,2-pyridyl | H | H | 7/9 | CH$_3$ | Cl |
| 3-CO$_2$CH$_3$,2-pyridyl | H | CH$_3$ | 7 | CH$_3$ | Cl |
| 3-CO$_2$CH$_3$,2-pyridyl | H | H | 7/9 | Cl | Cl |
| 3-CO$_2$CH$_3$,2-pyridyl | H | CH$_3$ | 7 | Cl | Cl |
| 3-CO$_2$CH$_3$,2-pyridyl | H | H | 7/9 | OCH$_3$ | OCH$_3$ |
| 3-CO$_2$CH$_3$,2-pyridyl | H | CH$_3$ | 7 | OCH$_3$ | OCH$_3$ |
| 3-CO$_2$CH$_3$,2-pyridyl | H | H | 7/9 | CH$_3$ | OCH$_3$ |
| 3-CO$_2$CH$_3$,2-pyridyl | H | CH$_3$ | 7 | CH$_3$ | OCH$_3$ |
| 3-CO$_2$CH$_3$,2-pyridyl | H | H | 7/9 | OCH$_3$ | CH$_3$ |
| 3-CO$_2$CH$_3$,2-pyridyl | H | CH$_3$ | 7 | OCH$_3$ | CH$_3$ |
| 3-CO$_2$CH$_3$,2-pyridyl | H | H | 7/9 | Cl | OCH$_3$ |
| 3-CO$_2$CH$_3$,2-pyridyl | H | CH$_3$ | 7 | Cl | OCH$_3$ |
| 3-CO$_2$CH$_3$,2-pyridyl | H | H | 7/9 | OCH$_3$ | Cl |
| 3-CO$_2$CH$_3$,2-pyridyl | H | CH$_3$ | 7 | OCH$_3$ | Cl |
| 3-CON(CH$_3$)$_2$,2-pyridyl | H | H | 7/9 | CH$_3$ | CH$_3$ |
| 3-CON(CH$_3$)$_2$,2-pyridyl | H | CH$_3$ | 7 | CH$_3$ | CH$_3$ |
| 3-CON(CH$_3$)$_2$,2-pyridyl | H | H | 7/9 | Cl | CH$_3$ |
| 3-CON(CH$_3$)$_2$,2-pyridyl | H | CH$_3$ | 7 | Cl | CH$_3$ |
| 3-CON(CH$_3$)$_2$,2-pyridyl | H | H | 7/9 | CH$_3$ | Cl |
| 3-CON(CH$_3$)$_2$,2-pyridyl | H | CH$_3$ | 7 | CH$_3$ | Cl |
| 3-CON(CH$_3$)$_2$,2-pyridyl | H | H | 7/9 | Cl | Cl |
| 3-CON(CH$_3$)$_2$,2-pyridyl | H | CH$_3$ | 7 | Cl | Cl |
| 3-CON(CH$_3$)$_2$,2-pyridyl | H | H | 7/9 | OCH$_3$ | OCH$_3$ |
| 3-CON(CH$_3$)$_2$,2-pyridyl | H | CH$_3$ | 7 | OCH$_3$ | OCH$_3$ |
| 3-CON(CH$_3$)$_2$,2-pyridyl | H | H | 7/9 | CH$_3$ | OCH$_3$ |
| 3-CON(CH$_3$)$_2$,2-pyridyl | H | CH$_3$ | 7 | CH$_3$ | OCH$_3$ |
| 3-CON(CH$_3$)$_2$,2-pyridyl | H | H | 7/9 | OCH$_3$ | CH$_3$ |
| 3-CON(CH$_3$)$_2$,2-pyridyl | H | CH$_3$ | 7 | OCH$_3$ | CH$_3$ |
| 3-CON(CH$_3$)$_2$,2-pyridyl | H | H | 7/9 | Cl | OCH$_3$ |
| 3-CON(CH$_3$)$_2$,2-pyridyl | H | CH$_3$ | 7 | Cl | OCH$_3$ |
| 3-CON(CH$_3$)$_2$,2-pyridyl | H | H | 7/9 | OCH$_3$ | Cl |
| 3-CON(CH$_3$)$_2$,2-pyridyl | H | CH$_3$ | 7 | OCH$_3$ | Cl |
| 3-CON(CH$_3$)$_2$,2-pyridyl | CH$_3$ | H | 7/9 | CH$_3$ | CH$_3$ |
| 3-CON(CH$_3$)$_2$,2-pyridyl | CH$_3$ | CH$_3$ | 7 | CH$_3$ | CH$_3$ |
| 3-CON(CH$_3$)$_2$,2-pyridyl | CH$_3$ | H | 7/9 | Cl | CH$_3$ |
| 3-CON(CH$_3$)$_2$,2-pyridyl | CH$_3$ | CH$_3$ | 7 | Cl | CH$_3$ |
| 3-CON(CH$_3$)$_2$,2-pyridyl | CH$_3$ | H | 7/9 | CH$_3$ | Cl |
| 3-CON(CH$_3$)$_2$,2-pyridyl | CH$_3$ | CH$_3$ | 7 | CH$_3$ | Cl |
| 3-CON(CH$_3$)$_2$,2-pyridyl | CH$_3$ | H | 7/9 | Cl | Cl |
| 3-CON(CH$_3$)$_2$,2-pyridyl | CH$_3$ | CH$_3$ | 7 | Cl | Cl |
| 3-CON(CH$_3$)$_2$,2-pyridyl | CH$_3$ | H | 7/9 | OCH$_3$ | OCH$_3$ |
| 3-CON(CH$_3$)$_2$,2-pyridyl | CH$_3$ | CH$_3$ | 7 | OCH$_3$ | OCH$_3$ |
| 3-CON(CH$_3$)$_2$,2-pyridyl | CH$_3$ | H | 7/9 | CH$_3$ | OCH$_3$ |
| 3-CON(CH$_3$)$_2$,2-pyridyl | CH$_3$ | CH$_3$ | 7 | CH$_3$ | OCH$_3$ |
| 3-CON(CH$_3$)$_2$,2-pyridyl | CH$_3$ | H | 7/9 | OCH$_3$ | CH$_3$ |
| 3-CON(CH$_3$)$_2$,2-pyridyl | CH$_3$ | CH$_3$ | 7 | OCH$_3$ | CH$_3$ |
| 3-CON(CH$_3$)$_2$,2-pyridyl | CH$_3$ | H | 7/9 | Cl | OCH$_3$ |
| 3-CON(CH$_3$)$_2$,2-pyridyl | CH$_3$ | CH$_3$ | 7 | Cl | OCH$_3$ |

TABLE I-continued

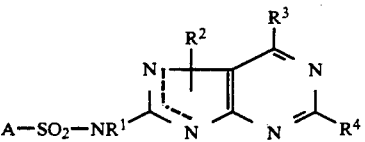

Ia

| A | R¹ | R² | Pos. | R³ | R⁴ |
|---|---|---|---|---|---|
| 3-CON(CH₃)₂,2-pyridyl | CH₃ | H | 7/9 | OCH₃ | Cl |
| 3-CON(CH₃)₂,2-pyridyl | CH₃ | CH₃ | 7 | OCH₃ | Cl |
| 3-CON(CH₃)₂,2-pyridyl | H | H | 7/9 | CF₃ | CF₃ |
| 3-CON(CH₃)₂,2-pyridyl | H | CH₃ | 7 | CF₃ | CF₃ |
| 3-CON(CH₃)₂,2-pyridyl | H | H | 7/9 | Cl | CF₃ |
| 3-CON(CH₃)₂,2-pyridyl | H | CH₃ | 7 | Cl | CF₃ |
| 3-CON(CH₃)₂,2-pyridyl | H | H | 7/9 | CF₃ | Cl |
| 3-CON(CH₃)₂,2-pyridyl | H | CH₃ | 7 | CF₃ | Cl |
| 3-CON(CH₃)₂,2-pyridyl | H | H | 7/9 | F | CF₃ |
| 3-CON(CH₃)₂,2-pyridyl | H | CH₃ | 7 | F | CF₃ |
| 3-CON(CH₃)₂,2-pyridyl | H | H | 7/9 | CF₃ | F |
| 3-CON(CH₃)₂,2-pyridyl | H | CH₃ | 7 | CF₃ | F |
| 3-CON(CH₃)₂,2-pyridyl | H | H | 7/9 | CH₃ | CF₃ |
| 3-CON(CH₃)₂,2-pyridyl | H | CH₃ | 7 | CH₃ | CF₃ |
| 3-CON(CH₃)₂,2-pyridyl | H | H | 7/9 | CF₃ | CH₃ |
| 3-CON(CH₃)₂,2-pyridyl | H | CH₃ | 7 | CF₃ | CH₃ |
| 3-CON(CH₃)₂,2-pyridyl | H | H | 7/9 | OCH₃ | CF₃ |
| 3-CON(CH₃)₂,2-pyridyl | H | CH₃ | 7 | OCH₃ | CF₃ |
| 3-CON(CH₃)₂,2-pyridyl | H | H | 7/9 | CF₃ | OCH₃ |
| 3-CON(CH₃)₂,2-pyridyl | H | CH₃ | 7 | CF₃ | OCH₃ |
| 3-CON(CH₃)₂,2-pyridyl | H | H | 7/9 | F | F |
| 3-CON(CH₃)₂,2-pyridyl | H | CH₃ | 7 | F | F |
| 3-CON(CH₃)₂,2-pyridyl | H | H | 7/9 | F | Cl |
| 3-CON(CH₃)₂,2-pyridyl | H | CH₃ | 7 | F | Cl |
| 3-CON(CH₃)₂,2-pyridyl | H | H | 7/9 | Cl | F |
| 3-CON(CH₃)₂,2-pyridyl | H | CH₃ | 7 | Cl | F |
| 3-CON(CH₃)₂,2-pyridyl | H | H | 7/9 | F | CH₃ |
| 3-CON(CH₃)₂,2-pyridyl | H | CH₃ | 7 | F | CH₃ |
| 3-CON(CH₃)₂,2-pyridyl | H | H | 7/9 | CH₃ | F |
| 3-CON(CH₃)₂,2-pyridyl | H | CH₃ | 7 | CH₃ | F |
| 3-CON(CH₃)₂,2-pyridyl | H | H | 7/9 | F | OCH₃ |
| 3-CON(CH₃)₂,2-pyridyl | H | CH₃ | 7 | F | OCH₃ |
| 3-CON(CH₃)₂,2-pyridyl | H | H | 7/9 | OCH₃ | F |
| 3-CON(CH₃)₂,2-pyridyl | H | CH₃ | 7 | OCH₃ | F |
| 3-CON(CH₃)₂,2-pyridyl | H | H | 7/9 | N(CH₃)₂ | Cl |
| 3-CON(CH₃)₂,2-pyridyl | H | CH₃ | 7 | N(CH₃)₂ | Cl |
| 3-CON(CH₃)₂,2-pyridyl | H | H | 7/9 | SCH₃ | Cl |
| 3-CON(CH₃)₂,2-pyridyl | H | CH₃ | 7 | SCH₃ | Cl |
| 3-pyridyl | H | H | 7/9 | CH₃ | CH₃ |
| 3-pyridyl | H | CH₃ | 7 | CH₃ | CH₃ |
| 3-pyridyl | H | H | 7/9 | Cl | CH₃ |
| 3-pyridyl | H | CH₃ | 7 | Cl | CH₃ |
| 3-pyridyl | H | H | 7/9 | CH₃ | Cl |
| 3-pyridyl | H | CH₃ | 7 | CH₃ | Cl |
| 3-pyridyl | H | H | 7/9 | Cl | Cl |
| 3-pyridyl | H | CH₃ | 7 | Cl | Cl |
| 3-pyridyl | H | H | 7/9 | OCH₃ | OCH₃ |
| 3-pyridyl | H | CH₃ | 7 | OCH₃ | OCH₃ |
| 3-pyridyl | H | H | 7/9 | CH₃ | OCH₃ |
| 3-pyridyl | H | CH₃ | 7 | CH₃ | OCH₃ |
| 3-pyridyl | H | H | 7/9 | OCH₃ | CH₃ |
| 3-pyridyl | H | CH₃ | 7 | OCH₃ | CH₃ |
| 3-pyridyl | H | H | 7/9 | Cl | OCH₃ |
| 3-pyridyl | H | CH₃ | 7 | Cl | OCH₃ |
| 3-pyridyl | H | H | 7/9 | OCH₃ | Cl |
| 3-pyridyl | H | CH₃ | 7 | OCH₃ | Cl |
| 8-quinolyl | H | H | 7/9 | CH₃ | CH₃ |
| 8-quinolyl | H | CH₃ | 7 | CH₃ | CH₃ |
| 8-quinolyl | H | H | 7/9 | Cl | CH₃ |
| 8-quinolyl | H | CH₃ | 7 | Cl | CH₃ |
| 8-quinolyl | H | H | 7/9 | CH₃ | Cl |
| 8-quinolyl | H | CH₃ | 7 | CH₃ | Cl |
| 8-quinolyl | H | H | 7/9 | Cl | Cl |
| 8-quinolyl | H | CH₃ | 7 | Cl | Cl |
| 8-quinolyl | H | H | 7/9 | OCH₃ | OCH₃ |
| 8-quinolyl | H | CH₃ | 7 | OCH₃ | OCH₃ |
| 8-quinolyl | H | H | 7/9 | CH₃ | OCH₃ |
| 8-quinolyl | H | CH₃ | 7 | CH₃ | OCH₃ |
| 8-quinolyl | H | H | 7/9 | OCH₃ | CH₃ |
| 8-quinolyl | H | CH₃ | 7 | OCH₃ | CH₃ |
| 8-quinolyl | H | H | 7/9 | Cl | OCH₃ |
| 8-quinolyl | H | CH₃ | 7 | Cl | OCH₃ |
| 8-quinolyl | H | H | 7/9 | OCH₃ | Cl |

TABLE I-continued

Formula Ia:
$A-SO_2-NR^1$ connected to a fused bicyclic system with $R^2$, $R^3$, $R^4$ substituents and ring nitrogens.

| A | $R^1$ | $R^2$ | Pos. | $R^3$ | $R^4$ |
|---|---|---|---|---|---|
| 8-quinolyl | H | CH₃ | 7 | OCH₃ | Cl |
| 7-CO₂CH₃,8-quinolyl | H | H | 7/9 | CH₃ | CH₃ |
| 7-CO₂CH₃,8-quinolyl | H | CH₃ | 7 | CH₃ | CH₃ |
| 7-CO₂CH₃,8-quinolyl | H | H | 7/9 | Cl | CH₃ |
| 7-CO₂CH₃,8-quinolyl | H | CH₃ | 7 | Cl | CH₃ |
| 7-CO₂CH₃,8-quinolyl | H | H | 7/9 | CH₃ | Cl |
| 7-CO₂CH₃,8-quinolyl | H | CH₃ | 7 | CH₃ | Cl |
| 7-CO₂CH₃,8-quinolyl | H | H | 7/9 | Cl | Cl |
| 7-CO₂CH₃,8-quinolyl | H | CH₃ | 7 | Cl | Cl |
| 7-CO₂CH₃,8-quinolyl | H | H | 7/9 | OCH₃ | OCH₃ |
| 7-CO₂CH₃,8-quinolyl | H | CH₃ | 7 | OCH₃ | OCH₃ |
| 7-CO₂CH₃,8-quinolyl | H | H | 7/9 | CH₃ | OCH₃ |
| 7-CO₂CH₃,8-quinolyl | H | CH₃ | 7 | CH₃ | OCH₃ |
| 7-CO₂CH₃,8-quinolyl | H | H | 7/9 | OCH₃ | CH₃ |
| 7-CO₂CH₃,8-quinolyl | H | CH₃ | 7 | OCH₃ | CH₃ |
| 7-CO₂CH₃,8-quinolyl | H | H | 7/9 | Cl | OCH₃ |
| 7-CO₂CH₃,8-quinolyl | H | CH₃ | 7 | Cl | OCH₃ |
| 7-CO₂CH₃,8-quinolyl | H | H | 7/9 | OCH₃ | Cl |
| 7-CO₂CH₃,8-quinolyl | H | CH₃ | 7 | OCH₃ | Cl |
| 7-Cl,8-quinolyl | H | H | 7/9 | CH₃ | CH₃ |
| 7-Cl,8-quinolyl | H | CH₃ | 7 | CH₃ | CH₃ |
| 7-Cl,8-quinolyl | H | H | 7/9 | Cl | CH₃ |
| 7-Cl,8-quinolyl | H | CH₃ | 7 | Cl | CH₃ |
| 7-Cl,8-quinolyl | H | H | 7/9 | CH₃ | Cl |
| 7-Cl,8-quinolyl | H | CH₃ | 7 | CH₃ | Cl |
| 7-Cl,8-quinolyl | H | H | 7/9 | Cl | Cl |
| 7-Cl,8-quinolyl | H | CH₃ | 7 | Cl | Cl |
| 7-Cl,8-quinolyl | H | H | 7/9 | OCH₃ | OCH₃ |
| 7-Cl,8-quinolyl | H | CH₃ | 7 | OCH₃ | OCH₃ |
| 7-Cl,8-quinolyl | H | H | 7/9 | CH₃ | OCH₃ |
| 7-Cl,8-quinolyl | H | CH₃ | 7 | CH₃ | OCH₃ |
| 7-Cl,8-quinolyl | H | H | 7/9 | OCH₃ | CH₃ |
| 7-Cl,8-quinolyl | H | CH₃ | 7 | OCH₃ | CH₃ |
| 7-Cl,8-quinolyl | H | H | 7/9 | Cl | OCH₃ |
| 7-Cl,8-quinolyl | H | CH₃ | 7 | Cl | OCH₃ |
| 7-Cl,8-quinolyl | H | H | 7/9 | OCH₃ | Cl |
| 7-Cl,8-quinolyl | H | CH₃ | 7 | OCH₃ | Cl |
| 7-Cl,8-quinolyl | H | H | 7/9 | CH₃ | CH₃ |
| 7-Cl,8-quinolyl | H | CH₃ | 7 | CH₃ | CH₃ |
| 7-Cl,8-quinolyl | H | H | 7/9 | Cl | CH₃ |
| 7-Cl,8-quinolyl | H | CH₃ | 7 | Cl | CH₃ |
| 7-Cl,8-quinolyl | H | H | 7/9 | CH₃ | Cl |
| 7-Cl,8-quinolyl | H | CH₃ | 7 | CH₃ | Cl |
| 7-Cl,8-quinolyl | H | H | 7/9 | Cl | Cl |
| 7-Cl,8-quinolyl | H | CH₃ | 7 | Cl | Cl |
| 7-Cl,8-quinolyl | H | H | 7/9 | OCH₃ | OCH₃ |
| 7-Cl,8-quinolyl | H | CH₃ | 7 | OCH₃ | OCH₃ |
| 7-Cl,8-quinolyl | H | H | 7/9 | CH₃ | OCH₃ |
| 7-Cl,8-quinolyl | H | CH₃ | 7 | CH₃ | OCH₃ |
| 7-Cl,8-quinolyl | H | H | 7/9 | OCH₃ | CH₃ |
| 7-Cl,8-quinolyl | H | CH₃ | 7 | OCH₃ | CH₃ |
| 7-Cl,8-quinolyl | H | H | 7/9 | Cl | OCH₃ |
| 7-Cl,8-quinolyl | H | CH₃ | 7 | Cl | OCH₃ |
| 7-Cl,8-quinolyl | H | H | 7/9 | OCH₃ | Cl |
| 7-Cl,8-quinolyl | H | CH₃ | 7 | OCH₃ | Cl |

TABLE II

Formula Ib: $A-CH_2-SO_2-NR^1$ attached to bicyclic heterocycle with $R^2$, $R^3$, $R^4$.

| A | $R^1$ | $R^2$ | Pos. | $R^3$ | $R^4$ |
|---|---|---|---|---|---|
| phenyl | H | H | 7/9 | CH₃ | CH₃ |
| phenyl | H | CH₃ | 7 | CH₃ | CH₃ |
| phenyl | H | H | 7/9 | Cl | CH₃ |
| phenyl | H | CH₃ | 7 | Cl | CH₃ |
| phenyl | H | H | 7/9 | CH₃ | Cl |
| phenyl | H | CH₃ | 7 | CH₃ | Cl |

TABLE II-continued

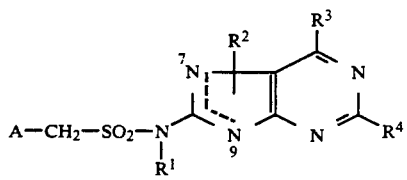
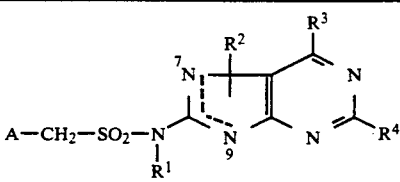

| A | R¹ | R² | Pos. | R³ | R⁴ |
|---|----|----|------|----|----|
| phenyl | H | H | 7/9 | Cl | Cl |
| phenyl | H | CH₃ | 7 | Cl | Cl |
| phenyl | H | H | 7/9 | OCH₃ | OCH₃ |
| phenyl | H | CH₃ | 7 | OCH₃ | OCH₃ |
| phenyl | H | H | 7/9 | CH₃ | OCH₃ |
| phenyl | H | CH₃ | 7 | CH₃ | OCH₃ |
| phenyl | H | H | 7/9 | OCH₃ | CH₃ |
| phenyl | H | CH₃ | 7 | OCH₃ | CH₃ |
| phenyl | H | H | 7/9 | Cl | OCH₃ |
| phenyl | H | CH₃ | 7 | Cl | OCH₃ |
| phenyl | H | H | 7/9 | OCH₃ | Cl |
| phenyl | H | CH₃ | 7 | OCH₃ | Cl |
| 2-Cl-phenyl | H | H | 7/9 | CH₃ | CH₃ |
| 2-Cl-phenyl | H | CH₃ | 7 | CH₃ | CH₃ |
| 2-Cl-phenyl | H | H | 7/9 | Cl | CH₃ |
| 2-Cl-phenyl | H | CH₃ | 7 | Cl | CH₃ |
| 2-Cl-phenyl | H | H | 7/9 | CH₃ | Cl |
| 2-Cl-phenyl | H | CH₃ | 7 | CH₃ | Cl |
| 2-Cl-phenyl | H | H | 7/9 | Cl | Cl |
| 2-Cl-phenyl | H | CH₃ | 7 | Cl | Cl |
| 2-Cl-phenyl | H | H | 7/9 | OCH₃ | OCH₃ |
| 2-Cl-phenyl | H | CH₃ | 7 | OCH₃ | OCH₃ |
| 2-Cl-phenyl | H | H | 7/9 | CH₃ | OCH₃ |
| 2-Cl-phenyl | H | CH₃ | 7 | CH₃ | OCH₃ |
| 2-Cl-phenyl | H | H | 7/9 | OCH₃ | CH₃ |
| 2-Cl-phenyl | H | CH₃ | 7 | OCH₃ | CH₃ |
| 2-Cl-phenyl | H | H | 7/9 | Cl | OCH₃ |
| 2-Cl-phenyl | H | CH₃ | 7 | Cl | OCH₃ |
| 2-Cl-phenyl | H | H | 7/9 | OCH₃ | Cl |
| 2-Cl-phenyl | H | CH₃ | 7 | OCH₃ | Cl |
| 2-F-phenyl | H | H | 7/9 | CH₃ | CH₃ |
| 2-F-phenyl | H | CH₃ | 7 | CH₃ | CH₃ |
| 2-F-phenyl | H | H | 7/9 | Cl | CH₃ |
| 2-F-phenyl | H | CH₃ | 7 | Cl | CH₃ |
| 2-F-phenyl | H | H | 7/9 | CH₃ | Cl |
| 2-F-phenyl | H | CH₃ | 7 | CH₃ | Cl |
| 2-F-phenyl | H | H | 7/9 | Cl | Cl |
| 2-F-phenyl | H | CH₃ | 7 | Cl | Cl |
| 2-F-phenyl | H | H | 7/9 | OCH₃ | OCH₃ |
| 2-F-phenyl | H | CH₃ | 7 | OCH₃ | OCH₃ |
| 2-F-phenyl | H | H | 7/9 | CH₃ | OCH₃ |
| 2-F-phenyl | H | CH₃ | 7 | CH₃ | OCH₃ |
| 2-F-phenyl | H | H | 7/9 | OCH₃ | CH₃ |
| 2-F-phenyl | H | CH₃ | 7 | OCH₃ | CH₃ |
| 2-F-phenyl | H | H | 7/9 | Cl | OCH₃ |
| 2-F-phenyl | H | CH₃ | 7 | Cl | OCH₃ |
| 2-F-phenyl | H | H | 7/9 | OCH₃ | Cl |
| 2-F-phenyl | H | CH₃ | 7 | OCH₃ | Cl |
| 2-CH₃-phenyl | H | H | 7/9 | CH₃ | CH₃ |
| 2-CH₃-phenyl | H | CH₃ | 7 | CH₃ | CH₃ |
| 2-CH₃-phenyl | H | H | 7/9 | Cl | CH₃ |
| 2-CH₃-phenyl | H | CH₃ | 7 | Cl | CH₃ |
| 2-CH₃-phenyl | H | H | 7/9 | CH₃ | Cl |
| 2-CH₃-phenyl | H | CH₃ | 7 | CH₃ | Cl |
| 2-CH₃-phenyl | H | H | 7/9 | Cl | Cl |
| 2-CH₃-phenyl | H | CH₃ | 7 | Cl | Cl |
| 2-CH₃-phenyl | H | H | 7/9 | OCH₃ | OCH₃ |
| 2-CH₃-phenyl | H | CH₃ | 7 | OCH₃ | OCH₃ |
| 2-CH₃-phenyl | H | H | 7/9 | CH₃ | OCH₃ |
| 2-CH₃-phenyl | H | CH₃ | 7 | CH₃ | OCH₃ |
| 2-CH₃-phenyl | H | H | 7/9 | OCH₃ | CH₃ |
| 2-CH₃-phenyl | H | CH₃ | 7 | OCH₃ | CH₃ |
| 2-CH₃-phenyl | H | H | 7/9 | Cl | OCH₃ |
| 2-CH₃-phenyl | H | CH₃ | 7 | Cl | OCH₃ |
| 2-CH₃-phenyl | H | H | 7/9 | OCH₃ | Cl |
| 2-CH₃-phenyl | H | CH₃ | 7 | OCH₃ | Cl |
| 2-CO₂CH₃-phenyl | H | H | 7/9 | CH₃ | CH₃ |
| 2-CO₂CH₃-phenyl | H | CH₃ | 7 | CH₃ | CH₃ |
| 2-CO₂CH₃-phenyl | H | H | 7/9 | Cl | CH₃ |
| 2-CO₂CH₃-phenyl | H | CH₃ | 7 | Cl | CH₃ |
| 2-CO₂CH₃-phenyl | H | H | 7/9 | CH₃ | Cl |
| 2-CO₂CH₃-phenyl | H | CH₃ | 7 | CH₃ | Cl |
| 2-CO₂CH₃-phenyl | H | H | 7/9 | Cl | Cl |
| 2-CO₂CH₃-phenyl | H | CH₃ | 7 | Cl | Cl |
| 2-CO₂CH₃-phenyl | H | H | 7/9 | OCH₃ | OCH₃ |
| 2-CO₂CH₃-phenyl | H | CH₃ | 7 | OCH₃ | OCH₃ |
| 2-CO₂CH₃-phenyl | H | H | 7/9 | CH₃ | OCH₃ |
| 2-CO₂CH₃-phenyl | H | CH₃ | 7 | CH₃ | OCH₃ |
| 2-CO₂CH₃-phenyl | H | H | 7/9 | OCH₃ | CH₃ |
| 2-CO₂CH₃-phenyl | H | CH₃ | 7 | OCH₃ | CH₃ |
| 2-CO₂CH₃-phenyl | H | H | 7/9 | Cl | OCH₃ |
| 2-CO₂CH₃-phenyl | H | CH₃ | 7 | Cl | OCH₃ |
| 2-CO₂CH₃-phenyl | H | H | 7/9 | OCH₃ | Cl |
| 2-CO₂CH₃-phenyl | H | CH₃ | 7 | OCH₃ | Cl |
| 2-CO₂C₂H₅-phenyl | H | H | 7/9 | CH₃ | CH₃ |
| 2-CO₂C₂H₅-phenyl | H | CH₃ | 7 | CH₃ | CH₃ |
| 2-CO₂C₂H₅-phenyl | H | H | 7/9 | Cl | CH₃ |
| 2-CO₂C₂H₅-phenyl | H | CH₃ | 7 | Cl | CH₃ |
| 2-CO₂C₂H₅-phenyl | H | H | 7/9 | CH₃ | Cl |
| 2-CO₂C₂H₅-phenyl | H | CH₃ | 7 | CH₃ | Cl |
| 2-CO₂C₂H₅-phenyl | H | H | 7/9 | Cl | Cl |
| 2-CO₂C₂H₅-phenyl | H | CH₃ | 7 | Cl | Cl |
| 2-CO₂C₂H₅-phenyl | H | H | 7/9 | OCH₃ | OCH₃ |
| 2-CO₂C₂H₅-phenyl | H | CH₃ | 7 | OCH₃ | OCH₃ |
| 2-CO₂C₂H₅-phenyl | H | H | 7/9 | CH₃ | OCH₃ |
| 2-CO₂C₂H₅-phenyl | H | CH₃ | 7 | CH₃ | OCH₃ |
| 2-CO₂C₂H₅-phenyl | H | H | 7/9 | OCH₃ | CH₃ |
| 2-CO₂C₂H₅-phenyl | H | CH₃ | 7 | OCH₃ | CH₃ |
| 2-CO₂C₂H₅-phenyl | H | H | 7/9 | Cl | OCH₃ |
| 2-CO₂C₂H₅-phenyl | H | CH₃ | 7 | Cl | OCH₃ |
| 2-CO₂C₂H₅-phenyl | H | H | 7/9 | OCH₃ | Cl |
| 2-CO₂C₂H₅-phenyl | H | CH₃ | 7 | OCH₃ | Cl |
| 2-OCH₃-phenyl | H | H | 7/9 | CH₃ | CH₃ |
| 2-OCH₃-phenyl | H | CH₃ | 7 | CH₃ | CH₃ |
| 2-OCH₃-phenyl | H | H | 7/9 | Cl | CH₃ |
| 2-OCH₃-phenyl | H | CH₃ | 7 | Cl | CH₃ |
| 2-OCH₃-phenyl | H | H | 7/9 | CH₃ | Cl |
| 2-OCH₃-phenyl | H | CH₃ | 7 | CH₃ | Cl |
| 2-OCH₃-phenyl | H | H | 7/9 | Cl | Cl |
| 2-OCH₃-phenyl | H | CH₃ | 7 | Cl | Cl |
| 2-OCH₃-phenyl | H | H | 7/9 | OCH₃ | OCH₃ |
| 2-OCH₃-phenyl | H | CH₃ | 7 | OCH₃ | OCH₃ |
| 2-OCH₃-phenyl | H | H | 7/9 | CH₃ | OCH₃ |
| 2-OCH₃-phenyl | H | CH₃ | 7 | CH₃ | OCH₃ |
| 2-OCH₃-phenyl | H | H | 7/9 | OCH₃ | CH₃ |
| 2-OCH₃-phenyl | H | CH₃ | 7 | OCH₃ | CH₃ |
| 2-OCH₃-phenyl | H | H | 7/9 | Cl | OCH₃ |
| 2-OCH₃-phenyl | H | CH₃ | 7 | Cl | OCH₃ |
| 2-OCH₃-phenyl | H | H | 7/9 | OCH₃ | Cl |
| 2-OCH₃-phenyl | H | CH₃ | 7 | OCH₃ | Cl |
| 2-OCH₂CH₂OCH₃-phenyl | H | H | 7/9 | CH₃ | CH₃ |
| 2-OCH₂CH₂OCH₃-phenyl | H | CH₃ | 7 | CH₃ | CH₃ |
| 2-OCH₂CH₂OCH₃-phenyl | H | H | 7/9 | Cl | CH₃ |
| 2-OCH₂CH₂OCH₃-phenyl | H | CH₃ | 7 | Cl | CH₃ |
| 2-OCH₂CH₂OCH₃-phenyl | H | H | 7/9 | CH₃ | Cl |
| 2-OCH₂CH₂OCH₃-phenyl | H | CH₃ | 7 | CH₃ | Cl |
| 2-OCH₂CH₂OCH₃-phenyl | H | H | 7/9 | Cl | Cl |
| 2-OCH₂CH₂OCH₃-phenyl | H | CH₃ | 7 | Cl | Cl |
| 2-OCH₂CH₂OCH₃-phenyl | H | H | 7/9 | OCH₃ | OCH₃ |
| 2-OCH₂CH₂OCH₃-phenyl | H | CH₃ | 7 | OCH₃ | OCH₃ |
| 2-OCH₂CH₂OCH₃-phenyl | H | H | 7/9 | CH₃ | OCH₃ |
| 2-OCH₂CH₂OCH₃-phenyl | H | CH₃ | 7 | CH₃ | OCH₃ |
| 2-OCH₂CH₂OCH₃-phenyl | H | H | 7/9 | OCH₃ | CH₃ |
| 2-OCH₂CH₂OCH₃-phenyl | H | CH₃ | 7 | OCH₃ | CH₃ |
| 2-OCH₂CH₂OCH₃-phenyl | H | H | 7/9 | Cl | OCH₃ |
| 2-OCH₂CH₂OCH₃-phenyl | H | CH₃ | 7 | Cl | OCH₃ |
| 2-OCH₂CH₂OCH₃-phenyl | H | H | 7/9 | OCH₃ | Cl |
| 2-OCH₂CH₂OCH₃-phenyl | H | CH₃ | 7 | OCH₃ | Cl |
| 2-OCH₂CH₂Cl-phenyl | H | H | 7/9 | CH₃ | CH₃ |
| 2-OCH₂CH₂Cl-phenyl | H | CH₃ | 7 | CH₃ | CH₃ |
| 2-OCH₂CH₂Cl-phenyl | H | H | 7/9 | Cl | CH₃ |
| 2-OCH₂CH₂Cl-phenyl | H | CH₃ | 7 | Cl | CH₃ |

TABLE II-continued

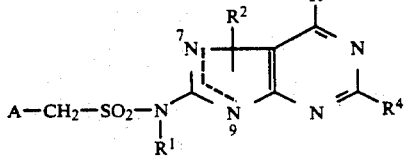

Ib

| A | R¹ | R² | Pos. | R³ | R⁴ |
|---|---|---|---|---|---|
| 2-OCH₂CH₂Cl-phenyl | H | H | 7/9 | CH₃ | Cl |
| 2-OCH₂CH₂Cl-phenyl | H | CH₃ | 7 | CH₃ | Cl |
| 2-OCH₂CH₂Cl-phenyl | H | H | 7/9 | Cl | Cl |
| 2-OCH₂CH₂Cl-phenyl | H | CH₃ | 7 | Cl | Cl |
| 2-OCH₂CH₂Cl-phenyl | H | H | 7/9 | OCH₃ | OCH₃ |
| 2-OCH₂CH₂Cl-phenyl | H | CH₃ | 7 | OCH₃ | OCH₃ |
| 2-OCH₂CH₂Cl-phenyl | H | H | 7/9 | CH₃ | OCH₃ |
| 2-OCH₂CH₂Cl-phenyl | H | CH₃ | 7 | CH₃ | OCH₃ |
| 2-OCH₂CH₂Cl-phenyl | H | H | 7/9 | OCH₃ | CH₃ |
| 2-OCH₂CH₂Cl-phenyl | H | CH₃ | 7 | OCH₃ | CH₃ |
| 2-OCH₂CH₂Cl-phenyl | H | H | 7/9 | Cl | OCH₃ |
| 2-OCH₂CH₂Cl-phenyl | H | CH₃ | 7 | Cl | OCH₃ |
| 2-OCH₂CH₂Cl-phenyl | H | H | 7/9 | OCH₃ | Cl |
| 2-OCH₂CH₂Cl-phenyl | H | CH₃ | 7 | OCH₃ | Cl |
| 2-OCH₂SO₂CH₃-phenyl | H | H | 7/9 | CH₃ | CH₃ |
| 2-OCH₂SO₂CH₃-phenyl | H | CH₃ | 7 | CH₃ | CH₃ |
| 2-OCH₂SO₂CH₃-phenyl | H | H | 7/9 | Cl | CH₃ |
| 2-OCH₂SO₂CH₃-phenyl | H | CH₃ | 7 | Cl | CH₃ |
| 2-OCH₂SO₂CH₃-phenyl | H | H | 7/9 | CH₃ | Cl |
| 2-OCH₂SO₂CH₃-phenyl | H | CH₃ | 7 | CH₃ | Cl |
| 2-OCH₂SO₂CH₃-phenyl | H | H | 7/9 | Cl | Cl |
| 2-OCH₂SO₂CH₃-phenyl | H | CH₃ | 7 | Cl | Cl |
| 2-OCH₂SO₂CH₃-phenyl | H | H | 7/9 | OCH₃ | OCH₃ |
| 2-OCH₂SO₂CH₃-phenyl | H | CH₃ | 7 | OCH₃ | OCH₃ |
| 2-OCH₂SO₂CH₃-phenyl | H | H | 7/9 | CH₃ | OCH₃ |
| 2-OCH₂SO₂CH₃-phenyl | H | CH₃ | 7 | CH₃ | OCH₃ |
| 2-OCH₂SO₂CH₃-phenyl | H | H | 7/9 | OCH₃ | CH₃ |
| 2-OCH₂SO₂CH₃-phenyl | H | CH₃ | 7 | OCH₃ | CH₃ |
| 2-OCH₂SO₂CH₃-phenyl | H | H | 7/9 | Cl | OCH₃ |
| 2-OCH₂SO₂CH₃-phenyl | H | CH₃ | 7 | Cl | OCH₃ |
| 2-OCH₂SO₂CH₃-phenyl | H | H | 7/9 | OCH₃ | Cl |
| 2-OCH₂SO₂CH₃-phenyl | H | CH₃ | 7 | OCH₃ | Cl |
| 2,6-Cl,Cl-phenyl | H | H | 7/9 | CH₃ | CH₃ |
| 2,6-Cl,Cl-phenyl | H | CH₃ | 7 | CH₃ | CH₃ |
| 2,6-Cl,Cl-phenyl | H | H | 7/9 | Cl | CH₃ |
| 2,6-Cl,Cl-phenyl | H | CH₃ | 7 | Cl | CH₃ |
| 2,6-Cl,Cl-phenyl | H | H | 7/9 | CH₃ | Cl |
| 2,6-Cl,Cl-phenyl | H | CH₃ | 7 | CH₃ | Cl |
| 2,6-Cl,Cl-phenyl | H | H | 7/9 | Cl | Cl |
| 2,6-Cl,Cl-phenyl | H | CH₃ | 7 | Cl | Cl |
| 2,6-Cl,Cl-phenyl | H | H | 7/9 | OCH₃ | OCH₃ |
| 2,6-Cl,Cl-phenyl | H | CH₃ | 7 | OCH₃ | OCH₃ |
| 2,6-Cl,Cl-phenyl | H | H | 7/9 | CH₃ | OCH₃ |
| 2,6-Cl,Cl-phenyl | H | CH₃ | 7 | CH₃ | OCH₃ |
| 2,6-Cl,Cl-phenyl | H | H | 7/9 | OCH₃ | CH₃ |
| 2,6-Cl,Cl-phenyl | H | CH₃ | 7 | OCH₃ | CH₃ |
| 2,6-Cl,Cl-phenyl | H | H | 7/9 | Cl | OCH₃ |
| 2,6-Cl,Cl-phenyl | H | CH₃ | 7 | Cl | OCH₃ |
| 2,6-Cl,Cl-phenyl | H | H | 7/9 | OCH₃ | Cl |
| 2,6-Cl,Cl-phenyl | H | CH₃ | 7 | OCH₃ | Cl |
| 2-Cl,6-CH₃-phenyl | H | H | 7/9 | CH₃ | CH₃ |
| 2-Cl,6-CH₃-phenyl | H | CH₃ | 7 | CH₃ | CH₃ |
| 2-Cl,6-CH₃-phenyl | H | H | 7/9 | Cl | CH₃ |
| 2-Cl,6-CH₃-phenyl | H | CH₃ | 7 | Cl | CH₃ |
| 2-Cl,6-CH₃-phenyl | H | H | 7/9 | CH₃ | Cl |
| 2-Cl,6-CH₃-phenyl | H | CH₃ | 7 | CH₃ | Cl |
| 2-Cl,6-CH₃-phenyl | H | H | 7/9 | Cl | Cl |
| 2-Cl,6-CH₃-phenyl | H | CH₃ | 7 | Cl | Cl |
| 2-Cl,6-CH₃-phenyl | H | H | 7/9 | OCH₃ | OCH₃ |
| 2-Cl,6-CH₃-phenyl | H | CH₃ | 7 | OCH₃ | OCH₃ |
| 2-Cl,6-CH₃-phenyl | H | H | 7/9 | CH₃ | OCH₃ |
| 2-Cl,6-CH₃-phenyl | H | CH₃ | 7 | CH₃ | OCH₃ |
| 2-Cl,6-CH₃-phenyl | H | H | 7/9 | OCH₃ | CH₃ |
| 2-Cl,6-CH₃-phenyl | H | CH₃ | 7 | OCH₃ | CH₃ |
| 2-Cl,6-CH₃-phenyl | H | H | 7/9 | Cl | OCH₃ |
| 2-Cl,6-CH₃-phenyl | H | CH₃ | 7 | Cl | OCH₃ |
| 2-Cl,6-CH₃-phenyl | H | H | 7/9 | OCH₃ | Cl |
| 2-Cl,6-CH₃-phenyl | H | CH₃ | 7 | OCH₃ | Cl |
| 2,5-Cl,Cl-phenyl | H | H | 7/9 | CH₃ | CH₃ |
| 2,5-Cl,Cl-phenyl | H | CH₃ | 7 | CH₃ | CH₃ |
| 2,5-Cl,Cl-phenyl | H | H | 7/9 | Cl | CH₃ |
| 2,5-Cl,Cl-phenyl | H | CH₃ | 7 | Cl | CH₃ |
| 2,5-Cl,Cl-phenyl | H | H | 7/9 | CH₃ | Cl |
| 2,5-Cl,Cl-phenyl | H | CH₃ | 7 | CH₃ | Cl |
| 2,5-Cl,Cl-phenyl | H | H | 7/9 | Cl | Cl |
| 2,5-Cl,Cl-phenyl | H | CH₃ | 7 | Cl | Cl |
| 2,5-Cl,Cl-phenyl | H | H | 7/9 | OCH₃ | OCH₃ |
| 2,5-Cl,Cl-phenyl | H | CH₃ | 7 | OCH₃ | OCH₃ |
| 2,5-Cl,Cl-phenyl | H | H | 7/9 | CH₃ | OCH₃ |
| 2,5-Cl,Cl-phenyl | H | CH₃ | 7 | CH₃ | OCH₃ |
| 2,5-Cl,Cl-phenyl | H | H | 7/9 | OCH₃ | CH₃ |
| 2,5-Cl,Cl-phenyl | H | CH₃ | 7 | OCH₃ | CH₃ |
| 2,5-Cl,Cl-phenyl | H | H | 7/9 | Cl | OCH₃ |
| 2,5-Cl,Cl-phenyl | H | CH₃ | 7 | Cl | OCH₃ |
| 2,5-Cl,Cl-phenyl | H | H | 7/9 | OCH₃ | Cl |
| 2,5-Cl,Cl-phenyl | H | CH₃ | 7 | OCH₃ | Cl |

TABLE III

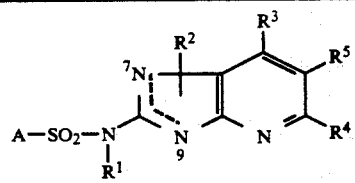

Ic

| A | R¹ | R² | Pos. | R³ | R⁴ | R⁵ |
|---|---|---|---|---|---|---|
| phenyl | H | H | 7/9 | CH₃ | CH₃ | H |
| phenyl | H | CH₃ | 7 | CH₃ | CH₃ | H |
| phenyl | H | H | 7/9 | Cl | CH₃ | H |
| phenyl | H | CH₃ | 7 | Cl | CH₃ | H |
| phenyl | H | H | 7/9 | CH₃ | Cl | H |
| phenyl | H | CH₃ | 7 | CH₃ | Cl | H |
| phenyl | H | H | 7/9 | Cl | Cl | H |
| phenyl | H | CH₃ | 7 | Cl | Cl | H |
| phenyl | H | H | 7/9 | OCH₃ | OCH₃ | H |
| phenyl | H | CH₃ | 7 | OCH₃ | OCH₃ | H |
| phenyl | H | H | 7/9 | CH₃ | OCH₃ | H |
| phenyl | H | CH₃ | 7 | CH₃ | OCH₃ | H |
| phenyl | H | H | 7/9 | OCH₃ | CH₃ | H |
| phenyl | H | CH₃ | 7 | OCH₃ | CH₃ | H |

TABLE III-continued

Ic structure: A—SO$_2$—N(R$^1$)—C(=N9)—N7(R$^2$)—[fused pyridine ring with R$^3$, R$^4$, R$^5$]

| A | R$^1$ | R$^2$ | Pos. | R$^3$ | R$^4$ | R$^5$ |
|---|---|---|---|---|---|---|
| phenyl | H | H | 7/9 | Cl | OCH$_3$ | H |
| phenyl | H | CH$_3$ | 7 | Cl | OCH$_3$ | H |
| phenyl | H | H | 7/9 | OCH$_3$ | Cl | H |
| phenyl | H | CH$_3$ | 7 | OCH$_3$ | Cl | H |
| 2-Cl-phenyl | H | H | 7/9 | CH$_3$ | CH$_3$ | H |
| 2-Cl-phenyl | H | CH$_3$ | 7 | CH$_3$ | CH$_3$ | H |
| 2-Cl-phenyl | H | H | 7/9 | Cl | CH$_3$ | H |
| 2-Cl-phenyl | H | CH$_3$ | 7 | Cl | CH$_3$ | H |
| 2-Cl-phenyl | H | H | 7/9 | CH$_3$ | Cl | H |
| 2-Cl-phenyl | H | CH$_3$ | 7 | CH$_3$ | Cl | H |
| 2-Cl-phenyl | H | H | 7/9 | Cl | Cl | H |
| 2-Cl-phenyl | H | CH$_3$ | 7 | Cl | Cl | H |
| 2-Cl-phenyl | H | H | 7/9 | OCH$_3$ | OCH$_3$ | H |
| 2-Cl-phenyl | H | CH$_3$ | 7 | OCH$_3$ | OCH$_3$ | H |
| 2-Cl-phenyl | H | H | 7/9 | CH$_3$ | OCH$_3$ | H |
| 2-Cl-phenyl | H | CH$_3$ | 7 | CH$_3$ | OCH$_3$ | H |
| 2-Cl-phenyl | H | H | 7/9 | OCH$_3$ | CH$_3$ | H |
| 2-Cl-phenyl | H | CH$_3$ | 7 | OCH$_3$ | CH$_3$ | H |
| 2-Cl-phenyl | H | H | 7/9 | Cl | OCH$_3$ | H |
| 2-Cl-phenyl | H | CH$_3$ | 7 | Cl | OCH$_3$ | H |
| 2-Cl-phenyl | H | H | 7/9 | OCH$_3$ | Cl | H |
| 2-Cl-phenyl | H | CH$_3$ | 7 | OCH$_3$ | Cl | H |
| 2-Cl-phenyl | H | CH$_3$ | 7 | OCH$_3$ | Cl | H |
| 2-Cl-phenyl | H | H | 7/9 | CF$_3$ | CF$_3$ | H |
| 2-Cl-phenyl | H | CH$_3$ | 7 | CF$_3$ | CF$_3$ | H |
| 2-Cl-phenyl | H | H | 7/9 | Cl | CF$_3$ | H |
| 2-Cl-phenyl | H | CH$_3$ | 7 | Cl | CF$_3$ | H |
| 2-Cl-phenyl | H | H | 7/9 | CF$_3$ | Cl | H |
| 2-Cl-phenyl | H | CH$_3$ | 7 | CF$_3$ | Cl | H |
| 2-Cl-phenyl | H | H | 7/9 | F | CF$_3$ | H |
| 2-Cl-phenyl | H | CH$_3$ | 7 | F | CF$_3$ | H |
| 2-Cl-phenyl | H | H | 7/9 | CF$_3$ | F | H |
| 2-Cl-phenyl | H | CH$_3$ | 7 | CF$_3$ | F | H |
| 2-Cl-phenyl | H | H | 7/9 | CH$_3$ | CF$_3$ | H |
| 2-Cl-phenyl | H | CH$_3$ | 7 | CH$_3$ | CF$_3$ | H |
| 2-Cl-phenyl | H | H | 7/9 | CF$_3$ | CH$_3$ | H |
| 2-Cl-phenyl | H | CH$_3$ | 7 | CF$_3$ | CH$_3$ | H |
| 2-Cl-phenyl | H | H | 7/9 | OCH$_3$ | CF$_3$ | H |
| 2-Cl-phenyl | H | CH$_3$ | 7 | OCH$_3$ | CF$_3$ | H |
| 2-Cl-phenyl | H | H | 7/9 | CF$_3$ | OCH$_3$ | H |
| 2-Cl-phenyl | H | CH$_3$ | 7 | CF$_3$ | OCH$_3$ | H |
| 2-Cl-phenyl | H | H | 7/9 | F | F | H |
| 2-Cl-phenyl | H | CH$_3$ | 7 | F | F | H |
| 2-Cl-phenyl | H | H | 7/9 | F | Cl | H |
| 2-Cl-phenyl | H | CH$_3$ | 7 | F | Cl | H |
| 2-Cl-phenyl | H | H | 7/9 | Cl | F | H |
| 2-Cl-phenyl | H | CH$_3$ | 7 | Cl | F | H |
| 2-Cl-phenyl | H | H | 7/9 | F | CH$_3$ | H |
| 2-Cl-phenyl | H | CH$_3$ | 7 | F | CH$_3$ | H |
| 2-Cl-phenyl | H | H | 7/9 | CH$_3$ | F | H |
| 2-Cl-phenyl | H | CH$_3$ | 7 | CH$_3$ | F | H |
| 2-Cl-phenyl | H | H | 7/9 | F | OCH$_3$ | H |
| 2-Cl-phenyl | H | CH$_3$ | 7 | F | OCH$_3$ | H |
| 2-Cl-phenyl | H | H | 7/9 | OCH$_3$ | F | H |
| 2-Cl-phenyl | H | CH$_3$ | 7 | OCH$_3$ | F | H |
| 2-Cl-phenyl | H | H | 7/9 | N(CH$_3$)$_2$ | Cl | H |
| 2-Cl-phenyl | H | CH$_3$ | 7 | N(CH$_3$)$_2$ | Cl | H |
| 2-Cl-phenyl | H | H | 7/9 | SCH$_3$ | Cl | H |
| 2-Cl-phenyl | H | CH$_3$ | 7 | SCH$_3$ | Cl | H |
| 2-F-phenyl | H | H | 7/9 | CH$_3$ | CH$_3$ | H |
| 2-F-phenyl | H | CH$_3$ | 7 | CH$_3$ | CH$_3$ | H |
| 2-F-phenyl | H | H | 7/9 | Cl | CH$_3$ | H |
| 2-F-phenyl | H | CH$_3$ | 7 | Cl | CH$_3$ | H |
| 2-F-phenyl | H | H | 7/9 | CH$_3$ | Cl | H |
| 2-F-phenyl | H | CH$_3$ | 7 | CH$_3$ | Cl | H |
| 2-F-phenyl | H | H | 7/9 | Cl | Cl | H |
| 2-F-phenyl | H | CH$_3$ | 7 | Cl | Cl | H |
| 2-F-phenyl | H | H | 7/9 | OCH$_3$ | OCH$_3$ | H |
| 2-F-phenyl | H | CH$_3$ | 7 | OCH$_3$ | OCH$_3$ | H |
| 2-F-phenyl | H | H | 7/9 | CH$_3$ | OCH$_3$ | H |
| 2-F-phenyl | H | CH$_3$ | 7 | CH$_3$ | OCH$_3$ | H |

TABLE III-continued

Ic

| A | $R^1$ | $R^2$ | Pos. | $R^3$ | $R^4$ | $R^5$ |
|---|---|---|---|---|---|---|
| 2-F-phenyl | H | H | 7/9 | $OCH_3$ | $CH_3$ | H |
| 2-F-phenyl | H | $CH_3$ | 7 | $OCH_3$ | $CH_3$ | H |
| 2-F-phenyl | H | H | 7/9 | Cl | $OCH_3$ | H |
| 2-F-phenyl | H | $CH_3$ | 7 | Cl | $OCH_3$ | H |
| 2-F-phenyl | H | H | 7/9 | $OCH_3$ | Cl | H |
| 2-F-phenyl | H | $CH_3$ | 7 | $OCH_3$ | Cl | H |
| 2-CN-phenyl | H | H | 7/9 | $CH_3$ | $CH_3$ | H |
| 2-CN-phenyl | H | $CH_3$ | 7 | $CH_3$ | $CH_3$ | H |
| 2-CN-phenyl | H | H | 7/9 | Cl | $CH_3$ | H |
| 2-CN-phenyl | H | $CH_3$ | 7 | Cl | $CH_3$ | H |
| 2-CN-phenyl | H | H | 7/9 | $CH_3$ | Cl | H |
| 2-CN-phenyl | H | $CH_3$ | 7 | $CH_3$ | Cl | H |
| 2-CN-phenyl | H | H | 7/9 | Cl | Cl | H |
| 2-CN-phenyl | H | $CH_3$ | 7 | Cl | Cl | H |
| 2-CN-phenyl | H | H | 7/9 | $OCH_3$ | $OCH_3$ | H |
| 2-CN-phenyl | H | $CH_3$ | 7 | $OCH_3$ | $OCH_3$ | H |
| 2-CN-phenyl | H | H | 7/9 | $CH_3$ | $OCH_3$ | H |
| 2-CN-phenyl | H | $CH_3$ | 7 | $CH_3$ | $OCH_3$ | H |
| 2-CN-phenyl | H | H | 7/9 | $OCH_3$ | $CH_3$ | H |
| 2-CN-phenyl | H | $CH_3$ | 7 | $OCH_3$ | $CH_3$ | H |
| 2-CN-phenyl | H | H | 7/9 | Cl | $OCH_3$ | H |
| 2-CN-phenyl | H | $CH_3$ | 7 | Cl | $OCH_3$ | H |
| 2-CN-phenyl | H | H | 7/9 | $OCH_3$ | Cl | H |
| 2-CN-phenyl | H | $CH_3$ | 7 | $OCH_3$ | Cl | H |
| 2-$CF_3$-phenyl | H | H | 7/9 | $CH_3$ | $CH_3$ | H |
| 2-$CF_3$-phenyl | H | $CH_3$ | 7 | $CH_3$ | $CH_3$ | H |
| 2-$CF_3$-phenyl | H | H | 7/9 | Cl | $CH_3$ | H |
| 2-$CF_3$-phenyl | H | $CH_3$ | 7 | Cl | $CH_3$ | H |
| 2-$CF_3$-phenyl | H | H | 7/9 | $CH_3$ | Cl | H |
| 2-$CF_3$-phenyl | H | $CH_3$ | 7 | $CH_3$ | Cl | H |
| 2-$CF_3$-phenyl | H | H | 7/9 | Cl | Cl | H |
| 2-$CF_3$-phenyl | H | $CH_3$ | 7 | Cl | Cl | H |
| 2-$CF_3$-phenyl | H | H | 7/9 | $OCH_3$ | $OCH_3$ | H |
| 2-$CF_3$-phenyl | H | $CH_3$ | 7 | $OCH_3$ | $OCH_3$ | H |
| 2-$CF_3$-phenyl | H | H | 7/9 | $CH_3$ | $OCH_3$ | H |
| 2-$CF_3$-phenyl | H | $CH_3$ | 7 | $CH_3$ | $OCH_3$ | H |
| 2-$CF_3$-phenyl | H | H | 7/9 | $OCH_3$ | $CH_3$ | H |
| 2-$CF_3$-phenyl | H | $CH_3$ | 7 | $OCH_3$ | $CH_3$ | H |
| 2-$CF_3$-phenyl | H | H | 7/9 | Cl | $OCH_3$ | H |
| 2-$CF_3$-phenyl | H | $CH_3$ | 7 | Cl | $OCH_3$ | H |
| 2-$CF_3$-phenyl | H | H | 7/9 | $OCH_3$ | Cl | H |
| 2-$CF_3$-phenyl | H | $CH_3$ | 7 | $OCH_3$ | Cl | H |
| 2-$NO_2$-phenyl | H | H | 7/9 | $CH_3$ | $CH_3$ | H |
| 2-$NO_2$-phenyl | H | $CH_3$ | 7 | $CH_3$ | $CH_3$ | H |
| 2-$NO_2$-phenyl | H | H | 7/9 | Cl | $CH_3$ | H |
| 2-$NO_2$-phenyl | H | $CH_3$ | 7 | Cl | $CH_3$ | H |
| 2-$NO_2$-phenyl | H | H | 7/9 | $CH_3$ | Cl | H |
| 2-$NO_2$-phenyl | H | $CH_3$ | 7 | $CH_3$ | Cl | H |
| 2-$NO_2$-phenyl | H | H | 7/9 | Cl | Cl | H |
| 2-$NO_2$-phenyl | H | $CH_3$ | 7 | Cl | Cl | H |
| 2-$NO_2$-phenyl | H | H | 7/9 | $OCH_3$ | $OCH_3$ | H |
| 2-$NO_2$-phenyl | H | $CH_3$ | 7 | $OCH_3$ | $OCH_3$ | H |
| 2-$NO_2$-phenyl | H | H | 7/9 | $CH_3$ | $OCH_3$ | H |
| 2-$NO_2$-phenyl | H | $CH_3$ | 7 | $CH_3$ | $OCH_3$ | H |
| 2-$NO_2$-phenyl | H | H | 7/9 | $OCH_3$ | $CH_3$ | H |
| 2-$NO_2$-phenyl | H | $CH_3$ | 7 | $OCH_3$ | $CH_3$ | H |
| 2-$NO_2$-phenyl | H | H | 7/9 | Cl | $OCH_3$ | H |
| 2-$NO_2$-phenyl | H | $CH_3$ | 7 | Cl | $OCH_3$ | H |
| 2-$NO_2$-phenyl | H | H | 7/9 | $OCH_3$ | Cl | H |
| 2-$NO_2$-phenyl | H | $CH_3$ | 7 | $OCH_3$ | Cl | H |
| 2-$CH_3$-phenyl | H | H | 7/9 | $CH_3$ | $CH_3$ | H |
| 2-$CH_3$-phenyl | H | $CH_3$ | 7 | $CH_3$ | $CH_3$ | H |
| 2-$CH_3$-phenyl | H | H | 7/9 | Cl | $CH_3$ | H |
| 2-$CH_3$-phenyl | H | $CH_3$ | 7 | Cl | $CH_3$ | H |
| 2-$CH_3$-phenyl | H | H | 7/9 | $CH_3$ | Cl | H |
| 2-$CH_3$-phenyl | H | $CH_3$ | 7 | $CH_3$ | Cl | H |
| 2-$CH_3$-phenyl | H | H | 7/9 | Cl | Cl | H |
| 2-$CH_3$-phenyl | H | $CH_3$ | 7 | Cl | Cl | H |
| 2-$CH_3$-phenyl | H | H | 7/9 | $OCH_3$ | $OCH_3$ | H |
| 2-$CH_3$-phenyl | H | $CH_3$ | 7 | $OCH_3$ | $OCH_3$ | H |
| 2-$CH_3$-phenyl | H | H | 7/9 | $CH_3$ | $OCH_3$ | H |

TABLE III-continued

Ic

| A | R¹ | R² | Pos. | R³ | R⁴ | R⁵ |
|---|---|---|---|---|---|---|
| 2-CH₃-phenyl | H | CH₃ | 7 | CH₃ | OCH₃ | H |
| 2-CH₃-phenyl | H | H | 7/9 | OCH₃ | CH₃ | H |
| 2-CH₃-phenyl | H | CH₃ | 7 | OCH₃ | CH₃ | H |
| 2-CH₃-phenyl | H | H | 7/9 | Cl | OCH₃ | H |
| 2-CH₃-phenyl | H | CH₃ | 7 | Cl | OCH₃ | H |
| 2-CH₃-phenyl | H | H | 7/9 | OCH₃ | Cl | H |
| 2-CH₃-phenyl | H | CH₃ | 7 | OCH₃ | Cl | H |
| 2-CO₂CH₃-phenyl | H | H | 7/9 | CH₃ | CH₃ | H |
| 2-CO₂CH₃-phenyl | H | CH₃ | 7 | CH₃ | CH₃ | H |
| 2-CO₂CH₃-phenyl | H | H | 7/9 | Cl | CH₃ | H |
| 2-CO₂CH₃-phenyl | H | CH₃ | 7 | Cl | CH₃ | H |
| 2-CO₂CH₃-phenyl | H | H | 7/9 | CH₃ | Cl | H |
| 2-CO₂CH₃-phenyl | H | CH₃ | 7 | CH₃ | Cl | H |
| 2-CO₂CH₃-phenyl | H | H | 7/9 | Cl | Cl | H |
| 2-CO₂CH₃-phenyl | H | CH₃ | 7 | Cl | Cl | H |
| 2-CO₂CH₃-phenyl | H | H | 7/9 | OCH₃ | OCH₃ | H |
| 2-CO₂CH₃-phenyl | H | CH₃ | 7 | OCH₃ | OCH₃ | H |
| 2-CO₂CH₃-phenyl | H | H | 7/9 | CH₃ | OCH₃ | H |
| 2-CO₂CH₃-phenyl | H | CH₃ | 7 | CH₃ | OCH₃ | H |
| 2-CO₂CH₃-phenyl | H | H | 7/9 | OCH₃ | CH₃ | H |
| 2-CO₂CH₃-phenyl | H | CH₃ | 7 | OCH₃ | CH₃ | H |
| 2-CO₂CH₃-phenyl | H | H | 7/9 | Cl | OCH₃ | H |
| 2-CO₂CH₃-phenyl | H | CH₃ | 7 | Cl | OCH₃ | H |
| 2-CO₂CH₃-phenyl | H | H | 7/9 | OCH₃ | Cl | H |
| 2-CO₂CH₃-phenyl | H | CH₃ | 7 | OCH₃ | Cl | H |
| 2-CO₂CH₃-phenyl | H | H | 7/9 | CF₃ | CF₃ | H |
| 2-CO₂CH₃-phenyl | H | CH₃ | 7 | CF₃ | CF₃ | H |
| 2-CO₂CH₃-phenyl | H | H | 7/9 | Cl | CF₃ | H |
| 2-CO₂CH₃-phenyl | H | CH₃ | 7 | Cl | CF₃ | H |
| 2-CO₂CH₃-phenyl | H | H | 7/9 | CF₃ | Cl | H |
| 2-CO₂CH₃-phenyl | H | CH₃ | 7 | CF₃ | Cl | H |
| 2-CO₂CH₃-phenyl | H | H | 7/9 | F | CF₃ | H |
| 2-CO₂CH₃-phenyl | H | CH₃ | 7 | F | CF₃ | H |
| 2-CO₂CH₃-phenyl | H | H | 7/9 | CF₃ | F | H |
| 2-CO₂CH₃-phenyl | H | CH₃ | 7 | CF₃ | F | H |
| 2-CO₂CH₃-phenyl | H | H | 7/9 | CH₃ | CF₃ | H |
| 2-CO₂CH₃-phenyl | H | CH₃ | 7 | CH₃ | CF₃ | H |
| 2-CO₂CH₃-phenyl | H | H | 7/9 | CF₃ | CH₃ | H |
| 2-CO₂CH₃-phenyl | H | CH₃ | 7 | CF₃ | CH₃ | H |
| 2-CO₂CH₃-phenyl | H | H | 7/9 | OCH₃ | CF₃ | H |
| 2-CO₂CH₃-phenyl | H | CH₃ | 7 | OCH₃ | CF₃ | H |
| 2-CO₂CH₃-phenyl | H | H | 7/9 | CF₃ | OCH₃ | H |
| 2-CO₂CH₃-phenyl | H | CH₃ | 7 | CF₃ | OCH₃ | H |
| 2-CO₂CH₃-phenyl | H | H | 7/9 | F | F | H |
| 2-CO₂CH₃-phenyl | H | CH₃ | 7 | F | F | H |
| 2-CO₂CH₃-phenyl | H | H | 7/9 | F | Cl | H |
| 2-CO₂CH₃-phenyl | H | CH₃ | 7 | F | Cl | H |
| 2-CO₂CH₃-phenyl | H | H | 7/9 | Cl | F | H |
| 2-CO₂CH₃-phenyl | H | CH₃ | 7 | Cl | F | H |
| 2-CO₂CH₃-phenyl | H | H | 7/9 | F | CH₃ | H |
| 2-CO₂CH₃-phenyl | H | CH₃ | 7 | F | CH₃ | H |
| 2-CO₂CH₃-phenyl | H | H | 7/9 | CH₃ | F | H |
| 2-CO₂CH₃-phenyl | H | CH₃ | 7 | CH₃ | F | H |
| 2-CO₂CH₃-phenyl | H | H | 7/9 | F | OCH₃ | H |
| 2-CO₂CH₃-phenyl | H | CH₃ | 7 | F | OCH₃ | H |
| 2-CO₂CH₃-phenyl | H | H | 7/9 | OCH₃ | F | H |
| 2-CO₂CH₃-phenyl | H | CH₃ | 7 | OCH₃ | F | H |
| 2-CO₂CH₃-phenyl | H | H | 7/9 | N(CH₃)₂ | Cl | H |
| 2-CO₂CH₃-phenyl | H | CH₃ | 7 | N(CH₃)₂ | Cl | H |
| 2-CO₂CH₃-phenyl | H | H | 7/9 | SCH₃ | Cl | H |
| 2-CO₂CH₃-phenyl | H | CH₃ | 7 | SCH₃ | Cl | H |
| 2-CO₂C₂H₅-phenyl | H | H | 7/9 | CH₃ | CH₃ | H |
| 2-CO₂C₂H₅-phenyl | H | CH₃ | 7 | CH₃ | CH₃ | H |
| 2-CO₂C₂H₅-phenyl | H | H | 7/9 | Cl | CH₃ | H |
| 2-CO₂C₂H₅-phenyl | H | CH₃ | 7 | Cl | CH₃ | H |
| 2-CO₂C₂H₅-phenyl | H | H | 7/9 | CH₃ | Cl | H |
| 2-CO₂C₂H₅-phenyl | H | CH₃ | 7 | CH₃ | Cl | H |
| 2-CO₂C₂H₅-phenyl | H | H | 7/9 | Cl | Cl | H |
| 2-CO₂C₂H₅-phenyl | H | CH₃ | 7 | Cl | Cl | H |
| 2-CO₂C₂H₅-phenyl | H | H | 7/9 | OCH₃ | OCH₃ | H |
| 2-CO₂C₂H₅-phenyl | H | CH₃ | 7 | OCH₃ | OCH₃ | H |

TABLE III-continued

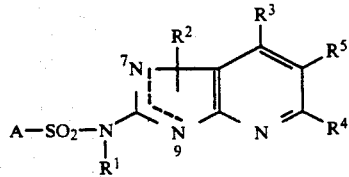

Ic

| A | R¹ | R² | Pos. | R³ | R⁴ | R⁵ |
|---|---|---|---|---|---|---|
| 2-CO₂C₂H₅-phenyl | H | H | 7/9 | CH₃ | OCH₃ | H |
| 2-CO₂C₂H₅-phenyl | H | CH₃ | 7 | CH₃ | OCH₃ | H |
| 2-CO₂C₂H₅-phenyl | H | H | 7/9 | OCH₃ | CH₃ | H |
| 2-CO₂C₂H₅-phenyl | H | CH₃ | 7 | OCH₃ | CH₃ | H |
| 2-CO₂C₂H₅-phenyl | H | H | 7/9 | Cl | OCH₃ | H |
| 2-CO₂C₂H₅-phenyl | H | CH₃ | 7 | Cl | OCH₃ | H |
| 2-CO₂C₂H₅-phenyl | H | H | 7/9 | OCH₃ | Cl | H |
| 2-CO₂C₂H₅-phenyl | H | CH₃ | 7 | OCH₃ | Cl | H |
| 2-COCH₃-phenyl | H | H | 7/9 | CH₃ | CH₃ | H |
| 2-COCH₃-phenyl | H | CH₃ | 7 | CH₃ | CH₃ | H |
| 2-COCH₃-phenyl | H | H | 7/9 | Cl | CH₃ | H |
| 2-COCH₃-phenyl | H | CH₃ | 7 | Cl | CH₃ | H |
| 2-COCH₃-phenyl | H | H | 7/9 | CH₃ | Cl | H |
| 2-COCH₃-phenyl | H | CH₃ | 7 | CH₃ | Cl | H |
| 2-COCH₃-phenyl | H | H | 7/9 | Cl | Cl | H |
| 2-COCH₃-phenyl | H | CH₃ | 7 | Cl | Cl | H |
| 2-COCH₃-phenyl | H | H | 7/9 | OCH₃ | OCH₃ | H |
| 2-COCH₃-phenyl | H | CH₃ | 7 | OCH₃ | OCH₃ | H |
| 2-COCH₃-phenyl | H | H | 7/9 | CH₃ | OCH₃ | H |
| 2-COCH₃-phenyl | H | CH₃ | 7 | CH₃ | OCH₃ | H |
| 2-COCH₃-phenyl | H | H | 7/9 | OCH₃ | CH₃ | H |
| 2-COCH₃-phenyl | H | CH₃ | 7 | OCH₃ | CH₃ | H |
| 2-COCH₃-phenyl | H | H | 7/9 | Cl | OCH₃ | H |
| 2-COCH₃-phenyl | H | CH₃ | 7 | Cl | OCH₃ | H |
| 2-COCH₃-phenyl | H | H | 7/9 | OCH₃ | Cl | H |
| 2-COCH₃-phenyl | H | CH₃ | 7 | OCH₃ | Cl | H |
| 2-OCH₃-phenyl | H | H | 7/9 | CH₃ | CH₃ | H |
| 2-OCH₃-phenyl | H | CH₃ | 7 | CH₃ | CH₃ | H |
| 2-OCH₃-phenyl | H | H | 7/9 | Cl | CH₃ | H |
| 2-OCH₃-phenyl | H | CH₃ | 7 | Cl | CH₃ | H |
| 2-OCH₃-phenyl | H | H | 7/9 | CH₃ | Cl | H |
| 2-OCH₃-phenyl | H | CH₃ | 7 | CH₃ | Cl | H |
| 2-OCH₃-phenyl | H | H | 7/9 | Cl | Cl | H |
| 2-OCH₃-phenyl | H | CH₃ | 7 | Cl | Cl | H |
| 2-OCH₃-phenyl | H | H | 7/9 | OCH₃ | OCH₃ | H |
| 2-OCH₃-phenyl | H | CH₃ | 7 | OCH₃ | OCH₃ | H |
| 2-OCH₃-phenyl | H | H | 7/9 | CH₃ | OCH₃ | H |
| 2-OCH₃-phenyl | H | CH₃ | 7 | CH₃ | OCH₃ | H |
| 2-OCH₃-phenyl | H | H | 7/9 | OCH₃ | CH₃ | H |
| 2-OCH₃-phenyl | H | CH₃ | 7 | OCH₃ | CH₃ | H |
| 2-OCH₃-phenyl | H | H | 7/9 | Cl | OCH₃ | H |
| 2-OCH₃-phenyl | H | CH₃ | 7 | Cl | OCH₃ | H |
| 2-OCH₃-phenyl | H | H | 7/9 | OCH₃ | Cl | H |
| 2-OCH₃-phenyl | H | CH₃ | 7 | OCH₃ | Cl | H |
| 2-OCH₂CH₂OCH₃-phenyl | H | H | 7/9 | CH₃ | CH₃ | H |
| 2-OCH₂CH₂OCH₃-phenyl | H | CH₃ | 7 | CH₃ | CH₃ | H |
| 2-OCH₂CH₂OCH₃-phenyl | H | H | 7/9 | Cl | CH₃ | H |
| 2-OCH₂CH₂OCH₃-phenyl | H | CH₃ | 7 | Cl | CH₃ | H |
| 2-OCH₂CH₂OCH₃-phenyl | H | H | 7/9 | CH₃ | Cl | H |
| 2-OCH₂CH₂OCH₃-phenyl | H | CH₃ | 7 | CH₃ | Cl | H |
| 2-OCH₂CH₂OCH₃-phenyl | H | H | 7/9 | Cl | Cl | H |
| 2-OCH₂CH₂OCH₃-phenyl | H | CH₃ | 7 | Cl | Cl | H |
| 2-OCH₂CH₂OCH₃-phenyl | H | H | 7/9 | OCH₃ | OCH₃ | H |
| 2-OCH₂CH₂OCH₃-phenyl | H | CH₃ | 7 | OCH₃ | OCH₃ | H |
| 2-OCH₂CH₂OCH₃-phenyl | H | H | 7/9 | CH₃ | OCH₃ | H |
| 2-OCH₂CH₂OCH₃-phenyl | H | CH₃ | 7 | CH₃ | OCH₃ | H |
| 2-OCH₂CH₂OCH₃-phenyl | H | H | 7/9 | OCH₃ | CH₃ | H |
| 2-OCH₂CH₂OCH₃-phenyl | H | CH₃ | 7 | OCH₃ | CH₃ | H |
| 2-OCH₂CH₂OCH₃-phenyl | H | H | 7/9 | Cl | OCH₃ | H |
| 2-OCH₂CH₂OCH₃-phenyl | H | CH₃ | 7 | Cl | OCH₃ | H |
| 2-OCH₂CH₂OCH₃-phenyl | H | H | 7/9 | OCH₃ | Cl | H |
| 2-OCH₂CH₂OCH₃-phenyl | H | CH₃ | 7 | OCH₃ | Cl | H |
| 2-OCH₂CO₂CH₃-phenyl | H | H | 7/9 | CH₃ | CH₃ | H |
| 2-OCH₂CO₂CH₃-phenyl | H | CH₃ | 7 | CH₃ | CH₃ | H |
| 2-OCH₂CO₂CH₃-phenyl | H | H | 7/9 | Cl | CH₃ | H |
| 2-OCH₂CO₂CH₃-phenyl | H | CH₃ | 7 | Cl | CH₃ | H |
| 2-OCH₂CO₂CH₃-phenyl | H | H | 7/9 | CH₃ | Cl | H |
| 2-OCH₂CO₂CH₃-phenyl | H | CH₃ | 7 | CH₃ | Cl | H |
| 2-OCH₂CO₂CH₃-phenyl | H | H | 7/9 | Cl | Cl | H |
| 2-OCH₂CO₂CH₃-phenyl | H | CH₃ | 7 | Cl | Cl | H |
| 2-OCH₂CO₂CH₃-phenyl | H | H | 7/9 | OCH₃ | OCH₃ | H |

TABLE III-continued

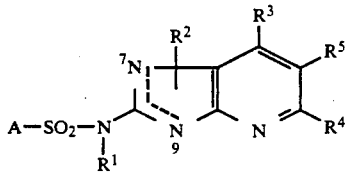

| A | R¹ | R² | Pos. | R³ | R⁴ | R⁵ |
|---|---|---|---|---|---|---|
| 2-OCH₂CO₂CH₃-phenyl | H | CH₃ | 7 | OCH₃ | OCH₃ | H |
| 2-OCH₂CO₂CH₃-phenyl | H | H | 7/9 | CH₃ | OCH₃ | H |
| 2-OCH₂CO₂CH₃-phenyl | H | CH₃ | 7 | CH₃ | OCH₃ | H |
| 2-OCH₂CO₂CH₃-phenyl | H | H | 7/9 | OCH₃ | CH₃ | H |
| 2-OCH₂CO₂CH₃-phenyl | H | CH₃ | 7 | OCH₃ | CH₃ | H |
| 2-OCH₂CO₂CH₃-phenyl | H | H | 7/9 | Cl | OCH₃ | H |
| 2-OCH₂CO₂CH₃-phenyl | H | CH₃ | 7 | Cl | OCH₃ | H |
| 2-OCH₂CO₂CH₃-phenyl | H | H | 7/9 | OCH₃ | Cl | H |
| 2-OCH₂CO₂CH₃-phenyl | H | CH₃ | 7 | OCH₃ | Cl | H |
| 2-OCH₂CH₂Cl-phenyl | H | H | 7/9 | CH₃ | CH₃ | H |
| 2-OCH₂CH₂Cl-phenyl | H | CH₃ | 7 | CH₃ | CH₃ | H |
| 2-OCH₂CH₂Cl-phenyl | H | H | 7/9 | Cl | CH₃ | H |
| 2-OCH₂CH₂Cl-phenyl | H | CH₃ | 7 | Cl | CH₃ | H |
| 2-OCH₂CH₂Cl-phenyl | H | H | 7/9 | CH₃ | Cl | H |
| 2-OCH₂CH₂Cl-phenyl | H | CH₃ | 7 | CH₃ | Cl | H |
| 2-OCH₂CH₂Cl-phenyl | H | H | 7/9 | Cl | Cl | H |
| 2-OCH₂CH₂Cl-phenyl | H | CH₃ | 7 | Cl | Cl | H |
| 2-OCH₂CH₂Cl-phenyl | H | H | 7/9 | OCH₃ | OCH₃ | H |
| 2-OCH₂CH₂Cl-phenyl | H | CH₃ | 7 | OCH₃ | OCH₃ | H |
| 2-OCH₂CH₂Cl-phenyl | H | H | 7/9 | CH₃ | OCH₃ | H |
| 2-OCH₂CH₂Cl-phenyl | H | CH₃ | 7 | CH₃ | OCH₃ | H |
| 2-OCH₂CH₂Cl-phenyl | H | H | 7/9 | OCH₃ | CH₃ | H |
| 2-OCH₂CH₂Cl-phenyl | H | CH₃ | 7 | OCH₃ | CH₃ | H |
| 2-OCH₂CH₂Cl-phenyl | H | H | 7/9 | Cl | OCH₃ | H |
| 2-OCH₂CH₂Cl-phenyl | H | CH₃ | 7 | Cl | OCH₃ | H |
| 2-OCH₂CH₂Cl-phenyl | H | H | 7/9 | OCH₃ | Cl | H |
| 2-OCH₂CH₂Cl-phenyl | H | CH₃ | 7 | OCH₃ | Cl | H |
| 2-OCH₂CH₂Cl-phenyl | H | H | 7/9 | CF₃ | CF₃ | H |
| 2-OCH₂CH₂Cl-phenyl | H | CH₃ | 7 | CF₃ | CF₃ | H |
| 2-OCH₂CH₂Cl-phenyl | H | H | 7/9 | Cl | CF₃ | H |
| 2-OCH₂CH₂Cl-phenyl | H | CH₃ | 7 | Cl | CF₃ | H |
| 2-OCH₂CH₂Cl-phenyl | H | H | 7/9 | CF₃ | Cl | H |
| 2-OCH₂CH₂Cl-phenyl | H | CH₃ | 7 | CF₃ | Cl | H |
| 2-OCH₂CH₂Cl-phenyl | H | H | 7/9 | F | CF₃ | H |
| 2-OCH₂CH₂Cl-phenyl | H | CH₃ | 7 | F | CF₃ | H |
| 2-OCH₂CH₂Cl-phenyl | H | H | 7/9 | CF₃ | F | H |
| 2-OCH₂CH₂Cl-phenyl | H | CH₃ | 7 | CF₃ | F | H |
| 2-OCH₂CH₂Cl-phenyl | H | H | 7/9 | CH₃ | CF₃ | H |
| 2-OCH₂CH₂Cl-phenyl | H | CH₃ | 7 | CH₃ | CF₃ | H |
| 2-OCH₂CH₂Cl-phenyl | H | H | 7/9 | CF₃ | CH₃ | H |
| 2-OCH₂CH₂Cl-phenyl | H | CH₃ | 7 | CF₃ | CH₃ | H |
| 2-OCH₂CH₂Cl-phenyl | H | H | 7/9 | OCH₃ | CF₃ | H |
| 2-OCH₂CH₂Cl-phenyl | H | CH₃ | 7 | OCH₃ | CF₃ | H |
| 2-OCH₂CH₂Cl-phenyl | H | H | 7/9 | CF₃ | OCH₃ | H |
| 2-OCH₂CH₂Cl-phenyl | H | CH₃ | 7 | CF₃ | OCH₃ | H |
| 2-OCH₂CH₂Cl-phenyl | H | H | 7/9 | F | F | H |
| 2-OCH₂CH₂Cl-phenyl | H | CH₃ | 7 | F | F | H |
| 2-OCH₂CH₂Cl-phenyl | H | H | 7/9 | F | Cl | H |
| 2-OCH₂CH₂Cl-phenyl | H | CH₃ | 7 | F | Cl | H |
| 2-OCH₂CH₂Cl-phenyl | H | H | 7/9 | Cl | F | H |
| 2-OCH₂CH₂Cl-phenyl | H | CH₃ | 7 | Cl | F | H |
| 2-OCH₂CH₂Cl-phenyl | H | H | 7/9 | F | CH₃ | H |
| 2-OCH₂CH₂Cl-phenyl | H | CH₃ | 7 | F | CH₃ | H |
| 2-OCH₂CH₂Cl-phenyl | H | H | 7/9 | CH₃ | F | H |
| 2-OCH₂CH₂Cl-phenyl | H | CH₃ | 7 | CH₃ | F | H |
| 2-OCH₂CH₂Cl-phenyl | H | H | 7/9 | F | OCH₃ | H |
| 2-OCH₂CH₂Cl-phenyl | H | CH₃ | 7 | F | OCH₃ | H |
| 2-OCH₂CH₂Cl-phenyl | H | H | 7/9 | OCH₃ | F | H |
| 2-OCH₂CH₂Cl-phenyl | H | CH₃ | 7 | OCH₃ | F | H |
| 2-OCH₂CH₂Cl-phenyl | H | H | 7/9 | N(CH₃)₂ | Cl | H |
| 2-OCH₂CH₂Cl-phenyl | H | CH₃ | 7 | N(CH₃)₂ | Cl | H |
| 2-OCH₂CH₂Cl-phenyl | H | H | 7/9 | SCH₃ | Cl | H |
| 2-OCH₂CH₂Cl-phenyl | H | CH₃ | 7 | SCH₃ | Cl | H |
| 2-SCH₃-phenyl | H | H | 7/9 | CH₃ | CH₃ | H |
| 2-SCH₃-phenyl | H | CH₃ | 7 | CH₃ | CH₃ | H |
| 2-SCH₃-phenyl | H | H | 7/9 | Cl | CH₃ | H |
| 2-SCH₃-phenyl | H | CH₃ | 7 | Cl | CH₃ | H |
| 2-SCH₃-phenyl | H | H | 7/9 | CH₃ | Cl | H |
| 2-SCH₃-phenyl | H | CH₃ | 7 | CH₃ | Cl | H |
| 2-SCH₃-phenyl | H | H | 7/9 | Cl | Cl | H |
| 2-SCH₃-phenyl | H | CH₃ | 7 | Cl | Cl | H |

TABLE III-continued

Ic structure: A—SO$_2$—N(R$^1$)—C(=N7)—... pyridine fused system with R$^2$, R$^3$, R$^4$, R$^5$ substituents, N9

| A | R$^1$ | R$^2$ | Pos. | R$^3$ | R$^4$ | R$^5$ |
|---|---|---|---|---|---|---|
| 2-SCH$_3$-phenyl | H | H | 7/9 | OCH$_3$ | OCH$_3$ | H |
| 2-SCH$_3$-phenyl | H | CH$_3$ | 7 | OCH$_3$ | OCH$_3$ | H |
| 2-SCH$_3$-phenyl | H | H | 7/9 | CH$_3$ | OCH$_3$ | H |
| 2-SCH$_3$-phenyl | H | CH$_3$ | 7 | CH$_3$ | OCH$_3$ | H |
| 2-SCH$_3$-phenyl | H | H | 7/9 | OCH$_3$ | CH$_3$ | H |
| 2-SCH$_3$-phenyl | H | CH$_3$ | 7 | OCH$_3$ | CH$_3$ | H |
| 2-SCH$_3$-phenyl | H | H | 7/9 | Cl | OCH$_3$ | H |
| 2-SCH$_3$-phenyl | H | CH$_3$ | 7 | Cl | OCH$_3$ | H |
| 2-SCH$_3$-phenyl | H | H | 7/9 | OCH$_3$ | Cl | H |
| 2-SCH$_3$-phenyl | H | CH$_3$ | 7 | OCH$_3$ | Cl | H |
| 2-SO$_2$CH$_3$-phenyl | H | H | 7/9 | CH$_3$ | CH$_3$ | H |
| 2-SO$_2$CH$_3$-phenyl | H | CH$_3$ | 7 | CH$_3$ | CH$_3$ | H |
| 2-SO$_2$CH$_3$-phenyl | H | H | 7/9 | Cl | CH$_3$ | H |
| 2-SO$_2$CH$_3$-phenyl | H | CH$_3$ | 7 | Cl | CH$_3$ | H |
| 2-SO$_2$CH$_3$-phenyl | H | H | 7/9 | CH$_3$ | Cl | H |
| 2-SO$_2$CH$_3$-phenyl | H | CH$_3$ | 7 | CH$_3$ | Cl | H |
| 2-SO$_2$CH$_3$-phenyl | H | H | 7/9 | Cl | Cl | H |
| 2-SO$_2$CH$_3$-phenyl | H | CH$_3$ | 7 | Cl | Cl | H |
| 2-SO$_2$CH$_3$-phenyl | H | H | 7/9 | OCH$_3$ | OCH$_3$ | H |
| 2-SO$_2$CH$_3$-phenyl | H | CH$_3$ | 7 | OCH$_3$ | OCH$_3$ | H |
| 2-SO$_2$CH$_3$-phenyl | H | H | 7/9 | CH$_3$ | OCH$_3$ | H |
| 2-SO$_2$CH$_3$-phenyl | H | CH$_3$ | 7 | CH$_3$ | OCH$_3$ | H |
| 2-SO$_2$CH$_3$-phenyl | H | H | 7/9 | OCH$_3$ | CH$_3$ | H |
| 2-SO$_2$CH$_3$-phenyl | H | CH$_3$ | 7 | OCH$_3$ | CH$_3$ | H |
| 2-SO$_2$CH$_3$-phenyl | H | H | 7/9 | Cl | OCH$_3$ | H |
| 2-SO$_2$CH$_3$-phenyl | H | CH$_3$ | 7 | Cl | OCH$_3$ | H |
| 2-SO$_2$CH$_3$-phenyl | H | H | 7/9 | OCH$_3$ | Cl | H |
| 2-SO$_2$CH$_3$-phenyl | H | CH$_3$ | 7 | OCH$_3$ | Cl | H |
| 2-SO$_2$N(CH$_3$)$_2$-phenyl | H | H | 7/9 | CH$_3$ | CH$_3$ | H |
| 2-SO$_2$N(CH$_3$)$_2$-phenyl | H | CH$_3$ | 7 | CH$_3$ | CH$_3$ | H |
| 2-SO$_2$N(CH$_3$)$_2$-phenyl | H | H | 7/9 | Cl | CH$_3$ | H |
| 2-SO$_2$N(CH$_3$)$_2$-phenyl | H | CH$_3$ | 7 | Cl | CH$_3$ | H |
| 2-SO$_2$N(CH$_3$)$_2$-phenyl | H | H | 7/9 | CH$_3$ | Cl | H |
| 2-SO$_2$N(CH$_3$)$_2$-phenyl | H | CH$_3$ | 7 | CH$_3$ | Cl | H |
| 2-SO$_2$N(CH$_3$)$_2$-phenyl | H | H | 7/9 | Cl | Cl | H |
| 2-SO$_2$N(CH$_3$)$_2$-phenyl | H | CH$_3$ | 7 | Cl | Cl | H |
| 2-SO$_2$N(CH$_3$)$_2$-phenyl | H | H | 7/9 | OCH$_3$ | OCH$_3$ | H |
| 2-SO$_2$N(CH$_3$)$_2$-phenyl | H | CH$_3$ | 7 | OCH$_3$ | OCH$_3$ | H |
| 2-SO$_2$N(CH$_3$)$_2$-phenyl | H | H | 7/9 | CH$_3$ | OCH$_3$ | H |
| 2-SO$_2$N(CH$_3$)$_2$-phenyl | H | CH$_3$ | 7 | CH$_3$ | OCH$_3$ | H |
| 2-SO$_2$N(CH$_3$)$_2$-phenyl | H | H | 7/9 | OCH$_3$ | CH$_3$ | H |
| 2-SO$_2$N(CH$_3$)$_2$-phenyl | H | CH$_3$ | 7 | OCH$_3$ | CH$_3$ | H |
| 2-SO$_2$N(CH$_3$)$_2$-phenyl | H | H | 7/9 | Cl | OCH$_3$ | H |
| 2-SO$_2$N(CH$_3$)$_2$-phenyl | H | CH$_3$ | 7 | Cl | OCH$_3$ | H |
| 2-SO$_2$N(CH$_3$)$_2$-phenyl | H | H | 7/9 | OCH$_3$ | Cl | H |
| 2-SO$_2$N(CH$_3$)$_2$-phenyl | H | CH$_3$ | 7 | OCH$_3$ | Cl | H |
| 2,6-Cl,Cl-phenyl | H | H | 7/9 | CH$_3$ | CH$_3$ | H |
| 2,6-Cl,Cl-phenyl | H | CH$_3$ | 7 | CH$_3$ | CH$_3$ | H |
| 2,6-Cl,Cl-phenyl | H | H | 7/9 | Cl | CH$_3$ | H |
| 2,6-Cl,Cl-phenyl | H | CH$_3$ | 7 | Cl | CH$_3$ | H |
| 2,6-Cl,Cl-phenyl | H | H | 7/9 | CH$_3$ | Cl | H |
| 2,6-Cl,Cl-phenyl | H | CH$_3$ | 7 | CH$_3$ | Cl | H |
| 2,6-Cl,Cl-phenyl | H | H | 7/9 | Cl | Cl | H |
| 2,6-Cl,Cl-phenyl | H | CH$_3$ | 7 | Cl | Cl | H |
| 2,6-Cl,Cl-phenyl | H | H | 7/9 | OCH$_3$ | OCH$_3$ | H |
| 2,6-Cl,Cl-phenyl | H | CH$_3$ | 7 | OCH$_3$ | OCH$_3$ | H |
| 2,6-Cl,Cl-phenyl | H | H | 7/9 | CH$_3$ | OCH$_3$ | H |
| 2,6-Cl,Cl-phenyl | H | CH$_3$ | 7 | CH$_3$ | OCH$_3$ | H |
| 2,6-Cl,Cl-phenyl | H | H | 7/9 | OCH$_3$ | CH$_3$ | H |
| 2,6-Cl,Cl-phenyl | H | CH$_3$ | 7 | OCH$_3$ | CH$_3$ | H |
| 2,6-Cl,Cl-phenyl | H | H | 7/9 | Cl | OCH$_3$ | H |
| 2,6-Cl,Cl-phenyl | H | CH$_3$ | 7 | Cl | OCH$_3$ | H |
| 2,6-Cl,Cl-phenyl | H | H | 7/9 | OCH$_3$ | Cl | H |
| 2,6-Cl,Cl-phenyl | H | CH$_3$ | 7 | OCH$_3$ | Cl | H |
| 2,6-Cl,Cl-phenyl | H | H | 7/9 | CF$_3$ | CF$_3$ | H |
| 2,6-Cl,Cl-phenyl | H | CH$_3$ | 7 | CF$_3$ | CF$_3$ | H |
| 2,6-Cl,Cl-phenyl | H | H | 7/9 | Cl | CF$_3$ | H |
| 2,6-Cl,Cl-phenyl | H | CH$_3$ | 7 | Cl | CF$_3$ | H |
| 2,6-Cl,Cl-phenyl | H | H | 7/9 | CF$_3$ | Cl | H |
| 2,6-Cl,Cl-phenyl | H | CH$_3$ | 7 | CF$_3$ | Cl | H |
| 2,6-Cl,Cl-phenyl | H | H | 7/9 | F | CF$_3$ | H |

TABLE III-continued

Ic $$\text{A}-\text{SO}_2-\underset{R^1}{\underset{|}{N}}-\text{...}$$ (structure with $R^2$, $R^3$, $R^4$, $R^5$, $N^7$, $N^9$)

| A | $R^1$ | $R^2$ | Pos. | $R^3$ | $R^4$ | $R^5$ |
|---|---|---|---|---|---|---|
| 2,6-Cl,Cl-phenyl | H | CH$_3$ | 7 | F | CF$_3$ | H |
| 2,6-Cl,Cl-phenyl | H | H | 7/9 | CF$_3$ | F | H |
| 2,6-Cl,Cl-phenyl | H | CH$_3$ | 7 | CF$_3$ | F | H |
| 2,6-Cl,Cl-phenyl | H | H | 7/9 | CH$_3$ | CF$_3$ | H |
| 2,6-Cl,Cl-phenyl | H | CH$_3$ | 7 | CH$_3$ | CF$_3$ | H |
| 2,6-Cl,Cl-phenyl | H | H | 7/9 | CF$_3$ | CH$_3$ | H |
| 2,6-Cl,Cl-phenyl | H | CH$_3$ | 7 | CF$_3$ | CH$_3$ | H |
| 2,6-Cl,Cl-phenyl | H | H | 7/9 | OCH$_3$ | CF$_3$ | H |
| 2,6-Cl,Cl-phenyl | H | CH$_3$ | 7 | OCH$_3$ | CF$_3$ | H |
| 2,6-Cl,Cl-phenyl | H | H | 7/9 | CF$_3$ | OCH$_3$ | H |
| 2,6-Cl,Cl-phenyl | H | CH$_3$ | 7 | CF$_3$ | OCH$_3$ | H |
| 2,6-Cl,Cl-phenyl | H | H | 7/9 | F | F | H |
| 2,6-Cl,Cl-phenyl | H | CH$_3$ | 7 | F | F | H |
| 2,6-Cl,Cl-phenyl | H | H | 7/9 | F | Cl | H |
| 2,6-Cl,Cl-phenyl | H | CH$_3$ | 7 | F | Cl | H |
| 2,6-Cl,Cl-phenyl | H | H | 7/9 | Cl | F | H |
| 2,6-Cl,Cl-phenyl | H | CH$_3$ | 7 | Cl | F | H |
| 2,6-Cl,Cl-phenyl | H | H | 7/9 | F | CH$_3$ | H |
| 2,6-Cl,Cl-phenyl | H | CH$_3$ | 7 | F | CH$_3$ | H |
| 2,6-Cl,Cl-phenyl | H | H | 7/9 | CH$_3$ | F | H |
| 2,6-Cl,Cl-phenyl | H | CH$_3$ | 7 | CH$_3$ | F | H |
| 2,6-Cl,Cl-phenyl | H | H | 7/9 | F | OCH$_3$ | H |
| 2,6-Cl,Cl-phenyl | H | CH$_3$ | 7 | F | OCH$_3$ | H |
| 2,6-Cl,Cl-phenyl | H | H | 7/9 | OCH$_3$ | F | H |
| 2,6-Cl,Cl-phenyl | H | CH$_3$ | 7 | OCH$_3$ | F | H |
| 2,6-Cl,Cl-phenyl | H | H | 7/9 | N(CH$_3$)$_2$ | Cl | H |
| 2,6-Cl,Cl-phenyl | H | CH$_3$ | 7 | N(CH$_3$)$_2$ | Cl | H |
| 2,6-Cl,Cl-phenyl | H | H | 7/9 | SCH$_3$ | Cl | H |
| 2,6-Cl,Cl-phenyl | H | CH$_3$ | 7 | SCH$_3$ | Cl | H |
| 2-Cl,6-CH$_3$-phenyl | H | H | 7/9 | CH$_3$ | CH$_3$ | H |
| 2-Cl,6-CH$_3$-phenyl | H | CH$_3$ | 7 | CH$_3$ | CH$_3$ | H |
| 2-Cl,6-CH$_3$-phenyl | H | H | 7/9 | Cl | CH$_3$ | H |
| 2-Cl,6-CH$_3$-phenyl | H | CH$_3$ | 7 | Cl | CH$_3$ | H |
| 2-Cl,6-CH$_3$-phenyl | H | H | 7/9 | CH$_3$ | Cl | H |
| 2-Cl,6-CH$_3$-phenyl | H | CH$_3$ | 7 | CH$_3$ | Cl | H |
| 2-Cl,6-CH$_3$-phenyl | H | H | 7/9 | Cl | Cl | H |
| 2-Cl,6-CH$_3$-phenyl | H | CH$_3$ | 7 | Cl | Cl | H |
| 2-Cl,6-CH$_3$-phenyl | H | H | 7/9 | OCH$_3$ | OCH$_3$ | H |
| 2-Cl,6-CH$_3$-phenyl | H | CH$_3$ | 7 | OCH$_3$ | OCH$_3$ | H |
| 2-Cl,6-CH$_3$-phenyl | H | H | 7/9 | CH$_3$ | OCH$_3$ | H |
| 2-Cl,6-CH$_3$-phenyl | H | CH$_3$ | 7 | CH$_3$ | OCH$_3$ | H |
| 2-Cl,6-CH$_3$-phenyl | H | H | 7/9 | OCH$_3$ | CH$_3$ | H |
| 2-Cl,6-CH$_3$-phenyl | H | CH$_3$ | 7 | OCH$_3$ | CH$_3$ | H |
| 2-Cl,6-CH$_3$-phenyl | H | H | 7/9 | Cl | OCH$_3$ | H |
| 2-Cl,6-CH$_3$-phenyl | H | CH$_3$ | 7 | Cl | OCH$_3$ | H |
| 2-Cl,6-CH$_3$-phenyl | H | H | 7/9 | OCH$_3$ | Cl | H |
| 2-Cl,6-CH$_3$-phenyl | H | CH$_3$ | 7 | OCH$_3$ | Cl | H |
| 2-Cl,6-CH$_3$-phenyl | H | H | 7/9 | CF$_3$ | CF$_3$ | H |
| 2-Cl,6-CH$_3$-phenyl | H | CH$_3$ | 7 | CF$_3$ | CF$_3$ | H |
| 2-Cl,6-CH$_3$-phenyl | H | H | 7/9 | Cl | CF$_3$ | H |
| 2-Cl,6-CH$_3$-phenyl | H | CH$_3$ | 7 | Cl | CF$_3$ | H |
| 2-Cl,6-CH$_3$-phenyl | H | H | 7/9 | CF$_3$ | Cl | H |
| 2-Cl,6-CH$_3$-phenyl | H | CH$_3$ | 7 | CF$_3$ | Cl | H |
| 2-Cl,6-CH$_3$-phenyl | H | H | 7/9 | F | CF$_3$ | H |
| 2-Cl,6-CH$_3$-phenyl | H | CH$_3$ | 7 | F | CF$_3$ | H |
| 2-Cl,6-CH$_3$-phenyl | H | H | 7/9 | CF$_3$ | F | H |
| 2-Cl,6-CH$_3$-phenyl | H | CH$_3$ | 7 | CF$_3$ | F | H |
| 2-Cl,6-CH$_3$-phenyl | H | H | 7/9 | CH$_3$ | CF$_3$ | H |
| 2-Cl,6-CH$_3$-phenyl | H | CH$_3$ | 7 | CH$_3$ | CF$_3$ | H |
| 2-Cl,6-CH$_3$-phenyl | H | H | 7/9 | CF$_3$ | CH$_3$ | H |
| 2-Cl,6-CH$_3$-phenyl | H | CH$_3$ | 7 | CF$_3$ | CH$_3$ | H |
| 2-Cl,6-CH$_3$-phenyl | H | H | 7/9 | OCH$_3$ | CF$_3$ | H |
| 2-Cl,6-CH$_3$-phenyl | H | CH$_3$ | 7 | OCH$_3$ | CF$_3$ | H |
| 2-Cl,6-CH$_3$-phenyl | H | H | 7/9 | CF$_3$ | OCH$_3$ | H |
| 2-Cl,6-CH$_3$-phenyl | H | CH$_3$ | 7 | CF$_3$ | OCH$_3$ | H |
| 2-Cl,6-CH$_3$-phenyl | H | H | 7/9 | F | F | H |
| 2-Cl,6-CH$_3$-phenyl | H | CH$_3$ | 7 | F | F | H |
| 2-Cl,6-CH$_3$-phenyl | H | H | 7/9 | F | Cl | H |
| 2-Cl,6-CH$_3$-phenyl | H | CH$_3$ | 7 | F | Cl | H |
| 2-Cl,6-CH$_3$-phenyl | H | H | 7/9 | Cl | F | H |
| 2-Cl,6-CH$_3$-phenyl | H | CH$_3$ | 7 | Cl | F | H |

TABLE III-continued $$\text{A}-\text{SO}_2-\underset{R^1}{\underset{|}{N}}-\text{[pyrido-imidazole with }R^2, R^3, R^4, R^5\text{]} \quad \text{Ic}$$

| A | R¹ | R² | Pos. | R³ | R⁴ | R⁵ |
|---|---|---|---|---|---|---|
| 2-Cl,6-CH₃-phenyl | H | H | 7/9 | F | CH₃ | H |
| 2-Cl,6-CH₃-phenyl | H | CH₃ | 7 | F | CH₃ | H |
| 2-Cl,6-CH₃-phenyl | H | H | 7/9 | CH₃ | F | H |
| 2-Cl,6-CH₃-phenyl | H | CH₃ | 7 | CH₃ | F | H |
| 2-Cl,6-CH₃-phenyl | H | H | 7/9 | F | OCH₃ | H |
| 2-Cl,6-CH₃-phenyl | H | CH₃ | 7 | F | OCH₃ | H |
| 2-Cl,6-CH₃-phenyl | H | H | 7/9 | OCH₃ | F | H |
| 2-Cl,6-CH₃-phenyl | H | CH₃ | 7 | OCH₃ | F | H |
| 2-Cl,6-CH₃-phenyl | H | H | 7/9 | N(CH₃)₂ | Cl | H |
| 2-Cl,6-CH₃-phenyl | H | CH₃ | 7 | N(CH₃)₂ | Cl | H |
| 2-Cl,6-CH₃-phenyl | H | H | 7/9 | SCH₃ | Cl | H |
| 2-Cl,6-CH₃-phenyl | H | CH₃ | 7 | SCH₃ | Cl | H |
| 2,5-Cl,Cl-phenyl | H | H | 7/9 | CH₃ | CH₃ | H |
| 2,5-Cl,Cl-phenyl | H | CH₃ | 7 | CH₃ | CH₃ | H |
| 2,5-Cl,Cl-phenyl | H | H | 7/9 | Cl | CH₃ | H |
| 2,5-Cl,Cl-phenyl | H | CH₃ | 7 | Cl | CH₃ | H |
| 2,5-Cl,Cl-phenyl | H | H | 7/9 | CH₃ | Cl | H |
| 2,5-Cl,Cl-phenyl | H | CH₃ | 7 | CH₃ | Cl | H |
| 2,5-Cl,Cl-phenyl | H | H | 7/9 | Cl | Cl | H |
| 2,5-Cl,Cl-phenyl | H | CH₃ | 7 | Cl | Cl | H |
| 2,5-Cl,Cl-phenyl | H | H | 7/9 | OCH₃ | OCH₃ | H |
| 2,5-Cl,Cl-phenyl | H | CH₃ | 7 | OCH₃ | OCH₃ | H |
| 2,5-Cl,Cl-phenyl | H | H | 7/9 | CH₃ | OCH₃ | H |
| 2,5-Cl,Cl-phenyl | H | CH₃ | 7 | CH₃ | OCH₃ | H |
| 2,5-Cl,Cl-phenyl | H | H | 7/9 | OCH₃ | CH₃ | H |
| 2,5-Cl,Cl-phenyl | H | CH₃ | 7 | OCH₃ | CH₃ | H |
| 2,5-Cl,Cl-phenyl | H | H | 7/9 | Cl | OCH₃ | H |
| 2,5-Cl,Cl-phenyl | H | CH₃ | 7 | Cl | OCH₃ | H |
| 2,5-Cl,Cl-phenyl | H | H | 7/9 | OCH₃ | Cl | H |
| 2,5-Cl,Cl-phenyl | H | CH₃ | 7 | OCH₃ | Cl | H |
| 2,5-Cl,Cl-phenyl | H | H | 7/9 | CF₃ | CF₃ | H |
| 2,5-Cl,Cl-phenyl | H | CH₃ | 7 | CF₃ | CF₃ | H |
| 2,5-Cl,Cl-phenyl | H | H | 7/9 | Cl | CF₃ | H |
| 2,5-Cl,Cl-phenyl | H | CH₃ | 7 | Cl | CF₃ | H |
| 2,5-Cl,Cl-phenyl | H | H | 7/9 | CF₃ | Cl | H |
| 2,5-Cl,Cl-phenyl | H | CH₃ | 7 | CF₃ | Cl | H |
| 2,5-Cl,Cl-phenyl | H | H | 7/9 | F | CF₃ | H |
| 2,5-Cl,Cl-phenyl | H | CH₃ | 7 | F | CF₃ | H |
| 2,5-Cl,Cl-phenyl | H | H | 7/9 | CF₃ | F | H |
| 2,5-Cl,Cl-phenyl | H | CH₃ | 7 | CF₃ | F | H |
| 2,5-Cl,Cl-phenyl | H | H | 7/9 | CH₃ | CF₃ | H |
| 2,5-Cl,Cl-phenyl | H | CH₃ | 7 | CH₃ | CF₃ | H |
| 2,5-Cl,Cl-phenyl | H | H | 7/9 | CF₃ | CH₃ | H |
| 2,5-Cl,Cl-phenyl | H | CH₃ | 7 | CF₃ | CH₃ | H |
| 2,5-Cl,Cl-phenyl | H | H | 7/9 | OCH₃ | CF₃ | H |
| 2,5-Cl,Cl-phenyl | H | CH₃ | 7 | OCH₃ | CF₃ | H |
| 2,5-Cl,Cl-phenyl | H | H | 7/9 | CF₃ | OCH₃ | H |
| 2,5-Cl,Cl-phenyl | H | CH₃ | 7 | CF₃ | OCH₃ | H |
| 2,5-Cl,Cl-phenyl | H | H | 7/9 | F | F | H |
| 2,5-Cl,Cl-phenyl | H | CH₃ | 7 | F | F | H |
| 2,5-Cl,Cl-phenyl | H | H | 7/9 | F | Cl | H |
| 2,5-Cl,Cl-phenyl | H | CH₃ | 7 | F | Cl | H |
| 2,5-Cl,Cl-phenyl | H | H | 7/9 | Cl | F | H |
| 2,5-Cl,Cl-phenyl | H | CH₃ | 7 | Cl | F | H |
| 2,5-Cl,Cl-phenyl | H | H | 7/9 | F | CH₃ | H |
| 2,5-Cl,Cl-phenyl | H | CH₃ | 7 | F | CH₃ | H |
| 2,5-Cl,Cl-phenyl | H | H | 7/9 | CH₃ | F | H |
| 2,5-Cl,Cl-phenyl | H | CH₃ | 7 | CH₃ | F | H |
| 2,5-Cl,Cl-phenyl | H | H | 7/9 | F | OCH₃ | H |
| 2,5-Cl,Cl-phenyl | H | CH₃ | 7 | F | OCH₃ | H |
| 2,5-Cl,Cl-phenyl | H | H | 7/9 | OCH₃ | F | H |
| 2,5-Cl,Cl-phenyl | H | CH₃ | 7 | OCH₃ | F | H |
| 2,5-Cl,Cl-phenyl | H | H | 7/9 | N(CH₃)₂ | Cl | H |
| 2,5-Cl,Cl-phenyl | H | CH₃ | 7 | N(CH₃)₂ | Cl | H |
| 2,5-Cl,Cl-phenyl | H | H | 7/9 | SCH₃ | Cl | H |
| 2,5-Cl,Cl-phenyl | H | CH₃ | 7 | SCH₃ | Cl | H |
| 2-CO₂CH₃,3-F-phenyl | H | H | 7/9 | CH₃ | CH₃ | H |
| 2-CO₂CH₃,3-F-phenyl | H | CH₃ | 7 | CH₃ | CH₃ | H |
| 2-CO₂CH₃,3-F-phenyl | H | H | 7/9 | Cl | CH₃ | H |
| 2-CO₂CH₃,3-F-phenyl | H | CH₃ | 7 | Cl | CH₃ | H |
| 2-CO₂CH₃,3-F-phenyl | H | H | 7/9 | CH₃ | Cl | H |

TABLE III-continued

Ic $A-SO_2-N(R^1)-$ [pyrazolo-pyridine with $R^2$, $R^3$, $R^4$, $R^5$; ring atoms $N^7$, $N^9$]

| A | $R^1$ | $R^2$ | Pos. | $R^3$ | $R^4$ | $R^5$ |
|---|---|---|---|---|---|---|
| 2-CO$_2$CH$_3$,3-F-phenyl | H | CH$_3$ | 7 | CH$_3$ | Cl | H |
| 2-CO$_2$CH$_3$,3-F-phenyl | H | H | 7/9 | Cl | Cl | H |
| 2-CO$_2$CH$_3$,3-F-phenyl | H | CH$_3$ | 7 | Cl | Cl | H |
| 2-CO$_2$CH$_3$,3-F-phenyl | H | H | 7/9 | OCH$_3$ | OCH$_3$ | H |
| 2-CO$_2$CH$_3$,3-F-phenyl | H | CH$_3$ | 7 | OCH$_3$ | OCH$_3$ | H |
| 2-CO$_2$CH$_3$,3-F-phenyl | H | H | 7/9 | CH$_3$ | OCH$_3$ | H |
| 2-CO$_2$CH$_3$,3-F-phenyl | H | CH$_3$ | 7 | CH$_3$ | OCH$_3$ | H |
| 2-CO$_2$CH$_3$,3-F-phenyl | H | H | 7/9 | OCH$_3$ | CH$_3$ | H |
| 2-CO$_2$CH$_3$,3-F-phenyl | H | CH$_3$ | 7 | OCH$_3$ | CH$_3$ | H |
| 2-CO$_2$CH$_3$,3-F-phenyl | H | H | 7/9 | Cl | OCH$_3$ | H |
| 2-CO$_2$CH$_3$,3-F-phenyl | H | CH$_3$ | 7 | Cl | OCH$_3$ | H |
| 2-CO$_2$CH$_3$,3-F-phenyl | H | H | 7/9 | OCH$_3$ | Cl | H |
| 2-CO$_2$CH$_3$,3-F-phenyl | H | CH$_3$ | 7 | OCH$_3$ | Cl | H |
| 2-CO$_2$CH$_3$,3-F-phenyl | H | H | 7/9 | F | F | H |
| 2-CO$_2$CH$_3$,3-F-phenyl | H | CH$_3$ | 7 | F | F | H |
| 2-CO$_2$CH$_3$,3-F-phenyl | H | H | 7/9 | F | Cl | H |
| 2-CO$_2$CH$_3$,3-F-phenyl | H | CH$_3$ | 7 | F | Cl | H |
| 2-CO$_2$CH$_3$,3-F-phenyl | H | H | 7/9 | Cl | F | H |
| 2-CO$_2$CH$_3$,3-F-phenyl | H | CH$_3$ | 7 | Cl | F | H |
| 2-CO$_2$CH$_3$,3-F-phenyl | H | H | 7/9 | F | CH$_3$ | H |
| 2-CO$_2$CH$_3$,3-F-phenyl | H | CH$_3$ | 7 | F | CH$_3$ | H |
| 2-CO$_2$CH$_3$,3-F-phenyl | H | H | 7/9 | CH$_3$ | F | H |
| 2-CO$_2$CH$_3$,3-F-phenyl | H | CH$_3$ | 7 | CH$_3$ | F | H |
| 2-CO$_2$CH$_3$,3-F-phenyl | H | H | 7/9 | F | OCH$_3$ | H |
| 2-CO$_2$CH$_3$,3-F-phenyl | H | CH$_3$ | 7 | F | OCH$_3$ | H |
| 2-CO$_2$CH$_3$,3-F-phenyl | H | H | 7/9 | OCH$_3$ | F | H |
| 2-CO$_2$CH$_3$,3-F-phenyl | H | CH$_3$ | 7 | OCH$_3$ | F | H |
| 2-CO$_2$CH$_3$,3-F-phenyl | H | H | 7/9 | N(CH$_3$)$_2$ | Cl | H |
| 2-CO$_2$CH$_3$,3-F-phenyl | H | CH$_3$ | 7 | N(CH$_3$)$_2$ | Cl | H |
| 2-CO$_2$CH$_3$,3-F-phenyl | H | H | 7/9 | SCH$_3$ | Cl | H |
| 2-CO$_2$CH$_3$,3-F-phenyl | H | CH$_3$ | 7 | SCH$_3$ | Cl | H |
| 2-CO$_2$CH$_3$,3-F-phenyl | H | H | 7/9 | CF$_3$ | CF$_3$ | H |
| 2-CO$_2$CH$_3$,3-F-phenyl | H | CH$_3$ | 7 | CF$_3$ | CF$_3$ | H |
| 2-CO$_2$CH$_3$,3-F-phenyl | H | H | 7/9 | Cl | CF$_3$ | H |
| 2-CO$_2$CH$_3$,3-F-phenyl | H | CH$_3$ | 7 | Cl | CF$_3$ | H |
| 2-CO$_2$CH$_3$,3-F-phenyl | H | H | 7/9 | CF$_3$ | Cl | H |
| 2-CO$_2$CH$_3$,3-F-phenyl | H | CH$_3$ | 7 | CF$_3$ | Cl | H |
| 2-CO$_2$CH$_3$,3-F-phenyl | H | H | 7/9 | F | CF$_3$ | H |
| 2-CO$_2$CH$_3$,3-F-phenyl | H | CH$_3$ | 7 | F | CF$_3$ | H |
| 2-CO$_2$CH$_3$,3-F-phenyl | H | H | 7/9 | CF$_3$ | F | H |
| 2-CO$_2$CH$_3$,3-F-phenyl | H | CH$_3$ | 7 | CF$_3$ | F | H |
| 2-CO$_2$CH$_3$,3-F-phenyl | H | H | 7/9 | CH$_3$ | CF$_3$ | H |
| 2-CO$_2$CH$_3$,3-F-phenyl | H | CH$_3$ | 7 | CH$_3$ | CF$_3$ | H |
| 2-CO$_2$CH$_3$,3-F-phenyl | H | H | 7/9 | CF$_3$ | CH$_3$ | H |
| 2-CO$_2$CH$_3$,3-F-phenyl | H | CH$_3$ | 7 | CF$_3$ | CH$_3$ | H |
| 2-CO$_2$CH$_3$,3-F-phenyl | H | H | 7/9 | OCH$_3$ | CF$_3$ | H |
| 2-CO$_2$CH$_3$,3-F-phenyl | H | CH$_3$ | 7 | OCH$_3$ | CF$_3$ | H |
| 2-CO$_2$CH$_3$,3-F-phenyl | H | H | 7/9 | CF$_3$ | OCH$_3$ | H |
| 2-CO$_2$CH$_3$,3-F-phenyl | H | CH$_3$ | 7 | CF$_3$ | OCH$_3$ | H |
| 3-Cl-thienyl | H | H | 7/9 | CH$_3$ | CH$_3$ | H |
| 3-Cl-thienyl | H | CH$_3$ | 7 | CH$_3$ | CH$_3$ | H |
| 3-Cl-thienyl | H | H | 7/9 | Cl | CH$_3$ | H |
| 3-Cl-thienyl | H | CH$_3$ | 7 | Cl | CH$_3$ | H |
| 3-Cl-thienyl | H | H | 7/9 | CH$_3$ | Cl | H |
| 3-Cl-thienyl | H | CH$_3$ | 7 | CH$_3$ | Cl | H |
| 3-Cl-thienyl | H | H | 7/9 | Cl | Cl | H |
| 3-Cl-thienyl | H | CH$_3$ | 7 | Cl | Cl | H |
| 3-Cl-thienyl | H | H | 7/9 | OCH$_3$ | OCH$_3$ | H |
| 3-Cl-thienyl | H | CH$_3$ | 7 | OCH$_3$ | OCH$_3$ | H |
| 3-Cl-thienyl | H | H | 7/9 | CH$_3$ | OCH$_3$ | H |
| 3-Cl-thienyl | H | CH$_3$ | 7 | CH$_3$ | OCH$_3$ | H |
| 3-Cl-thienyl | H | H | 7/9 | OCH$_3$ | CH$_3$ | H |
| 3-Cl-thienyl | H | CH$_3$ | 7 | OCH$_3$ | CH$_3$ | H |
| 3-Cl-thienyl | H | H | 7/9 | Cl | OCH$_3$ | H |
| 3-Cl-thienyl | H | CH$_3$ | 7 | Cl | OCH$_3$ | H |
| 3-Cl-thienyl | H | H | 7/9 | OCH$_3$ | Cl | H |
| 3-Cl-thienyl | H | CH$_3$ | 7 | OCH$_3$ | Cl | H |
| 2-CO$_2$CH$_3$,3-thienyl | H | H | 7/9 | CH$_3$ | CH$_3$ | H |
| 2-CO$_2$CH$_3$,3-thienyl | H | CH$_3$ | 7 | CH$_3$ | CH$_3$ | H |
| 2-CO$_2$CH$_3$,3-thienyl | H | H | 7/9 | Cl | CH$_3$ | H |
| 2-CO$_2$CH$_3$,3-thienyl | H | CH$_3$ | 7 | Cl | CH$_3$ | H |

TABLE III-continued

Ic

A—SO$_2$—N(R$^1$)—[structure with R$^2$, R$^3$, R$^4$, R$^5$, 7N, N9]

| A | R$^1$ | R$^2$ | Pos. | R$^3$ | R$^4$ | R$^5$ |
|---|---|---|---|---|---|---|
| 2-CO$_2$CH$_3$,3-thienyl | H | H | 7/9 | CH$_3$ | Cl | H |
| 2-CO$_2$CH$_3$,3-thienyl | H | CH$_3$ | 7 | CH$_3$ | Cl | H |
| 2-CO$_2$CH$_3$,3-thienyl | H | H | 7/9 | Cl | Cl | H |
| 2-CO$_2$CH$_3$,3-thienyl | H | CH$_3$ | 7 | Cl | Cl | H |
| 2-CO$_2$CH$_3$,3-thienyl | H | H | 7/9 | OCH$_3$ | OCH$_3$ | H |
| 2-CO$_2$CH$_3$,3-thienyl | H | CH$_3$ | 7 | OCH$_3$ | OCH$_3$ | H |
| 2-CO$_2$CH$_3$,3-thienyl | H | H | 7/9 | CH$_3$ | OCH$_3$ | H |
| 2-CO$_2$CH$_3$,3-thienyl | H | CH$_3$ | 7 | CH$_3$ | OCH$_3$ | H |
| 2-CO$_2$CH$_3$,3-thienyl | H | H | 7/9 | OCH$_3$ | CH$_3$ | H |
| 2-CO$_2$CH$_3$,3-thienyl | H | CH$_3$ | 7 | OCH$_3$ | CH$_3$ | H |
| 2-CO$_2$CH$_3$,3-thienyl | H | H | 7/9 | Cl | OCH$_3$ | H |
| 2-CO$_2$CH$_3$,3-thienyl | H | CH$_3$ | 7 | Cl | OCH$_3$ | H |
| 2-CO$_2$CH$_3$,3-thienyl | H | H | 7/9 | OCH$_3$ | Cl | H |
| 2-CO$_2$CH$_3$,3-thienyl | H | CH$_3$ | 7 | OCH$_3$ | Cl | H |
| 2-CO$_2$CH$_3$,3-thienyl | H | H | 7/9 | CF$_3$ | CF$_3$ | H |
| 2-CO$_2$CH$_3$,3-thienyl | H | CH$_3$ | 7 | CF$_3$ | CF$_3$ | H |
| 2-CO$_2$CH$_3$,3-thienyl | H | H | 7/9 | Cl | CF$_3$ | H |
| 2-CO$_2$CH$_3$,3-thienyl | H | CH$_3$ | 7 | Cl | CF$_3$ | H |
| 2-CO$_2$CH$_3$,3-thienyl | H | H | 7/9 | CF$_3$ | Cl | H |
| 2-CO$_2$CH$_3$,3-thienyl | H | CH$_3$ | 7 | CF$_3$ | Cl | H |
| 2-CO$_2$CH$_3$,3-thienyl | H | H | 7/9 | F | CF$_3$ | H |
| 2-CO$_2$CH$_3$,3-thienyl | H | CH$_3$ | 7 | F | CF$_3$ | H |
| 2-CO$_2$CH$_3$,3-thienyl | H | H | 7/9 | CF$_3$ | F | H |
| 2-CO$_2$CH$_3$,3-thienyl | H | CH$_3$ | 7 | CF$_3$ | F | H |
| 2-CO$_2$CH$_3$,3-thienyl | H | H | 7/9 | CH$_3$ | CF$_3$ | H |
| 2-CO$_2$CH$_3$,3-thienyl | H | CH$_3$ | 7 | CH$_3$ | CF$_3$ | H |
| 2-CO$_2$CH$_3$,3-thienyl | H | H | 7/9 | CF$_3$ | CH$_3$ | H |
| 2-CO$_2$CH$_3$,3-thienyl | H | CH$_3$ | 7 | CF$_3$ | CH$_3$ | H |
| 2-CO$_2$CH$_3$,3-thienyl | H | H | 7/9 | OCH$_3$ | CF$_3$ | H |
| 2-CO$_2$CH$_3$,3-thienyl | H | CH$_3$ | 7 | OCH$_3$ | CF$_3$ | H |
| 2-CO$_2$CH$_3$,3-thienyl | H | H | 7/9 | CF$_3$ | OCH$_3$ | H |
| 2-CO$_2$CH$_3$,3-thienyl | H | CH$_3$ | 7 | CF$_3$ | OCH$_3$ | H |
| 2-CO$_2$CH$_3$,3-thienyl | H | H | 7/9 | F | F | H |
| 2-CO$_2$CH$_3$,3-thienyl | H | CH$_3$ | 7 | F | F | H |
| 2-CO$_2$CH$_3$,3-thienyl | H | H | 7/9 | F | Cl | H |
| 2-CO$_2$CH$_3$,3-thienyl | H | CH$_3$ | 7 | F | Cl | H |
| 2-CO$_2$CH$_3$,3-thienyl | H | H | 7/9 | Cl | F | H |
| 2-CO$_2$CH$_3$,3-thienyl | H | CH$_3$ | 7 | Cl | F | H |
| 2-CO$_2$CH$_3$,3-thienyl | H | H | 7/9 | F | CH$_3$ | H |
| 2-CO$_2$CH$_3$,3-thienyl | H | CH$_3$ | 7 | F | CH$_3$ | H |
| 2-CO$_2$CH$_3$,3-thienyl | H | H | 7/9 | CH$_3$ | F | H |
| 2-CO$_2$CH$_3$,3-thienyl | H | CH$_3$ | 7 | CH$_3$ | F | H |
| 2-CO$_2$CH$_3$,3-thienyl | H | H | 7/9 | F | OCH$_3$ | H |
| 2-CO$_2$CH$_3$,3-thienyl | H | CH$_3$ | 7 | F | OCH$_3$ | H |
| 2-CO$_2$CH$_3$,3-thienyl | H | H | 7/9 | OCH$_3$ | F | H |
| 2-CO$_2$CH$_3$,3-thienyl | H | CH$_3$ | 7 | OCH$_3$ | F | H |
| 2-CO$_2$CH$_3$,3-thienyl | H | H | 7/9 | N(CH$_3$)$_2$ | Cl | H |
| 2-CO$_2$CH$_3$,3-thienyl | H | CH$_3$ | 7 | N(CH$_3$)$_2$ | Cl | H |
| 2-CO$_2$CH$_3$,3-thienyl | H | H | 7/9 | SCH$_3$ | Cl | H |
| 2-CO$_2$CH$_3$,3-thienyl | H | CH$_3$ | 7 | SCH$_3$ | Cl | H |
| 1-CH$_3$,4-CO$_2$CH$_3$,5-pyrazolyl | H | H | 7/9 | CH$_3$ | CH$_3$ | H |
| 1-CH$_3$,4-CO$_2$CH$_3$,5-pyrazolyl | H | CH$_3$ | 7 | CH$_3$ | CH$_3$ | H |
| 1-CH$_3$,4-CO$_2$CH$_3$,5-pyrazolyl | H | H | 7/9 | Cl | CH$_3$ | H |
| 1-CH$_3$,4-CO$_2$CH$_3$,5-pyrazolyl | H | CH$_3$ | 7 | Cl | CH$_3$ | H |
| 1-CH$_3$,4-CO$_2$CH$_3$,5-pyrazolyl | H | H | 7/9 | CH$_3$ | Cl | H |
| 1-CH$_3$,4-CO$_2$CH$_3$,5-pyrazolyl | H | CH$_3$ | 7 | CH$_3$ | Cl | H |
| 1-CH$_3$,4-CO$_2$CH$_3$,5-pyrazolyl | H | H | 7/9 | Cl | Cl | H |
| 1-CH$_3$,4-CO$_2$CH$_3$,5-pyrazolyl | H | CH$_3$ | 7 | Cl | Cl | H |
| 1-CH$_3$,4-CO$_2$CH$_3$,5-pyrazolyl | H | H | 7/9 | OCH$_3$ | OCH$_3$ | H |
| 1-CH$_3$,4-CO$_2$CH$_3$,5-pyrazolyl | H | CH$_3$ | 7 | OCH$_3$ | OCH$_3$ | H |
| 1-CH$_3$,4-CO$_2$CH$_3$,5-pyrazolyl | H | H | 7/9 | CH$_3$ | OCH$_3$ | H |
| 1-CH$_3$,4-CO$_2$CH$_3$,5-pyrazolyl | H | CH$_3$ | 7 | CH$_3$ | OCH$_3$ | H |
| 1-CH$_3$,4-CO$_2$CH$_3$,5-pyrazolyl | H | H | 7/9 | OCH$_3$ | CH$_3$ | H |
| 1-CH$_3$,4-CO$_2$CH$_3$,5-pyrazolyl | H | CH$_3$ | 7 | OCH$_3$ | CH$_3$ | H |
| 1-CH$_3$,4-CO$_2$CH$_3$,5-pyrazolyl | H | H | 7/9 | Cl | OCH$_3$ | H |
| 1-CH$_3$,4-CO$_2$CH$_3$,5-pyrazolyl | H | CH$_3$ | 7 | Cl | OCH$_3$ | H |
| 1-CH$_3$,4-CO$_2$CH$_3$,5-pyrazolyl | H | H | 7/9 | OCH$_3$ | Cl | H |
| 1-CH$_3$,4-CO$_2$CH$_3$,5-pyrazolyl | H | CH$_3$ | 7 | OCH$_3$ | Cl | H |
| 1-CH$_3$,4-CO$_2$CH$_3$,5-pyrazolyl | H | H | 7/9 | CF$_3$ | CF$_3$ | H |
| 1-CH$_3$,4-CO$_2$CH$_3$,5-pyrazolyl | H | CH$_3$ | 7 | CF$_3$ | CF$_3$ | H |
| 1-CH$_3$,4-CO$_2$CH$_3$,5-pyrazolyl | H | H | 7/9 | Cl | CF$_3$ | H |

TABLE III-continued

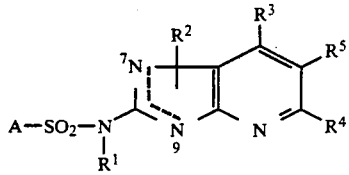

Ic

| A | $R^1$ | $R^2$ | Pos. | $R^3$ | $R^4$ | $R^5$ |
|---|---|---|---|---|---|---|
| 1-CH₃,4-CO₂CH₃,5-pyrazolyl | H | CH₃ | 7 | Cl | CF₃ | H |
| 1-CH₃,4-CO₂CH₃,5-pyrazolyl | H | H | 7/9 | CF₃ | Cl | H |
| 1-CH₃,4-CO₂CH₃,5-pyrazolyl | H | CH₃ | 7 | CF₃ | Cl | H |
| 1-CH₃,4-CO₂CH₃,5-pyrazolyl | H | H | 7/9 | F | CF₃ | H |
| 1-CH₃,4-CO₂CH₃,5-pyrazolyl | H | CH₃ | 7 | F | CF₃ | H |
| 1-CH₃,4-CO₂CH₃,5-pyrazolyl | H | H | 7/9 | CF₃ | F | H |
| 1-CH₃,4-CO₂CH₃,5-pyrazolyl | H | CH₃ | 7 | CF₃ | F | H |
| 1-CH₃,4-CO₂CH₃,5-pyrazolyl | H | H | 7/9 | CH₃ | CF₃ | H |
| 1-CH₃,4-CO₂CH₃,5-pyrazolyl | H | CH₃ | 7 | CH₃ | CF₃ | H |
| 1-CH₃,4-CO₂CH₃,5-pyrazolyl | H | H | 7/9 | CF₃ | CH₃ | H |
| 1-CH₃,4-CO₂CH₃,5-pyrazolyl | H | CH₃ | 7 | CF₃ | CH₃ | H |
| 1-CH₃,4-CO₂CH₃,5-pyrazolyl | H | H | 7/9 | OCH₃ | CF₃ | H |
| 1-CH₃,4-CO₂CH₃,5-pyrazolyl | H | CH₃ | 7 | OCH₃ | CF₃ | H |
| 1-CH₃,4-CO₂CH₃,5-pyrazolyl | H | H | 7/9 | CF₃ | OCH₃ | H |
| 1-CH₃,4-CO₂CH₃,5-pyrazolyl | H | CH₃ | 7 | CF₃ | OCH₃ | H |
| 1-CH₃,4-CO₂CH₃,5-pyrazolyl | H | H | 7/9 | F | F | H |
| 1-CH₃,4-CO₂CH₃,5-pyrazolyl | H | CH₃ | 7 | F | F | H |
| 1-CH₃,4-CO₂CH₃,5-pyrazolyl | H | H | 7/9 | F | Cl | H |
| 1-CH₃,4-CO₂CH₃,5-pyrazolyl | H | CH₃ | 7 | F | Cl | H |
| 1-CH₃,4-CO₂CH₃,5-pyrazolyl | H | H | 7/9 | Cl | F | H |
| 1-CH₃,4-CO₂CH₃,5-pyrazolyl | H | CH₃ | 7 | Cl | F | H |
| 1-CH₃,4-CO₂CH₃,5-pyrazolyl | H | H | 7/9 | F | CH₃ | H |
| 1-CH₃,4-CO₂CH₃,5-pyrazolyl | H | CH₃ | 7 | F | CH₃ | H |
| 1-CH₃,4-CO₂CH₃,5-pyrazolyl | H | H | 7/9 | CH₃ | F | H |
| 1-CH₃,4-CO₂CH₃,5-pyrazolyl | H | CH₃ | 7 | CH₃ | F | H |
| 1-CH₃,4-CO₂CH₃,5-pyrazolyl | H | H | 7/9 | F | OCH₃ | H |
| 1-CH₃,4-CO₂CH₃,5-pyrazolyl | H | CH₃ | 7 | F | OCH₃ | H |
| 1-CH₃,4-CO₂CH₃,5-pyrazolyl | H | H | 7/9 | OCH₃ | F | H |
| 1-CH₃,4-CO₂CH₃,5-pyrazolyl | H | CH₃ | 7 | OCH₃ | F | H |
| 1-CH₃,4-CO₂CH₃,5-pyrazolyl | H | H | 7/9 | N(CH₃)₂ | Cl | H |
| 1-CH₃,4-CO₂CH₃,5-pyrazolyl | H | CH₃ | 7 | N(CH₃)₂ | Cl | H |
| 1-CH₃,4-CO₂CH₃,5-pyrazolyl | H | H | 7/9 | SCH₃ | Cl | H |
| 1-CH₃,4-CO₂CH₃,5-pyrazolyl | H | CH₃ | 7 | SCH₃ | Cl | H |
| 3-CON(CH₃)₂,2-pyridyl | H | H | 7/9 | CH₃ | CH₃ | H |
| 3-CON(CH₃)₂,2-pyridyl | H | CH₃ | 7 | CH₃ | CH₃ | H |
| 3-CON(CH₃)₂,2-pyridyl | H | H | 7/9 | Cl | CH₃ | H |
| 3-CON(CH₃)₂,2-pyridyl | H | CH₃ | 7 | Cl | CH₃ | H |
| 3-CON(CH₃)₂,2-pyridyl | H | H | 7/9 | CH₃ | Cl | H |
| 3-CON(CH₃)₂,2-pyridyl | H | CH₃ | 7 | CH₃ | Cl | H |
| 3-CON(CH₃)₂,2-pyridyl | H | H | 7/9 | Cl | Cl | H |
| 3-CON(CH₃)₂,2-pyridyl | H | CH₃ | 7 | Cl | Cl | H |
| 3-CON(CH₃)₂,2-pyridyl | H | H | 7/9 | OCH₃ | OCH₃ | H |
| 3-CON(CH₃)₂,2-pyridyl | H | CH₃ | 7 | OCH₃ | OCH₃ | H |
| 3-CON(CH₃)₂,2-pyridyl | H | H | 7/9 | CH₃ | OCH₃ | H |
| 3-CON(CH₃)₂,2-pyridyl | H | CH₃ | 7 | CH₃ | OCH₃ | H |
| 3-CON(CH₃)₂,2-pyridyl | H | H | 7/9 | OCH₃ | CH₃ | H |
| 3-CON(CH₃)₂,2-pyridyl | H | CH₃ | 7 | OCH₃ | CH₃ | H |
| 3-CON(CH₃)₂,2-pyridyl | H | H | 7/9 | Cl | OCH₃ | H |
| 3-CON(CH₃)₂,2-pyridyl | H | CH₃ | 7 | Cl | OCH₃ | H |
| 3-CON(CH₃)₂,2-pyridyl | H | H | 7/9 | OCH₃ | Cl | H |
| 3-CON(CH₃)₂,2-pyridyl | H | CH₃ | 7 | OCH₃ | Cl | H |
| 3-CON(CH₃)₂,2-pyridyl | H | H | 7/9 | CF₃ | CF₃ | H |
| 3-CON(CH₃)₂,2-pyridyl | H | CH₃ | 7 | CF₃ | CF₃ | H |
| 3-CON(CH₃)₂,2-pyridyl | H | H | 7/9 | Cl | CF₃ | H |
| 3-CON(CH₃)₂,2-pyridyl | H | CH₃ | 7 | Cl | CF₃ | H |
| 3-CON(CH₃)₂,2-pyridyl | H | H | 7/9 | CF₃ | Cl | H |
| 3-CON(CH₃)₂,2-pyridyl | H | CH₃ | 7 | CF₃ | Cl | H |
| 3-CON(CH₃)₂,2-pyridyl | H | H | 7/9 | F | CF₃ | H |
| 3-CON(CH₃)₂,2-pyridyl | H | CH₃ | 7 | F | CF₃ | H |
| 3-CON(CH₃)₂,2-pyridyl | H | H | 7/9 | CF₃ | F | H |
| 3-CON(CH₃)₂,2-pyridyl | H | CH₃ | 7 | CF₃ | F | H |
| 3-CON(CH₃)₂,2-pyridyl | H | H | 7/9 | CH₃ | CF₃ | H |
| 3-CON(CH₃)₂,2-pyridyl | H | CH₃ | 7 | CH₃ | CF₃ | H |
| 3-CON(CH₃)₂,2-pyridyl | H | H | 7/9 | CF₃ | CH₃ | H |
| 3-CON(CH₃)₂,2-pyridyl | H | CH₃ | 7 | CF₃ | CH₃ | H |
| 3-CON(CH₃)₂,2-pyridyl | H | H | 7/9 | OCH₃ | CF₃ | H |
| 3-CON(CH₃)₂,2-pyridyl | H | CH₃ | 7 | OCH₃ | CF₃ | H |
| 3-CON(CH₃)₂,2-pyridyl | H | H | 7/9 | CF₃ | OCH₃ | H |
| 3-CON(CH₃)₂,2-pyridyl | H | CH₃ | 7 | CF₃ | OCH₃ | H |
| 3-CON(CH₃)₂,2-pyridyl | H | H | 7/9 | F | F | H |
| 3-CON(CH₃)₂,2-pyridyl | H | CH₃ | 7 | F | F | H |

TABLE III-continued

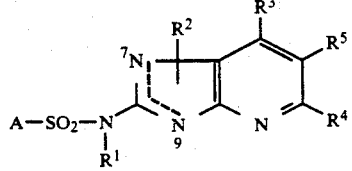

| A | R¹ | R² | Pos. | R³ | R⁴ | R⁵ |
|---|---|---|---|---|---|---|
| 3-CON(CH₃)₂,2-pyridyl | H | H | 7/9 | F | Cl | H |
| 3-CON(CH₃)₂,2-pyridyl | H | CH₃ | 7 | F | Cl | H |
| 3-CON(CH₃)₂,2-pyridyl | H | H | 7/9 | Cl | F | H |
| 3-CON(CH₃)₂,2-pyridyl | H | CH₃ | 7 | Cl | F | H |
| 3-CON(CH₃)₂,2-pyridyl | H | H | 7/9 | F | CH₃ | H |
| 3-CON(CH₃)₂,2-pyridyl | H | CH₃ | 7 | F | CH₃ | H |
| 3-CON(CH₃)₂,2-pyridyl | H | H | 7/9 | CH₃ | F | H |
| 3-CON(CH₃)₂,2-pyridyl | H | CH₃ | 7 | CH₃ | F | H |
| 3-CON(CH₃)₂,2-pyridyl | H | H | 7/9 | F | OCH₃ | H |
| 3-CON(CH₃)₂,2-pyridyl | H | CH₃ | 7 | F | OCH₃ | H |
| 3-CON(CH₃)₂,2-pyridyl | H | H | 7/9 | OCH₃ | F | H |
| 3-CON(CH₃)₂,2-pyridyl | H | CH₃ | 7 | OCH₃ | F | H |
| 3-CON(CH₃)₂,2-pyridyl | H | H | 7/9 | N(CH₃)₂ | Cl | H |
| 3-CON(CH₃)₂,2-pyridyl | H | CH₃ | 7 | N(CH₃)₂ | Cl | H |
| 3-CON(CH₃)₂,2-pyridyl | H | H | 7/9 | SCH₃ | Cl | H |
| 3-CON(CH₃)₂,2-pyridyl | H | CH₃ | 7 | SCH₃ | Cl | H |

TABLE IV

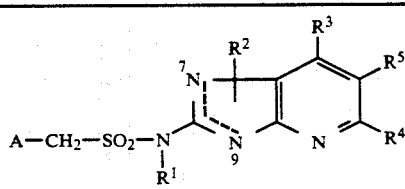
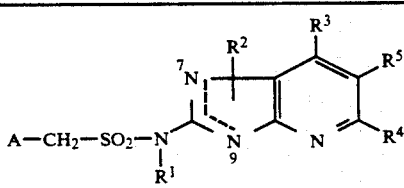

| A | R¹ | R² | Pos. | R³ | R⁴ | R⁵ |
|---|---|---|---|---|---|---|
| phenyl | H | H | 7/9 | CH₃ | CH₃ | H |
| phenyl | H | CH₃ | 7 | CH₃ | CH₃ | H |
| phenyl | H | H | 7/9 | Cl | CH₃ | H |
| phenyl | H | CH₃ | 7 | Cl | CH₃ | H |
| phenyl | H | H | 7/9 | CH₃ | Cl | H |
| phenyl | H | CH₃ | 7 | CH₃ | Cl | H |
| phenyl | H | H | 7/9 | Cl | Cl | H |
| phenyl | H | CH₃ | 7 | Cl | Cl | H |
| phenyl | H | H | 7/9 | OCH₃ | OCH₃ | H |
| phenyl | H | CH₃ | 7 | OCH₃ | OCH₃ | H |
| phenyl | H | H | 7/9 | CH₃ | OCH₃ | H |
| phenyl | H | CH₃ | 7 | CH₃ | OCH₃ | H |
| phenyl | H | H | 7/9 | OCH₃ | CH₃ | H |
| phenyl | H | CH₃ | 7 | OCH₃ | CH₃ | H |
| phenyl | H | H | 7/9 | Cl | OCH₃ | H |
| phenyl | H | CH₃ | 7 | Cl | OCH₃ | H |
| phenyl | H | H | 7/9 | OCH₃ | Cl | H |
| phenyl | H | CH₃ | 7 | OCH₃ | Cl | H |
| 2-Cl-phenyl | H | H | 7/9 | CH₃ | CH₃ | H |
| 2-Cl-phenyl | H | CH₃ | 7 | CH₃ | CH₃ | H |
| 2-Cl-phenyl | H | H | 7/9 | Cl | CH₃ | H |
| 2-Cl-phenyl | H | CH₃ | 7 | Cl | CH₃ | H |
| 2-Cl-phenyl | H | H | 7/9 | CH₃ | Cl | H |
| 2-Cl-phenyl | H | CH₃ | 7 | CH₃ | Cl | H |
| 2-Cl-phenyl | H | H | 7/9 | Cl | Cl | H |
| 2-Cl-phenyl | H | CH₃ | 7 | Cl | Cl | H |
| 2-Cl-phenyl | H | H | 7/9 | OCH₃ | OCH₃ | H |
| 2-Cl-phenyl | H | CH₃ | 7 | OCH₃ | OCH₃ | H |
| 2-Cl-phenyl | H | H | 7/9 | CH₃ | OCH₃ | H |
| 2-Cl-phenyl | H | CH₃ | 7 | CH₃ | OCH₃ | H |
| 2-Cl-phenyl | H | H | 7/9 | OCH₃ | CH₃ | H |
| 2-Cl-phenyl | H | CH₃ | 7 | OCH₃ | CH₃ | H |
| 2-Cl-phenyl | H | H | 7/9 | Cl | OCH₃ | H |
| 2-Cl-phenyl | H | CH₃ | 7 | Cl | OCH₃ | H |
| 2-Cl-phenyl | H | H | 7/9 | OCH₃ | Cl | H |
| 2-Cl-phenyl | H | CH₃ | 7 | OCH₃ | Cl | H |
| 2-F-phenyl | H | H | 7/9 | CH₃ | CH₃ | H |
| 2-F-phenyl | H | CH₃ | 7 | CH₃ | CH₃ | H |
| 2-F-phenyl | H | H | 7/9 | Cl | CH₃ | H |
| 2-F-phenyl | H | CH₃ | 7 | Cl | CH₃ | H |
| 2-F-phenyl | H | H | 7/9 | CH₃ | Cl | H |
| 2-F-phenyl | H | CH₃ | 7 | CH₃ | Cl | H |
| 2-F-phenyl | H | H | 7/9 | Cl | Cl | H |
| 2-F-phenyl | H | CH₃ | 7 | Cl | Cl | H |
| 2-F-phenyl | H | H | 7/9 | OCH₃ | OCH₃ | H |
| 2-F-phenyl | H | CH₃ | 7 | OCH₃ | OCH₃ | H |
| 2-F-phenyl | H | H | 7/9 | CH₃ | OCH₃ | H |
| 2-F-phenyl | H | CH₃ | 7 | CH₃ | OCH₃ | H |
| 2-F-phenyl | H | H | 7/9 | OCH₃ | CH₃ | H |
| 2-F-phenyl | H | CH₃ | 7 | OCH₃ | CH₃ | H |
| 2-F-phenyl | H | H | 7/9 | Cl | OCH₃ | H |
| 2-F-phenyl | H | CH₃ | 7 | Cl | OCH₃ | H |
| 2-F-phenyl | H | H | 7/9 | OCH₃ | Cl | H |
| 2-F-phenyl | H | CH₃ | 7 | OCH₃ | Cl | H |
| 2-CH₃-phenyl | H | H | 7/9 | CH₃ | CH₃ | H |
| 2-CH₃-phenyl | H | CH₃ | 7 | CH₃ | CH₃ | H |
| 2-CH₃-phenyl | H | H | 7/9 | Cl | CH₃ | H |
| 2-CH₃-phenyl | H | CH₃ | 7 | Cl | CH₃ | H |
| 2-CH₃-phenyl | H | H | 7/9 | CH₃ | Cl | H |
| 2-CH₃-phenyl | H | CH₃ | 7 | CH₃ | Cl | H |
| 2-CH₃-phenyl | H | H | 7/9 | Cl | Cl | H |
| 2-CH₃-phenyl | H | CH₃ | 7 | Cl | Cl | H |
| 2-CH₃-phenyl | H | H | 7/9 | OCH₃ | OCH₃ | H |
| 2-CH₃-phenyl | H | CH₃ | 7 | OCH₃ | OCH₃ | H |
| 2-CH₃-phenyl | H | H | 7/9 | CH₃ | OCH₃ | H |
| 2-CH₃-phenyl | H | CH₃ | 7 | CH₃ | OCH₃ | H |
| 2-CH₃-phenyl | H | H | 7/9 | OCH₃ | CH₃ | H |
| 2-CH₃-phenyl | H | CH₃ | 7 | OCH₃ | CH₃ | H |
| 2-CH₃-phenyl | H | H | 7/9 | Cl | OCH₃ | H |
| 2-CH₃-phenyl | H | CH₃ | 7 | Cl | OCH₃ | H |
| 2-CH₃-phenyl | H | H | 7/9 | OCH₃ | Cl | H |
| 2-CH₃-phenyl | H | CH₃ | 7 | OCH₃ | Cl | H |
| 2-CO₂CH₃-phenyl | H | H | 7/9 | CH₃ | CH₃ | H |
| 2-CO₂CH₃-phenyl | H | CH₃ | 7 | CH₃ | CH₃ | H |
| 2-CO₂CH₃-phenyl | H | H | 7/9 | Cl | CH₃ | H |
| 2-CO₂CH₃-phenyl | H | CH₃ | 7 | Cl | CH₃ | H |
| 2-CO₂CH₃-phenyl | H | H | 7/9 | CH₃ | Cl | H |
| 2-CO₂CH₃-phenyl | H | CH₃ | 7 | CH₃ | Cl | H |
| 2-CO₂CH₃-phenyl | H | H | 7/9 | Cl | Cl | H |
| 2-CO₂CH₃-phenyl | H | CH₃ | 7 | Cl | Cl | H |

TABLE IV-continued

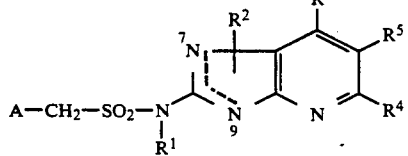

| A | R¹ | R² | Pos. | R³ | R⁴ | R⁵ |
|---|---|---|---|---|---|---|
| 2-CO₂CH₃-phenyl | H | H | 7/9 | OCH₃ | OCH₃ | H |
| 2-CO₂CH₃-phenyl | H | CH₃ | 7 | OCH₃ | OCH₃ | H |
| 2-CO₂CH₃-phenyl | H | H | 7/9 | CH₃ | OCH₃ | H |
| 2-CO₂CH₃-phenyl | H | CH₃ | 7 | CH₃ | OCH₃ | H |
| 2-CO₂CH₃-phenyl | H | H | 7/9 | OCH₃ | CH₃ | H |
| 2-CO₂CH₃-phenyl | H | CH₃ | 7 | OCH₃ | CH₃ | H |
| 2-CO₂CH₃-phenyl | H | H | 7/9 | Cl | OCH₃ | H |
| 2-CO₂CH₃-phenyl | H | CH₃ | 7 | Cl | OCH₃ | H |
| 2-CO₂CH₃-phenyl | H | H | 7/9 | OCH₃ | Cl | H |
| 2-CO₂CH₃-phenyl | H | CH₃ | 7 | OCH₃ | Cl | H |
| 2-CO₂C₂H₅-phenyl | H | H | 7/9 | CH₃ | CH₃ | H |
| 2-CO₂C₂H₅-phenyl | H | CH₃ | 7 | CH₃ | CH₃ | H |
| 2-CO₂C₂H₅-phenyl | H | H | 7/9 | Cl | CH₃ | H |
| 2-CO₂C₂H₅-phenyl | H | CH₃ | 7 | Cl | CH₃ | H |
| 2-CO₂C₂H₅-phenyl | H | H | 7/9 | CH₃ | Cl | H |
| 2-CO₂C₂H₅-phenyl | H | CH₃ | 7 | CH₃ | Cl | H |
| 2-CO₂C₂H₅-phenyl | H | H | 7/9 | Cl | Cl | H |
| 2-CO₂C₂H₅-phenyl | H | CH₃ | 7 | Cl | Cl | H |
| 2-CO₂C₂H₅-phenyl | H | H | 7/9 | OCH₃ | OCH₃ | H |
| 2-CO₂C₂H₅-phenyl | H | CH₃ | 7 | OCH₃ | OCH₃ | H |
| 2-CO₂C₂H₅-phenyl | H | H | 7/9 | OCH₃ | CH₃ | H |
| 2-CO₂C₂H₅-phenyl | H | CH₃ | 7 | OCH₃ | CH₃ | H |
| 2-CO₂C₂H₅-phenyl | H | H | 7/9 | Cl | OCH₃ | H |
| 2-CO₂C₂H₅-phenyl | H | CH₃ | 7 | Cl | OCH₃ | H |
| 2-CO₂C₂H₅-phenyl | H | H | 7/9 | OCH₃ | Cl | H |
| 2-CO₂C₂H₅-phenyl | H | CH₃ | 7 | OCH₃ | Cl | H |
| 2-OCH₃-phenyl | H | H | 7/9 | CH₃ | CH₃ | H |
| 2-OCH₃-phenyl | H | CH₃ | 7 | CH₃ | CH₃ | H |
| 2-OCH₃-phenyl | H | H | 7/9 | Cl | CH₃ | H |
| 2-OCH₃-phenyl | H | CH₃ | 7 | Cl | CH₃ | H |
| 2-OCH₃-phenyl | H | H | 7/9 | CH₃ | Cl | H |
| 2-OCH₃-phenyl | H | CH₃ | 7 | CH₃ | Cl | H |
| 2-OCH₃-phenyl | H | H | 7/9 | Cl | Cl | H |
| 2-OCH₃-phenyl | H | CH₃ | 7 | Cl | Cl | H |
| 2-OCH₃-phenyl | H | H | 7/9 | OCH₃ | OCH₃ | H |
| 2-OCH₃-phenyl | H | CH₃ | 7 | OCH₃ | OCH₃ | H |
| 2-OCH₃-phenyl | H | H | 7/9 | CH₃ | OCH₃ | H |
| 2-OCH₃-phenyl | H | CH₃ | 7 | CH₃ | OCH₃ | H |
| 2-OCH₃-phenyl | H | H | 7/9 | OCH₃ | CH₃ | H |
| 2-OCH₃-phenyl | H | CH₃ | 7 | OCH₃ | CH₃ | H |
| 2-OCH₃-phenyl | H | H | 7/9 | Cl | OCH₃ | H |
| 2-OCH₃-phenyl | H | CH₃ | 7 | Cl | OCH₃ | H |
| 2-OCH₃-phenyl | H | H | 7/9 | OCH₃ | Cl | H |
| 2-OCH₃-phenyl | H | CH₃ | 7 | OCH₃ | Cl | H |
| 2-OCH₂CH₂OCH₃-phenyl | H | H | 7/9 | CH₃ | CH₃ | H |
| 2-OCH₂CH₂OCH₃-phenyl | H | CH₃ | 7 | CH₃ | CH₃ | H |
| 2-OCH₂CH₂OCH₃-phenyl | H | H | 7/9 | Cl | CH₃ | H |
| 2-OCH₂CH₂OCH₃-phenyl | H | CH₃ | 7 | Cl | CH₃ | H |
| 2-OCH₂CH₂OCH₃-phenyl | H | H | 7/9 | CH₃ | Cl | H |
| 2-OCH₂CH₂OCH₃-phenyl | H | CH₃ | 7 | CH₃ | Cl | H |
| 2-OCH₂CH₂OCH₃-phenyl | H | H | 7/9 | Cl | Cl | H |
| 2-OCH₂CH₂OCH₃-phenyl | H | CH₃ | 7 | Cl | Cl | H |
| 2-OCH₂CH₂OCH₃-phenyl | H | H | 7/9 | OCH₃ | OCH₃ | H |
| 2-OCH₂CH₂OCH₃-phenyl | H | CH₃ | 7 | OCH₃ | OCH₃ | H |
| 2-OCH₂CH₂OCH₃-phenyl | H | H | 7/9 | CH₃ | OCH₃ | H |
| 2-OCH₂CH₂OCH₃-phenyl | H | CH₃ | 7 | CH₃ | OCH₃ | H |
| 2-OCH₂CH₂OCH₃-phenyl | H | H | 7/9 | OCH₃ | CH₃ | H |
| 2-OCH₂CH₂OCH₃-phenyl | H | CH₃ | 7 | OCH₃ | CH₃ | H |
| 2-OCH₂CH₂OCH₃-phenyl | H | H | 7/9 | Cl | OCH₃ | H |
| 2-OCH₂CH₂OCH₃-phenyl | H | CH₃ | 7 | Cl | OCH₃ | H |
| 2-OCH₂CH₂OCH₃-phenyl | H | H | 7/9 | OCH₃ | Cl | H |
| 2-OCH₂CH₂OCH₃-phenyl | H | CH₃ | 7 | OCH₃ | Cl | H |
| 2-OCH₂CH₂Cl-phenyl | H | H | 7/9 | CH₃ | CH₃ | H |
| 2-OCH₂CH₂Cl-phenyl | H | CH₃ | 7 | CH₃ | CH₃ | H |
| 2-OCH₂CH₂Cl-phenyl | H | H | 7/9 | Cl | CH₃ | H |
| 2-OCH₂CH₂Cl-phenyl | H | CH₃ | 7 | Cl | CH₃ | H |
| 2-OCH₂CH₂Cl-phenyl | H | H | 7/9 | CH₃ | Cl | H |
| 2-OCH₂CH₂Cl-phenyl | H | CH₃ | 7 | CH₃ | Cl | H |
| 2-OCH₂CH₂Cl-phenyl | H | H | 7/9 | Cl | Cl | H |
| 2-OCH₂CH₂Cl-phenyl | H | CH₃ | 7 | Cl | Cl | H |
| 2-OCH₂CH₂Cl-phenyl | H | H | 7/9 | OCH₃ | OCH₃ | H |
| 2-OCH₂CH₂Cl-phenyl | H | CH₃ | 7 | OCH₃ | OCH₃ | H |
| 2-OCH₂CH₂Cl-phenyl | H | H | 7/9 | CH₃ | OCH₃ | H |
| 2-OCH₂CH₂Cl-phenyl | H | CH₃ | 7 | CH₃ | OCH₃ | H |
| 2-OCH₂CH₂Cl-phenyl | H | H | 7/9 | OCH₃ | CH₃ | H |
| 2-OCH₂CH₂Cl-phenyl | H | CH₃ | 7 | OCH₃ | CH₃ | H |
| 2-OCH₂CH₂Cl-phenyl | H | H | 7/9 | Cl | OCH₃ | H |
| 2-OCH₂CH₂Cl-phenyl | H | CH₃ | 7 | Cl | OCH₃ | H |
| 2-OCH₂CH₂Cl-phenyl | H | H | 7/9 | OCH₃ | Cl | H |
| 2-OCH₂CH₂Cl-phenyl | H | CH₃ | 7 | OCH₃ | Cl | H |
| 2-OCH₂CO₂CH₃-phenyl | H | H | 7/9 | CH₃ | CH₃ | H |
| 2-OCH₂CO₂CH₃-phenyl | H | CH₃ | 7 | CH₃ | CH₃ | H |
| 2-OCH₂CO₂CH₃-phenyl | H | H | 7/9 | Cl | CH₃ | H |
| 2-OCH₂CO₂CH₃-phenyl | H | CH₃ | 7 | Cl | CH₃ | H |
| 2-OCH₂CO₂CH₃-phenyl | H | H | 7/9 | CH₃ | Cl | H |
| 2-OCH₂CO₂CH₃-phenyl | H | CH₃ | 7 | CH₃ | Cl | H |
| 2-OCH₂CO₂CH₃-phenyl | H | H | 7/9 | Cl | Cl | H |
| 2-OCH₂CO₂CH₃-phenyl | H | CH₃ | 7 | Cl | Cl | H |
| 2-OCH₂CO₂CH₃-phenyl | H | H | 7/9 | OCH₃ | OCH₃ | H |
| 2-OCH₂CO₂CH₃-phenyl | H | CH₃ | 7 | OCH₃ | OCH₃ | H |
| 2-OCH₂CO₂CH₃-phenyl | H | H | 7/9 | CH₃ | OCH₃ | H |
| 2-OCH₂CO₂CH₃-phenyl | H | CH₃ | 7 | CH₃ | OCH₃ | H |
| 2-OCH₂CO₂CH₃-phenyl | H | H | 7/9 | OCH₃ | CH₃ | H |
| 2-OCH₂CO₂CH₃-phenyl | H | CH₃ | 7 | OCH₃ | CH₃ | H |
| 2-OCH₂CO₂CH₃-phenyl | H | H | 7/9 | Cl | OCH₃ | H |
| 2-OCH₂CO₂CH₃-phenyl | H | CH₃ | 7 | Cl | OCH₃ | H |
| 2-OCH₂CO₂CH₃-phenyl | H | H | 7/9 | OCH₃ | Cl | H |
| 2-OCH₂CO₂CH₃-phenyl | H | CH₃ | 7 | OCH₃ | Cl | H |
| 2,6-Cl,Cl-phenyl | H | H | 7/9 | CH₃ | CH₃ | H |
| 2,6-Cl,Cl-phenyl | H | CH₃ | 7 | CH₃ | CH₃ | H |
| 2,6-Cl,Cl-phenyl | H | H | 7/9 | Cl | CH₃ | H |
| 2,6-Cl,Cl-phenyl | H | CH₃ | 7 | Cl | CH₃ | H |
| 2,6-Cl,Cl-phenyl | H | H | 7/9 | CH₃ | Cl | H |
| 2,6-Cl,Cl-phenyl | H | CH₃ | 7 | CH₃ | Cl | H |
| 2,6-Cl,Cl-phenyl | H | H | 7/9 | Cl | Cl | H |
| 2,6-Cl,Cl-phenyl | H | CH₃ | 7 | Cl | Cl | H |
| 2,6-Cl,Cl-phenyl | H | H | 7/9 | OCH₃ | OCH₃ | H |
| 2,6-Cl,Cl-phenyl | H | CH₃ | 7 | OCH₃ | OCH₃ | H |
| 2,6-Cl,Cl-phenyl | H | H | 7/9 | CH₃ | OCH₃ | H |
| 2,6-Cl,Cl-phenyl | H | CH₃ | 7 | CH₃ | OCH₃ | H |
| 2,6-Cl,Cl-phenyl | H | H | 7/9 | OCH₃ | CH₃ | H |
| 2,6-Cl,Cl-phenyl | H | CH₃ | 7 | OCH₃ | CH₃ | H |
| 2,6-Cl,Cl-phenyl | H | H | 7/9 | Cl | OCH₃ | H |
| 2,6-Cl,Cl-phenyl | H | CH₃ | 7 | Cl | OCH₃ | H |
| 2,6-Cl,Cl-phenyl | H | H | 7/9 | OCH₃ | Cl | H |
| 2,6-Cl,Cl-phenyl | H | CH₃ | 7 | OCH₃ | Cl | H |
| 2-Cl,6-CH₃-phenyl | H | H | 7/9 | CH₃ | CH₃ | H |
| 2-Cl,6-CH₃-phenyl | H | CH₃ | 7 | CH₃ | CH₃ | H |
| 2-Cl,6-CH₃-phenyl | H | H | 7/9 | Cl | CH₃ | H |
| 2-Cl,6-CH₃-phenyl | H | CH₃ | 7 | Cl | CH₃ | H |
| 2-Cl,6-CH₃-phenyl | H | H | 7/9 | CH₃ | Cl | H |
| 2-Cl,6-CH₃-phenyl | H | CH₃ | 7 | CH₃ | Cl | H |

TABLE IV-continued

Id $$A-CH_2-SO_2-N(R^1)-C(R^2)=N-[\text{pyridine with } R^3, R^4, R^5]$$

(positions 7, 9 on the fused ring system)

| A | $R^1$ | $R^2$ | Pos. | $R^3$ | $R^4$ | $R^5$ |
|---|---|---|---|---|---|---|
| 2-Cl,6-CH$_3$-phenyl | H | H | 7/9 | Cl | Cl | H |
| 2-Cl,6-CH$_3$-phenyl | H | CH$_3$ | 7 | Cl | Cl | H |
| 2-Cl,6-CH$_3$-phenyl | H | H | 7/9 | OCH$_3$ | OCH$_3$ | H |
| 2-Cl,6-CH$_3$-phenyl | H | CH$_3$ | 7 | OCH$_3$ | OCH$_3$ | H |
| 2-Cl,6-CH$_3$-phenyl | H | H | 7/9 | CH$_3$ | OCH$_3$ | H |
| 2-Cl,6-CH$_3$-phenyl | H | CH$_3$ | 7 | CH$_3$ | OCH$_3$ | H |
| 2-Cl,6-CH$_3$-phenyl | H | H | 7/9 | OCH$_3$ | CH$_3$ | H |
| 2-Cl,6-CH$_3$-phenyl | H | CH$_3$ | 7 | OCH$_3$ | CH$_3$ | H |
| 2-Cl,6-CH$_3$-phenyl | H | H | 7/9 | Cl | OCH$_3$ | H |
| 2-Cl,6-CH$_3$-phenyl | H | CH$_3$ | 7 | Cl | OCH$_3$ | H |
| 2-Cl,6-CH$_3$-phenyl | H | H | 7/9 | OCH$_3$ | Cl | H |
| 2-Cl,6-CH$_3$-phenyl | H | CH$_3$ | 7 | OCH$_3$ | Cl | H |
| 2,5-Cl,Cl-phenyl | H | H | 7/9 | CH$_3$ | CH$_3$ | H |
| 2,5-Cl,Cl-phenyl | H | CH$_3$ | 7 | CH$_3$ | CH$_3$ | H |
| 2,5-Cl,Cl-phenyl | H | H | 7/9 | Cl | CH$_3$ | H |
| 2,5-Cl,Cl-phenyl | H | CH$_3$ | 7 | Cl | CH$_3$ | H |
| 2,5-Cl,Cl-phenyl | H | H | 7/9 | CH$_3$ | Cl | H |
| 2,5-Cl,Cl-phenyl | H | CH$_3$ | 7 | CH$_3$ | Cl | H |
| 2,5-Cl,Cl-phenyl | H | H | 7/9 | Cl | Cl | H |
| 2,5-Cl,Cl-phenyl | H | CH$_3$ | 7 | Cl | Cl | H |
| 2,5-Cl,Cl-phenyl | H | H | 7/9 | OCH$_3$ | OCH$_3$ | H |
| 2,5-Cl,Cl-phenyl | H | CH$_3$ | 7 | OCH$_3$ | OCH$_3$ | H |
| 2,5-Cl,Cl-phenyl | H | H | 7/9 | CH$_3$ | OCH$_3$ | H |
| 2,5-Cl,Cl-phenyl | H | CH$_3$ | 7 | CH$_3$ | OCH$_3$ | H |
| 2,5-Cl,Cl-phenyl | H | H | 7/9 | OCH$_3$ | CH$_3$ | H |
| 2,5-Cl,Cl-phenyl | H | CH$_3$ | 7 | OCH$_3$ | CH$_3$ | H |
| 2,5-Cl,Cl-phenyl | H | H | 7/9 | Cl | OCH$_3$ | H |
| 2,5-Cl,Cl-phenyl | H | CH$_3$ | 7 | Cl | OCH$_3$ | H |
| 2,5-Cl,Cl-phenyl | H | H | 7/9 | OCH$_3$ | Cl | H |
| 2,5-Cl,Cl-phenyl | H | CH$_3$ | 7 | OCH$_3$ | Cl | H |

The substituted sulfonamides I, and herbicidal agents containing them, may be applied for instance in the form of directly sprayable solutions, powders, suspensions (including high-percentage aqueous, oily or other suspensions); dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows

I. 90 parts by weight of compound no. 1.005 is mixed with 10 parts by weight of N-methyl-alpha-pyrrolidone. A mixture is obtained which is suitable for application in the form of very fine drops.

II. 20 parts by weight of compound no. 1.006 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.007 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.008 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.009 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.010 is intimately mixed with 97 parts by weight of particulate kaolin. A dust is obtained containing 3% by weight of the active ingredient.

VII. 30 parts by weight of compound no. 1.011 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.012 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the numerous application methods possible, the compounds according to the invention, or agents containing them, may be used in a large number of crops for removing unwanted plants.

Some of the sulfonamides of the general formula I may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

Of practical importance is the reduction in vegetative growth in fruit trees and other woody plants, thus saving pruning costs.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The sulfonamides of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a disinfectant), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 1, g per kg of seed are generally required. For foliage and soil treatment, amounts of from 0.01 to 10, and preferably from 0.1 to 5, kg/ha are generally considered to be sufficient.

To increase the spectrum of action and to achieve synergistic effects, the sulfonamides of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, imidazolinones, sulfonylureas, cyclohexane-1,3-dione derivatives, quinolinecarboxylic acid derivatives, phenyloxy- or (hetero)-aryloxyphenylpropionic acid derivatives (salts, esters, amides), etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The directions given in the synthesis examples below were used, after appropriate modifications of the starting materials, to produce further compounds I. The compounds obtained are given in Tables 1 to 3 with their physical data.

EXAMPLE 1

Synthesis of $N^1$-(2,6-dichloro-7-methyl-8-purinyl)-benzenesulfonamide (process A)

10.8 g (50.0 mmol) of the sodium salt of benzenesulfonamide was suspended in 100 ml of DMF; at 60° C., 11.9 g (50.0 mmol) of 7-methyl-2,6,8-trichloropurine was added. After 8 hours at 80° C. and cooling to room temperature, $H_2O$/ice was added, the mixture was acidified with 10% strength hydrochloric acid and the precipitate was suction filtered and dried.

11.7 g of colorless crystals (65%) (active ingredient 1.001).

$^1$H-NMR (250 MHz, $d^6$DMSO, $\delta$ in ppm): 3.60 (s, 3H, N-CH$_3$); 7.60 (mc, 3H, aryl-H); 7.95 (mc, 2H, aryl-H).

EXAMPLE 2

Synthesis of $N^1$-(2-chloro-6-methoxy-7-methyl-8-purinyl)-benzenesulfonamide (process F)

3.00 g (8.00 mmol) of the sulfonamide prepared in Example 1 and 2.90 g (16.0 mmol) of 30% strength sodium methylate solution were stirred in 50 ml of methanol for 12 hours at room temperature, and then evaporated down in a rotary evaporator. Stirring the residue in $H_2O$ and acidifying with dilute HCl gave 2.30 g (81%) of the desired product in the form of colorless crystals (active ingredient 1.002).

$^1$H-NMR (250 MHz, $d^6$-DMSO, $\delta$ in ppm): 3.50 (s, 3H, N-CH$_3$); 4.05 (s, 3H, OCH$_3$); 7.55 (mc, 3H, aryl-H); 7.95 (mc, 2H, aryl-H).

EXAMPLE 3

Synthesis of $N^1$-(2,6-dimethoxy-7-methyl-8-purinyl)-benzenesulfonamide (process G)

3.60 g (10.0 mmol) of the sulfonamide synthesized in Example 1 and 5.40 g (30.0 mmol) of 30% strength sodium methylate solution were heated in 200 ml of methanol in an autoclave for 12 hours at 120° C.; after the mixture had been cooled to room temperature it was evaporated in a rotary evaporator. Stirring the residue in $H_2O$ and acidifying with 10% strength HCl gave 3.20 g of colorless crystals in a yield of 92% (active ingredient 1.003).

$^1$H-NMR (250 MHz, $d^6$-DMSO, $\delta$ in ppm): 3.45 (s, 3H, N-CH$_3$); 3.90 (s, 3H, OCH$_3$); 4.05 (s, 3H, OCH$_3$); 7.50 (mc, 3H, aryl-H); 7.95 (mc, 2H, aryl-H).

EXAMPLE 4

Synthesis of $N^1$-(2,6-dichloro-7-methyl-8-purinyl)-2-carbomethoxybenzenesulfonamide (process B)

At 70° C., 6.60 g (28 mmol) of 2-carbomethoxybenzenesulfonamide was added to a suspension of 3.00 g (14.0 mmol) of 8-amino-2,6-dichloro-7-methylpurine in 150 ml of pyridine. After 3 hours at 70°-80° C., the reaction mixture was evaporated down in a rotary evaporator, and the residue was stirred into ice/$H_2O$ and acidified with dilute HCl. The desired product was obtained in the form of a brown powder having the following physical data (active ingredient 1.020)

$^1$H-NMR (250 MHz, $d^6$-DMSO, $\delta$ in ppm): 3.60 (s, 3H, N-CH$_3$); 3.80 (s, 3H, CO$_2$CH$_3$); 7.60 (mc, 1H, aryl-H); 7.70 (mc, 2H, aryl-H); 8.10 (mc, 1H, aryl-H).

EXAMPLE 5

Synthesis of
N¹-(2,6-dimethoxy-8-purinyl)-benzenesulfonamide
(process C)

While stirring and at room temperature, 3.00 g (13.0 mmol) of benzenesulfonylisocyanide dichloride was slowly dripped into 2.20 (13.0 mmol) of 4,5-diamino-2,6-dimethoxypyrimidine and 2.60 g (26.0 mmol) of triethylamine in 50 ml of dioxane. After 5 hours at 100° C., the mixture was cooled to room temperature, the solid which had formed was filtered off and the filtrate was evaporated down in a rotary evaporator. The desired product was isolated from the residue by crystallization with methylene chloride/methyl tert-butyl ether (active ingredient 1.004).

¹H-NMR (250 MHz, d⁶-DMSO, δ in ppm): 3.90 (s, 3H, OCH₃); 4.00 (s, 3H, OCH₃); 7.55 (mc, 3H, aryl-H); 7.95 (mc, 2H, aryl-H).

TABLE 1

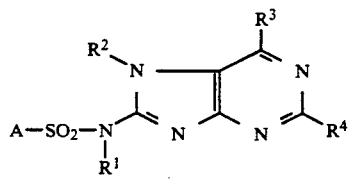

Ia

| No. | A | R¹ | R² | R³ | R⁴ | ¹HNMR[d⁶ DMSO, δ(ppm)]; mp[°C.] |
|---|---|---|---|---|---|---|
| 1.001 | phenyl | H | CH₃ | Cl | Cl | 3.60(s, 3H); 7.60(mc, 3H); 7.95(mc, 2H); |
| 1.002 | phenyl | H | CH₃ | OCH₃ | Cl | 3.50(s, 3H); 4.05(s, 3H); 7.55(mc, 3H); 7.95(mc, 2H) |
| 1.003 | phenyl | H | CH₃ | OCH₃ | OCH₃ | 3.45(s, 3H); 3.90(s, 3H); 4.05(s, 3H); 7.50(mc, 3H); 7.95(mc, 2H); |
| 1.004 | phenyl | H | H | OCH₃ | OCH₃ | 3.90(s, 3H); 4.00(s, 3H); 7.55(mc, 3H); 7.95(mc, 2H); |
| 1.005 | 2-Cl-phenyl | H | CH₃ | Cl | Cl | 3.60(s, 3H); 7.50-7.60(m, 3H); 8.15(mc, 1H); |
| 1.006 | 2-Cl-phenyl | H | CH₃ | OCH₃ | Cl | 3.55(s, 3H); 4.05(s, 3H); 7.45-7.60(m, 3H); 8.15(mc, 1H); |
| 1.007 | 2-Cl-phenyl | H | CH₃ | OCH₃ | OCH₃ | 3.50(s, 3H); 3.90(s, 3H); 4.05(s, 3H); 7.45-7.60(m, 3H); 8.15(mc, 1H); |
| 1.008 | 2,6-Cl,Cl-phenyl | H | CH₃ | Cl | Cl | 3.60(s, 3H); 7.45-7.60(m, 3H); |
| 1.009 | 2,6-Cl,Cl-phenyl | H | CH₃ | OCH₃ | Cl | 3.55(s, 3H); 4.10(s, 3H); 7.50-7.65(m, 3H); |
| 1.010 | 2,6-Cl,Cl-phenyl | H | CH₃ | OCH₃ | OCH₃ | 3.50(s, 3H); 3.80(s, 3H); 3.95(s, 3H); 7.40-7.50(m, 3H); |
| 1.011 | 2,6-Cl,Cl-phenyl | H | CH₃ | N(CH₃)₂ | Cl | 3.05(s, 6H); 3.55(s, 3H); 7.40-7.55(m, 3H); |
| 1.012 | 2,5-Cl,Cl-phenyl | H | CH₃ | Cl | Cl | 3.60(s, 3H); 7.60(mc, 2H); 8.20(mc, 1H); |
| 1.013 | 2,5-Cl,Cl-phenyl | H | CH₃ | OCH₃ | Cl | 3.55(s, 3H); 4.05(s, 3H); 7.65(mc, 2H); 8.20(mc, 1H); |
| 1.014 | 2,5-Cl,Cl-phenyl | H | CH₃ | OCH₃ | OCH₃ | 3.55(s, 3H); 3.90(s, 3H); 4.05(s, 3H); 7.65(mc, 2H); 8.20(mc, 1H); |
| 1.015 | 3-F-phenyl | H | CH₃ | Cl | Cl | 3.65(s, 3H); 7.40(mc, 1H); 7.60(mc, 1H); 7.80(mc, 2H); |
| 1.016 | 3-F-phenyl | H | CH₃ | OCH₃ | Cl | 3.50(s, 3H); 4.10(s, 3H); 7.40(mc, 1H); 7.60(mc, 1H); 7.80(mc, 2H); |
| 1.017 | 3-F-phenyl | H | CH₃ | OCH₃ | OCH₃ | 3.50(s, 3H); 3.90(s, 3H); 4.00(s, 3H); 7.40(mc, 1H); 7.60(mc, 1H); 7.80(mc, 2H); |
| 1.018 | 4-F-phenyl | H | CH₃ | Cl | Cl | 3.60(s, 3H); 7.40(mc, 2H); 8.05(mc, 2H); |
| 1.019 | 4-F-phenyl | H | CH₃ | OCH₃ | Cl | 3.50(s, 3H); 4.05(s, 3H); 7.30(mc, 2H); 8.00(mc, 2H); |
| 1.020 | 2-CO₂CH₃-phenyl | H | CH₃ | Cl | Cl | 3.60(s, 3H); 3.80(s, 3H); 7.60(mc, 1H); 7.70(mc, 2H); 8.10(mc, 1H); |
| 1.021 | 2-Cl,6-CH₃-phenyl | H | CH₃ | Cl | Cl | 2.70(s, 3H); 3.55(s, 3H); 7.30-7.50(m, 3H); |
| 1.022 | 2-Cl,6-CH₃-phenyl | H | CH₃ | OCH₃ | Cl | 2.70(s, 3H); 3.50(s, 3H); 4.00(s, 3H); 7.30-7.50(m, 3H); |
| 1.023 | 2-Cl,6-CH₃-phenyl | H | CH₃ | OCH₃ | OCH₃ | 2.70(s, 3H); 3.50(s, 3H); 3.90(s, 3H); 4.00(s, 3H); 7.20-7.40(m, 3H); |
| 1.024 | 2-OCH₃-phenyl | H | CH₃ | Cl | Cl | 3.55(s, 3H); 3.70(s, 3H); 7.05(t, 1H); 7.15(d, 1H);7.55 (t, 1H); 7.85(d, 1H); |
| 1.025 | 2-OCH₃-phenyl | H | CH₃ | OCH₃ | Cl | 3.45(s, 3H); 3.65(s, 3H); 4.05(s, 3H); 7.05(t, 1H); 7.15(d, 1H); 7.55(t, 1H); 7.85(d, 1H); |
| 1.026 | 2-OCH₃-phenyl | H | CH₃ | OCH₃ | OCH₃ | 3.45(s, 3H); 3.60(s, 3H); 3.90(s, 3H); 4.05(s, 3H); 7.00(t, 1H); 7.10(d, 1H); 7.50(t, 1H); 7.85(d, 1H); |
| 1.027 | 2-OCH₃-phenyl | H | CH₃ | N(CH₃)₂ | Cl | 3.00(s, 6H); 3.45(s, 3H); 3.60(s, 3H); 7.05(t, 1H); 7.15(d, 1H); 7.55(t, 1H); 7.85(d, 1H); |
| 1.028 | 4-OCH₃-phenyl | H | CH₃ | OCH₃ | OCH₃ | 3.50(s, 3H); 3.80(s, 3H); 3.90(s, 3H); 4.00(s, 3H); 6.95(mc, 2H); 7.90(mc, 2H); |
| 1.029 | 2-naphthyl | H | CH₃ | Cl | Cl | 3.60(s, 3H); 7.70(mc, 2H); 7.90-8.15(m, 4H); 8.65(s, 1H); |
| 1.030 | 2-naphthyl | H | CH₃ | OCH₃ | Cl | 3.50(s, 3H); 4.00(s, 3H); 7.55(mc, 2H); 7.90-8.15 (m, 4H); 8.65(s, 1H); |
| 1.031 | 2-naphthyl | H | CH₃ | OCH₃ | OCH₃ | 3.50(s, 3H); 3.85(s, 3H); 3.95(s, 3H); 7.60(mc, 2H); 7.90-8.10(m, 4H); 8.60(s, 1H); |
| 1.032 | 1-naphthyl | H | CH₃ | Cl | Cl | 3.55(s, 3H); 7.60-7.75(m, 3H); 8.00(mc, 1H); 8.15(mc, 1H); 8.40(mc, 1H); 8.80(mc, 1H); |
| 1.033 | 1-naphthyl | H | CH₃ | OCH₃ | Cl | 3.45(s, 3H); 3.95(s, 3H); 7.55-7.70(m, 3H); 7.95(mc, 1H); 7.95(mc, 1H); 8.05(mc, 1H); 8.20(mc, 1H); 8.35(mc, 1H); 8.85(mc, 1H); |
| 1.034 | 1-naphthyl | H | CH₃ | OCH₃ | OCH₃ | 3.50(s, 3H); 3.80(s, 3H); 3.90(s, 3H); 7.45-7.60 (m, 3H); 8.15(mc, 1H); |
| 1.035 | 8-quinolyl | H | CH₃ | Cl | Cl | 3.50(s, 3H); 7.65(mc, 1H); 7.80(mc, 1H); 8.30(mc, 1H); 8.50(mc, 1H); 8.55(mc, 1H); 8.80(mc, 1H); |
| 1.036 | 8-quinolyl | H | CH₃ | OCH₃ | Cl | 3.40(s, 3H); 4.10(s, 3H); 7.55(mc, 1H); 7.70(mc, 1H); 8.20(mc, 1H); 8.50(mc, 2H); 8.70(mc, 1H); |
| 1.037 | 2-thienyl | H | CH₃ | Cl | Cl | 3.65(s, 3H); 7.10(mc, 1H); 7.75(mc, 1H); 7.85(mc, 1H); |
| 1.038 | 2-thienyl | H | CH₃ | OCH₃ | Cl | 3.55(s, 3H); 4.05(s, 3H); 7.10(mc, 1H); 7.75(mc, 2H); |
| 1.039 | 2-thienyl | H | CH₃ | OCH₃ | OCH₃ | 3.50(s, 3H); 3.95(s, 3H); 4.05(s, 3H); 7.10(mc, 1H); |

TABLE 1-continued

Ia $$A-SO_2-N(R^1)-C(=NR^2)-...-R^3, R^4$$

| No. | A | R¹ | R² | R³ | R⁴ | ¹HNMR[d⁶ DMSO, δ(ppm)]; mp[°C.] |
|---|---|---|---|---|---|---|
| | | | | | | 7.80(mc, 2H); |
| 1.040 | 3-Cl,2-thienyl | H | CH₃ | Cl | Cl | 3.70(s, 3H); 7.10(d, 1H); 7.90(d, 1H); |
| 1.041 | 3-Cl,2-thienyl | H | CH₃ | OCH₃ | Cl | 3.50(s, 3H),4.10(s, 3H); 7.10(d, 1H); 7.90(d, 1H); |
| 1.042 | 3-Cl,2-thienyl | H | CH₃ | OCH₃ | OCH₃ | 3.55(s, 3H); 3.90(s, 3H); 4.05(s, 3H); 7.10(d, 1H), 7.85(d, 1H); |
| 1.043 | 4-CO₂CH₃,3-thienyl | H | CH₃ | Cl | Cl | 3.55(s, 3H); 3.70(s, 3H); 8.35(mc, 2H); |
| 1.044 | 4-CO₂CH₃,3-thienyl | H | CH₃ | OCH₃ | Cl | 3.50(s, 3H); 3.70(s, 3H); 4.10(s, 3H); 8.30(mc, 2H); |
| 1.045 | 4-CO₂CH₃,3-thienyl | H | CH₃ | OCH₃ | OCH₃ | 3.45(s, 3H); 3.70(s, 3H); 3.90(s, 3H); 4.05(s, 3H) 8.30(mc, 2H); |
| 1.046 | 2-chlorophenyl | H | H | OCH₃ | CH₃ | 2.48(s, 3H); 34.00s, 3H); 7.51(mc, 3H); 8.19(d, 1H); 12.50(s; 1H); 12.70(s; 1H); |
| 1.047 | 2-chlorophenyl | H | H | OCH₃ | OCH₃ | 3.90(s, 3H); 4.05(s, 3H); 7.51(mc, 3H); 8.15(d, 1H); 12.30(s, 1H); 12.60(s, 1H); |
| 1.048 | 2-chlorophenyl | H | CH₃ | F | F | 193 |
| 1.049 | 2-chlorophenyl | H | CH₃ | OCH₃ | F | 3.53(s, 3H); 7.37(mc, 2H); 7.63(mc, 1H); 7.97(mc, 1H); 13.0(m, 1H); |
| 1.050 | 2,6-Cl,Cl-phenyl | H | CH₃ | F | F | 3.53(s, 3H); 7.22-7.63(m, 3H); |
| 1.051 | 2,6-Cl,Cl-phenyl | H | CH₃ | OCH₃ | F | 3.53(s, 3H); 7.51(mc, 1H); 7.60(mc, 2H); |
| 1.052 | 2,6-Cl,Cl-phenyl | H | CH₃ | OCH₂CF₃ | Cl | 3.53(s, 3H); 5.19(q, 2H); 7.54(mc, 3H); |
| 1.053 | 2,3-Cl,Cl-phenyl | H | CH₃ | Cl | Cl | 244 |
| 1.054 | 2,3-Cl,Cl-phenyl | H | CH₃ | OCH₃ | Cl | 215 |
| 1.055 | 2,4,5,-Cl,Cl,Cl-phenyl | H | CH₃ | Cl | Cl | 255-227 |
| 1.056 | 2-F-phenyl | H | CH₃ | Cl | Cl | 115-119 |
| 1.057 | 2-F-phenyl | H | CH₃ | OCH₃ | Cl | 210-212 |
| 1.058 | 2-F-phenyl | H | CH₃ | F | F | 3.53(s, 33H); 7.53(mc, 1H); 7.64(mc, 2H); 8.19(d, 1H); |
| 1.059 | 2,6-F,F-phenyl | H | CH₃ | Cl | Cl | 3.65(s, 3H); 7.63(mc, 1H); 8.05(mc, 1H); 8.91(mc, 1H); |
| 1.060 | 2,6-F,F-phenyl | H | CH₃ | OCH₃ | Cl | *3.61(s, 3H); 4.15(s, 3H); 6.91(mc, 2H); 7.41(mc, 2H); |
| 1.061 | 2,6-F,F-phenyl | H | CH₃ | F | F | 167-169 |
| 1.062 | 2,6-F,F-phenyl | H | CH₃ | OCH₃ | F | 3.56(s, 3H); 4.08(s, 3H); 7.23(mc, 2H); 7.64(mc, 2H); |
| 1.063 | 2-CO₂CH₃-phenyl | H | CH₃ | OCH₃ | Cl | 203-205 |
| 1.064 | 2-CH₃-phenyl | H | CH₃ | Cl | Cl | 2.63(s, 3H); 3.61(s, 3H); 7.40(mc, 3H); 8.07(d, 1H); |
| 1.065 | 2-CH₃-phenyl | H | CH₃ | OCH₃ | Cl | 2.61(s, 3H); 3.49(s, 3H); 4.03(s, 3H); 7.39(mc, 3H); 8.05(d, 1H); 0.87(s, 1H); |
| 1.066 | 2-CH₃-phenyl | H | CH₃ | OCH₃ | OCH₃ | 2.63(s, 3H); 3.50(s, 3H); 3.89(s, 3H); 4.01(s, 3H); 7.38(mc, 3H); 8.09(d, 1H); 12.45(s, 1H); |
| 1.067 | 2,5-CH₃,CH₃-phenyl | H | CH₃ | Cl | Cl | 189-190 |
| 1.068 | 2,5-CH₃,CH₃-phenyl | H | CH₃ | OCH₃ | Cl | 206-208 |
| 1.069 | 2,5-CH₃,CH₃-phenyl | H | CH₃ | OCH₃ | OCH₃ | 182-184 |
| 1.070 | 2-CF₃-phenyl | H | CH₃ | Cl | Cl | 208-210 |
| 1.071 | 2-CF₃-phenyl | H | CH₃ | OCH₃ | Cl | 205-206 |
| 1.072 | 2-CF₃-phenyl | H | CH₃ | OCH₃ | OCH₃ | 199-203 |
| 1.073 | 2-O(CH₂)₂Cl-phenyl | H | CH₃ | Cl | Cl | 115-119 |
| 1.074 | 2-O(CH₂)₂OCH₃-phenyl | H | CH₃ | Cl | Cl | 191-193 |
| 1.075 | 2-O(CH₂)₂OCH₃-phenyl | H | CH₃ | OCH₃ | Cl | 188 |
| 1.076 | 2,5-OCH₃,OCH₃-phenyl | H | CH₃ | Cl | Cl | 3.54(s, 3H); 3.61(s, 3H):3.76(s, 3H); 7.11(s, 2H); 7.44(s, 1H); 12.85(s, 1H); |
| 1.077 | 2,5-OCH₃,OCH₃-phenyl | H | CH₃ | OCH₃ | Cl | 3.46(s, 3H); 3.61(s, 3H); 3.76(s, 3H); 4.04(s, 3H); 7.07(s, 2H); 7.44(s, 1, H); 12.62(s, 1H); |
| 1.078 | 2-OCH₃,5-Br-phenyl | H | CH₃ | Cl | Cl | 3.57(s, 3H); 3.71(s-3H); 7.13(mc, 1H); 7.73(mc-1H); 7.98(mc, 1H); |

*¹H NMR spectrum using CDCl₃ as solvent

TABLE 2

Ib $$A-CH_2-SO_2-N(R^1)-C(=NR^2)-...-R^3, R^4$$

| No. | A | R¹ | R² | R³ | R⁴ | ¹HNMR[d⁶ DMSO, δ(ppm)]; mp[°C.] |
|---|---|---|---|---|---|---|
| 2.001 | 2,6-Cl,Cl-phenyl | H | CH₃ | Cl | Cl | 3.60(s, 3H); 4.70(s, 2H); 7.40(mc, 1H); 7.55(mc, 2H); |
| 2.002 | 2,6-Cl,Cl-phenyl | H | CH₃ | OCH₃ | Cl | 3.50(s, 3H); 4.05(s, 2H), 4.70(s, 2H), |

TABLE 2-continued

Ib

A—CH$_2$—SO$_2$—N(R$^1$)—C(NR$^2$)=... [structure with R$^3$, R$^4$]

| No. | A | R$^1$ | R$^2$ | R$^3$ | R$^4$ | $^1$HNMR[d$^6$ DMSO, δ(ppm)]; mp[°C.] |
|---|---|---|---|---|---|---|
| 2.003 | 2-F-phenyl | H | CH$_3$ | Cl | Cl | 7.40(mc, 1H); 7.55(mc, 2H) 3.57(s, 3H); 4.49(s, 2H); 7.08-7.60(m-4H); |
| 2.004 | 2-F-phenyl | H | CH$_3$ | OCH$_3$ | Cl | 3.48(s, 3H); 4.07(s, 3H); 4.44(s, 2H); 7.18(mc, 2H); 7.35(mc, 1H); 7.52(mc, 1H); |

TABLE 3

Ic

A—SO$_2$—N(R$^1$)—C(NR$^2$)=... [structure with R$^3$, R$^4$, R$^5$]

| No. | A | R$^1$ | R$^2$ | R$^3$ | R$^4$ | R$^5$ | $^1$HNMR[d$^6$ DMSO, δ(ppm)]; mp[°C.] |
|---|---|---|---|---|---|---|---|
| 3.001 | phenyl | H | H | H | H | H | 7.15(dd, 1H); 7.55(mc, 3H); 7.65(dd, 1H); 7.90(mc, 2H); 8.05(dd, 1H); |

The herbicidal action of the sulfonamides of the formula I on the growth of plants is demonstrated by the following greenhouse experiments.

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before the compounds, suspended or emulsified in water, were sprayed on to them through finely distributing nozzles. The application rate for postemergence treatment was 0.5 kg/ha.

The pots wer set up in the greenhouse, heat-loving species at 20° to 35° C., and species from moderate climates at 10° to 20° C. The experiments were run for from 2 to 4 weeks. During this period the plants were tended and their reactions to the various treatments assessed. The assessment scale ws 0 to 100, 100 denoting nonemergence or complete destruction of at least the visible plant parts, and 0 denoting no damage or normal growth.

The plants employed for the experiments were *Chenopodium album, Chrysanthemum corinarium, Matricaria inodora, Sinapis alba,* and *Zea mays.*

Compounds 1.009 and 1.057, applied postemergence at a rate of 0.5 kg/ha, combated unwanted broadleaved plants very well and were tolerated by Indian corn.

We claim:

1. A sulfonamide of the formulae

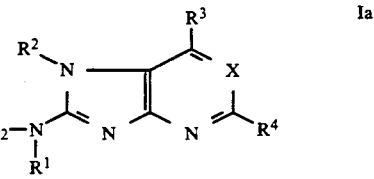

Ia

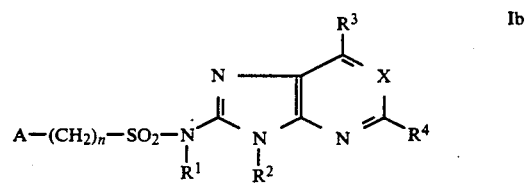

Ib where
R$^1$ is hydrogen or C$_1$-C$_4$-alkyl,
R$^2$ is
  C$_1$-C$_6$-alkyl which can be substituted by one to five halogens and/or one of the following:
  C$_1$-C$_4$-alkoxy, C$_1$-C$_4$-haloalkoxy, C$_1$-C$_4$-alkylthio, C$_1$-C$_4$-haloalkylthio, phenyl, phenoxy or phenylthio;
  C$_3$-C$_4$-alkenyl, C$_3$-C$_4$-alkynyl; a saturated or singly unsaturated 5- to 7-membered heterocycle which contains one or two nitrogen, oxygen and/or sulfur atoms and which can have one to three of the following substituents: halogen, C$_1$-C$_4$-alkyl, C$_1$-C$_4$-alkoxy, C$_1$-C$_4$-haloalkyl, C$_1$-C$_4$-haloalkoxy, C$_1$-C$_4$-alkylthio, C$_1$-C$_4$-haloalkylthio, and/or phenyl, phenoxy and/or phenylthio;
R$^3$ and R$^4$ are halogen;
  C$_1$-C$_4$-alkoxy, C$_1$-C$_4$-alkylthio, C$_2$-C$_6$-alkenyl, C$_2$-C$_6$-alkenyloxy, C$_2$-C$_6$-alkenylthio, C$_2$-C$_6$-alkynyl, C$_2$-C$_6$-alkynyloxy and/or C$_2$-C$_6$-alkynylthio, it being possible for these radicals to be substituted by one to five halogens and/or by one of the following groups: C$_1$-C$_4$-alkoxy, C$_1$-C$_4$-haloalkoxy, C$_2$-C$_4$-alkylthio, C$_1$-C$_4$-haloalkylthio, phenyl, phenoxy or phenylthio; C$_3$-C$_6$-cycloalkyl, C$_3$-C$_6$-cycloalkylthio, C$_5$-C$_6$-cycloalkenyl, C$_3$-C$_6$-cycloalkoxy, C$_5$-C$_6$- cyclokenyloxy, C₅–C₆-cycloalkenylthio, phenyl, phenoxy, phenylthio, benzyl, benzyloxy or benzylthio, it being possible for these cyclic groups to be substituted by one to five halogens and/or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, phenyl, phenoxy, phenylthio, benzyl, benzyloxy and/or benzylthio;

the groups mentioned under $R^2$ or $NR^7R^8$, where $R^7$ and $R^8$ are hydrogen, $C_1$–$C_6$-alkyl, $C_3$–$C_6$-alkenyl, $C_3$–$C_6$-alkynyl, $C_3$–$C_6$-cycloalkyl, $C_5$–$C_6$-cycloalkenyl, phenyl and/or benzyl, it being possible for the aromatic rings in turn to be substituted once to five times by halogen and/or once to three times by $C_1$–$C_4$-alkyl, $C_1$–$C_4$-haloalkyl, $C_1$–$C_4$-alkoxy and/or $C_1$–$C_4$-haloalkoxy, or together are a $C_4$–$C_6$-alkylene bridge which can be interrupted by an oxygen, sulfur or a nitrogen atom, it being possible for these bridges in turn to carry one to three $C_1$–$C_4$-alkyl groups;

X is nitrogen or $=CR^5-$, where $R^5$ is one of the radicals $R^3$, n is 0 or 1 and A is phenyl, naphthyl, pyridyl, pyridazinyl, pyrimidinyl, pyrazinyl, 1,3,5-triazinyl, 1,2,4-triazinyl, 1,2,3-triazinyl, tetrazinyl, pyrrolyl, furyl, thienyl, pyrazolyl, imidazolyl, oxazolyl, isoxazolyl, thiazolyl, isothiazolyl, 1,2,3-triazolyl, 1,2,4-triazolyl, tetrazolyl, thiadiazolyl, indolyl, isoindolyl, thionaphthyl, quinolyl, isoquinolyl, cinnolinyl, phthalazinyl, quinazolyl, quinoxalyl, indazolyl, naphthyridinyl, benzothiazolyl, benzimidazolyl, benzofuryl, benzoxazolyl and benzotriazolyl, and these aromatic rings substituted by one to five of the halogens, fluorine, chlorine and bromine, and/or one to three of the following: cyano, nitro, thiocyanato, $-COR^6$ where $R^6$ is hydroxyl, amino or one of the radicals $R^3$, $-SO_mR^6$ where m is 1 or 2, and/or the radicals mentioned for $R^3$.

2. A sulfonamide of the formulae

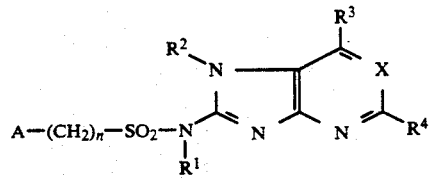

Ia

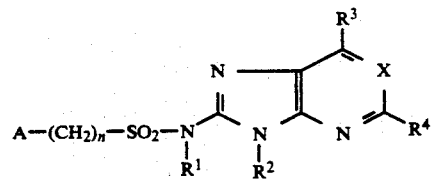

Ib where $R^1$ is hydrogen or $C_1$–$C_4$-alkyl, $R^2$ is hydrogen $R^3$ and $R^4$ are halogen;

$C_1$–$C_4$-alkoxy, $C_1$–$C_4$-alkylthio, $C_2$–$C_6$-alkenyl, $C_2$–$C_6$-alkenyloxy, $C_2$–$C_6$-alkenylthio, $C_2$–$C_6$-alkynyl, $C_2$–$C_6$-alkynyloxy and/or $C_2$–$C_6$-alkynylthio, it being possible for these radicals to be substituted by one to five halogens and/or by one of the following groups: $C_1$–$C_4$-alkoxy, $C_1$–$C_4$-haloalkoxy, $C_2$–$C_4$-alkylthio, $C_1$–$C_4$-haloalkylthio, phenyl, phenoxy or phenylthio; $C_3$–$C_6$-cycloalkyl, $C_3$–$C_6$-cycloalkylthio, $C_5$–$C_6$-cycloalkenyl, $C_3$–$C_6$-cycloalkoxy, $C_5$–$C_6$-cyclokenyloxy, $C_5$–$C_6$-cycloalkenylthio, phenyl, phenoxy, phenylthio, benzyl, benzyloxy or benzylthio, it being possible for these cyclic groups to be substituted by one to five halogens and/or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, phenyl, phenoxy, phenylthio, benzyl, benzyloxy and/or benzylthio;

$C_1$–$C_6$-alkyl which can be substituted by one to five halogens and/or one of the following:

$C_1$–$C_4$-alkoxy, $C_1$–$C_4$-haloalkoxy, $C_1$–$C_4$-alkylthio, $C_1$–$C_4$-haloalkylthio, phenyl, phenoxy or phenylthio;

$C_3$–$C_4$-alkenyl, $C_3$–$C_4$-alkynyl;

a suturated or singly unsaturated 5- to 7-membered heterocycle which contains one or two nitrogen, oxygen and/or sulfur atoms and which can have one to three of the following substituents; halogen, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-haloalkylthio and/or phenyl, phenoxy and/or phenylthio; or $NR^7R^8$, where $R^7$ and $R^8$ are hydrogen, $C_1$–$C_6$-alkyl, $C_3$–$C_6$-alkenyl, $C_3$–$C_6$-alkynyl, $C_3$–$C_6$-cycloalkyl, $C_5$–$C_6$-cycloalkenyl, phenyl and/or benzyl, it being possible for the aromatic rings in turn to be substituted once to five times by halogen and/or once to three times by $C_1$–$C_4$-alkyl, $C_1$–$C_4$-haloalkyl, $C_1$–$C_4$-alkoxy and/or $C_1$–$C_4$-haloalkoxy, or together are a $C_4$–$C_6$-alkylene bridge which can be interrupted by an oxygen, sulfur or a nitrogen atom, it being possible for these bridges in turn to carry one to three $C_1$–$C_4$-alkyl groups;

X is nitrogen or $=CR^5-$, where $R^5$ is one of the radicals $R^3$, n is 0 or 1 and A is phenyl, pyridyl, naphthyl, quinolyl, thienyl, pyrazolyl or N-methyl-pyrazolyl, and one of these aromatic radicals substituted by one to three of the following, in particular: nitro, cyano, fluorine, chlorine, bromine, ethyl, propyl, isopropyl, trifluoromethyl, methoxy, ethoxy, 1-methylethoxy, 1,1-dimethylethoxy, trifluoromethoxy, trifluoroethoxy, chloroethoxy, methoxymethyl, ethoxymethyl, methoxyethyl, ethoxyethyl, methoxyethoxy, ethoxyethoxy, methylthio, ethylthio, methyl- and ethylsulfonyl, methoxycarbonyl, ethoxycarbonyl, iso-propoxycarbonyl, methyl- and ethylcarbonyl, N,N-dimethylsulfamoyl and N,N—dimethylcarbamoyl, and agriculturally useful salts thereof.

3. A sulfonamide of the formulae I or Ib as defined in claim 1, wherein

A is phenyl, pyridyl, naphthyl, quinolyl, thienyl or pyrazolyl, and one of these aromatic radicals substituted by one to three of the following, in particular: nitro, cyano, fluorine, chlorine, ethyl, propyl, isopropyl, trifluoromethyl, methoxy, ethoxy, 1-methylethoxy, 1,1-dimethylethoxy, trifluoromethoxy, trifluoroethoxy, chloroethoxy, methoxymethyl, ethoxymethyl, methoxyethyl, ethoxyethyl, methoxyethoxy, ethoxyethoxy, methylthio, ethylthio, methyl- and ethylsulfonyl, methoxycarbonyl, ethoxycarbonyl, iso-propoxycarbonyl, methyl- and ethylcarbonyl, N,N-dimethylsulfamoyl and N,N-dimethylcarbamoyl, and agriculturally useful salts thereof.

4. A herbicidal composition containing a sulfonamide of the formula Ia or Ib as set forth in claim 2, or in agriculturally useful salt thereof, and conventional formulation auxiliaries.

5. A herbicidal composition containing a sulfonamide of the formula Ia or Ib as set forth in claim 1, or an agriculturally useful salt thereof, and conventional formulation auxiliaries.

6. A process for combating the growth of unwanted plants, wherein a sulfonamide of the formula Ia or Ib as set forth in claim 1 is allowed to act on the plants and/or their habitat.

7. A composition for influencing plant growth, containing a sulfonamide of the formula Ia or Ib as set forth in claim 1, or an agriculturally useful salt thereof, and conventional formulation auxiliaries.

8. A process for influencing plant growth, wherein a sulfonamide of the formula Ia or Ib as set forth in claim 1 or a salt thereof, is allowed to act on the plants and/or their habitat.

* * * * *

UNITED STATES PATENT AND TRADEMARK OFFICE
CERTIFICATE OF CORRECTION

PATENT NO. : 5,171,353
DATED : December 15, 1992
INVENTOR(S) : Fischer et al

It is certified that error appears in the above-indentified patent and that said Letters Patent is hereby corrected as shown below:

On the title page, item [57] Abstract, line 9, after "$C_1-C_4$-alkoxy" insert --,--; line 16, "the group", should read --the groups--; and line 23, "$=CR^5 14$," should read --$=CR^5-$,--.

In claim 4, column 111, line 10, "2, or in" should read --2, or an--.

Signed and Sealed this

Twenty-second Day of February, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,171,353
DATED : Dec. 15, 1992
INVENTOR(S) : FISCHER et al.

It is certified that error appears in the above-identified patent and that said Letters Patent is hereby corrected as shown below:

IN THE CLAIMS

Claim 2, column 110, line 6, "$C_5$-$C_6$-cyclokenyloxy" should read -- $C_5$-$C_6$-cycloalkenyloxy --.

Claim 2, column 110, line 21, "suturated" should read --saturated--.

Signed and Sealed this

Fifth Day of July, 1994

Attest:

BRUCE LEHMAN

Attesting Officer      Commissioner of Patents and Trademarks